United States Patent
Saha

(10) Patent No.: US 7,326,567 B2
(45) Date of Patent: Feb. 5, 2008

(54) PLASMID SYSTEM FOR MULTIGENE EXPRESSION

(75) Inventor: Deba P. Saha, Nutley, NJ (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 10/986,498

(22) Filed: Nov. 10, 2004

(65) Prior Publication Data

US 2005/0176099 A1   Aug. 11, 2005

Related U.S. Application Data

(60) Provisional application No. 60/519,230, filed on Nov. 12, 2003.

(51) Int. Cl.
- C12N 15/63 (2006.01)
- C12Q 1/68 (2006.01)
- G01N 33/53 (2006.01)
- C12N 15/85 (2006.01)

(52) U.S. Cl. .................. 435/320.1; 435/6; 435/7.1

(58) Field of Classification Search ............ None
See application file for complete search history.

(56) References Cited

U.S. PATENT DOCUMENTS

| | | |
|---|---|---|
| 4,543,439 A | 9/1985 | Frackelton, Jr. et al. |
| 5,198,340 A | 3/1993 | Mukku |
| 5,262,308 A | 11/1993 | Baserga |
| 5,942,412 A | 8/1999 | Prager et al. |
| 5,958,872 A | 9/1999 | O'Connor et al. |
| 5,977,307 A | 11/1999 | Friden et al. |
| 6,022,711 A | 2/2000 | Cunningham et al. |
| 6,084,085 A | 7/2000 | Baserga et al. |
| 6,294,330 B1 | 9/2001 | Michnick et al. |
| 6,300,129 B1 | 10/2001 | Lonberg et al. |
| 6,316,462 B1 | 11/2001 | Bishop et al. |
| 6,333,031 B1 | 12/2001 | Olsson et al. |
| 6,346,390 B1 | 2/2002 | Olsson et al. |
| 6,372,250 B1 | 4/2002 | Pardridge |
| 6,537,988 B2 | 3/2003 | Lee |
| 6,645,775 B1 | 11/2003 | Clark et al. |
| 2002/0022023 A1 | 2/2002 | Ullrich et al. |
| 2002/0025313 A1 | 2/2002 | Micklus et al. |
| 2002/0107187 A1 | 8/2002 | Kingston et al. |
| 2002/0132275 A1 | 9/2002 | Fidler et al. |
| 2002/0155095 A1 | 10/2002 | Nagabhushan et al. |
| 2002/0164333 A1 | 11/2002 | Nemerow et al. |
| 2002/0169116 A1 | 11/2002 | Kingston et al. |
| 2002/0187925 A1 | 12/2002 | Kingston et al. |
| 2002/0197262 A1 | 12/2002 | Hasan et al. |
| 2003/0021780 A1 | 1/2003 | Smith et al. |
| 2003/0031658 A1 | 2/2003 | Brodt et al. |
| 2003/0045676 A1 | 3/2003 | Kingston et al. |
| 2003/0087342 A1 | 5/2003 | Mermod et al. ......... 435/69.1 |
| 2003/0088061 A1 | 5/2003 | Staunton |
| 2003/0092631 A1 | 5/2003 | Deshayes et al. |
| 2003/0138430 A1 | 7/2003 | Stimmel et al. |
| 2003/0165502 A1 | 9/2003 | Fujita-Yamaguchi |
| 2003/0195147 A1 | 10/2003 | Pillutla et al. |
| 2003/0235582 A1 | 12/2003 | Singh et al. |
| 2003/0236190 A1 | 12/2003 | Pillutla et al. |
| 2004/0009154 A1 | 1/2004 | Khan et al. |
| 2004/0009906 A1 | 1/2004 | Kakkis et al. |
| 2004/0023887 A1 | 2/2004 | Pillutla et al. |
| 2004/0047835 A1 | 3/2004 | Bianco |
| 2004/0057950 A1 | 3/2004 | Waksal et al. |
| 2004/0086511 A1 | 5/2004 | Zack et al. |
| 2004/0102360 A1 | 5/2004 | Barnett et al. |
| 2004/0116330 A1 | 6/2004 | Naito et al. |
| 2004/0142381 A1 | 7/2004 | Hubbard et al. |
| 2004/0228859 A1 | 11/2004 | Graus et al. |
| 2004/0265307 A1 | 12/2004 | Singh et al. |
| 2005/0008642 A1 | 1/2005 | Graus et al. |
| 2005/0048050 A1 | 3/2005 | Fujita-Yamaguchi |
| 2005/0069539 A1 | 3/2005 | Cohen et al. |
| 2005/0081812 A1 | 4/2005 | Toedter et al. |
| 2005/0084906 A1 | 4/2005 | Goetsch et al. |
| 2005/0186203 A1 | 8/2005 | Singh et al. |
| 2005/0244408 A1 | 11/2005 | Cohen et al. |
| 2005/0249728 A1 | 11/2005 | Singh et al. |
| 2005/0249730 A1 | 11/2005 | Goetsch et al. |
| 2005/0255493 A1 | 11/2005 | Macaulay et al. |
| 2005/0272637 A1 | 12/2005 | Clinton et al. |
| 2005/0272755 A1 | 12/2005 | Denis et al. |

(Continued)

FOREIGN PATENT DOCUMENTS

FR   2 834 900   7/2003

(Continued)

OTHER PUBLICATIONS

Oberholzer et al., Increased survival in sepsis by in vivo adenovirus-induced expression of IL-10 in dendritic cells. J Immunol. Apr. 1, 2002;168(7):3412-8.

Wahle, The end of the message: 3'-end processing leading to polyadenylated messenger RNA. Bioessays. Feb. 1992;14(2):113-8.

Ju et al., Nucleotide sequence analysis of the long terminal repeat (LTR) of avain retroviruses: structural similarities with transposable elements. Nov. 1980;22(Pt 2):379-86.

Kaufman, Selection and coamplification of heterologous genes in mammalian cells. Methods Enzymol. 1990;185:537-66.

Takebe et al., SR alpha promoter: an efficient and versatile mammalian cDNA expression system composed of the simian virus 40 early promoter and the R-U5 segment of human T-cell leukemia virus type 1 long terminal repeat. Mol Cell Biol. Jan. 1988;8(1):466-72.

(Continued)

Primary Examiner—Nancy Vogel
Assistant Examiner—Michele K. Joike

(57) ABSTRACT

The present invention provides a plasmid system which facilitates the construction of a single amplifiable plasmid that, having the potential to accommodate many independent expression cassettes, has the ability to express multi-subunit complex proteins such as antibodies and receptors.

39 Claims, 16 Drawing Sheets

U.S. PATENT DOCUMENTS

| | | | |
|---|---|---|---|
| 2005/0281812 A1 | 12/2005 | Cohen et al. | |
| 2006/0018910 A1 | 1/2006 | Gualberto et al. | |

FOREIGN PATENT DOCUMENTS

| | | |
|---|---|---|
| FR | 2 834 990 | 7/2003 |
| FR | 2 834 991 | 7/2003 |
| WO | WO 91/04014 | 4/1991 |
| WO | WO 91/13160 | 9/1991 |
| WO | WO 91/14438 | 10/1991 |
| WO | WO 97/44352 | 11/1997 |
| WO | WO98/17801 | 4/1998 |
| WO | WO 98/22092 | 5/1998 |
| WO | WO 98/45427 | 10/1998 |
| WO | WO 99/25378 | 5/1999 |
| WO | WO 99/28347 | 6/1999 |
| WO | WO 99/42127 | 8/1999 |
| WO | WO 99/60023 | 11/1999 |
| WO | WO 00/22130 | 4/2000 |
| WO | WO 00/50067 | 8/2000 |
| WO | WO 00/69454 | 11/2000 |
| WO | WO 01/07084 A1 | 2/2001 |
| WO | WO 01/30964 A2 | 5/2001 |
| WO | WO 01/36632 A2 | 5/2001 |
| WO | WO 01/70268 A1 | 9/2001 |
| WO | WO 01/70930 A2 | 9/2001 |
| WO | WO 01/72771 A2 | 10/2001 |
| WO | WO 01/75064 A2 | 10/2001 |
| WO | WO 01/88121 A1 | 11/2001 |
| WO | WO 02/04522 A2 | 1/2002 |
| WO | WO 02/07783 A2 | 1/2002 |
| WO | WO 02/14525 A2 | 2/2002 |
| WO | WO 02/27017 A2 | 4/2002 |
| WO | WO 02/31500 A2 | 4/2002 |
| WO | WO 02/43758 A2 | 6/2002 |
| WO | WO 02/053596 A2 | 7/2002 |
| WO | WO 02/054066 A2 | 7/2002 |
| WO | WO 02/072780 A2 | 9/2002 |
| WO | WO 2004/087756 A2 | 10/2002 |
| WO | WO 02/088752 A2 | 11/2002 |
| WO | WO 02/092599 A1 | 11/2002 |
| WO | WO 02/102854 A2 | 12/2002 |
| WO | WO 02/102972 A2 | 12/2002 |
| WO | WO 02/102973 A2 | 12/2002 |
| WO | WO 03/000928 A2 | 1/2003 |
| WO | WO 03/014696 A2 | 2/2003 |
| WO | WO 03/027246 A2 | 4/2003 |
| WO | WO 03/039538 A1 | 5/2003 |
| WO | WO 03/059951 A2 | 7/2003 |
| WO | WO 03/088910 A2 | 10/2003 |
| WO | WO 03/100008 | 12/2003 |
| WO | WO 03/100008 A2 | 12/2003 |
| WO | WO 03/100059 A2 | 12/2003 |
| WO | WO 03/106621 A2 | 12/2003 |
| WO | WO 03/106621 A2 | 12/2003 |
| WO | WO 2004/030625 A2 | 4/2004 |
| WO | WO 2004/030627 A2 | 4/2004 |
| WO | WO 2004/056865 A2 | 7/2004 |
| WO | WO 2004/071529 A2 | 8/2004 |
| WO | WO 2004/083248 A1 | 9/2004 |
| WO | WO2004/096224 A2 | 11/2004 |
| WO | WO2004/096224 A3 | 11/2004 |
| WO | WO 2005/005635 A2 | 1/2005 |
| WO | WO 2005/016967 A2 | 2/2005 |
| WO | WO 2005/016970 A2 | 2/2005 |
| WO | WO 2005/061541 A1 | 7/2005 |
| WO | WO2005/117980 A1 | 12/2005 |
| WO | WO2006/013472 | 2/2006 |
| WO | WO 2006/013472 A2 | 2/2006 |
| WO | WO2006/020258 | 2/2006 |
| WO | WO 2006/020258 A2 | 2/2006 |

OTHER PUBLICATIONS

Norderhaug et al., "Versatile vectors for transient and stable expression of recombinant antibody molecules in mammalian cells", Journal of Immunological Methods, (1997), pp.77-87, vol. 204.

Zhang et al., "An adenoviral vector expressing functional heterogeneous proteins herpes simplex viral thymidine kinase and human interleukin-2 . . . ", Endocrine-Related Cancer, (2001), pp. 315-325, vol. 8.

Flamez et al., "Production in *Escherichia coli* of a functional murine and murine::human chimeric F(ab')2 fragment and mature antibody directed against . . . ", Journal of Biotechnology, (1995), pp. 133-143, vol. 42.

Christopher R.Bebbington, "Expression of Antibody Genes in Nonlymphoid Mammalian Cells", METHODS: A Companion to Methods in Enzymology, Apr. 1991, pp. 136-145, vol. 2, No. 2.

Page et al., "High level expression of the humanized monoclonal antibody campath-1H Chinese hamster ovary cells", BIOTECHNOLOGY, Jan. 1991, pp. 64-68, vol. 9.

Patent Cooperation Treaty PCT International Search Report, PCT Application No.: PCT/US2004/037721.

Li et al., "Single-chain antibodies against human insulin-like growth factor I receptor: expression, purification, and effect on tumor growth", Cancer Immunol. Immunother. 49: 243-252 (2000).

Burtrum et al., "A fully human monoclonal antibody to the insulin-like growth factor I receptor blocks ligand-dependent signaling and inhibits human tumor growth in vivo." Cancer Res. Dec. 15, 2003;63(24):8912-21.

Business Wire, "Imclone systems incorporated reports advancements in several pipeline programs" (Jul. 14, 2003).

Zhu, "Monoclonal Antibodies in Cancer-Fourth International Congress (Part II), Colorado Springs, CO, USA" Investigational Drug Database Meeting Report (Sep. 3-6, 2004).

Williams, "American Association for Cancer Research-94th Annual Meeting (Part III)-Overnight Report, Washington, D.C., USA" Investigational Drug Database Meeting Report (Jul. 11-14, 2003).

Imclone Systems, Inc. Form 10-K (filed Mar. 15, 2004).

Holt et al., Domain antibodies: proteins for therapy, Trends in Biotechnology 21(11): 484-490 (2003).

Maloney et al., An Anti-Insulin-like Growth Factor I Receptor Antibody That is a Potent Inhibitor of Cancer Cell Proliferation, Cancer Research 63, 5073-5083 (2003).

Lu et al., Simultaneous Blockade of Both the Epidermal Grown Factor Receptor and the Insulin-like Growth factor receptor signaling pathways in cancer cells with a XXX human recombinant XXX antibody, J. Bio. Chem.279(4):2856-65 (2004).

Tang et al., Use of a peptide mimotope to guide the humanization of MRK-16, an anti-P-glycoprotein monoclonal antibody. J Biol Chem. Sep. 24, 1999:274(39):27371-8.

Boylan et al., The anti-proliferative effect of suramin towards tamoxifen-sensitive and resistant human breast cancer cell lines in relation to expression of receptors for epidermal growth factor and insulin-like growth factor-I: growth stimulation in the presence of tamoxifen. Ann Oncol. Feb. 1999;9(2):205-11.

Happerfield et al., The localization of the insulin-like growth factor receptor 1 (IGFR-1) in benign and malignant breast tissue. J Pathol. Dec. 1997;183(4):412-7.

Clarke et al., Type I insulin-like growth factor receptor gene expression in normal human breast tissue treated with oestrogen and progesterone. Br J Cancer. 1997;75(2):251-7.

Van Den Berg et al., Expression of receptors for epidermal growth factor and insulin-like growth factor I by ZR-75-1 human breast cancer cell variants is inversely related: the effect of steroid hormones on insulin-like growth factor I receptor expression. Br J Cancer. Feb. 1996;73(4):477-81.

Lebon et al., Purification of insulin-like growth factor I receptor from human placental membranes. J Biol Chem. Jun. 15, 1986;261(17):7685-9.

Warren et al., Induction of vascular endothelial growth factor by insulin-like growth factor 1 in colorectal carcinoma. J Biol Chem. Nov. 15, 1996;271(46):29483-8.

Auclair et al., Antiinsulin receptor autoantibodies induce insulin receptors to constitutively associate with insulin receptor substrate-1 and -2 and cause severe cell resistance to both insulin and insulin-like growth factor I, J Clin Endocrinol Metab. Sep. 1999;84(9):3197-3206.

Gori et al., Effects of androgens on the insulin-like growth factor system in an androgen-responsive human osteoblastic cell line. Endocrinology. Dec. 1999;140(12):5579-86.

Kasprzyk et al., Therapy of an animal model of human gastric cancer using a combination of anti-erbB-2 monoclonal antibodies. Cancer Res. May 15, 1992;52(10):2771-6.

Drebin et al., Monoclonal antibodies reactive with distinct domains of the neu oncogene-encoded p185 molecule exert synergistic anti-tumor effects in vivo. Oncogene. Mar. 1988;2(3):273-7.

Shin et al., Proapoptotic activity of cell-permeable anti-Akt single-chain antibodies. Cancer Res. Apr. 1, 2005;65(7):2815-24.

Lu et al., A fully human recombinant lgG-like bispecific antibody to both the epidermal growth factor receptor and the insulin-like growth factor receptor for enhanced antitumor activity. J Biol Chem. May 20, 2005;280(20):19665-72.

Cohen et al., Combination therapy enhances the inhibition of tumor growth with the fully human anti-type 1 insulin-like growth factor receptor monoclonal antibody CP-751,871. Clin Cancer Res. Mar. 1, 2005;11(5):2063-73.

Wu et al., In vivo effects of the human type I insulin-like growth factor receptor antibody A12 on androgen-dependent and androgen-independent xenograft human prostate tumors. Clin Cancer Res. Apr. 15, 2005;11(8):3065-74.

Goetsch et al., A recombinant humanized anti-insulin-like growth factor receptor type I antibody (h7C10) enhances the antitumor activity of vinorelbine and anti-epidermal growth factor receptor therapy against human cancer xenografts. Int J Cancer. Jan. 10, 2005;113(2):316-28.

Granerus et al., Effects of insulin-like growth factor-binding protein 2 and an IGF-type I receptor-blocking antibody on apoptosis in human teratocarcinoma cells in vitro. Cell Biol Int. 2001;25(8):825-8.

Kaliman et al., Antipeptide antibody to the insulin-like growth factor-I receptor sequence 1232-1246 inhibits the receptor kinase activity. J Biol Chem. May 25, 1992;267(15):10645-51.

Rodeck et al., Interactions between growth factor receptors and corresponding monoclonal antibodies in human tumors. J Cell Biochem. Dec. 1987;35(4):315-20.

Iwakiri et al., Autocrine growth of Epstein-Barr virus-positive gastric carcinoma cells mediated by an Epstein-Barr virus-encoded small RNA. Cancer Res. Nov. 1, 2003;63(21):7062-7

Kiess et al., Human neuroblastoma cells use either insulin-like growth factor-I or insulin-like growth factor-II in an autocrine pathway via the IGF-I receptor: variability of IGF, IGF binding protein (IGFBP) and IGF receptor gene expression and IGF and IGFBP secretion in human neuroblastoma cells in relation to cellular proliferation. Regul Pept. Sep. 26, 1997;72(1):19-29.

Pritchard et al., Synovial fibroblasts from patients with rheumatoid arthritis, like fibroblasts from Graves' disease, express high levels of IL-16 when treated with Igs against insulin-like growth factor-1 receptor. J Immunol. Sep. 1, 2004;173(5):3564-9.

Jackson-Booth et al., Inhibition of the biologic response to insulin-like growth factor I in MCF-7 breast cancer cells by a new monoclonal antibody to the insulin-like growth factor-I receptor. The importance of receptor down-regulation. Horm Metab Res. Nov.-Dec. 2003;35(11-12):850-6.

Carboni et al., Tumor development by transgenic expression of a constitutively active insulin-like growth factor I-receptor. Cancer Res. May 1, 2005;65(9):3781-7.

Remacle-Bonnet et al., Insulin-like growth factor-I protects colon cancer cells from death factor-induced apoptosis by potentiating tumor necrosis factor alpha-induced mitogen-activated protein kinase and nuclear factor kappaB signaling pathways. Cancer Res. Apr. 1, 2005;60(7):2007-17.

Lahm et al., Blockade of the insulin-like growth-factor-I receptor inhibits growth of human colorectal cancer cells: evidence of a functional IGF-II-mediated autocrine loop. Int J Cancer. Aug. 1, 1994;58(3):452-9.

Steele-Perkins et al., Monoclonal antibody alpha IR-3 inhibits the ability of insulin-like growth factor II to stimulate a signal from the type I receptor without inhibiting its binding. Biochem Biophys Res Commun. Sep. 28, 1990;171(3):1244-51.

Scotlandi et al., Prognostic and therapeutic relevance of HER2 expression in osteosarcoma and Ewing's sarcoma. Eur J Cancer. Jun. 2005;41(9):1349-61.

Agus et al., Response of prostate cancer to anti-Her-2/neu antibody in androgen-dependent and -independent human xenograft models. Cancer Res. Oct. 1, 1999;59(19):4761-4.

Pietras et al., Monoclonal antibody to HER-2/neureceptor modulates repair of radiation-induced DNA damage and enhances radiosensitivity of human breast cancer cells overexpressing this oncogene. Cancer Res. Mar. 15, 1999;59(6):1347-55.

Goldenberg, Trastuzumab, a recombinant DNA-derived humanized monoclonal antibody, a novel agent for the treatment of metastatic breast cancer. Clin Ther. Feb. 1999;21(2):309-18. Review.

Seely et al., Retroviral expression of a kinase-defective IGF-I receptor suppresses growth and causes apoptosis of CHO and U87 cells in-vivo. BMC Cancer. May 31, 2002;2:15.

Soos et al., A penal of monoclonal antibodies for the type I insulin-like growth factor receptor. Epitope mapping, effects on ligand binding, and biological activity. J Biol Chem. Jun. 25, 1992;267(18):12955-63.

Kalebic et al., In vivo treatment with antibody against IGF-1 receptor suppresses growth of human rhabdomyosarcoma and down-regulates p34cdc2. Cancer Res. Nov. 1, 1994;54(21):5531-4.

Baserga, The insulin-like growth factor I receptor: a key to tumor growth? Cancer Res. Jan. 15, 1995;55(2):249-52.

Rubini et al., Characterization of an antibody that can detect an activated IGF-I receptor in human cancers. Exp Cell Res. Aug. 25, 1999;251(1):22-32.

Lin et al., Structure-function relationships in glucagon: properties of highly purified des-His-1-, monoiodo-, and (des-Asn- 28, Thr - 29)(homoserine lactone-27)-glucagon, Biochemistry. Apr. 22, 1975;14(8):1559-63.

Acland et al., Subcellular fate of the int-2 oncoprotein is determined by choice of initiation codon, Nature. Feb. 15, 1990;343(6259):662-5.

Cordera et al., Inhibition of insulin and epidermal growth factor (EGF) receptor autophosphorylation by a human polyclonal lgG, Biochem Biophys Res Commun. Nov. 15, 1985;132(3):991-1000.

Freund et al., Functional insulin and insulin-like growth factor-1 receptors are preferentially expressed in multiple myeloma cells lines as compared to B-lymphoblastoid cells lines, Cancer Res. Jun. 15, 1994;54(12):3179-85.

Rudikoff et al., Single amino acid substitution altering antigen-binding specificity, Proc Natl Acad Sci U S A. Mar. 1982;79(6):1979-83.

Burgess et al., Possible dissociation of the heparin-binding and mitogenic activities of heparin-binding (acidic fibroblast) growth factor-1 from its receptor-binding activities by site-directed mutagenesis of a single lysine residue, J Cell Biol. Nov. 1990;111:2129-38.

Lazar et al., Transforming growth factor alpha:mutation of aspartic acid 47 and leucine 48 results in different biological activities, Mol Cell Biol. Mar. 1988;8(3):1247-52.

Schwartz et al., A superactive insulin: [B10-aspartic acid]insulin(human), Proc Natl Acad Sci U S A. Sep. 1987;84(18):6408-11.

Jackson et al., Insulin receptor substrate-1 is the predominant signaling molecule activated by insulin-like growth factor-I, insulin, and interleukin-4 in estrogen receptor-positive human breast cancer cells. J Biol Chem. Apr. 17, 1998;273(16):9994-10003.

Desnoyers et al., Novel non-isotopic method for the localization of receptors in tissue sections. J Histochem Cytochem. Dec. 2001;49(12):1509-18.

Ricort et al. Insulin-like growth factor (IGF) binding protein-3 inhibits type 1 IGF receptor activation independently of its IGF binding affinity, Endocrinology. Jan. 2001;142(1):108-13.

Stefania Benini et al., Inhibition of Insulin-like Growth Factor I Receptor Increases the Antitumor Activity of Doxorubicin and Vincristine Against Ewing's Sarcoma Cells, Clinical Cancer Research, vol. 7, 1790-1797, Jun. 2001.

V.M. MacAulay, Insulin-like Growth Factors and Cancer, Br. J. Cancer, 65, 311-320, 1992.

Mariana Resnicoff et al., The Role of the Insulin-like Growth Factor I Receptor in Transformation and Apoptosis, Kimmel Cancer Institute, Thomas Jefferson University pp. 76-81, 1998.

Xiangdang Liu et al., Inhibition of Insulin-like Growth Factor I Receptor Expression in Neuroblastoma Cells Induces the Regression of Established Tumors in Mice, Cancer Research 58, 5432-5438, Dec. 1, 1998.

Jamie L. Resnik et al., Elevated Insulin-like Growth Factor I Receptor Autophosphorylation and Kinase Activity in Human Breast Cancer, Cancer Research 58, 1159-1164, Mar. 15, 1998.

Fredrika Pekonen et al., Receptors for Epidermal Growth Factor and Insulin-like Growth Factor I and Their Relation to Steroid Receptors in Human Breast Cancer, Cancer Research 48, 1343-1347, Mar. 1, 1988.

Quynh T. Rohlik et al., An Antibody to the Receptor for Insulin-like Growth Factor I Inhibits the Growth of MCF-7 Cells in Tissue Culture, Biochemical and Biophysical Research Communications, vol. 149, No. 1, 276-281, 1987.

Carlos L. Arteaga et al., Blockade of the Type I Somatomedin Receptor Inhibits Growth of Human Breast Cancer Cells in Athymic Mice, J. Clin. Invest., vol. 84, 1418-1423, Nov. 1989.

Ted Gansler et al., Rapid Communication Antibody to Type I Insulinlike Growth Factor Receptor Inhibits Growth of Wilms' Tumor in Culture and in Athymic Mice, American Journal of Pathology, vol. 135, No. 6, 961-966, Dec. 1989.

Krzysztof Reiss et al., Inhibition of Tumor Growth by a Dominant Negative Mutant of the Insulin-like Growth Factor I Receptor with a Bystander Effect, Clinical Cancer Research, vol. 4, 2647-2655, Nov. 1998.

Carlos L. Arteaga et al., Growth Inhibition of Human Breast Cancer Cells in Vitro with an Antibody Against the Type I Somatomedin Receptor, Cancer Research, 49, 6237-6241, Nov. 15, 1989.

Sandra E. Dunn et al., A Dominant Negative Mutant of the Insulin-like Growth Factor-I Receptor Inhibits the Adhesion, Invasion, and Metastasis of Breast Cancer, Cancer Research, 58, 3353-3361, Aug. 1, 1998.

Peter Burfeind, Antisense RNA to the Type I Insulin-like Growth Factor Receptor Suppresses Tumor Growth and Prevents Invasion by Rate Prostate Cancer Cells In Vivo, Proc. Natl. Acad. Sci. USA, vol. 93 7263-7268, Jul. 1996.

Diane Prager et al., Dominant Negative Inhibition of Tumorigenesis In Vivo by Human Insulin-like Growth Factor I Receptor Mutant, Proc. Natl. Acad. Sci. USA, vol. 91, 2181-2185, Mar. 1994.

Deepali Sachdev, A Chimeric Humanized Single-Chain Antibody Against the Type I Insulin-like Growth Factor (IGF) Receptor Renders Breast Cancer Cells Refractory to the Mitogenic Effects of IGF-1, Cancer Research 63, 627-635, 2003.

Hakam et al., "Expression of insulin-like growth factor-1 receptor in human colorectal cancer", Human Pathology (1999) 30(10): 1128-1133.

Sepp-Lorenzino, "Structure and function of the insulin-like growth factor I receptor", Breast Cancer Research and Treatment (1998) 47: 235-253.

R&D Systems catalogue pages-monoclonal Anti-human IGF-IR Antibody MAB391, 2004.

Xiong et al., "Growth-stimulatory monoclonal antibodies against human insulin-like growth factor I receptor" Proc. Nat. Acad. Sci. 89: 5356-5360 (1992).

Li et al., "Two new monoclonal antibodies against the α subunit of the human insulin-like growth factor-I receptor" Biochem. Biophys. Res. Comm. 196(1):92-98 (1993).

Kull et al., "Monoclonal antibodies to receptors for insulin and somatomedin-C" J. Biol. Chem. 258(10):6561-6566 (1983).

Buttler et al., "Insulin-like growth factor-I receptor signal transduction: at the interface between physiology and cell biology" Comp. Biochem. Physiol. Part (B) 121 (1):19-26 (1998).

Chan et al., "Plasma insulin-like growth factor-I and prostate cancer risk: a prospective study" Science. 279(5350):563-566 (1998).

Xie et al., "Expression of insulin-like growth factor-1 receptor in synovial sarcoma: association with an aggressive phenotype" Cancer Res. 59(15):3588-3591 (1999).

Steller et al., "Overexpression of the insulin-like growth factor-1 receptor and autocrine stimulation in human cervical cancer cells" Cancer Res. 56(8):1761-1765 (1996).

Pandini et al., "Insulin and insulin-like growth factor-I (IGF-I) receptor overexpression in breast cancers leads to insulin/IGF-I hybrid receptor overexpression: evidence for a second mechanism of IGF-I signaling" Clin. Cancer Res. 5(7):1935-1944 (1999).

Webster et al., "Repression of the insulin receptor promoter by the tumor suppressor gene product p53: a possible mechanism for receptor overexpression in breast cancer" Cancer Res. 56(12):2781-2788 (1996).

Ben-Schlomo et al., "Acromegaly" Endocrin. Metab. Clin. N. America 30(3):565-583 (2001).

SEQUENCE LISTING

<160> NUMBER OF SEQ ID NOS: 27

<210> SEQ ID NO 1
<211> LENGTH: 2941
<212> TYPE: DNA
<213> ORGANISM: Artificial sequence
<220> FEATURE:
<223> OTHER INFORMATION: pULLs plasmid

<400> SEQUENCE: 1

```
ctaaattgta agcgttaata ttttgttaaa attcgcgtta aatttttgtt aaatcagctc      60
attttttaac caataggccg aaatcggcaa atcccttat  aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
```

```
ctaatcaagt ttttgggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcggcgcta gggcgctggc aagtgtagcg gtcacgctgc gcgtaaccac     420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggt ttttcccagt cacgacgttg    600
taaaacgacg gccagtgagc gcgccaccgg tgcccgggc cggtccgact agttacgtaa     660
agcttggtac cctcgaggtc gacatcgatg atatcgaatt cctgcagggg ccctccggag    720
gatccgcggc cgctctagag agctccatat gtggccatcg cgattaatta agcgcgcttg    780
gcgtaatcat ggtcatagct gtttcctgtg tgaaattgtt atccgctcac aattccacac    840
aacatacgag ccggaagcat aaagtgtaaa gcctggggtg cctaatgagt gagctaactc    900
acattaattg cgttgcgctc actgcccgct ttccagtcgg gaaacctgtc gtgccagctg    960
cattaatgaa tcggccaacg cgcggggaga ggcggtttgc gtattgggcg ctcttccgct   1020
tcctcgctca ctgactcgct gcgctcggtc gttcggctgc ggcgagcggt atcagctcac   1080
tcaaaggcgg taatacggtt atccacagaa tcaggggata acgcaggaaa gaacatgtga   1140
gcaaaaggcc agcaaaaggc caggaaccgt aaaaaggccg cgttgctggc gttttttccat  1200 aggctccgcc cccctgacga gcatcacaaa aatcgacgct caagtcagag gtggcgaaac   1260
ccgacaggac tataaagata ccaggcgttt ccccctggaa gctccctcgt gcgctctcct   1320
gttccgaccc tgccgcttac cggatacctg tccgcctttc tcccttcggg aagcgtggcg   1380
ctttctcata gctcacgctg taggtatctc agttcggtgt aggtcgttcg ctccaagctg   1440
ggctgtgtgc acgaaccccc cgttcagccc gaccgctgcg ccttatccgg taactatcgt   1500
cttgagtcca acccggtaag acacgactta tcgccactgg cagcagccac tggtaacagg   1560
attagcagag cgaggtatgt aggcggtgct acagagttct tgaagtggtg gcctaactac   1620
ggctacacta aaggacagt atttggtatc tgcgctctgc tgaagccagt taccttcgga   1680
aaaagagttg gtagctcttg atccggcaaa caaaccaccg ctggtagcgg tggttttttt   1740
gtttgcaagc agcagattac gcgcagaaaa aaaggatctc aagaagatcc tttgatcttt   1800
tctacggggt ctgacgctca gtggaacgaa aactcacgtt aagggatttt ggtcatgaga   1860
ttatcaaaaa ggatcttcac ctagatcctt ttaaattaaa aatgaagttt taaatcaatc   1920
taaagtatat atgagtaaac ttggtctgac agttaccaat gcttaatcag tgaggcacct   1980
atctcagcga tctgtctatt tcgttcatcc atagttgcct gactccccgt cgtgtagata   2040
actacgatac gggagggctt accatctggc cccagtgctg caatgatacc gcgagaccca   2100
cgctcaccgg ctccagattt atcagcaata aaccagccag ccggaagggc cgagcgcaga   2160
agtggtcctg caactttatc cgcctccatc cagtctatta attgttgccg ggaagctaga   2220
gtaagtagtt cgccagttaa tagtttcgc aacgttgttg ccattgctac aggcatcgtg   2280
gtgtcacgct cgtcgtttgg tatggcttca ttcagctccg gttcccaacg atcaaggcga   2340
gttacatgat cccccatgtt gtgcaaaaaa gcggttagct ccttcggtcc tccgatcgtt   2400
gtcagaagta agttggccgc agtgttatca ctcatggtta tggcagcact gcataattct   2460
cttactgtca tgccatccgt aagatgcttt tctgtgactg gtgagtactc aaccaagtca   2520
ttctgagaat agtgtatgcg gcgaccgagt tgctcttgcc cggcgtcaat acgggataat   2580
accgcgccac atagcagaac tttaaaagtg ctcatcattg gaaaacgttc ttcggggcga   2640
```

-continued

| | |
|---|---|
| aaactctcaa ggatcttacc gctgttgaga tccagttcga tgtaacccac tcgtgcaccc | 2700 |
| aactgatctt cagcatcttt tactttcacc agcgtttctg ggtgagcaaa aacaggaagg | 2760 |
| caaaatgccg caaaaaggg aataagggcg cacggaaat gttgaatact catactcttc | 2820 |
| cttttttcaat attattgaag catttatcag ggttattgtc tcatgagcgg atacatattt | 2880 |
| gaatgtattt agaaaaataa acaaataggg gttccgcgca catttccccg aaaagtgcca | 2940 |
| c | 2941 |

<210> SEQ ID NO 2
<211> LENGTH: 2935
<212> TYPE: DNA
<213> ORGANISM: Artificial sequence
<220> FEATURE:
<223> OTHER INFORMATION: pUHLS plasmid

<400> SEQUENCE: 2

| | |
|---|---|
| ctaaattgta agcgttaata ttttgttaaa attcgcgtta aattttttgtt aaatcagctc | 60 |
| atttttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgccgtttta acccctcagc tacgtaaagc ttggtaccct | 660 |
| cgaggtcgac atcgatgata tcgaattcct gcaggggccc cccgggtccg gaggatccgc | 720 |
| ggccgctcta gagagctcac gcgttgatca tgtacaggcc ggccagcgcg cttggcgtaa | 780 |
| tcatggtcat agctgtttcc tgtgtgaaat tgttatccgc tcacaattcc acacaacata | 840 |
| cgagccggaa gcataaagtg taaagcctgg ggtgcctaat gagtgagcta actcacatta | 900 |
| attgcgttgc gctcactgcc cgctttccag tcgggaaacc tgtcgtgcca gctgcattaa | 960 |
| tgaatcggcc aacgcgcggg gagaggcggt ttgcgtattg ggcgctcttc cgcttcctcg | 1020 |
| ctcactgact cgctgcgctc ggtcgttcgg ctgcggcgag cggtatcagc tcactcaaag | 1080 |
| gcggtaatac ggttatccac agaatcaggg gataacgcag gaaagaacat gtgagcaaaa | 1140 |
| ggccagcaaa aggccaggaa ccgtaaaaag gccgcgttgc tggcgttttt ccataggctc | 1200 |
| cgcccccctg acgagcatca caaaaatcga cgctcaagtc agaggtggcg aaacccgaca | 1260 |
| ggactataaa gataccaggc gtttccccct ggaagctccc tcgtgcgctc tcctgttccg | 1320 |
| accctgccgc ttaccggata cctgtccgcc tttctccctt cgggaagcgt ggcgctttct | 1380 |
| catagctcac gctgtaggta tctcagttcg gtgtaggtcg ttcgctccaa gctgggctgt | 1440 |
| gtgcacgaac cccccgttca gcccgaccgc tgcgccttat ccggtaacta tcgtcttgag | 1500 |
| tccaacccgg taagacacga cttatcgcca ctggcagcag ccactggtaa caggattagc | 1560 |
| agagcgaggt atgtaggcgg tgctacagag ttcttgaagt ggtggcctaa ctacggctac | 1620 |
| actagaagga cagtatttgg tatctgcgct ctgctgaagc cagttacctt cggaaaaaga | 1680 |

```
gttggtagct cttgatccgg caaacaaacc accgctggta gcggtggttt ttttgtttgc   1740
aagcagcaga ttacgcgcag aaaaaaagga tctcaagaag atcctttgat cttttctacg   1800
gggtctgacg ctcagtggaa cgaaaactca cgttaaggga ttttggtcat gagattatca   1860
aaaaggatct tcacctagat ccttttaaat taaaaatgaa gttttaaatc aatctaaagt   1920
atatatgagt aaacttggtc tgacagttac caatgcttaa tcagtgaggc acctatctca   1980
gcgatctgtc tatttcgttc atccatagtt gcctgactcc ccgtcgtgta gataactacg   2040
atacgggagg gcttaccatc tggccccagt gctgcaatga taccgcgaga cccacgctca   2100
ccggctccag atttatcagc aataaaccag ccagccggaa gggccgagcg cagaagtggt   2160
cctgcaactt tatccgcctc catccagtct attaattgtt gccgggaagc tagagtaagt   2220
agttcgccag ttaatagttt gcgcaacgtt gttgccattg ctacaggcat cgtggtgtca   2280
cgctcgtcgt ttggtatggc ttcattcagc tccggttccc aacgatcaag gcgagttaca   2340
tgatccccca tgttgtgcaa aaaagcggtt agctccttcg gtcctccgat cgttgtcaga   2400
agtaagttgg ccgcagtgtt atcactcatg gttatggcag cactgcataa ttctcttact   2460
gtcatgccat ccgtaagatg cttttctgtg actggtgagt actcaaccaa gtcattctga   2520
gaatagtgta tgcggcgacc gagttgctct tgcccggcgt caatacggga taataccgcg   2580
ccacatagca gaactttaaa agtgctcatc attggaaaac gttcttcggg gcgaaaactc   2640
tcaaggatct taccgctgtt gagatccagt tcgatgtaac ccactcgtgc acccaactga   2700
tcttcagcat cttttacttt caccagcgtt tctgggtgag caaaaacagg aaggcaaaat   2760
gccgcaaaaa agggaataag ggcgacacgg aaatgttgaa tactcatact cttcctttt   2820 caatattatt gaagcattta tcagggttat tgtctcatga gcggatacat atttgaatgt   2880
atttagaaaa ataaacaaat aggggttccg cgcacatttc cccgaaaagt gccac       2935

<210> SEQ ID NO 3
<211> LENGTH: 5444
<212> TYPE: DNA
<213> ORGANISM: Artificial sequence
<220> FEATURE:
<223> OTHER INFORMATION: pXBLS plasmid

<400> SEQUENCE: 3
gcactataca tcaaatattc cttattaacc cctttacaaa ttaaaaagct aaaggtacac     60
aatttttgag catagttatt aatagcagac actctatgcc tgtgtggagt aagaaaaaac    120
agtatgttat gattataact gttatgccta cttataaagg ttacagaata ttttttccata  180 attttcttgt atagcagtgc agcttttttc tttgtggtgt aaatagcaaa gcaagcaaga    240
gttctattac taaacacagc atgactcaaa aaacttagca attctgaagg aaagtccttg    300
gggtcttcta cctttctctt cttttttgga ggagtagaat gttgagagtc agcagtagcc    360
tcatcatcac tagatggcat ttcttctgag caaaacaggt ttcctcatt aaaggcattc     420 caccactgct cccattcatc agttccatag gttggaatct aaaatacaca acaattaga     480 atcagtagtt taacacatta tacttaaa attttatat ttaccttaga gctttaaatc       540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
```

-continued

```
cacaaagagt ctgaggtggc ctggttgatt catggcttcc tggtaaacag aactgcctcc      900
gactatccaa accatgtcta ctttacttgc caattccggt tgttcaataa gtcttaaggc      960
atcatccaaa cttttggcaa gaaaatgagc tcctcgtggt ggttctttga gttctctact     1020
gagaactata ttaattctgt cctttaaagg tcgattcttc tcaggaatgg agaaccaggt     1080
tttcctaccc ataatcacca gattctgttt accttccact gaagaggttg tggtcattct     1140
ttggaagtac ttgaactcgt tcctgagcgg aggccagggt aggtctccgt tcttgccaat     1200
ccccatattt tgggacacgg cgacgatgca gttcaatggt cgaaccatga tggcagcggg     1260
gataaaatcc taccagcctt cacgctagga ttgccgtcaa gtttggcgcg aaatcgcagc     1320
cctgagctgt ccccccccc aagctcagat ctgagcttgg tccctatggt gagtccgttc     1380
cgctcttgtg atgatagcca gacaagaaag agacaataca agacaaacac caaatagtag     1440
aaatagagac aagggtcact tatccgaggg tccctgttcg ggcgccagct gccgcagtcg     1500
gccgacctga gggtcgccgg ggtctgcggg gggaccctct ggaaagtgaa ggataagtga     1560
cgagcggaga cgggatggcg aacagacaca aacacacaag aggtgaatgt taggactgtt     1620
gcaagtttac tcaaaaaatc agcactcttt tatatcttgg tttacataag catttacata     1680
agatttggat aaattccaaa agaacatagg aaaatagaac actcagagct cagatcagaa     1740
cctttgatac caaaccaagt caggaaacca cttgtctcac atcctcgttt taagaacagt     1800
ttgtaaccaa aaacttactt aagccctggg aaccgcaagg ttgggccaat aaaggctatt     1860
cataataact catgccatga gttttttgcag aataatgttc tattagtcca gccactgtcc     1920
cctccttggt atggaaaatc tttccccaaa agtgcattcc tgttcctaga taaatataat     1980
catgtacctg ttgtttcatg tcgtcttttt cttcttgaga caacatacac caaggaggtc     2040
tagctctggc gagtctttca cgaaaaggga gggatctata taacacttta tagccattga     2100
ctgtaaccca cctatcccaa tttaagtcat atcttcctgt atatggtaag ggggcatctg     2160
ttggtctgta gatgtaaggt cccctataag tccctggttg ccaccacctg tctcctattt     2220
tgacaaaaac actctttttt ccctttttta cttctaggcc tgtggtcaat agtccttgca     2280
cctgttcttc aattgaggtt gagcgtctct ttctattttc tattcccatt tctaacttct     2340
gaatttgagt aaaaatagta ctaaaagata atgattcatt tcttaacata gtaactaata     2400
atctacctat tggattggtc ttattggtaa aaatataatt tttagcaagc attcttatt     2460
ctatttctga aggacaaaat cgatgcggct tgtaagagga agttggctgt ggtccttgcc     2520
tcaggaggaa ggtcgagttc tccgaattgt ttagattgta atcttgcaca gaagagctat     2580
taaaagagtc aagggtgaga gccctgcgag cacgaaccgc aacttccccc aatagcccca     2640
ggcaaagcag agctatgcca agtttgcagc agagaatgaa tatgtctttg tctgatgggc     2700
tcatccgttt gtgcgcagac gggtcgtcct tggtgggaaa caacccttg gctgcttctc     2760
ccctaggtgt aggacactct cgggagttca accatttctg cccaagctca gatctgagct     2820
ttaatgcggt agtttatcac agttaaattg ctaacgcagt caggcaccgt gtatgaaatc     2880
taacaatgcg ctcatcgtca tcctcggcac cgtcaccctg gatgctgtag catagcctt     2940
ggttatgccg gtactgccgg gcctcttgcg ggatatcgtc cattccgaca gcatcgccag     3000
tcactatggc gtgctgctag cgctcttccg cttcctcgct cactgactcg ctgcgctcgg     3060
tcgttcggct gcggcgagcg gtatcagctc actcaaaggc ggtaatacgg ttatccacag     3120
aatcagggga taacgcagga agaacatgt gagcaaaagg ccagcaaaag gccaggaacc     3180
```

-continued

```
gtaaaaaggc cgcgttgctg gcgttttcc ataggctccg ccccctgac gagcatcaca    3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaagagt tggtagctct tgatccggca    3720
aacaaaccac cgctggtagc ggtggttttt tgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata ataccgcgcc acatagcaga actttaaaag    4620
tgctcatcat tggaaaacgt tcttcgggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct ccttttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgcc gtttaaaccc tcagctgatc atccggatgt acagcgcgcg gccggccggt    5100
accacgcgtt ggccacatat ggcggccgct cgcgattaat taacgaccg ccgcggacta    5160 gtgcccgggc caccggtgct cgaagcttgg atcgatccag acatgataag atacattgat    5220
gagtttggac aaaccacaac tagaatgcag tgaaaaaaat gctttatttg tgaaatttgt    5280
gatgctattg ctttatttgt aaccattata agctgcaata acaagttaa caacaacaat    5340 tgcattcatt ttatgtttca ggttcagggg gaggtgtggg aggttttta aagcaagtaa    5400 aacctctaca aatgtggtat ggctgattat gatctctagt caag                     5444
```

<210> SEQ ID NO 4
<211> LENGTH: 3176

<212> TYPE: DNA
<213> ORGANISM: Artificial sequence
<220> FEATURE:
<223> OTHER INFORMATION: pULstopLs plasmid

<400> SEQUENCE: 4

| | |
|---|---|
| ctaaattgta agcgttaata ttttgttaaa attcgcgtta aattttgtt aaatcagctc | 60 |
| atttttaac caataggccg aaatcggcaa atcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta atcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaagggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgccaccgg tgcccgggc cggtccgact agttacgtaa | 660 |
| agcttggtac cctcgaggtc gacatcgatg atatcgaatt cctgcagggg ccctccggag | 720 |
| gatccagatc cccctcgctt tcttgctgtc caatttctat taaaggttcc tttgttccct | 780 |
| aagtccaact actaaactgg gggatattat gaagggcctt gagcatctgg attctgccta | 840 |
| ataaaaaaca tttattttca ttgcaatgat gtatttaaat tatttctgaa tattttacta | 900 |
| aaaagggaat gtgggaggtc agtgcattta aaacataaag aaatgaagag ggggatctgt | 960 |
| cgacaagctc tagagagctc catatgtggc catcgcgatt aattaagcgc gcttggcgta | 1020 |
| atcatggtca tagctgtttc ctgtgtgaaa ttgttatccg ctcacaattc cacacaacat | 1080 |
| acgagccgga agcataaagt gtaaagcctg gggtgcctaa tgagtgagct aactcacatt | 1140 |
| aattgcgttg cgctcactgc ccgctttcca gtcgggaaac ctgtcgtgcc agctgcatta | 1200 |
| atgaatcggc caacgcgcgg ggagaggcgg tttgcgtatt gggcgctctt ccgcttcctc | 1260 |
| gctcactgac tcgctgcgct cggtcgttcg gctgcggcga gcggtatcag ctcactcaaa | 1320 |
| ggcggtaata cggttatcca cagaatcagg ggataacgca ggaaagaaca tgtgagcaaa | 1380 |
| aggccagcaa aaggccagga accgtaaaaa ggccgcgttg ctggcgtttt tccataggct | 1440 |
| ccgcccccct gacgagcatc acaaaaatcg acgctcaagt cagaggtggc gaaacccgac | 1500 |
| aggactataa agataccagg cgtttccccc tggaagctcc ctcgtgcgct ctcctgttcc | 1560 |
| gaccctgccg cttaccggat acctgtccgc ctttctccct tcgggaagcg tggcgctttc | 1620 |
| tcatagctca cgctgtaggt atctcagttc ggtgtaggtc gttcgctcca agctgggctg | 1680 |
| tgtgcacgaa ccccccgttc agcccgaccg ctgcgcctta ccggtaact atcgtcttga | 1740 |
| gtccaacccg gtaagacacg acttatcgcc actggcagca gccactggta acaggattag | 1800 |
| cagagcgagg tatgtaggcg gtgctacaga gttcttgaag tggtggccta actacggcta | 1860 |
| cactagaagg acagtatttg gtatctgcgc tctgctgaag ccagttacct tcggaaaaag | 1920 |
| agttggtagc tcttgatccg gcaaacaaac caccgctggt agcggtggtt ttttgtttg | 1980 |
| caagcagcag attacgcgca gaaaaaaagg atctcaagaa gatcctttga tcttttctac | 2040 |
| ggggtctgac gctcagtgga acgaaaactc acgttaaggg attttggtca tgagattatc | 2100 |
| aaaaaggatc ttcacctaga tccttttaaa ttaaaaatga agttttaaat caatctaaag | 2160 |

```
tatatatgag taaacttggt ctgacagtta ccaatgctta atcagtgagg cacctatctc    2220
agcgatctgt ctatttcgtt catccatagt tgcctgactc cccgtcgtgt agataactac    2280
gatacgggag ggcttaccat ctggccccag tgctgcaatg ataccgcgag acccacgctc    2340
accggctcca gatttatcag caataaacca gccagccgga agggccgagc gcagaagtgg    2400
tcctgcaact ttatccgcct ccatccagtc tattaattgt tgccgggaag ctagagtaag    2460
tagttcgcca gttaatagtt tgcgcaacgt tgttgccatt gctacaggca tcgtggtgtc    2520
acgctcgtcg tttggtatgg cttcattcag ctccggttcc caacgatcaa ggcgagttac    2580
atgatccccc atgttgtgca aaaaagcggt tagctccttc ggtcctccga tcgttgtcag    2640
aagtaagttg gccgcagtgt tatcactcat ggttatggca gcactgcata attctcttac    2700
tgtcatgcca tccgtaagat gcttttctgt gactggtgag tactcaacca agtcattctg    2760
agaatagtgt atgcggcgac cgagttgctc ttgcccggcg tcaatacggg ataataccgc    2820
gccacatagc agaactttaa aagtgctcat cattggaaaa cgttcttcgg ggcgaaaact    2880
ctcaaggatc ttaccgctgt tgagatccag ttcgatgtaa cccactcgtg cacccaactg    2940
atcttcagca tcttttactt tcaccagcgt ttctgggtga gcaaaaacag gaaggcaaaa    3000
tgccgcaaaa aagggaataa gggcgacacg gaaatgttga atactcatac tcttcctttt    3060
tcaatattat tgaagcattt atcagggtta ttgtctcatg agcggataca tatttgaatg    3120
tatttagaaa aataaacaaa tagggggttcc gcgcacattt ccccgaaaag tgccac      3176
```

<210> SEQ ID NO 5
<211> LENGTH: 3170
<212> TYPE: DNA
<213> ORGANISM: Artificial sequence
<220> FEATURE:
<223> OTHER INFORMATION: pUHstopLS plasmid

<400> SEQUENCE: 5

```
ctaaattgta agcgttaata ttttgttaaa attcgcgtta aattttttgtt aaatcagctc      60 atttttttaac caataggccg aaatcggcaa aatcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaaccc taaagggag      300 ccccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcggc ctcttcgcta ttacgccagc tggcgaaagg     540
gggatgtgct gcaaggcgat taagttgggt aacgccaggg ttttcccagt cacgacgttg    600
taaaacgacg gccagtgagc gcgccgttta accctcagc tacgtaaagc ttggtaccct     660
cgaggtcgac atcgatgata tcgaattcct gcaggggccc cccgggtccg gaggatccag     720
atcccccctc ctttcttgct gtccaatttc tattaaaggt tcctttgttc cctaagtcca     780
actactaaac tgggggatat tatgaagggc cttgagcatc tggattctgc ctaataaaaa      840
acatttattt tcattgcaat gatgtattta aattatttct gaatatttta ctaaaagggg     900
aatgtgggag gtcagtgcat ttaaaacata agaaatgaa gagggggatc tgtcgacaag     960
ctctagagag ctcacgcgtt gatcatgtac aggccggcca gcgcgcttgg cgtaatcatg    1020
gtcatagctg tttcctgtgt gaaattgtta tccgctcaca attccacaca acatacgagc    1080
```

-continued

```
cggaagcata aagtgtaaag cctggggtgc ctaatgagtg agctaactca cattaattgc    1140
gttgcgctca ctgcccgctt tccagtcggg aaacctgtcg tgccagctgc attaatgaat    1200
cggccaacgc gcggggagag gcggtttgcg tattgggcgc tcttccgctt cctcgctcac    1260
tgactcgctg cgctcggtcg ttcggctgcg gcgagcggta tcagctcact caaaggcggt    1320
aatacggtta tccacagaat caggggataa cgcaggaaag aacatgtgag caaaaggcca    1380
gcaaaaggcc aggaaccgta aaaaggccgc gttgctggcg ttttttccata ggctccgccc    1440
ccctgacgag catcacaaaa atcgacgctc aagtcagagg tggcgaaacc cgacaggact    1500
ataaagatac caggcgtttc ccctggaag ctccctcgtg cgctctcctg ttccgacccct    1560
gccgcttacc ggatacctgt ccgcctttct cccttcggga agcgtggcgc tttctcatag    1620
ctcacgctgt aggtatctca gttcggtgta ggtcgttcgc tccaagctgg gctgtgtgca    1680
cgaaccccc gttcagcccg accgctgcgc cttatccggt aactatcgtc ttgagtccaa    1740
cccggtaaga cacgacttat cgccactggc agcagccact ggtaacagga ttagcagagc    1800
gaggtatgta ggcggtgcta cagagttctt gaagtggtgg cctaactacg gctacactag    1860
aaggacagta tttggtatct gcgctctgct gaagccagtt accttcggaa aaagagttgg    1920
tagctcttga tccggcaaac aaaccaccgc tggtagcggt ggtttttttg tttgcaagca    1980
gcagattacg cgcagaaaaa aaggatctca agaagatcct ttgatctttt ctacgggtc    2040
tgacgctcag tggaacgaaa actcacgtta agggattttg gtcatgagat tatcaaaaag    2100
gatcttcacc tagatccttt taaattaaaa atgaagtttt aaatcaatct aaagtatata    2160
tgagtaaact tggtctgaca gttaccaatg cttaatcagt gaggcaccta tctcagcgat    2220
ctgtctattt cgttcatcca tagttgcctg actccccgtc gtgtagataa ctacgatacg    2280
ggagggctta ccatctggcc ccagtgctgc aatgataccg cgagacccac gctcaccggc    2340
tccagattta tcagcaataa accagccagc cggaagggcc gagcgcagaa gtggtcctgc    2400
aactttatcc gcctccatcc agtctattaa ttgttgccgg gaagctagag taagtagttc    2460
gccagttaat agtttgcgca acgttgttgc cattgctaca ggcatcgtgg tgtcacgctc    2520
gtcgtttggt atggcttcat tcagctccgg ttcccaacga tcaaggcgag ttacatgatc    2580
ccccatgttg tgcaaaaaag cggttagctc cttcggtcct ccgatcgttg tcagaagtaa    2640
gttggccgca gtgttatcac tcatggttat ggcagcactg cataattctc ttactgtcat    2700
gccatccgta agatgctttt ctgtgactgg tgagtactca accaagtcat tctgagaata    2760
gtgtatgcgg cgaccgagtt gctcttgccc ggcgtcaata cgggataata ccgcgccaca    2820
tagcagaact ttaaaagtgc tcatcattgg aaaacgttct cgggggcgaa aactctcaag    2880
gatcttaccg ctgttgagat ccagttcgat gtaacccact cgtgcaccca actgatcttc    2940
agcatctttt actttcacca gcgtttctgg gtgagcaaaa acaggaaggc aaaatgccgc    3000
aaaaaaggga ataagggcga cacggaaatg ttgaatactc atactcttcc ttttcaata    3060
ttattgaagc atttatcagg gttattgtct catgagcgga tacatatttg aatgtattta    3120
gaaaaataaa caaataggg ttccgcgcac atttccccga aaagtgccac    3170
```

<210> SEQ ID NO 6
<211> LENGTH: 12190
<212> TYPE: DNA
<213> ORGANISM: Artificial sequence
<220> FEATURE:
<223> OTHER INFORMATION: pAIL5V1 plasmid -continued

<400> SEQUENCE: 6

```
gcactataca tcaaatattc cttattaacc cctttacaaa ttaaaaagct aaaggtacac      60
aatttttgag catagttatt aatagcagac actctatgcc tgtgtggagt aagaaaaaac     120
agtatgttat gattataact gttatgccta cttataaagg ttacagaata tttttccata    180
attttcttgt atagcagtgc agcttttttcc tttgtggtgt aaatagcaaa gcaagcaaga    240
gttctattac taaacacagc atgactcaaa aacttagca attctgaagg aaagtccttg     300
gggtcttcta cctttctctt ctttttttgga ggagtagaat gttgagagtc agcagtagcc    360
tcatcatcac tagatggcat ttcttctgag caaaacaggt tttcctcatt aaaggcattc    420
caccactgct cccattcatc agttccatag gttggaatct aaaatacaca aacaattaga    480
atcagtagtt taacacatta tacacttaaa aatttttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720 gatgccttttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt ccccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gttttttgcag aataatgttc tattagtcca gccactgtcc   1920
cctccttggt atggaaaatc tttccccaaa agtgcattcc tgttcctaga taaatataat   1980
catgtacctg ttgtttcatg tcgtctttttt cttcttgaga caacatacac caaggaggtc   2040
tagctctggc gagtcttttca cgaaaaggga gggatctata taacacttta tagccattga   2100
ctgtaaccca cctatcccaa tttaagtcat atccttcctgt atatggtaag ggggcatctg   2160
ttggtctgta gatgtaaggt cccctataag tccctggttg ccaccacctg tctcctatttt   2220 tgacaaaaac actcttttttt ccctttttta cttctaggcc tgtggtcaat agtccttgca   2280
cctgttcttc aattgaggtt gagcgtctct ttctattttc tattcccatt tctaacttct   2340
```

-continued

```
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caaccccttg ctgcttctc     2760 ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag gcataggctt    2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc     3180
gtaaaaaggc cgcgttgctg gcgttttttcc ataggctccg ccccctgac gagcatcaca    3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc aacccggta agacacgact     3540 tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaagagt tggtagctct tgatccggca     3720
aacaaaccac cgctggtagc ggtggttttt tgtttgcaa gcagcagatt acgcgcagaa     3780 aaaaggatc tcaagaagat cctttgatct tttctacggg gtctgacgct cagtggaacg     3840
aaaactcacg ttaagggatt ttggtcatga gattatcaaa aaggatcttc acctagatcc    3900 tttttaaatta aaaatgaagt tttaaatcaa tctaaagtat atatgagtaa acttggtctg   3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata ataccgcgcc acatagcaga actttaaaag     4620
tgctcatcat tggaaaacgt tcttcggggc gaaaactctc aaggatctta ccgctgttga    4680
```

-continued

```
gatccagttc gatgtaaccc actcgtgcac ccaactgatc ttcagcatct tttactttca    4740
ccagcgtttc tgggtgagca aaacaggaa ggcaaaatgc cgcaaaaaag ggaataaggg     4800
cgacacggaa atgttgaata ctcatactct tccttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgcc gtttaaaccc tcagctaccg atgtacgggc cagatatacg cgttgacatt    5100
gattattgac tagttattaa tagtaatcaa ttacggggtc attagttcat agcccatata    5160
tggagttccg cgttacataa cttacggtaa atggcccgcc tggctgaccg cccaacgacc    5220
cccgcccatt gacgtcaata atgacgtatg ttcccatagt aacgccaata gggactttcc    5280
attgacgtca atgggtggac tatttacggt aaactgccca cttggcagta catcaagtgt    5340
atcatatgcc aagtacgccc cctattgacg tcaatgacgg taaatggccc gcctggcatt    5400
atgcccagta catgacctta tgggactttc ctacttggca gtacatctac gtattagtca    5460
tcgctattac catggtgatg cggttttggc agtacatcaa tgggcgtgga tagcggtttg    5520
actcacgggg atttccaagt ctccacccca ttgacgtcaa tgggagtttg ttttggcacc    5580
aaaatcaacg ggactttcca aaatgtcgta acaactccgc cccattgacg caaatgggcg    5640
gtaggcgtgt acggtgggag gtctatataa gcagagctct ctggctaact agagaaccca    5700
ctgcttactg gcttatcgaa attaatacga ctcactatag ggagacccaa gctggctagc    5760
gtttaaactt aagcttggta ccgagctcgg atccactagt ccagtgtggt ggaattccag    5820
agagaactca ccatggagtt tgggctgagc tggcttttc ttgtggctat tttaaaaggt    5880
gtccagtgtg aggtgcagct gttggagtct ggggggaggct tggtacagcc tggggggtcc    5940
ctgagactct cctgtgcagc ctctggattc acctttagca gctatgccat gagctgggtc    6000
cgccaggctc cagggaaggg gctggagtgg gtctcaacta ttagtggtag tggtggtagc    6060
acatactacg cagactccgt gaagggccgg ttcaccatct ccagagacaa ttccaagaac    6120
acgctgtatc tgcaaatgaa cagcctgaga gccgaggaca cggccgtata ttactgtgcg    6180
aaagagaggt ataactggaa ctacctacac tactggggcc agggaaccct ggtcaccgtc    6240
tcctcagcta gcaccaaggg cccatccgtc ttccccctgg cgccctgctc caggagcacc    6300
tccgagagca gccgccct gggctgcctg gtcaaggact acttccccga accggtgacg    6360
gtgtcgtgga actcaggcgc cctgaccagc ggcgtgcaca ccttcccggc tgtcctacag    6420
tcctcaggac tctactccct cagcagcgtg gtgaccgtgc cctccagcag cttgggcacg    6480
aagacctaca cctgcaacgt agatcacaag cccagcaaca ccaaggtgga caagagagtt    6540
ggtgagaggc cagcacaggg agggagggtg tctgctggaa gccaggctca gccctcctgc    6600
ctggacgcac cccggctgtg cagccccagc ccagggcagc aaggcatgcc ccatctgtct    6660
cctcacccgg aggcctctga ccaccccact catgctcagg gagagggtct tctggatttt    6720
tccaccaggc tccgggcagc cacaggctgg atgcccctac cccaggccct gcgcatacag    6780 ggcaggtgc tgcgctcaga cctgccaaga gccatatccg ggaggaccct gcccctgacc    6840
taagcccacc ccaaaggcca aactctccac tccctcagct cagacacctt ctctcctccc    6900
agatctgagt aactcccaat cttctctctg cagagtccaa atatggtccc ccatgcccat    6960
catgcccagg taagccaacc caggcctcgc cctccagctc aaggcgggac aggtgcccta    7020
gagtagcctg catccaggga caggccccag ccgggtgctg acgcatccac ctccatctct    7080
```

-continued

```
tcctcagcac ctgagttcct ggggggacca tcagtcttcc tgttcccccc aaaacccaag   7140
gacactctca tgatctcccg gacccctgag gtcacgtgcg tggtggtgga cgtgagccag   7200
gaagaccccg aggtccagtt caactggtac gtggatggcg tggaggtgca taatgccaag   7260
acaaagccgc gggaggagca gttcaacagc acgtaccgtg tggtcagcgt cctcaccgtc   7320
ctgcaccagg actggctgaa cggcaaggag tacaagtgca aggtctccaa caaaggcctc   7380
ccgtcctcca tcgagaaaac catctccaaa gccaaaggtg ggacccacgg ggtgcgaggg   7440
ccacatggac agaggtcagc tcggcccacc ctctgccctg ggagtgaccg ctgtgccaac   7500
ctctgtccct acagggcagc cccgagagcc acaggtgtac accctgcccc catcccagga   7560
ggagatgacc aagaaccagg tcagcctgac ctgcctggtc aaaggcttct acccccagcga   7620
catcgccgtg gagtgggaga gcaatgggca gccggagaac aactacaaga ccacgcctcc   7680
cgtgctggac tccgacggct ccttcttcct ctacagcagg ctaaccgtgg acaagagcag   7740
gtggcaggag gggaatgtct tctcatgctc cgtgatgcat gaggctctgc acaaccacta   7800
cacacagaaa agcctctccc tgtctctggg taaatgagtg ccaggccggg caagcccccg   7860
ctccccgggt ccggaggatc cagatccccc tcgctttctt gctgtccaat ttctattaaa   7920
ggttcctttg ttccctaagt ccaactacta aactggggga tattatgaag ggccttgagc   7980
atctggattc tgcctaataa aaaacattta ttttcattgc aatgatgtat ttaaattatt   8040
tctgaatatt ttactaaaaa gggaatgtgg gaggtcagtg catttaaaac ataaagaaat   8100
gaagaggggg atctgtcgac aagctctaga gagctcacgc gttgatcatg tacaggccgg   8160
cctgtgccac tgggcgccag aaatccgcgc ggtggttttt ggggtcgggg ggtgtttggc   8220
agccacagac gcccggtgtt cgtgtcgcgc cagtacatgc ggtccatgcc caggccatcc   8280
aaaaaccatg ggtctgtctg ctcagtccag tcgtggacca gaccccacgc aacgcccaaa   8340
ataataaccc ccacgaacca taaaccattc cccatggggg accccgtccc taacccacgg   8400
ggccagtggc tatggcaggg cctgccgccc cgacgttggc tgcgagccct gggccttcac   8460
ccgaacttgg ggggtggggt ggggaaaagg aagaaacgcg ggcgtattgg ccccaatggg   8520
gtctcggtgg ggtatcgaca gagtgccagc cctgggaccg aaccccgcgt ttatgaacaa   8580
acgacccaac cccgtgcgt tttattctgt cttttttattg ccgtcatagc gcggttcct   8640
tccggtattg tctccttccg tgtttcagtt agcctccccc atctccccta ttcctttgcc   8700
ctcggacgag tgctggggcg tcggtttcca ctatcggcga gtacttctac acagccatcg   8760
gtccagacgg ccgcgcttct gcgggcgatt tgtgtacgcc cgacagtccc ggctccggat   8820
cggacgattg cgtcgcatcg accctgcgcc aagctgcat catcgaaatt gccgtcaacc   8880
aagctctgat agagttggtc aagaccaatg cggagcatat acgcccggag ccgcggcgat   8940
cctgcaagct ccggatgcct ccgctcgaag tagcgcgtct gctgctccat acaagccaac   9000
cacggcctcc agaagaagat gttggcgacc tcgtattggg aatccccgaa catcgcctcg   9060
ctccagtcaa tgaccgctgt tatgcggcca ttgtccgtca ggacattgtt ggagccgaaa   9120
tccgcgtgca cgaggtgccg gacttcgggg cagtcctcgg cccaaagcat cagctcatcg   9180
agagcctgcg cgacggacgc actgacggtg tcgtccatca cagtttgcca gtgatacaca   9240
tggggatcag caatcgcgca tatgaaatca cgccatgtag tgtattgacc gattccttgc   9300
ggtccgaatg ggccgaaccc gctcgtctgg ctaagatcgg ccgcagcgat cgcatccatg   9360
gcctccgcga ccggctgcag aacagcgggc agttcggttt caggcaggtc ttgcaacgtg   9420
```

-continued

```
acaccctgtg cacggcggga gatgcaatag gtcaggctct cgctgaattc cccaatgtca   9480
agcacttccg gaatcgggag cgcggccgat gcaaagtgcc gataaacata acgatctttg   9540
tagaaaccat cggcgcagct atttacccgc aggacatatc cacgccctcc tacatcgaag   9600
ctgaaagcac gagattcttc gccctccgag agctgcatca ggtcggagac gctgtcgaac   9660
ttttcgatca gaaacttctc gacagacgtc gcggtgagtt caggcttttt catatctcat   9720
tgcccgggat ctgcggcacg ctgttgacgc tgttaagcgg gtcgctgcag ggtcgctcgg   9780
tgttcgaggc cacacgcgtc accttaatat gcgaagtgga cctgggaccg cgccgccccg   9840
actgcatctg cgtgttcgaa ttcgccaatg acaagacgct gggcgggtt tgtgtcatca    9900
tagaactaaa gacatgcaaa tatatttctt ccggggacac cgccagcaaa cgcgagcaac   9960
gggccacggg gatgaagcag ggcatggcgg ccgacgcgct gggctacgtc ttgctggcgt   10020
tcgcacaggc cggccagcgc gcggccggcc ggtaccacgc gttggccaca tatggcggcc   10080
gctcgcgatt aattaatcgc gatggccaca tatggagctc tctagagctt gtcgacagat   10140
cccctcttc atttctttat gttttaaatg cactgacctc ccacattccc tttttagtaa    10200
aatattcaga ataatttaa atacatcatt gcaatgaaaa taaatgtttt ttattaggca    10260
gaatccagat gctcaaggcc cttcataata tcccccagtt tagtagttgg acttagggaa   10320
caaaggaacc tttaatagaa attggacagc aagaaagcga gggggatctg gatcctccgg   10380
agggccccctt ctccctctaa cactctcccc tgttgaagct ctttgtgacg ggcgagctca   10440
ggccctgatg ggtgacttcg caggcgtaga ctttgtgttt ctcgtagtct gctttgctca   10500
gcgtcagggt gctgctgagg ctgtaggtgc tgtccttgct gtcctgctct gtgacactct   10560
cctgggagtt acccgattgg agggcgttat ccaccttcca ctgtactttg gcctctctgg   10620
gatagaagtt attcagcagg cacacaacag aggcagttcc agatttcaac tgctcatcag   10680
atggcgggaa gatgaagaca gatggtgcag ccacagttcg tctgatctcc accttggtcc   10740
ctccgccgaa agtgagcggg tgattatcat actgttgaca ataatatgtt gcaatatctt   10800
caggctgcag gctgctgatg gtgaaagtaa aatctgtccc agaaccactt ccactgaacc   10860
ttgatgggac tcttgtttcc aaattggaag cactgtagat caggagttta ggggctttcc   10920
ctggtttctg ctgataccaa tttaaatagt tgataatgtc ctgactcgcc tgcaagtga    10980
tggtgactct gtctcccaca gatgcagaca gggaggatgg agactgggtc atctggatgt   11040
cacatctggc acctgagagc cagagcagca ggagccccag gagctgagca gggaccctca   11100
tgtccatgct gtgtcccggt tgggactgac tcctgcacag ggtgaattcc accacactgg   11160
actagtggat ccgagctcgg taccaagctt aagtttaaac gctagccagc ttgggtctcc   11220
ctatagtgag tcgtattaat ttcgataagc cagtaagcag tgggttctct agttagccag   11280
agagctctgc ttatatagac ctcccaccgt acacgcctac cgcccatttg cgtcaatggg   11340
gcggagttgt tacgacattt tggaaagtcc cgttgatttt ggtgccaaaa caaactccca   11400
ttgacgtcaa tggggtggag acttggaaat ccccgtgagt caaaccgcta tccacgccca   11460
ttgatgtact gccaaaaccg catcaccatg gtaaatagcga tgactaatac gtagatgtac   11520
tgccaagtag gaaagtccca taaggtcatg tactgggcat aatgccaggc gggccattta   11580
ccgtcattga cgtcaatagg gggcgtactt ggcatatgat acacttgatg tactgccaag   11640
tgggcagttt accgtaaata gtccacccat tgacgtcaat ggaaagtccc tattggcgtt   11700
actatgggaa catacgtcat tattgacgtc aatgggcggg ggtcgttggg cggtcagcca   11760
ggcgggccat ttaccgtaag ttatgtaacg cggaactcca tatatgggct atgaactaat   11820
```

-continued

| | |
|---|---|
| gaccccgtaa ttgattacta ttaataacta gtcaataatc aatgtcaacg cgtatatctg | 11880 |
| gcccgtacat cggtaactag tcggaccggc ccgggccacc ggtgctcgaa gcttggatcg | 11940 |
| atccagacat gataagatac attgatgagt ttggacaaac cacaactaga atgcagtgaa | 12000 |
| aaaaatgctt tatttgtgaa atttgtgatg ctattgcttt atttgtaacc attataagct | 12060 |
| gcaataaaca agttaacaac aacaattgca ttcattttat gtttcaggtt cagggggagg | 12120 |
| tgtgggaggt tttttaaagc aagtaaaacc tctacaaatg tggtatggct gattatgatc | 12180 |
| tctagtcaag | 12190 |

<210> SEQ ID NO 7
<211> LENGTH: 12225
<212> TYPE: DNA
<213> ORGANISM: Artificial sequence
<220> FEATURE:
<223> OTHER INFORMATION: pAIGFRV3 plasmid

<400> SEQUENCE: 7

| | |
|---|---|
| gcactataca tcaaatattc cttattaacc cctttacaaa ttaaaaagct aaaggtacac | 60 |
| aatttttgag catagttatt aatagcagac actctatgcc tgtgtggagt aagaaaaaac | 120 |
| agtatgttat gattataact gttatgccta cttataaagg ttacagaata tttttccata | 180 |
| attttcttgt atagcagtgc agctttttcc tttgtggtgt aaatagcaaa gcaagcaaga | 240 |
| gttctattac taaacacagc atgactcaaa aacttagca attctgaagg aaagtccttg | 300 |
| gggtcttcta cctttctctt ctttttttgga ggagtagaat gttgagagtc agcagtagcc | 360 |
| tcatcatcac tagatggcat ttcttctgag caaaacaggt tttcctcatt aaaggcattc | 420 |
| caccactgct cccattcatc agttccatag gttggaatct aaaatacaca acaattaga | 480 |
| atcagtagtt taacacatta tacttaaa aattttatat ttaccttaga gctttaaatc | 540 |
| tctgtaggta gtttgtccaa ttatgtcaca ccacagaagt aaggttcctt cacaaagatc | 600 |
| gatctaaagc cagcaaaagt cccatggtct tataaaaatg catagcttta ggaggggagc | 660 |
| agagaacttg aaagcatctt cctgttagtc tttcttctcg tagacttcaa acttatactt | 720 |
| gatgcctttt tcctcctgga cctcagagag gacgcctggg tattctggga gaagtttata | 780 |
| tttccccaaa tcaatttctg ggaaaaacgt gtcactttca aattcctgca tgatccttgt | 840 |
| cacaaagagt ctgaggtggc ctggttgatt catggcttcc tggtaaacag aactgcctcc | 900 |
| gactatccaa accatgtcta ctttacttgc caattccggt tgttcaataa gtcttaaggc | 960 |
| atcatccaaa cttttggcaa gaaaatgagc tcctcgtggt ggttctttga gttctctact | 1020 |
| gagaactata ttaattctgt cctttaaagg tcgattcttc tcaggaatgg agaaccaggt | 1080 |
| tttcctaccc ataatcacca gattctgttt accttccact gaagaggttg tggtcattct | 1140 |
| ttggaagtac ttgaactcgt tcctgagcgg aggccaggag aggtctccgt tcttgccaat | 1200 |
| ccccatattt tgggacacgg cgacgatgca gttcaatggt cgaaccatga tggcagcggg | 1260 |
| gataaaatcc taccagcctt cacgctagga ttgccgtcaa gtttggcgcg aaatcgcagc | 1320 |
| cctgagctgt ccccccccc aagctcagat ctgagcttgg tccctatggt gagtccgttc | 1380 |
| cgctcttgtg atgatagcca gacaagaaag agacaataca agacaaacac caaatagtag | 1440 |
| aaatagagac aagggtcact tatccgaggg tccctgttcg ggcgccagct gccgcagtcg | 1500 |
| gccgacctga gggtcgccgg ggtctgcggg gggaccctct ggaaagtgaa ggataagtga | 1560 |
| cgagcggaga cgggatggcg aacagacaca aacacacaag aggtgaatgt taggactgtt | 1620 |

-continued

```
gcaagtttac tcaaaaaatc agcactcttt tatatcttgg tttacataag catttacata    1680
agatttggat aaattccaaa agaacatagg aaaatagaac actcagagct cagatcagaa    1740
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc   1920
cctccttggt atggaaaatc tttccccaaa agtgcattcc tgttcctaga taaatataat    1980
catgtacctg ttgtttcatg tcgtcttttt cttcttgaga caacatacac caaggaggtc    2040
tagctctggc gagtctttca cgaaaaggga gggatctata taacacttta tagccattga    2100
ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actcttttt ccctttttta cttctaggcc tgtggtcaat agtccttgca     2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca gtttgcagc agagaatgaa tatgtctttg tctgatgggc     2700
tcatccgttt gtgcgcagac gggtcgtcct tggtgggaaa caacccttg gctgcttctc     2760 ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggctt     2940 ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc    3180
gtaaaaaggc cgcgttgctg gcgttttcc ataggctccg ccccctgac gagcatcaca     3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca gctcacgc tgtaggtatc      3420 tcagttcggt gtaggtcgtt cgctccaagc tgggctgtgt gcacgaaccc ccgttcagc     3480 ccgaccgctg cgccttatcc ggtaactatc gtcttgagtc aacccggta agacacgact     3540 tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt ttgtttgcaa gcagcagatt acgcgcagaa    3780
aaaaaggatc tcaagaagat cctttgatct ttttctacgg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
```

```
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata taccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag gaataaggg   4800 cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct ggccggcctg tgcgaacgcc agcaagacga gcccagcgc gtcggccgcc   5100 atgccctgct tcatccccgt ggcccgttgc tcgcgtttgc tggcggtgtc cccggaagaa   5160
atatatttgc atgtctttag ttctatgatg acacaaaccc cgcccagcgt cttgtcattg   5220
gcgaattcga acacgcagat gcagtcgggg cggcgcggtc ccaggtccac ttcgcatatt   5280
aaggtgacgc gtgtggcctc gaacaccgag cgaccctgca gcgacccgct taacagcgtc   5340
aacagcgtgc cgcagatccc gggcaatgag atatgaaaaa gcctgaactc accgcgacgt   5400
ctgtcgagaa gtttctgatc gaaaagttcg acagcgtctc cgacctgatg cagctctcgg   5460
agggcgaaga atctcgtgct ttcagcttcg atgtaggagg gcgtggatat gtcctgcggg   5520
taaatagctg cgccgatggt ttctacaaag atcgttatgt ttatcggcac tttgcatcgg   5580
ccgcgctccc gattccggaa gtgcttgaca ttggggaatt cagcgagagc ctgacctatt   5640
gcatctcccg ccgtgcacag ggtgtcacgt tgcaagacct gcctgaaacc gaactgcccg   5700
ctgttctgca gccggtcgcg gaggccatgg atgcgatcgc tgcggccgat cttagccaga   5760
cgagcgggtt cggcccattc ggaccgcaag gaatcggtca atacactaca tggcgtgatt   5820
tcatatgcgc gattgctgat ccccatgtgt atcactggca aactgtgatg gacgacaccg   5880
tcagtgcgtc cgtcgcgcag gctctcgatg agctgatgct ttgggccgag gactgccccg   5940
aagtccggca cctcgtgcac gcggatttcg gctccaacaa tgtcctgacg gacaatggcc   6000
gcataacagc ggtcattgac tggagcgagg cgatgttcgg ggattcccaa tacgaggtcg   6060
ccaacatctt cttctggagg ccgtggttgg cttgtatgga gcagcagacg cgctacttcg   6120
agcggaggca tccggagctt gcaggatcgc cgcggctccg gcgtatatg ctccgcattg   6180 gtcttgacca actctatcag agcttggttg acggcaattt cgatgatgca gcttgggcgc   6240
agggtcgatg cgacgcaatc gtccgatccg gagccgggac tgtcgggcgt acacaaatcg   6300
cccgcagaag cgcggccgtc tggaccgatg gctgtgtaga agtactcgcc gatagtggaa   6360
```

-continued

```
accgacgccc cagcactcgt ccgagggcaa aggaataggg gagatggggg aggctaactg    6420
aaacacggaa ggagacaata ccggaaggaa cccgcgctat gacggcaata aaaagacaga    6480
ataaaacgca cggtgttggg gtcgtttgtt cataaacgcg gggttcggtc ccagggctgg    6540
cactctgtcg atacccacc gagaccccat tggggccaat acgcccgcgt ttcttccttt     6600
tccccacccc acccccaag ttcgggtgaa ggcccagggc tcgcagccaa cgtcggggcg    6660
gcaggccctg ccatagccac tggccccgtg gttagggac ggggtccccc atggggaatg    6720
gtttatggtt cgtggggtt attattttgg gcgttgcgtg gggtctggtc cacgactgga     6780
ctgagcagac agacccatgg tttttggatg gcctgggcat ggaccgcatg tactggcgcg    6840
acacgaacac cgggcgtctg tggctgccaa acacccccga cccccaaaaa ccaccgcgcg    6900
gatttctggc gcccagtggc acaggccggc ctgtacatga tcaacgcgtg agctctctag    6960
agcttgtcga cagatccccc tcttcatttc tttatgtttt aaatgcactg acctcccaca    7020 ttccctttt agtaaaatat tcagaaataa tttaaataca tcattgcaat gaaaataaat     7080
gttttttatt aggcagaatc cagatgctca aggcccttca taatatcccc cagtttagta    7140
gttggactta gggaacaaag gaacctttaa tagaaattgg acagcaagaa agcgaggggg    7200
atctggatcc tccggacccg gggagcgggg gcttgccggc cctggcactc atttacccag    7260
agacagggag aggctcttct gtgtgtagtg gttgtgcaga gcctcatgca tcacggagca    7320
tgagaagaca ttcccctcct gccacctgct cttgtccacg gttagcctgc tgtagaggaa    7380
gaaggagccg tcggagtcca gcacgggagg cgtggtcttg tagttgttct ccggctgccc    7440
attgctctcc cactccacgg cgatgtcgct ggggtagaag cctttgacca ggcaggtcag    7500 gctgacctg ttcttggtca tctcctcctg ggatgggggc agggtgtaca cctgtggctc     7560
tcggggctgc cctgtaggga cagaggttgg cacagcggtc actcccaggg cagagggtgg    7620
gccgagctga cctctgtcca tgtggccctc gcacccgtg gtcccacct ttggctttgg      7680 agatggtttt ctcgatggag gacgggaggc ctttgttgga gaccttgcac ttgtactcct    7740
tgccgttcag ccagtcctgg tgcaggacg tgaggacgct gaccacacgg tacgtgctgt     7800
tgaactgctc ctcccgcggc tttgtcttgg cattatgcac ctccacgcca tccacgtacc    7860
agttgaactg gacctcgggg tcttcctggc tcacgtccac caccacgcac gtgacctcag    7920
gggtccggga gatcatgaga gtgtccttgg gttttggggg gaacaggaag actgatggtc    7980
cccccaggaa ctcaggtgct gaggaagaga tggaggtgga tgcgtcagca cccggctggg    8040
gcctgtccct ggatgcaggc tactctaggg cacctgtccc gccttgagct ggagggcgag    8100
gcctggggtg gcttacctgg gcatgatggg catgggggac catatttgga ctctgcagag    8160
agaagattgg gagttactca gatctgggag gagagaaggt gtctgagctg agggagtgga    8220
gagtttggcc tttggggtgg gcttaggtca ggggcagggt cctcccggat atggctcttg    8280
gcaggtctga gcgcagcacc tgccccctgta tgcgcagggc ctggggtagg ggcatccagc    8340
ctgtggctgc ccggagcctg gtggaaaaat ccagaagacc ctctccctga gcatgagtgg    8400
ggtggtcaga ggcctccggg tgaggagaca gatgggcat gccttgctgc cctgggctgg     8460
ggctgcacag ccggggtgcg tccaggcagg agggctgagc ctggcttcca gcagacaccc    8520
tccctccctg tgctgcctc tcaccaactc tcttgtccac cttggtgttg ctgggcttgt     8580
gatctacgtt gcaggtgtag gtcttcgtgc ccaagctgct ggagggcacg gtcaccacgc    8640
tgctgaggga gtagagtcct gaggactgta ggacagccgg gaaggtgtgc acgccgctgt    8700
tcagggcgcc tgagttccac gacaccgtca ccggttcggg gaagtagtcc ttgaccaggc    8760
```

```
agcccagggc ggctgtgctc tcggaggtgc tcctggagca gggcgccagg gggaagacgg    8820
atgggccctt ggtggaagct gaggagacgg tgaccgtggt cccttggccc cagacgtcca    8880
taccgtagta gaagttcccc agtcttgcac agtaatacac agccatgtcc tcggctctca    8940
ggctgttcat ttgaagatac aaggagttct tggcattgtc tctggagatg gtgaatcggc    9000
ccttcacgga gtctgcatag tatgtggcac cacgagtatc aataactgat atccactcca    9060 gacctttttcc tggagcctgg cgaacccagt gcatagcaaa gctactgaag gtgaatccag   9120
aggctgcaca ggagagtctc agggaccccc caggatgtac caagcctccc ccagactgca    9180
ccagctgaac ctcacactgg acaccttttta atatagcaac aaggaaaacc cagctcagcc   9240
caaactccat aagggcgaat tccaccacac tggactagtg gatccgagct cggtaccaag    9300
cttaagttta aacgctagcc agcttgggtc tccctatagt gagtcgtatt aatttcgata    9360
agccagtaag cagtgggttc tctagttagc cagagagctc tgcttatata gacctcccac    9420
cgtacacgcc taccgcccat ttgcgtcaat ggggcggagt tgttacgaca ttttggaaag    9480
tcccgttgat tttggtgcca aaacaaactc ccattgacgt caatgggtg gagacttgga    9540 aatccccgtg agtcaaaccg ctatccacgc ccattgatgt actgccaaaa ccgcatcacc    9600
atggtaatag cgatgactaa tacgtagatg tactgccaag taggaaagtc ccataaggtc    9660
atgtactggg cataatgcca ggcgggccat ttaccgtcat tgacgtcaat aggggcgta    9720 cttggcatat gatacacttg atgtactgcc aagtgggcag tttaccgtaa atagtccacc    9780
cattgacgtc aatggaaagt ccctattggc gttactatgg gaacatacgt cattattgac    9840
gtcaatgggc ggggtcgtt gggcggtcag ccaggcgggc catttaccgt aagttatgta    9900
acgcggaact ccatatatgg gctatgaact aatgaccccg taattgatta ctattaataa    9960
ctagtcaata atcaatgtca acgcgtatat ctggcccgta catcggtagc tgagggttta   10020
aacggcgcgc ggccggccgg taccacgcgt tggccacata tggcggccgc tcgcgattaa   10080
ttaatcgcga tggccacata tggagctctc tagagcttgt cgacagatcc cctcttcat    10140 ttctttatgt tttaaatgca ctgacctccc acattccctt tttagtaaaa tattcagaaa   10200
taatttaaat acatcattgc aatgaaaata atgtttttt attaggcaga atccagatgc     10260 tcaaggcccct tcataatatc ccccagttta gtagttggac ttaggaaca aaggaacctt   10320 taatagaaat tggacagcaa gaaagcgagg gggatctgga tcctccggag ggccccttct   10380
ccctctaaca ctctcccctg ttgaagctct ttgtgacggg cgagctcagg ccctgatggg   10440
tgacttcgca ggcgtagact ttgtgtttct cgtagtctgc tttgctcagc gtcagggtgc   10500
tgctgaggct gtaggtgctg tccttgctgt cctgctctgt gacactctcc tgggagttac   10560
ccgattggag ggcgttatcc accttccact gtactttggc ctctctggga tagaagttat   10620
tcagcaggca cacaacagag gcagttccag atttcaactg ctcatcagat ggcgggaaga   10680
tgaagacaga tggtgcagcc acagttcgtt tgatctccac cttggtccct ccgccgaaag   10740
tgtgaggtaa acgactactc tgatgacagt aatacgctgc agcatcttca gcttccaggc   10800
tattgatggt gagggtgaaa tctgtcccag atccactgcc actgaacctc gagggaccc    10860 ctgagaggga ctgggaagca tacttgatga ggagctttgg agactgatct ggtttctgct   10920
ggtaccagtg taagctacta ccaatgctct gactggcccg gcaggtgatg gtgactttct   10980
cctttggagt cacagactga aagtctggaa cctgagtcag cacaatttca cccctggagg   11040
ctggaaccca gagcagcaga aacccaatga gttgtgatgg cgacatcttc ctgccttgac   11100
```

-continued

```
ttgtcagttt tgctcatgcc cccgcgtact ctgcgttgtt accactgctt gccctatagt    11160
gagtcgtatt agaagggcga attccaccac actggactag tggatccgag ctcggtacca    11220
agcttaagtt taaacgctag ccagcttggg tctccctata gtgagtcgta ttaatttcga    11280
taagccagta agcagtgggt tctctagtta gccagagagc tctgcttata tagacctccc    11340
accgtacacg cctaccgccc atttgcgtca atgggcgga gttgttacga cattttggaa    11400
agtcccgttg attttggtgc caaaacaaac tcccattgac gtcaatgggg tggagacttg    11460 gaaatcccg tgagtcaaac cgctatccac gcccattgat gtactgccaa accgcatca    11520 ccatggtaat agcgatgact aatacgtaga gtactgcca gtaggaaag tcccataagg    11580 tcatgtactg gcataatgc caggcgggcc atttaccgtc attgacgtca ataggggcg    11640 tacttggcat atgatacact tgatgtactg ccaagtgggc agtttaccgt aaatagtcca    11700
cccattgacg tcaatggaaa gtccctattg gcgttactat gggaacatac gtcattattg    11760
acgtcaatgg gcggggtcg ttgggcggtc agccaggcgg gccatttacc gtaagttatg    11820
taacgcggaa ctccatatat gggctatgaa ctaatgaccc cgtaattgat tactattaat    11880
aactagtcaa taatcaatgt caacgcgtat atctggcccg tacatcggta actagtcgga    11940 ccggccgg ccaccggtgc tcgaagcttg gatcgatcca gacatgataa gatacattga    12000
tgagtttgga caaaccacaa ctagaatgca gtgaaaaaaa tgctttattt gtgaaatttg    12060
tgatgctatt gctttatttg taaccattat aagctgcaat aaacaagtta acaacaacaa    12120
ttgcattcat tttatgtttc aggttcaggg ggaggtgtgg gaggtttttt aaagcaagta    12180
aaacctctac aaatgtggta tggctgatta tgatctctag tcaag                    12225
```

<210> SEQ ID NO 8
<211> LENGTH: 13079
<212> TYPE: DNA
<213> ORGANISM: Artificial sequence
<220> FEATURE:
<223> OTHER INFORMATION: pAIG1FR(-)IL2LS plasmid

<400> SEQUENCE: 8

```
gcactataca tcaaatattc cttattaacc cctttacaaa ttaaaaagct aaaggtacac      60 aattttttgag catagttatt aatagcagac actctatgcc tgtgtggagt aagaaaaaac    120
agtatgttat gattataact gttatgccta cttataaagg ttacagaata ttttttccata   180 atttctcttgt atagcagtgc agcttttttcc tttgtggtgt aaatagcaaa gcaagcaaga   240
gttctattac taaacacagc atgactcaaa aaacttagca attctgaagg aaagtccttg    300
gggtcttcta cctttctctt ctttttggaa ggagtagaat gttgagagtc agcagtagcc    360
tcatcatcac tagatggcat tcttctgag caaaacaggt tttcctcatt aaaggcattc     420
caccactgct cccattcatc agttccatag gttggaatct aaaatacaca acaattaga     480 atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag acgcctgggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
```

-continued

```
atcatccaaa cttttggcaa gaaaatgagc tcctcgtggt ggttctttga gttctctact    1020
gagaactata ttaattctgt cctttaaagg tcgattcttc tcaggaatgg agaaccaggt    1080
tttcctaccc ataatcacca gattctgttt accttccact gaagaggttg tggtcattct    1140
ttggaagtac ttgaactcgt tcctgagcgg aggccagggt aggtctccgt tcttgccaat    1200
ccccatattt tgggacacgg cgacgatgca gttcaatggt cgaaccatga tggcagcggg    1260
gataaaatcc taccagcctt cacgctagga ttgccgtcaa gtttggcgcg aaatcgcagc    1320
cctgagctgt ccccccccccc aagctcagat ctgagcttgg tccctatggt gagtccgttc    1380
cgctcttgtg atgatagcca gacaagaaag agacaataca agacaaacac caaatagtag    1440
aaatagagac aagggtcact tatccgaggg tccctgttcg ggcgccagct gccgcagtcg    1500
gccgacctga gggtcgccgg ggtctgcggg gggaccctct ggaaagtgaa ggataagtga    1560
cgagcggaga cgggatggcg aacagacaca aacacacaag aggtgaatgt taggactgtt    1620
gcaagtttac tcaaaaaatc agcactcttt tatatcttgg tttacataag catttacata    1680
agatttggat aaattccaaa gaacatagg aaaatagaac actcagagct cagatcagaa    1740
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc    1920
cctccttggt atggaaaatc tttccccaaa agtgcattcc tgttcctaga taaatataat    1980
catgtacctg ttgtttcatg tcgtcttttt cttcttgaga caacatacac caaggaggtc    2040
tagctctggc gagtctttca cgaaaaggga gggatctata taacacttta tagccattga    2100
ctgtaaccca cctatcccaa tttaagtcat atcttcctgt atatggtaag ggggcatctg    2160
ttggtctgta gatgtaaggt cccctataag tccctggttg ccaccacctg tctcctatt    2220 tgacaaaaac actcttttt ccctttttta cttctaggcc tgtggtcaat agtccttgca    2280
cctgttcttc aattgaggtt gagcgtctct ttctatttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca gtttgcagc agagaatgaa tatgtctttg tctgatgggc    2700
tcatccgttt gtgcgcagac gggtcgtcct tggtgggaaa caacccttg gctgcttctc    2760 ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag catagcctt    2940 ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgtt gagcaaaagg ccagcaaaag gccaggaacc    3180
gtaaaaaggc cgcgttgctg gcgttttttcc ataggctccg ccccccctgac gagcatcaca    3240 aaaatcgacg ctcaagtcag aggtggcgaa acccgacagg actataaaga taccaggcgt    3300
```

```
ttcccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc ccgttcagc    3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt tgtttgcaa gcagcagatt acgcgcagaa    3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
tttaaatta aaaatgaagt tttaaatcaa tctaaagtat atatgagtaa acttggtctg    3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgt tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca cacgggata ataccgcgcc acatagcaga actttaaaag    4620
tgctcatcat tggaaaacgt tcttcgggc gaaaactctc aaggatctta ccgctgttga    4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct ccttttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct ggccggcctg tgcgaacgcc agcaagacgt agcccagcgc gtcggccgcc   5100
atgccctgct tcatccccgt ggcccgttgc tcgcgtttgc tggcggtgtc cccggaagaa   5160
atatatttgc atgtctttag ttctatgatg acacaaaccc cgcccagcgt cttgtcattg   5220
gcgaattcga acacgcagat gcagtcgggg cggcgcggtc ccaggtccac ttcgcatatt   5280
aaggtgacgc gtgtggcctc gaacaccgag cgaccctgca gcgacccgct taacagcgtc   5340
aacagcgtgc cgcagatccc gggcaatgag atatgaaaaa gcctgaactc accgcgacgt   5400
ctgtcgagaa gtttctgatc gaaaagttcg acagcgtctc cgacctgatg cagctctcgg   5460
agggcgaaga atctcgtgct ttcagcttcg atgtaggagg gcgtggatat gtcctgcggg   5520
taaatagctg cgccgatggt ttctacaaag atcgttatgt ttatcggcac tttgcatcgg   5580
ccgcgctccc gattccggaa gtgcttgaca ttggggaatt cagcgagagc ctgacctatt   5640
gcatctcccg ccgtgcacag ggtgtcacgt tgcaagacct gcctgaaacc gaactgcccg   5700
```

```
ctgttctgca gccggtcgcg gaggccatgg atgcgatcgc tgcggccgat cttagccaga    5760
cgagcgggtt cggcccattc ggaccgcaag gaatcggtca atacactaca tggcgtgatt    5820
tcatatgcgc gattgctgat ccccatgtgt atcactggca aactgtgatg gacgacaccg    5880
tcagtgcgtc cgtcgcgcag gctctcgatg agctgatgct ttgggccgag gactgccccg    5940
aagtccggca cctcgtgcac gcggatttcg gctccaacaa tgtcctgacg gacaatggcc    6000
gcataacagc ggtcattgac tggagcgagg cgatgttcgg ggattcccaa tacgaggtcg    6060
ccaacatctt cttctggagg ccgtggttgg cttgtatgga gcagcagacg cgctacttcg    6120
agcggaggca tccggagctt gcaggatcgc cgcggctccg ggcgtatatg ctccgcattg    6180
gtcttgacca actctatcag agcttggttg acggcaattt cgatgatgca gcttgggcgc    6240
agggtcgatg cgacgcaatc gtccgatccg gagccgggac tgtcgggcgt acacaaatcg    6300
cccgcagaag cgcggccgtc tggaccgatg gctgtgtaga agtactcgcc gatagtggaa    6360
accgacgccc cagcactcgt ccgagggcaa aggaataggg gagatggggg aggctaactg    6420
aaacacggaa ggagacaata ccggaaggaa cccgcgctat gacggcaata aaaagacaga    6480
ataaaacgca cgggtgttgg gtcgtttgtt cataaacgcg gggttcggtc ccagggctgg    6540
cactctgtcg ataccccacc gagacccat tggggccaat acgcccgcgt tcttcctttt    6600
tccccacccc accccccaag ttcgggtgaa ggcccagggc tcgcagccaa cgtcggggcg    6660
gcaggccctg ccatagccac tggccccgtg ggttagggac ggggtccccc atggggaatg    6720
gtttatggtt cgtgggggtt attattttgg gcgttgcgtg gggtctggtc cacgactgga    6780
ctgagcagac agacccatgg ttttggatg gcctgggcat ggaccgcatg tactggcgcg    6840
acacgaacac cgggcgtctg tggctgccaa acaccccga cccccaaaaa ccaccgcgcg    6900
gatttctggc gcccagtggc acaggccggc ctgtacatga tcaacgcgtg agctctctag    6960
agcttgtcga cagatccccc tcttcatttc tttatgtttt aaatgcactg acctcccaca    7020
ttcccttttt agtaaaatat tcagaaataa tttaaataca tcattgcaat gaaaataaat    7080
gttttttatt aggcagaatc cagatgctca aggcccttca taatatcccc cagtttagta    7140
gttggactta gggaacaaag gaaccttaa tagaaattgg acagcaagaa agcgaggggg    7200
atctggatcc tccggacccg tatctagaat catcgattca tttacccgga gacagggaga    7260
ggctcttctg cgtgtagtgg ttgtgcagag cctcatgcat cacggagcat gagaagacgt    7320
tcccctgctg ccacctgctc ttgtccacgt gagcttgct gtagaggaag aaggagccgt    7380
cggagtccag cacgggaggc gtggtcttgt agttgttctc cggctgccca ttgctctccc    7440
actccacggc gatgtcgctg ggatagaagc ctttgaccag gcaggtcagg ctgacctggt    7500
tcttggtcag ctcatcccgg gatggggca gggtgtacac ctgtggttct cggggctgcc    7560
cttggctttt ggagatggtt ttctcgatgg gggctgggag ggctttgttg gagaccttgc    7620
acttgtactc cttgccattc agccagtcct ggtgcaggac ggtgaggacg ctgaccacac    7680
ggtacgtgct gttgtactgc tcctcccgcg ctttgtcttg gcattatgc acctccacgc    7740
cgtccacgta ccagttgaac ttgacctcag ggtcttcgtg gctcacgtcc accaccacgc    7800
atgtgacctc aggggtccgg gagatcatga gggtgtcctt gggttttggg gggaagagga    7860
agactgacgg tcccccagg agttcaggtg ctgggcacgg tgggcatgtg tgagttttgt    7920
cacaagattt gggctcaact ttcttgtcca ccttggtgtt gctgggcttg tgattcacgt    7980
tgcagatgta ggtctgggtg cccaagctgc tggagggcac ggtcaccacg ctgctgaggg    8040
```

```
agtagagtcc tgaggactgt aggacagccg ggaaggtgtg cacgccgctg gtcagggcgc   8100
ctgagttcca cgacaccgtc accggttcgg ggaagtagtc cttgaccagg cagcccaggg   8160
ccgctgtgcc cccagaggtg ctcttggagg agggtgccag ggggaagacc gatgggccct   8220
tggtggaagc tgaggagacg gtgaccgtgg tcccttggcc ccagacgtcc ataccgtagt   8280
agaagttccc cagtcttgca cagtaataca cagcagtgtc ctcggctctc aggctgttca   8340
tttgaagata caaggagttc ttggcattgt ctctggagat ggtgaatcgg cccttcacgg   8400
agtctgcata gtatgtggca ccacgagtat caataactga tatccactcc agaccttttc   8460
ctggagcctg gcgaacccag tgcatagcaa agctactgaa ggtgaatcca gaggctgcac   8520
aggagagtct cagggacccc ccaggcttta ccaagcctcc cccagactgc accagctgaa   8580
cctcacactg gacacctttt aatatagcaa caaggaaaac ccagctcagc ccaaactcca   8640
taagggcgaa ttccaccaca ctggactagt ggatccgagc tcggtaccaa gcttaagttt   8700
aaacgctagc cagcttgggt ctccctatag tgagtcgtat taatttcgat aagccagtaa   8760
gcagtgggtt ctctagttag ccagagagct ctgcttatat agacctccca ccgtacacgc   8820
ctaccgccca tttgcgtcaa tggggcggag ttgttacgac attttggaaa gtcccgttga   8880
ttttggtgcc aaaacaaact cccattgacg tcaatggggt ggagacttgg aaatccccgt   8940
gagtcaaacc gctatccacg cccattgatg tactgccaaa accgcatcac catggtaata   9000
gcgatgacta atacgtagat gtactgccaa gtaggaaagt cccataaggt catgtactgg   9060
gcataatgcc aggcgggcca tttaccgtca ttgacgtcaa tagggggcgt acttggcata   9120
tgatacactt gatgtactgc caagtgggca gtttaccgta aatagtccac ccattgacgt   9180
caatggaaag tccctattgg cgttactatg ggaacatacg tcattattga cgtcaatggg   9240 cggggtcgt tgggcggtca gccaggcggg ccatttaccg taagttatgt aacgcggaac   9300
tccatatatg gctatgaac taatgacccc gtaattgatt actattaata actagtcaat   9360
aatcaatgtc aacgcgtata tctggcccgt acatcggtag ctgagggttt aaacggcgcg   9420
cggccggccg gtaccacgcg ttggccacat atggcggccg ctcgcgatta attaatcgcg   9480
atggccacat atggagctct ctagagcttg tcgacagatc cccctcttca tttctttatg   9540
ttttaaatgc actgacctcc cacattccct ttttagtaaa atattcagaa ataatttaaa   9600
tacatcattg caatgaaaat aaatgttttt tattaggcag aatccagatg ctcaaggccc   9660
ttcataatat cccccagttt agtagttgga cttaggaaac aaaggaacct taatagaaa    9720 ttggacagca agaaagcgag ggggatctgg atcctccgga gggcccctgc aggaattcga   9780
tggccgctag attgttcttc tactcttcct ctgtctccgc tgccaggtga gcccactcag   9840
gaggaggacg ctgatcagca ggaaaacaca gccggccact gctacctggt actctgttgt   9900
aaatatggac gtctccatgg ttgcagccat ttctgtctgt atttgaaaat ctgttgttgt   9960
gacgaggcag gaagtctcac tctcaggacg gccttcgggg cttgcctgag gcttctcttc  10020
acctggaaac tgactggtct ccatttcacc tgtgcatatg agctggggct gggtccacct  10080
tgtcttcccg tgggtcattt tgcagacgct ctcagcagga cctctgtgta gagccctgta  10140
tccctggacg cactgataat aaaccatctg ccccaccacg aaatgataaa ttctctctgt  10200
ggcttcattt tcccatggtg gaggttccct gcagtgacct ggaaggctcg cttggtccac  10260
tggctgcatt ggactttgca tttctgtggt tttccttttct ttctgttctt caggttgagg  10320
tgtcacttgt ttcgttgtgt tccgagtggc agagcttgtg cattgacatt ggttgtccca  10380
ggacgagtgg ctagagtttc ctgtacagag catatagagt gacccgcttt ttattctgcg  10440
```

```
gaaacctctc ttgcattcac agttcaacat ggttccttcc ttgtaggcca tggctttgaa   10500
tgtggcgtgt gggatctctg gcgggtcatc gtcacagagc tctgcctggc agccaggcac   10560
catgatgaac gtgagcagtc cccacatcag caggtatgaa tccatggtgg cggcaaccgg   10620
ttatcatcgt gttttttcaaa ggaaaaccac gtccccgtgg ttcgggggggc ctagacgttt   10680
tttaacctcg actaaacaca tgtaaagcat gtgcaccgag gccccagatc agatcccata   10740
caatggggta ccttctgggc atccttcagc cccttgttga atacgcttga ggagagccat   10800
ttgactcttt ccacaactat ccaactcaca acgtggcact ggggttgtgc cgcctttgca   10860
ggtgtatctt atacacgtgg cttttggccg cagaggcacc tgtcgccagg tggggggttc   10920
cgctgcctgc aaagggtcgc tacagacgtt gtttgtcttc aagaagcttc cagaggaact   10980
gcttccttca cgacattcaa cagaccttgc attcctttgg cgagagggga aagacccta    11040
ggaatgctcg tcaagaagac agggccaggt ttccgggccc tcacattgcc aaaagacggc   11100
aatatggtgg aaaataacat atagacaaac gcacaccggc cttattccaa gcggcttcgg   11160
ccagtaacgt tagggggggg ggagggagag gggcgctcga gactagccgg agggcccctt   11220
ctccctctaa cactctcccc tgttgaagct cttttgtgacg ggcgagctca ggccctgatg   11280
ggtgacttcg caggcgtaga ctttgtgttt ctcgtagtct gctttgctca gcgtcagggt   11340
gctgctgagg ctgtaggtgc tgtccttgct gtcctgctct gtgacactct cctgggagtt   11400
acccgattgg agggcgttat ccaccttcca ctgtactttg gcctctctgg gatagaagtt   11460
attcagcagg cacacaacag aggcagttcc agatttcaac tgctcatcag atggcgggaa   11520
gatgaagaca gatggtgcag ccacagttcg tttgatctcc accttggtcc ctccgccgaa   11580
agtgtgaggt aaacgactac tctgatgaca gtaatacgct gcagcatctt cagcttccag   11640
gctattgatg gtgagggtga atctgtccc agatccactg ccactgaacc tcgaggggac    11700
ccctgagagg gactgggaag catacttgat gaggagcttt ggagactgat ctggtttctg   11760
ctggtaccag tgtaagctac taccaatgct ctgactggcc cggcaggtga tggtgacttt   11820
ctccttttgga gtcacagact gaaagtctgg aacctgagtc agcacaattt caccccctgga   11880
ggctggaacc cagagcagca gaaacccaat gagttgtgat ggcgacatct tcctgccttg   11940
acttgtcagt tttgctcatg cccccgcgta ctctgcgttg ttaccactgc ttgccctata   12000
gtgagtcgta ttagaagggc gaattccacc acactggact agtggatccg agctcggtac   12060
caagcttaag tttaaacgct agccagcttg ggtctcccta tagtgagtcg tattaatttc   12120
gataagccag taagcagtgg gttctctagt tagccagaga gctctgctta tatagacctc   12180
ccaccgtaca cgcctaccgc ccatttgcgt caatggggcg gagttgttac gacattttgg   12240
aaagtcccgt tgattttggt gccaaaacaa actcccattg acgtcaatgg ggtggagact   12300
tggaaatccc cgtgagtcaa accgctatcc acgcccattg atgtactgcc aaaaccgcat   12360
caccatggta atagcgatga ctaatacgta gatgtactgc caagtaggaa agtcccataa   12420
ggtcatgtac tgggcataat gccaggcggg ccatttaccg tcattgacgt caataggggg   12480
cgtacttggc atatgataca cttgatgtac tgccaagtgg gcagtttacc gtaaatagtc   12540
cacccattga cgtcaatgga aagtccctat tggcgttact atgggaacat acgtcattat   12600
tgacgtcaat gggcgggggt cgttgggcgg tcagccaggc gggccattta ccgtaagtta   12660
tgtaacgcgg aactccatat atgggctatg aactaatgac cccgtaattg attactatta   12720
ataactagtc aataatcaat gtcaacgcgt atatctggcc cgtacatcgg taactagtcg   12780
```

-continued

| | |
|---|---|
| gaccgccgcg gactagtgcc cgggccaccg gtgctcgaag cttggatcga tccagacatg | 12840 |
| ataagataca ttgatgagtt tggacaaacc acaactagaa tgcagtgaaa aaaatgcttt | 12900 |
| atttgtgaaa tttgtgatgc tattgcttta tttgtaacca ttataagctg caataaacaa | 12960 |
| gttaacaaca acaattgcat tcattttatg tttcaggttc agggggaggt gtgggaggtt | 13020 |
| ttttaaagca agtaaaacct ctacaaatgt ggtatggctg attatgatct ctagtcaag | 13079 |

<210> SEQ ID NO 9
<211> LENGTH: 11520
<212> TYPE: DNA
<213> ORGANISM: Artificial sequence
<220> FEATURE:
<223> OTHER INFORMATION: pAIL10V3 plasmid

<400> SEQUENCE: 9

| | |
|---|---|
| gcactataca tcaaatattc cttattaacc cctttacaaa ttaaaaagct aaaggtacac | 60 |
| aattttttgag catagttatt aatagcgagac actctatgcc tgtgtggagt aagaaaaaac | 120 |
| agtatgttat gattataact gttatgccta cttataaagg ttacagaata ttttttccata | 180 |
| attttcttgt atagcagtgc agcttttttcc tttgtggtgt aaatagcaaa gcaagcaaga | 240 |
| gttctattac taaacacagc atgactcaaa aaacttagca attctgaagg aaagtccttg | 300 |
| gggtcttcta cctttctctt cttttttgga ggagtagaat gttgagagtc agcagtagcc | 360 |
| tcatcatcac tagatggcat tcttctgag caaaacaggt tttcctcatt aaaggcattc | 420 |
| caccactgct cccattcatc agttccatag gttggaatct aaaatacaca acaattaga | 480 |
| atcagtagtt taacacatta tacacttaaa aatttatat ttaccttaga gctttaaatc | 540 |
| tctgtaggta gtttgtccaa ttatgtcaca ccacagaagt aaggttcctt cacaaagatc | 600 |
| gatctaaagc cagcaaaagt cccatggtct tataaaaatg catagcttta ggaggggagc | 660 |
| agagaacttg aaagcatctt cctgttagtc tttcttctcg tagacttcaa acttatactt | 720 |
| gatgcctttt tcctcctgga cctcagagag gacgcctggg tattctggga aagtttata | 780 |
| tttccccaaa tcaatttctg ggaaaaacgt gtcactttca aattcctgca tgatccttgt | 840 |
| cacaaagagt ctgaggtggc ctggttgatt catggcttcc tggtaaacag aactgcctcc | 900 |
| gactatccaa accatgtcta ctttacttgc caattccggt tgttcaataa gtcttaaggc | 960 |
| atcatccaaa cttttggcaa gaaatgagc tcctcgtggt ggttctttga gttctctact | 1020 |
| gagaactata ttaattctgt cctttaaagg tcgattcttc tcaggaatgg agaaccaggt | 1080 |
| tttcctaccc ataatcacca gattctgttt accttccact gaagaggttg tggtcattct | 1140 |
| ttggaagtac ttgaactcgt tcctgagcgg aggccaggt aggtctccgt tcttgccaat | 1200 |
| ccccatattt tgggacacgg cgacgatgca gttcaatggt cgaaccatga tggcagcggg | 1260 |
| gataaaatcc taccagcctt cacgctagga ttgccgtcaa gtttggcgcg aaatcgcagc | 1320 |
| cctgagctgt ccccccccc aagctcagat ctgagcttgg tccctatggt gagtccgttc | 1380 |
| cgctcttgtg atgatagcca gacaagaaag agacaataca agacaaacac caaatagtag | 1440 |
| aaatagagac aagggtcact tatccgaggg tccctgttcg ggcgccagct gccgcagtcg | 1500 |
| gccgacctga gggtcgccgg ggtctgcggg gggaccctct ggaaagtgaa ggataagtga | 1560 |
| cgagcggaga cggatggcg aacagacaca acacacaag aggtgaatgt taggactgtt | 1620 |
| gcaagtttac tcaaaaaatc agcactcttt tatatcttgg tttacataag catttacata | 1680 |
| agatttggat aaattccaaa agaacatagg aaaatagaac actcagagct cagatcagaa | 1740 |
| cctttgatac caaaccaagt caggaaacca cttgtctcac atcctcgttt taagaacagt | 1800 |

```
ttgtaaccaa aaacttactt aagccctggg aaccgcaagg ttgggccaat aaaggctatt    1860
cataataact catgccatga gtttttgcag aataatgttc tattagtcca gccactgtcc    1920
cctccttggt atggaaaatc tttccccaaa agtgcattcc tgttcctaga taaatataat    1980
catgtacctg ttgtttcatg tcgtctttt cttcttgaga caacatacac caaggaggtc     2040
tagctctggc gagtctttca cgaaaaggga gggatctata taacactta tagccattga     2100 ctgtaaccca cctatcccaa tttaagtcat atcttcctgt atatggtaag ggggcatctg    2160
ttggtctgta gatgtaaggt cccctataag tccctggttg ccaccacctg tctcctattt    2220
tgacaaaaac actcttttt ccctttttta cttctaggcc tgtggtcaat agtccttgca     2280
cctgttcttc aattgaggtt gagcgtctct ttctattttc tattcccatt tctaacttct    2340
gaatttgagt aaaaatagta ctaaaagata atgattcatt tcttaacata gtaactaata    2400
atctacctat tggattggtc ttattggtaa aaatataatt tttagcaagc attcttattt    2460
ctatttctga aggacaaaat cgatgcggct tgtaagagga agttggctgt ggtccttgcc    2520
tcaggaggaa ggtcgagttc tccgaattgt ttagattgta atcttgcaca gaagagctat    2580
taaaagagtc aagggtgaga gccctgcgag cacgaaccgc aacttccccc aatagcccca    2640
ggcaaagcag agctatgcca agtttgcagc agagaatgaa tatgtctttg tctgatgggc    2700
tcatccgttt gtgcgcagac gggtcgtcct tggtgggaaa caaccccttg gctgcttctc    2760
ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag catagggctt    2940
ggttatgccg gtactgccgg gcctcttgcg ggatatcgtc cattccgaca gcatcgccag    3000
tcactatggc gtgctgctag cgctcttccg cttcctcgct cactgactcg ctgcgctcgg    3060
tcgttcggct gcggcgagcg gtatcagctc actcaaaggc ggtaatacgg ttatccacag    3120
aatcagggga taacgcagga agaacatgt gagcaaaagg ccagcaaaag gccaggaacc     3180
gtaaaaaggc cgcgttgctg gcgtttttcc ataggctccg ccccctgac gagcatcaca     3240 aaaatcgacg ctcaagtcag aggtggcgaa acccgacagg actataaaga taccaggcgt    3300
ttccccctgg aagctccctc gtgcgctctc ctgttccgac cctgccgctt accggatacc    3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc ccgttcagc     3480 ccgaccgctg cgccttatcc ggtaactatc gtcttgagtc aacccggta agacacgact     3540 tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt tgtttgcaa gcagcagatt acgcgcagaa     3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
```

-continued

```
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag gaataagggg    4800
cgacacggaa atgttgaata ctcatactct tccttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgct ggccggcctg tgcgaacgcc agcaagacgt agcccagcgc gtcggccgcc    5100
atgccctgct tcatccccgt ggcccgttgc tcgcgtttgc tggcggtgtc cccggaagaa    5160
atatatttgc atgtctttag ttctatgatg acacaaaccc cgcccagcgt cttgtcattg    5220
gcgaattcga acacgcagat gcagtcgggg cggcgcggtc ccaggtccac ttcgcatatt    5280
aaggtgacgg tgtggcctc gaacaccgag cgacccctgca cgacccgct taacagcgtc    5340 aacagcgtgc cgcagatccc gggcaatgag atatgaaaaa gcctgaactc accgcgacgt    5400
ctgtcgagaa gtttctgatc gaaaagttcg acagcgtctc cgacctgatg cagctctcgg    5460
agggcgaaga atctcgtgct ttcagcttcg atgtaggagg gcgtggatat gtcctgcggg    5520
taaatagctg cgccgatggt ttctacaaag atcgttatgt ttatcggcac tttgcatcgg    5580
ccgcgctccc gattccggaa gtgcttgaca ttggggaatt cagcgagagc ctgacctatt    5640
gcatctcccg ccgtgcacag ggtgtcacgt tgcaagacct gcctgaaacc gaactgcccg    5700
ctgttctgca gccggtcgcg gaggccatgg atgcgatcgc tgcggccgat cttagccaga    5760
cgagcgggtt cggcccattc ggaccgcaag gaatcggtca atacactaca tggcgtgatt    5820
tcatatgcgc gattgctgat ccccatgtgt atcactggca aactgtgatg gacgacaccg    5880
tcagtgcgtc cgtcgcgcag gctctcgatg agctgatgct ttgggccgag gactgccccg    5940
aagtccggca cctcgtgcac gcggatttcg gctccaacaa tgtcctgacg gacaatggcc    6000
gcataacagc ggtcattgac tggagcgagg cgatgttcgg ggattcccaa tacgaggtcg    6060
ccaacatctt cttctggagg ccgtggttgg cttgtatgga gcagcagacg cgctacttcg    6120
agcggaggca tccggagctt gcaggatcgc cgcggctccg gcgtatatg ctccgcattg    6180 gtcttgacca actctatcag agcttggttg acggcaattt cgatgatgca gcttgggcgc    6240
agggtcgatg cgacgcaatc gtccgatccg gagccgggac tgtcgggcgt acacaaatcg    6300
cccgcagaag cgcggccgtc tggaccgatg gctgtgtaga agtactcgcc gatagtggaa    6360
accgacgccc cagcactcgt ccgagggcaa aggaataggg gagatggggg aggctaactg    6420
aaacacggaa ggagacaata ccggaaggaa cccgcgctat gacggcaata aaaagacaga    6480
ataaaacgca cgggtgttgg gtcgtttgtt cataaacgcg gggttcggtc ccagggctgg    6540
```

-continued

```
cactctgtcg ataccccacc gagacccat tggggccaat acgcccgcgt ttcttccttt    6600
tccccacccc accccccaag ttcgggtgaa ggcccagggc tcgcagccaa cgtcggggcg    6660
gcaggccctg ccatagccac tggccccgtg ggtagggac ggggtccccc atggggaatg    6720
gtttatggtt cgtgggggtt attattttgg gcgttgcgtg gggtctggtc cacgactgga    6780
ctgagcagac agaccatgg tttttggatg gcctgggcat ggaccgcatg tactggcgcg    6840
acacgaacac cgggcgtctg tggctgccaa acaccccga cccccaaaaa ccaccgcgcg    6900
gatttctggc gcccagtggc acaggccggc ctgtacatga tcaacgcgtg agctctctag    6960
agcttgtcga cagatccccc tcttcatttc tttatgtttt aaatgcactg acctcccaca    7020 ttccctttt agtaaaatat tcagaaataa tttaaataca tcattgcaat gaaaataaat    7080
gttttttatt aggcagaatc cagatgctca aggcccttca taatatcccc cagtttagta    7140
gttggactta gggaacaaag gaacctttaa tagaaattgg acagcaagaa agcgaggggg    7200
atctggatcc tccggacccg tatctagaat catcgattca tttacccgga gacagggaga    7260
ggctcttctg cgtgtagtgg ttgtgcagag cctcatgcat cacggagcat gagaagacgt    7320
tcccctgctg ccacctgctc ttgtccacgg tgagcttgct gtagaggaag aaggagccgt    7380
cggagtccag cacgggaggc gtggtcttgt agttgttctc cggctgccca ttgctctccc    7440
actccacggc gatgtcgctg ggatagaagc ctttgaccag gcaggtcagg ctgacctggt    7500
tcttggtcag ctcatcccgg gatgggggca gggtgtacac ctgtggttct cggggctgcc    7560 cttttggcttt ggagatggtt ttctcgatgg gggctgggag ggctttgttg gagaccttgc    7620
acttgtactc cttgccattc agccagtcct ggtgcaggac ggtgaggacg ctgaccacac    7680
ggtacgtgct gttgtactgc tcctcccgcg gctttgtctt ggcattatgc acctccacgc    7740
cgtccacgta ccagttgaac ttgacctcag ggtcttcgtg gctcacgtcc accaccacgc    7800
atgtgaccct aggggtccgg gagatcatga gggtgtcctt gggttttggg gggaagagga    7860
agactgacgg tcccccagg agttcaggtg ctgggcacgg tgggcatgtg tgagttttgt    7920
cacaagattt gggctcaact ttcttgtcca ccttggtgtt gctgggcttg tgattcacgt    7980
tgcagatgta ggtctgggtg cccaagctgc tggagggcac ggtcaccacg ctgctgaggg    8040
agtagagtcc tgaggactgt aggacagccg ggaaggtgtg cacgccgctg gtcagggcgc    8100
ctgagttcca cgacaccgtc accggttcgg ggaagtagtc cttgaccagg cagcccaggg    8160
ccgctgtgcc cccagaggtg ctcttggagg agggtgccag ggggaagacc gatgggccct    8220
tggtgctagc cgacgagacg gtgaccaggg tgccttggcc ccagtaatca agccagacgc    8280
taaagcctcg atgtctcgca cagtaataca cagccgtgtc ctcagctctc aggctgttca    8340
tttgcagata cagcgtgttc ttggaattgt ctctggagat ggtgaagcgg ccgcgcacgg    8400
agtcgcgata gtaagtgtag gtagcatcaa gagtaatgct tgccacccac tccagcccct    8460
tgcctggagc ctggcggacc caggccatat gatagtcact gaaagtgaat ccagaggctg    8520
cacaggagag tctcagggac ctcccaggct ggaccacgcc tccccagac tccaccagct    8580 gcacctggga taggacacag cttgggaatg tcaccaggca gaagagcagc cccaagacag    8640
ccatgttaac tttctggtac caagcttaag tttaaacgct agccagcttg ggtctcccta    8700
tagtgagtcg tattaatttc gataagccag taagcagtgg gttctctagt tagccagaga    8760
gctctgctta tatagacctc ccaccgtaca cgcctaccgc ccatttgcgt caatggggcg    8820
gagttgttac gacattttgg aaagtcccgt tgatttggt gccaaaacaa actcccattg    8880
```

```
acgtcaatgg ggtggagact tggaaatccc cgtgagtcaa accgctatcc acgcccattg   8940
atgtactgcc aaaaccgcat caccatggta atagcgatga ctaatacgta gatgtactgc   9000
caagtaggaa agtcccataa ggtcatgtac tgggcataat gccaggcggg ccatttaccg   9060
tcattgacgt caataggggg cgtacttggc atatgataca cttgatgtac tgccaagtgg   9120
gcagtttacc gtaaatagtc cacccattga cgtcaatgga agtccctat ggcgttact    9180
atgggaacat acgtcattat tgacgtcaat gggcggggt cgttgggcgg tcagccaggc    9240
gggccattta ccgtaagtta tgtaacgcgg aactccatat atgggctatg aactaatgac   9300
cccgtaattg attactatta ataactagtc aataatcaat gtcaacgcgt atatctggcc   9360
cgtacatcgg tagctgaggg tttaaacggc gcgcggccgg ccggtaccac gcgttggcca   9420
catatggcgg ccgctcgcga ttaattaatc gcgatggcca catatggagc tctctagagc   9480
ttgtcgacag atcccctct tcatttcttt atgttttaaa tgcactgacc tcccacattc    9540
cctttttagt aaaatattca gaaataattt aaatacatca ttgcaatgaa ataaatgtt    9600
ttttattagg cagaatccag atgctcaagg cccttcataa tatcccccag tttagtagtt   9660
ggacttaggg aacaaaggaa cctttaatag aaattggaca gcaagaaagc gaggggggatc  9720
tggatcctcc ggagggccct ggatcctcct acgtatctag aatcatcgat taacactctc   9780
ccctgttgaa gctctttgtg acgggcgagc tcaggccctg atgggtgact cgcaggcgt    9840
agactttgtg tttctcgtag tctgctttgc tcagcgtcag ggtgctgctg aggctgtagg   9900
tgctgtcctt gctgtcctgc tctgtgacac tctcctggga gttacccgat tggagggcgt   9960
tatccacctt ccactgtact ttggcctctc tgggatagaa gttattcagc aggcacacaa  10020
cagaggcagt tccagatttc aactgctcat cagatggcgg gaagatgaag acagatggtg  10080
cagccaccgt acgtttcagt tccagcttgg tcccaggtcc aaacgtgtac ccgctataat  10140
actggtgaca gtagtaagtt gcaaaatctt caggttgcag actgctgatg gtgagagtga  10200
aatctgtccc agatccactg ccactgaacc ttgatgggac ccccgcttgc aaagggcttg  10260
cattatagat caggagctta ggggcttttcc ctggtttctg ctgataccag gccaagttct  10320
caaaaatgtt ctgacttgtc ttgcaagtga tggtgactct gtctcctaca gatgcagaca  10380
gggaggatgg agactgggtc atctggatgt cacatctcat ggctgggagg aagagccacca 10440
aaagccctaa aagttgaact ggagccatct cgagaattcc accacactgg actagtggat  10500
ccgagctcgg taccaagctt aagtttaaac gctagccagc ttgggtctcc ctatagtgag  10560
tcgtattaat ttcgataagc cagtaagcag tgggttctct agttagccag agagctctgc  10620
ttatatagac ctcccaccgt acacgcctac cgcccatttg cgtcaatggg gcggagttgt  10680
tacgacattt tggaaagtcc cgttgatttt ggtgccaaaa caaactccca ttgacgtcaa  10740
tggggtggag acttggaaat ccccgtgagt caaaccgcta ccacgcccca ttgatgtact  10800
gccaaaaccg catcaccatg gtaatagcga tgactaatac gtagatgtac tgccaagtag  10860
gaaagtccca aaggtcatg tactgggcat aatgccaggc gggccattta ccgtcattga   10920
cgtcaatagg gggcgtactt ggcatatgat acacttgatg tactgccaag tgggcagttt  10980
accgtaaata gtccacccat tgacgtcaat ggaaagtccc tattggcgtt actatgggaa  11040
catacgtcat tattgacgtc aatgggcggg gtcgttggg cggtcagcca ggcgggccat    11100
ttaccgtaag ttatgtaacg cggaactcca tatatgggct atgaactaat gaccccgtaa  11160
ttgattacta ttaataacta gtcaataatc aatgtcaacg cgtatatctg gcccgtacat  11220
cggtaactag tcggaccggc ccgggccacc ggtgctcgaa gcttggatcg atccagacat  11280
```

-continued

| gataagatac attgatgagt ttggacaaac cacaactaga atgcagtgaa aaaaatgctt | 11340 |
| tatttgtgaa atttgtgatg ctattgcttt atttgtaacc attataagct gcaataaaca | 11400 |
| agttaacaac aacaattgca ttcattttat gtttcaggtt caggggggagg tgtgggaggt | 11460 |
| ttttttaaagc aagtaaaacc tctacaaatg tggtatggct gattatgatc tctagtcaag | 11520 |

<210> SEQ ID NO 10
<211> LENGTH: 155
<212> TYPE: DNA
<213> ORGANISM: Artificial sequence
<220> FEATURE:
<223> OTHER INFORMATION: multiple cloning site

<400> SEQUENCE: 10

| aaatctagag gcgcgccgtt taaaccctca gctgatcatc cggatgtaca gcgcgcggcc | 60 |
| ggccggtacc acgcgttggc cacatatggc ggccgctcgc gattaattaa cggaccgccg | 120 |
| cggactagtg cccgggccac cggtgctcga gaaaa | 155 |

<210> SEQ ID NO 11
<211> LENGTH: 160
<212> TYPE: DNA
<213> ORGANISM: Artificial sequence
<220> FEATURE:
<223> OTHER INFORMATION: multiple cloning site

<400> SEQUENCE: 11

| ggggcgcgc cgtttaaacc ctcagctacg taaagcttgg taccctcgag gtcgacatcg | 60 |
| atgatatcga attcctgcag gggccccccg gtccggagg atccgcggcc gctctagaga | 120 |
| gctcacgcgt tgatcatgta caggccggcc agcgcgcccc | 160 |

<210> SEQ ID NO 12
<211> LENGTH: 166
<212> TYPE: DNA
<213> ORGANISM: Artificial sequence
<220> FEATURE:
<223> OTHER INFORMATION: multiple cloning site

<400> SEQUENCE: 12

| ggggcgcgc caccggtggc ccgggccggt ccgactagtt acgtaaagct tggtaccctc | 60 |
| gaggtcgaca tcgatgatat cgaattcctg caggggccct ccggaggatc cgcggccgct | 120 |
| ctagagagct ccatatgtgg ccatcgcgat taattaagcg cgcccc | 166 |

<210> SEQ ID NO 13
<211> LENGTH: 6078
<212> TYPE: DNA
<213> ORGANISM: Artificial sequence
<220> FEATURE:
<223> OTHER INFORMATION: pSRXBLS plasmid

<400> SEQUENCE: 13

| gcactataca tcaaatattc cttattaacc cctttacaaa ttaaaaagct aaaggtacac | 60 |
| aattttttgag catagttatt aatagcagac actctatgcc tgtgtggagt aagaaaaaac | 120 |
| agtatgttat gattataact gttatgccta cttataaagg ttacagaata ttttttccata | 180 |
| attttcttgt atagcagtgc agcttttttcc tttgtggtgt aaatagcaaa gcaagcaaga | 240 |
| gttctattac taaacacagc atgactcaaa aaacttagca attctgaagg aaagtccttg | 300 |
| gggtcttcta cctttctctt cttttttgga ggagtagaat gttgagagtc agcagtagcc | 360 |

-continued

| | |
|---|---|
| tcatcatcac tagatggcat ttcttctgag caaaacaggt tttcctcatt aaaggcattc | 420 |
| caccactgct cccattcatc agttccatag gttggaatct aaaatacaca aacaattaga | 480 |
| atcagtagtt taacacatta tacacttaaa aattttatat ttaccttaga gctttaaatc | 540 |
| tctgtaggta gtttgtccaa ttatgtcaca ccacagaagt aaggttcctt cacaaagatc | 600 |
| gatctaaagc cagcaaaagt cccatggtct tataaaaatg catagcttta ggaggggagc | 660 |
| agagaacttg aaagcatctt cctgttagtc tttcttctcg tagacttcaa acttatactt | 720 |
| gatgcctttt tcctcctgga cctcagagag gacgcctggg tattctggga gaagtttata | 780 |
| tttccccaaa tcaatttctg ggaaaaacgt gtcacttttca aattcctgca tgatccttgt | 840 |
| cacaaagagt ctgaggtggc ctggttgatt catggcttcc tggtaaacag aactgcctcc | 900 |
| gactatccaa accatgtcta ctttacttgc caattccggt tgttcaataa gtcttaaggc | 960 |
| atcatccaaa cttttggcaa gaaaatgagc tcctcgtggt ggttctttga gttctctact | 1020 |
| gagaactata ttaattctgt cctttaaagg tcgattcttc tcaggaatgg agaaccaggt | 1080 |
| tttcctaccc ataatcacca gattctgttt accttccact gaagaggttg tggtcattct | 1140 |
| ttggaagtac ttgaactcgt tcctgagcgg aggccagggg aggtctccgt tcttgccaat | 1200 |
| ccccatattt tgggacacgg cgacgatgca gttcaatggt cgaaccatga tggcagcggg | 1260 |
| gataaaatcc taccagcctt cacgctagga ttgccgtcaa gtttggcgcg aaatcgcagc | 1320 |
| cctgagctgt ccccccccccc aagctcagat ctgagcttgg tccctatggt gagtccgttc | 1380 |
| cgctcttgtg atgatagcca gacaagaaag agacaataca agacaaacac caaatagtag | 1440 |
| aaatagagac aagggtcact tatccgaggg tccctgttcg ggcgccagct gccgcagtcg | 1500 |
| gccgacctga gggtcgccgg ggtctgcggg gggaccctct ggaaagtgaa ggataagtga | 1560 |
| cgagcggaga cgggatggcg aacagacaca acacacaag aggtgaatgt taggactgtt | 1620 |
| gcaagtttac tcaaaaaatc agcactcttt tatatcttgg tttacataag catttacata | 1680 |
| agatttggat aaattccaaa agaacatagg aaaatagaac actcagagct cagatcagaa | 1740 |
| cctttgatac caaaccaagt caggaaaacca cttgtctcac atcctcgttt taagaacagt | 1800 |
| ttgtaaccaa aaacttactt aagccctggg aaccgcaagg ttgggccaat aaaggctatt | 1860 |
| cataataact catgccatga gttttttgcag aataatgttc tattagtcca gccactgtcc | 1920 |
| cctccttggt atggaaaatc tttccccaaa agtgcattcc tgttcctaga taaatataat | 1980 |
| catgtacctg ttgtttcatg tcgtcttttt cttcttgaga caacatacac caaggaggtc | 2040 |
| tagctctggc gagtctttca cgaaaaggga gggatctata taacactttta tagccattga | 2100 |
| ctgtaaccca cctatcccaa tttaagtcat atcttcctgt atatggtaag ggggcatctg | 2160 |
| ttggtctgta gatgtaaggt cccctataag tccctggttg ccaccacctg tctcctattt | 2220 |
| tgacaaaaac actctttttt ccctttttta cttctaggcc tgtggtcaat agtccttgca | 2280 |
| cctgttcttc aattgaggtt gagcgtctct ttctattttc tattcccatt tctaacttct | 2340 |
| gaatttgagt aaaaatagta ctaaagata atgattcatt tcttaacata gtaactaata | 2400 |
| atctacctat tggattggtc ttattggtaa aaatataatt tttagcaagc attcttattt | 2460 |
| ctatttctga aggacaaaat cgatgcggct tgtaagagga agttggctgt ggtccttgcc | 2520 |
| tcaggaggaa ggtcgagttc tccgaattgt ttagattgta atcttgcaca gaagagctat | 2580 |
| taaaagagtc aagggtgaga gccctgcgag cacgaaccgc aacttccccc aatagcccca | 2640 |
| ggcaaagcag agctatgcca gtttgcagc agagaatgaa tatgtctttg tctgatgggc | 2700 |
| tcatccgttt gtgcgcagac gggtcgtcct tggtgggaaa caacccccttg gctgcttctc | 2760 |

```
ccctaggtgt aggacactct cgggagttca accatttctg cccaagctca gatctgagct    2820
ttaatgcggt agtttatcac agttaaattg ctaacgcagt caggcaccgt gtatgaaatc    2880
taacaatgcg ctcatcgtca tcctcggcac cgtcaccctg gatgctgtag cataggctt    2940 ggttatgccg gtactgccgg gcctcttgcg ggatatcgtc cattccgaca gcatcgccag    3000
tcactatggc gtgctgctag cgtcttccg cttcctcgct cactgactcg ctgcgctcgg     3060
tcgttcggct gcggcgagcg gtatcagctc actcaaaggc ggtaatacgg ttatccacag    3120
aatcagggga taacgcagga aagaacatgt gagcaaaagg ccagcaaaag gccaggaacc    3180
gtaaaaaggc cgcgttgctg gcgttttcc ataggctccg ccccctgac gagcatcaca      3240 aaaatcgacg ctcaagtcag aggtggcgaa acccgacagg actataaaga taccaggcgt    3300 ttcccctgg aagctccctc gtgcgctctc ctgttccgac cctgccgctt accggatacc     3360
tgtccgcctt tctcccttcg ggaagcgtgg cgctttctca tagctcacgc tgtaggtatc    3420
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt tgtttgcaa gcagcagatt acgcgcagaa     3780 aaaaggatc tcaagaagat cctttgatct tttctacggg gtctgacgct cagtggaacg     3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag gaataaggg     4800 cgacacggaa atgttgaata ctcatactct tcctttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgcc gtttaaaccc tcagctgatc atccggatgt acagcgcgcg gccggccggt    5100
```

```
accacgcgtt ggccacatat ggcggccgct cgcgattaat taacggaccg ccgcggacta    5160
gtgcccgggc caccggtgct cgaggagctt ggatctgtaa cggcgcagaa cagaaaacga    5220
aacaaagacg tagagttgag caagcagggt caggcaaagc gtggagagcc ggctgagtct    5280
aggtaggctc caagggagcg ccggacaaag gcccggtctc gacctgagct ttaaacttac    5340
ctagacggcg gacgcagttc aggaggcacc acaggcggga ggcggcagaa cgcgactcaa    5400
ccggcgtgga tggcggcctc aggtagggcg gcgggcgcgt gaaggagaga tgcgagcccc    5460
tcgatcgagg agcttttgc aaaagcctag gcctccaaaa aagcctcctc actacttctg    5520
gaatagctca gaggccgagg cggcctcggc tctgcataa ataaaaaaaa ttagtcagcc    5580
atggggcgga gaatgggcgg aactgggcgg agttaggggc gggatgggcg gagttagggg    5640
cgggactatg gttgctgact aattgagatg catgctttgc atacttctgc ctgctgggga    5700
gcctggggac tttccacacc tggttgctga ctaattgaga tgcatgcttt gcatacttct    5760
gcctgctggg gagcctgggg actttccaca ccctaactga cacacattcc acagccaagc    5820
ttggatcgat ccagacatga taagatacat tgatgagttt ggacaaacca aactagaat    5880 gcagtgaaaa aaatgcttta tttgtgaaat ttgtgatgct attgctttat ttgtaaccat    5940
tataagctgc aataaacaag ttaacaacaa caattgcatt cattttatgt ttcaggttca    6000
gggggaggtg tgggaggttt tttaaagcaa gtaaaacctc tacaaatgtg gtatggctga    6060
ttatgatctc tagtcaag                                                  6078

<210> SEQ ID NO 14
<211> LENGTH: 6384
<212> TYPE: DNA
<213> ORGANISM: Artificial sequence
<220> FEATURE:
<223> OTHER INFORMATION: pDSRG plasmid

<400> SEQUENCE: 14
gcactataca tcaaatattc cttattaacc cctttacaaa ttaaaaagct aaaggtacac      60 aattttttgag catagttatt aatagcagac actctatgcc tgtgtggagt aagaaaaaac   120
agtatgttat gattataact gttatgccta cttataaagg ttacagaata ttttttccata   180 atttttcttgt atagcagtgc agcttttttcc tttgtggtgt aaatagcaaa gcaagcaaga   240
gttctattac taaacacagc atgactcaaa aaacttagca attctgaagg aaagtccttg    300
gggtcttcta cctttctctt cttttttgga ggagtagaat gttgagagtc agcagtagcc    360
tcatcatcac tagatggcat tcttctgag caaaacaggt tttcctcatt aaaggcattc     420
caccactgct cccattcatc agttccatag gttggaatct aaaatacaca aacaattaga    480
atcagtagtt taacacatta tacacttaaa aatttttatat ttaccttaga gctttaaatc   540
tctgtaggta gtttgtccaa ttatgtcaca ccacagaagt aaggttcctt cacaaagatc    600
gatctaaagc cagcaaaagt cccatggtct tataaaaatg catagctta ggaggggagc    660 agagaacttg aaagcatctt cctgttagtc ttttcttctcg tagacttcaa acttatactt     720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttcttga gttctctact   1020 gagaactata ttaattctgt cctttaaagg tcgattcttc tcaggaatgg agaaccaggt  1080
```

```
tttcctaccc ataatcacca gattctgttt accttccact gaagaggttg tggtcattct      1140
ttggaagtac ttgaactcgt tcctgagcgg aggccagggt aggtctccgt tcttgccaat      1200
ccccatattt tgggacacgg cgacgatgca gttcaatggt cgaaccatga tggcagcggg      1260
gataaaatcc taccagcctt cacgctagga ttgccgtcaa gtttggcgcg aaatcgcagc      1320
cctgagctgt ccccccccccc aagctcagat ctgagcttgg tccctatggt gagtccgttc      1380
cgctcttgtg atgatagcca gacaagaaag agacaataca agacaaacac caaatagtag      1440
aaatagagac aagggtcact tatccgaggg tccctgttcg ggcgccagct gccgcagtcg      1500
gccgacctga gggtcgccgg ggtctgcggg gggaccctct ggaaagtgaa ggataagtga      1560
cgagcggaga cgggatggcg aacagacaca aacacacaag aggtgaatgt taggactgtt      1620
gcaagtttac tcaaaaaatc agcactcttt tatatcttgg tttacataag catttacata      1680
agatttggat aaattccaaa agaacatagg aaaatagaac actcagagct cagatcagaa      1740
cctttgatac caaccaagt caggaaacca cttgtctcac atcctcgttt taagaacagt       1800
ttgtaaccaa aaacttactt aagccctggg aaccgcaagg ttgggccaat aaaggctatt      1860
cataataact catgccatga gttttttgcag aataatgttc tattagtcca gccactgtcc     1920
cctccttggt atggaaaatc tttccccaaa agtgcattcc tgttcctaga taaatataat     1980
catgtacctg ttgtttcatg tcgtcttttt cttcttgaga caacatacac caaggaggtc     2040
tagctctggc gagtctttca cgaaaaggga gggatctata taacactta tagccattga     2100 ctgtaaccca cctatcccaa tttaagtcat atcttcctgt atatggtaag ggggcatctg     2160
ttggtctgta gatgtaaggt cccctataag tccctggttg ccaccacctg tctcctattt     2220
tgacaaaaac actctttttt ccctttttta cttctaggcc tgtggtcaat agtccttgca    2280
cctgttcttc aattgaggtt gagcgtctct ttctattttc tattcccatt tctaacttct     2340
gaatttgagt aaaaatagta ctaaaagata atgattcatt tcttaacata gtaactaata     2400
atctacctat tggattggtc ttattggtaa aaatataatt tttagcaagc attcttattt      2460
ctatttctga aggacaaaat cgatgcggct tgtaagagga agttggctgt ggtccttgcc     2520
tcaggaggaa ggtcgagttc tccgaattgt ttagattgta atcttgcaca gaagagctat      2580
taaaagagtc aagggtgaga gccctgcgag cacgaaccgc aacttccccc aatagccccca   2640 ggcaaagcag agctatgcca agtttgcagc agagaatgaa tatgtctttg tctgatgggc     2700
tcatccgttt gtgcgcagac gggtcgtcct tggtgggaaa caaccccttg gctgcttctc     2760
ccctaggtgt aggacactct cgggagttca accatttctg cccaagctca gatctgagct     2820
ttaatgcggt agtttatcac agttaaattg ctaacgcagt caggcaccgt gtatgaaatc     2880
taacaatgcg ctcatcgtca tcctcggcac cgtcaccctg gatgctgtag gcataggctt     2940
ggttatgccg gtactgccgg gcctcttgcg ggatatcgtc cattccgaca gcatcgccag     3000
tcactatggc gtgctgctag cgctcttccg cttcctcgct cactgactcg ctgcgctcgg     3060
tcgttcggct gcggcgagcg gtatcagctc actcaaaggc ggtaatacgg ttatccacag     3120
aatcagggga taacgcagga agaacatgt gagcaaaagg ccagcaaaag gccaggaacc     3180
gtaaaaaggc cgcgttgctg gcgttttttcc ataggctccg ccccctgac gagcatcaca     3240 aaaatcgacg ctcaagtcag aggtggcgaa acccgacagg actataaaga taccaggcgt    3300
ttccccctgg aagctccctc gtgcgctctc ctgttccgac cctgccgctt accggatacc     3360
tgtccgcctt tctcccttcg ggaagcgtgg cgctttctca tagctcacgc tgtaggtatc     3420
```

```
tcagttcggt gtaggtcgtt cgctccaagc tgggctgtgt gcacgaaccc cccgttcagc    3480
ccgaccgctg cgccttatcc ggtaactatc gtcttgagtc caacccggta agacacgact    3540
tatcgccact ggcagcagcc actggtaaca ggattagcag agcgaggtat gtaggcggtg    3600
ctacagagtt cttgaagtgg tggcctaact acggctacac tagaaggaca gtatttggta    3660
tctgcgctct gctgaagcca gttaccttcg gaaaaagagt tggtagctct tgatccggca    3720
aacaaaccac cgctggtagc ggtggttttt ttgtttgcaa gcagcagatt acgcgcagaa    3780
aaaaaggatc tcaagaagat cctttgatct tttctacggg gtctgacgct cagtggaacg    3840
aaaactcacg ttaagggatt ttggtcatga gattatcaaa aaggatcttc acctagatcc    3900
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca acacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct ccttttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gagcttgtcg acagatcccc ctcttcattt ctttatgttt taaatgcact gacctcccac    5100
attccctttt tagtaaaata ttcagaaata atttaaatac atcattgcaa tgaaaataaa    5160 tgtttttttat taggcagaat ccagatgctc aaggcccttc ataatatccc ccagtttagt    5220
agttggactt agggaacaaa ggaacctttta atagaaattg gacagcaaga aagcgagggg    5280
gatctggatc cctcgaggaa ttcccgggga tccgtcgacc tgcagcagct tttagagcag    5340
aagtaacact tccgtacagg cctagaagta aaggcaacat ccactgagga gcagttcttt    5400
gatttgcacc accaccggat ccgggacctg aaataaaaga caaaaagact aaacttacca    5460
gttaactttc tggtttttca gttcctcgag gagcttggat ctgtaacggc gcagaacaga    5520
aaacgaaaca aagacgtaga gttgagcaag cagggtcagg caaagcgtgg agagccggct    5580
gagtctaggt aggctccaag ggagcgccgg acaaaggccc ggtctcgacc tgagctttaa    5640
acttacctag acggcggacg cagttcagga ggcaccacag gcgggaggcg gcagaacgcg    5700
actcaaccgg cgtggatggc ggcctcaggt agggcggcgg gcgcgtgaag gagagatgcg    5760
agcccctcga tcgaggagct ttttgcaaaa gcctaggcct ccaaaaaagc ctcctcacta    5820
```

```
cttctggaat agctcagagg ccgaggcggc ctcggcctct gcataaataa aaaaaattag    5880
tcagccatgg ggcggagaat gggcggaact gggcggagtt aggggcggga tgggcggagt    5940 tagggcggg  actatggttg ctgactaatt gagatgcatg cttttgcatac ttctgcctgc   6000 tggggagcct ggggactttc cacacctggt tgctgactaa ttgagatgca tgctttgcat    6060
acttctgcct gctggggagc ctggggactt tccacaccct aactgacaca cattccacag    6120
ccaagcttgg atcgatccag acatgataag atacattgat gagtttggac aaaccacaac    6180
tagaatgcag tgaaaaaaat gctttatttg tgaaatttgt gatgctattg ctttatttgt    6240
aaccattata agctgcaata acaagttaa  caacaacaat tgcattcatt ttatgtttca    6300
ggttcagggg gaggtgtggg aggtttttta aagcaagtaa aacctctaca aatgtggtat    6360
ggctgattat gatctctagt caag                                           6384
```

<210> SEQ ID NO 15
<211> LENGTH: 384
<212> TYPE: DNA
<213> ORGANISM: Homo sapiens
<220> FEATURE:
<221> NAME/KEY: CDS
<222> LOCATION: 1..384
<223> OTHER INFORMATION:
<220> FEATURE:
<221> NAME/KEY: sig_peptide
<222> LOCATION: 1..57
<223> OTHER INFORMATION:

<400> SEQUENCE: 15

```
atg tcg cca tca caa ctc att ggg ttt ctg ctg ctc tgg gtt cca gcc         48
Met Ser Pro Ser Gln Leu Ile Gly Phe Leu Leu Leu Trp Val Pro Ala
1               5                   10                  15 tcc agg ggt gaa att gtg ctg act cag gtt cca gac ttt cag tct gtg         96
Ser Arg Gly Glu Ile Val Leu Thr Gln Val Pro Asp Phe Gln Ser Val
            20                  25                  30 act cca aag gag aaa gtc acc atc acc tgc cgg gcc agt cag agc att        144
Thr Pro Lys Glu Lys Val Thr Ile Thr Cys Arg Ala Ser Gln Ser Ile
        35                  40                  45 ggt agt agc tta cac tgg tac cag cag aaa cca gat cag tct cca aag        192
Gly Ser Ser Leu His Trp Tyr Gln Gln Lys Pro Asp Gln Ser Pro Lys
    50                  55                  60 ctc ctc atc aag tat gct tcc cag tcc ctc tca ggg gtc ccc tcg agg        240
Leu Leu Ile Lys Tyr Ala Ser Gln Ser Leu Ser Gly Val Pro Ser Arg
65                  70                  75                  80 ttc agt ggc agt gga tct ggg aca gat ttc acc ctc acc atc aat agc        288
Phe Ser Gly Ser Gly Ser Gly Thr Asp Phe Thr Leu Thr Ile Asn Ser
                85                  90                  95 ctg gaa gct gaa gat gct gca gcg tat tac tgt cat cag agt agt cgt        336
Leu Glu Ala Glu Asp Ala Ala Ala Tyr Tyr Cys His Gln Ser Ser Arg
            100                 105                 110 tta cct cac act ttc ggc gga ggg acc aag gtg gag atc aaa cga act        384
Leu Pro His Thr Phe Gly Gly Gly Thr Lys Val Glu Ile Lys Arg Thr
        115                 120                 125
```

<210> SEQ ID NO 16
<211> LENGTH: 128
<212> TYPE: PRT
<213> ORGANISM: Homo sapiens

<400> SEQUENCE: 16

Met Ser Pro Ser Gln Leu Ile Gly Phe Leu Leu Leu Trp Val Pro Ala
1               5                   10                  15

```
Ser Arg Gly Glu Ile Val Leu Thr Gln Val Pro Asp Phe Gln Ser Val
         20                  25                  30

Thr Pro Lys Glu Lys Val Thr Ile Thr Cys Arg Ala Ser Gln Ser Ile
         35                  40                  45

Gly Ser Ser Leu His Trp Tyr Gln Gln Lys Pro Asp Gln Ser Pro Lys
         50                  55                  60

Leu Leu Ile Lys Tyr Ala Ser Gln Ser Leu Ser Gly Val Pro Ser Arg
 65                  70                  75                  80

Phe Ser Gly Ser Gly Ser Gly Thr Asp Phe Thr Leu Thr Ile Asn Ser
                 85                  90                  95

Leu Glu Ala Glu Asp Ala Ala Ala Tyr Tyr Cys His Gln Ser Ser Arg
             100                 105                 110

Leu Pro His Thr Phe Gly Gly Gly Thr Lys Val Glu Ile Lys Arg Thr
         115                 120                 125
```

<210> SEQ ID NO 17
<211> LENGTH: 411
<212> TYPE: DNA
<213> ORGANISM: Homo sapiens
<220> FEATURE:
<221> NAME/KEY: CDS
<222> LOCATION: 1..411
<223> OTHER INFORMATION:
<220> FEATURE:
<221> NAME/KEY: sig_peptide
<222> LOCATION: 1..57
<223> OTHER INFORMATION:

<400> SEQUENCE: 17

```
atg gag ttt ggg ctg agc tgg gtt ttc ctt gtt gct ata tta aaa ggt     48
Met Glu Phe Gly Leu Ser Trp Val Phe Leu Val Ala Ile Leu Lys Gly
 1               5                  10                  15 gtc cag tgt gag gtt cag ctg gtg cag tct ggg gga ggc ttg gta cat     96
Val Gln Cys Glu Val Gln Leu Val Gln Ser Gly Gly Gly Leu Val His
             20                  25                  30 cct ggg ggg tcc ctg aga ctc tcc tgt gca gcc tct gga ttc acc ttc    144
Pro Gly Gly Ser Leu Arg Leu Ser Cys Ala Ala Ser Gly Phe Thr Phe
         35                  40                  45 agt agc ttt gct atg cac tgg gtt cgc cag gct cca gga aaa ggt ctg    192
Ser Ser Phe Ala Met His Trp Val Arg Gln Ala Pro Gly Lys Gly Leu
     50                  55                  60 gag tgg ata tca gtt att gat act cgt ggt gcc aca tac tat gca gac    240
Glu Trp Ile Ser Val Ile Asp Thr Arg Gly Ala Thr Tyr Tyr Ala Asp
 65                  70                  75                  80 tcc gtg aag ggc cga ttc acc atc tcc aga gac aat gcc aag aac tcc    288
Ser Val Lys Gly Arg Phe Thr Ile Ser Arg Asp Asn Ala Lys Asn Ser
                 85                  90                  95 ttg tat ctt caa atg aac agc ctg aga gcc gag gac atg gct gtg tat    336
Leu Tyr Leu Gln Met Asn Ser Leu Arg Ala Glu Asp Met Ala Val Tyr
            100                 105                 110 tac tgt gca aga ctg ggg aac ttc tac tac ggt atg gac gtc tgg ggc    384
Tyr Cys Ala Arg Leu Gly Asn Phe Tyr Tyr Gly Met Asp Val Trp Gly
        115                 120                 125 caa ggg acc acg gtc acc gtc tcc tca                                411
Gln Gly Thr Thr Val Thr Val Ser Ser
        130                 135
```

<210> SEQ ID NO 18
<211> LENGTH: 137
<212> TYPE: PRT
<213> ORGANISM: Homo sapiens

<400> SEQUENCE: 18

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
                20                  25                  30

Pro Gly Gly Ser Leu Arg Leu Ser Cys Ala Ala Ser Gly Phe Thr Phe
            35                  40                  45

Ser Ser Phe Ala Met His Trp Val Arg Gln Ala Pro Gly Lys Gly Leu
50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 19
<211> LENGTH: 384
<212> TYPE: DNA
<213> ORGANISM: Homo sapiens
<220> FEATURE:
<221> NAME/KEY: CDS
<222> LOCATION: (1)..(384)
<223> OTHER INFORMATION:

<400> SEQUENCE: 19 atg tcg cca tca caa ctc att ggg ttt ctg ctg ctc tgg gtt cca gcc      48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg      96
Ser Arg Gly Glu Ile Val Leu Thr Gln Ser Pro Gly Thr Leu Ser Val
                20                  25                  30 tct cca ggc gag aga gcc acc ctc tcc tgc cgg gcc agt cag agc att     144
Ser Pro Gly Glu Arg Ala Thr Leu Ser Cys Arg Ala Ser Gln Ser Ile
            35                  40                  45 ggt agt agc tta cac tgg tac cag cag aaa cca ggt cag gct cca agg     192
Gly Ser Ser Leu His Trp Tyr Gln Gln Lys Pro Gly Gln Ala Pro Arg
50                  55                  60 ctt ctc atc aag tat gca tcc cag tcc ctc tca ggg atc ccc gat agg     240
Leu Leu Ile Lys Tyr Ala Ser Gln Ser Leu Ser Gly Ile Pro Asp Arg
65                  70                  75                  80 ttc agt ggc agt gga tct ggg aca gat ttc acc ctc acc atc agt aga     288
Phe Ser Gly Ser Gly Ser Gly Thr Asp Phe Thr Leu Thr Ile Ser Arg
                85                  90                  95 ctg gag cct gaa gat ttc gca gtg tat tac tgt cat cag agt agt cgt     336
Leu Glu Pro Glu Asp Phe Ala Val Tyr Tyr Cys His Gln Ser Ser Arg
            100                 105                 110 tta cct cac act ttc ggc caa ggg acc aag gtg gag atc aaa cgt aca     384
Leu Pro His Thr Phe Gly Gln Gly Thr Lys Val Glu Ile Lys Arg Thr
        115                 120                 125

<210> SEQ ID NO 20
<211> LENGTH: 128
<212> TYPE: PRT
<213> ORGANISM: Homo sapiens -continued

<400> SEQUENCE: 20

Met Ser Pro Ser Gln Leu Ile Gly Phe Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 21
<211> LENGTH: 411
<212> TYPE: DNA
<213> ORGANISM: Homo sapiens
<220> FEATURE:
<221> NAME/KEY: CDS
<222> LOCATION: (1)..(411)
<223> OTHER INFORMATION:

<400> SEQUENCE: 21 atg gag ttt ggg ctg agc tgg gtt ttc ctt gtt gct ata tta aaa ggt     48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta aag     96
Val Gln Cys Glu Val Gln Leu Val Gln Ser Gly Gly Gly Leu Val Lys
            20                  25                  30 cct ggg ggg tcc ctg aga ctc tcc tgt gca gcc tct gga ttc acc ttc    144
Pro Gly Gly Ser Leu Arg Leu Ser Cys Ala Ala Ser Gly Phe Thr Phe
        35                  40                  45 agt agc ttt gct atg cac tgg gtt cgc cag gct cca gga aaa ggt ctg    192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac    240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc    288
Ser Val Lys Gly Arg Phe Thr Ile Ser Arg Asp Asn Ala Lys Asn Ser
                85                  90                  95 ttg tat ctt caa atg aac agc ctg aga gcc gag gac act gct gtg tat    336
Leu Tyr Leu Gln Met Asn Ser Leu Arg Ala Glu Asp Thr Ala Val Tyr
            100                 105                 110 tac tgt gca aga ctg ggg aac ttc tac tac ggt atg gac gtc tgg ggc    384
Tyr Cys Ala Arg Leu Gly Asn Phe Tyr Tyr Gly Met Asp Val Trp Gly
        115                 120                 125 caa ggg acc acg gtc acc gtc tcc tca                                411
Gln Gly Thr Thr Val Thr Val Ser Ser
    130                 135

<210> SEQ ID NO 22
<211> LENGTH: 137
<212> TYPE: PRT

<213> ORGANISM: Homo sapiens

<400> SEQUENCE: 22

```
Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135
```

<210> SEQ ID NO 23
<211> LENGTH: 2960
<212> TYPE: DNA
<213> ORGANISM: Artificial Sequence
<220> FEATURE:
<223> OTHER INFORMATION: Nucleotide sequence of chicken lysozyme MAR element

<400> SEQUENCE: 23

| | | |
|---|---|---|
| gatccgtaat acaattgtac caggttttgg tttattacat gtgactgacg gcttcctgtg | 60 |
| cgtgctcagg aaacggcagt tgggcactgc actgcccggt gatggtgcca cggtggctcc | 120 |
| tgccgccttc tttgatattc actctgttgt atttcatctc ttcttgccga tgaaaggata | 180 |
| taacagtctg tgaggaaata cttggtattt cttctgatca gcgtttttat aagtaatgtt | 240 |
| gaatattgga taaggctgtg tgtcctttgt cttgggagac aaagcccaca gcaggtggtg | 300 |
| gttgggg tgg tggcagctca gtgacaggag aggtttttt gcctgttttt tttgttgttt | 360 |
| ttttttttta agtaaggtgt tcttttttct tagtaaaatt tctactggac tgtatgtttt | 420 |
| gacaggtcag aaacatttct tcaaaagaag aaccttttgg aaactgtaca gcccttttct | 480 |
| ttcattccct ttttgctttc tgtgccaatg cctttggttc tgatttgcat tatgcaaaac | 540 |
| gttgatcgga acttgaggtt tttatttata gtgtggcttg aaagcttgga tagctgttgt | 600 |
| tacatgagat accttattaa gtttaggcca gcttgatgct ttattttttt ccctttgaag | 660 |
| tagtgagcgt tctctggttt ttttcctttg aaactggcga ggcttagatt tttctaatgg | 720 |
| gatttttttac ctgatgatct agttgcatac ccaaatgctt gtaaatgttt tcctagttaa | 780 |
| catgttgata acttcggatt tacatgttgt atatacttgt catctgtgtt tctagtaaaa | 840 |
| atatatggca tttatagaaa tacgtaattc ctgatttcct tttttttttta tctctatgct | 900 |
| ctgtgtgtac aggtcaaaca gacttcactc ctatttttat ttatagaatt ttatatgcag | 960 |
| tctgtcgttg gttcttgtgt tgtaaggata cagccttaaa tttcctagag cgatgctcag | 1020 |
| taaggcgggt tgtcacatgg gttcaaatgt aaaacgggca cgtttggctg ctgccttccc | 1080 |
| gagatccagg acactaaact gcttctgcac tgaggtataa atcgcttcag atcccaggga | 1140 |

```
agtgtagatc cacgtgcata ttcttaaaga agaatgaata ctttctaaaa tattttggca    1200
taggaagcaa gctgcatgga tttgtttggg acttaaatta ttttggtaac ggagtgcata    1260
ggttttaaac acagttgcag catgctaacg agtcacagca tttatgcaga agtgatgcct    1320
gttgcagctg tttacggcac tgccttgcag tgagcgattt gcagataggg gtgggtgct    1380 ttgtgtcgtg ttcccacacg ctgccacaca gccacctccc ggaacacatc tcacctgctg    1440 ggtactttc aaaccatctt agcagtagta gatgagttac tatgaaacag agaagttcct    1500
cagttggata ttctcatggg atgtcttttt tcccatgttg ggcaaagtat gataaagcat    1560
ctctatttgt aaattatgca cttgttagtt cctgaatcct ttctatagca ccacttattg    1620
cagcaggtgt aggctctggt gtggcctgtg tctgtgcttc aatcttttaa gcttctttgg    1680
aaatacactg acttgattga agtctcttga agatagtaaa cagtacttac ctttgatccc    1740
aatgaaatcg agcatttcag ttgtaaaaga attccgccta ttcataccat gtaatgtaat    1800
tttacacccc cagtgctgac actttggaat atattcaagt aatagacttt ggcctcaccc    1860
tcttgtgtac tgtattttgt aatagaaaat attttaaact gtgcatatga ttattacatt    1920
atgaaagaga cattctgctg atcttcaaat gtaagaaaat gaggagtgcg tgtgcttta    1980 taaatacaag tgattgcaaa ttagtgcagg tgtccttaaa aaaaaaaaaa agtaatataa    2040
aaaggaccag gtgttttaca agtgaaatac attcctattt ggtaaacagt tacatttta    2100 tgaagattac cagcgctgct gactttctaa acataaggct gtattgtctt cctgtaccat    2160
tgcatttcct cattcccaat ttgcacaagg atgtctgggt aaactattca agaaatggct    2220
ttgaaataca gcatgggagc ttgtctgagt tggaatgcag agttgcactg caaaatgtca    2280
ggaaatggat gtctctcaga atgcccaact ccaaaggatt ttatatgtgt atatagtaag    2340
cagtttcctg attccagcag gccaaagagt ctgctgaatg ttgcgttgcc ggagacctgt    2400
atttctcaac aaggtaagat ggtatcctag caactgcgga ttttaataca ttttcagcag    2460
aagtacttag ttaatctcta cctttaggga tcgtttcatc attttagat gttatacttg    2520 aaatactgca taacttttag ctttcatggg ttccttttt tcagccttta ggagactgtt    2580
aagcaatttg ctgtccaact tttgtgttgg tcttaaactg caatagtagt ttaccttgta    2640
ttgaagaaat aaagaccatt tttatattaa aaaatacttt tgtctgtctt catttgact    2700 tgtctgatat ccttgcagtg ctcattatgt cagttctgtc agatattcag acatcaaaac    2760
ttaacgtgag ctcagtggag ttacagctgc ggttttgatg ctgttattat ttctgaaact    2820
agaaatgatg ttgtcttcat ctgctcatca aacacttcat gcagagttta aggctagtga    2880
gaaatgcata catttattga tactttttta aagtcaactt tttatcagat ttttttttca    2940
tttggaaata tattgttttc                                                2960
```

<210> SEQ ID NO 24
<211> LENGTH: 14910
<212> TYPE: DNA
<213> ORGANISM: Artificial Sequence
<220> FEATURE:
<223> OTHER INFORMATION: Nucleotide sequence of pinAIL10/MAR(-)

<400> SEQUENCE: 24

```
gcactataca tcaaatattc cttattaacc cctttacaaa ttaaaaagct aaaggtacac     60 aattttgag catagttatt aatagcagac actctatgcc tgtgtggagt aagaaaaaac    120
agtatgttat gattataact gttatgccta cttataaagg ttacagaata ttttccata    180
```

-continued

| | | | | |
|---|---|---|---|---|
| attttcttgt | atagcagtgc | agcttttcc | tttgtggtgt | aaatagcaaa gcaagcaaga | 240 |
| gttctattac | taaacacagc | atgactcaaa | aacttagca | attctgaagg aaagtccttg | 300 |
| gggtcttcta | cctttctctt | cttttttgga | ggagtagaat | gttgagagtc agcagtagcc | 360 |
| tcatcatcac | tagatggcat | ttcttctgag | caaaacaggt | tttcctcatt aaaggcattc | 420 |
| caccactgct | cccattcatc | agttccatag | gttggaatct | aaaatacaca acaattaga | 480 |
| atcagtagtt | taacacatta | tacacttaaa | aattttatat | ttaccttaga gctttaaatc | 540 |
| tctgtaggta | gtttgtccaa | ttatgtcaca | ccacagaagt | aaggttcctt cacaaagatc | 600 |
| gatctaaagc | cagcaaaagt | cccatggtct | tataaaaatg | catagcttta ggaggggagc | 660 |
| agagaacttg | aaagcatctt | cctgttagtc | tttcttctcg | tagacttcaa acttatactt | 720 |
| gatgcctttt | tcctcctgga | cctcagagag | gacgcctggg | tattctggga gaagtttata | 780 |
| tttccccaaa | tcaatttctg | ggaaaaacgt | gtcactttca | aattcctgca tgatccttgt | 840 |
| cacaaagagt | ctgaggtggc | ctggttgatt | catggcttcc | tggtaaacag aactgcctcc | 900 |
| gactatccaa | accatgtcta | ctttacttgc | caattccggt | tgttcaataa gtcttaaggc | 960 |
| atcatccaaa | cttttggcaa | gaaaatgagc | tcctcgtggt | ggttctttga gttctctact | 1020 |
| gagaactata | ttaattctgt | cctttaaagg | tcgattcttc | tcaggaatgg agaaccaggt | 1080 |
| tttcctaccc | ataatcacca | gattctgttt | accttccact | gaagaggttg tggtcattct | 1140 |
| ttggaagtac | ttgaactcgt | tcctgagcgg | aggccagggt | aggtctccgt tcttgccaat | 1200 |
| ccccatattt | tgggacacgg | cgacgatgca | gttcaatggt | cgaaccatga tggcagcggg | 1260 |
| gataaaatcc | taccagcctt | cacgctagga | ttgccgtcaa | gtttggcgcg aaatcgcagc | 1320 |
| cctgagctgt | ccccccccc | aagctcagat | ctgagcttgg | tccctatggt gagtccgttc | 1380 |
| cgctcttgtg | atgatagcca | gacaagaaag | agacaataca | agacaaacac caaatagtag | 1440 |
| aaatagagac | aagggtcact | tatccgaggg | tccctgttcg | ggcgccagct gccgcagtcg | 1500 |
| gccgacctga | gggtcgccgg | ggtctgcggg | gggaccctct | ggaaagtgaa ggataagtga | 1560 |
| cgagcggaga | cgggatggcg | aacagacaca | aacacacaag | aggtgaatgt taggactgtt | 1620 |
| gcaagtttac | tcaaaaaatc | agcactcttt | tatatcttgg | tttacataag catttacata | 1680 |
| agatttggat | aaaattccaaa | agaacatagg | aaaatagaac | actcagagct cagatcagaa | 1740 |
| cctttgatac | caaaccaagt | caggaaacca | cttgtctcac | atcctcgttt taagaacagt | 1800 |
| ttgtaaccaa | aaacttactt | aagccctggg | aaccgcaagg | ttgggccaat aaaggctatt | 1860 |
| cataataact | catgccatga | gttttttgcag | aataatgttc | tattagtcca gccactgtcc | 1920 |
| cctccttggt | atggaaaatc | tttccccaaa | agtgcattcc | tgttcctaga taaatataat | 1980 |
| catgtacctg | ttgtttcatg | tcgtcttttt | cttcttgaga | caacatacac caaggaggtc | 2040 |
| tagctctggc | gagtctttca | cgaaaaggga | gggatctata | taacacttta tagccattga | 2100 |
| ctgtaaccca | cctatcccaa | tttaagtcat | atcttcctgt | atatggtaag ggggcatctg | 2160 |
| ttggtctgta | gatgtaaggt | cccctataag | tccctggttg | ccaccacctg tctcctattt | 2220 |
| tgacaaaaac | actctttttt | ccctttttta | cttctaggcc | tgtggtcaat agtccttgca | 2280 |
| cctgttcttc | aattgaggtt | gagcgtctct | ttctattttc | tattcccatt tctaacttct | 2340 |
| gaatttgagt | aaaatagta | ctaaaagata | atgattcatt | tcttaacata gtaactaata | 2400 |
| atctacctat | tggattggtc | ttattggtaa | aaatataatt | tttagcaagc attcttattt | 2460 |
| ctatttctga | aggacaaaat | cgatgcggct | tgtaagagga | agttggctgt ggtccttgcc | 2520 |
| tcaggaggaa | ggtcgagttc | tccgaattgt | ttagattgta | atcttgcaca gaagagctat | 2580 |

| | |
|---|---|
| taaaagagtc aagggtgaga gccctgcgag cacgaaccgc aacttccccc aatagcccca | 2640 |
| ggcaaagcag agctatgcca agtttgcagc agagaatgaa tatgtctttg tctgatgggc | 2700 |
| tcatccgttt gtgcgcagac gggtcgtcct tggtgggaaa caaccccttg gctgcttctc | 2760 |
| ccctaggtgt aggacactct cgggagttca accatttctg cccaagctca gatctgagct | 2820 |
| ttaatgcggt agtttatcac agttaaattg ctaacgcagt caggcaccgt gtatgaaatc | 2880 |
| taacaatgcg ctcatcgtca tcctcggcac cgtcaccctg gatgctgtag gcataggctt | 2940 |
| ggttatgccg gtactgccgg gcctcttgcg ggatatcgtc cattccgaca gcatcgccag | 3000 |
| tcactatggc gtgctgctag cgctcttccg cttcctcgct cactgactcg ctgcgctcgg | 3060 |
| tcgttcggct gcggcgagcg gtatcagctc actcaaaggc ggtaatacgg ttatccacag | 3120 |
| aatcagggga taacgcagga agaacatgt gagcaaaagg ccagcaaaag gccaggaacc | 3180 |
| gtaaaaaggc cgcgttgctg gcgtttttcc ataggctccg ccccctgac gagcatcaca | 3240 |
| aaaatcgacg ctcaagtcag aggtggcgaa acccgacagg actataaaga taccaggcgt | 3300 |
| ttccccctgg aagctccctc gtgcgctctc ctgttccgac cctgccgctt accggatacc | 3360 |
| tgtccgcctt tctcccttcg ggaagcgtgg cgctttctca tagctcacgc tgtaggtatc | 3420 |
| tcagttcggt gtaggtcgtt cgctccaagc tgggctgtgt gcacgaaccc cccgttcagc | 3480 |
| ccgaccgctg cgccttatcc ggtaactatc gtcttgagtc caacccggta agacacgact | 3540 |
| tatcgccact ggcagcagcc actggtaaca ggattagcag agcgaggtat gtaggcggtg | 3600 |
| ctacagagtt cttgaagtgg tggcctaact acggctacac tagaaggaca gtatttggta | 3660 |
| tctgcgctct gctgaagcca gttaccttcg aaaaagagt tggtagctct tgatccggca | 3720 |
| aacaaaccac cgctggtagc ggtggttttt tgtttgcaa gcagcagatt acgcgcagaa | 3780 |
| aaaaaggatc tcaagaagat cctttgatct tttctacggg gtctgacgct cagtggaacg | 3840 |
| aaaactcacg ttaagggatt ttggtcatga gattatcaaa aaggatcttc acctagatcc | 3900 |
| ttttaaatta aaaatgaagt tttaaatcaa tctaaagtat atatgagtaa acttggtctg | 3960 |
| acagttacca atgcttaatc agtgaggcac ctatctcagc gatctgtcta tttcgttcat | 4020 |
| ccatagttgc ctgactcccc gtcgtgtaga taactacgat acgggagggc ttaccatctg | 4080 |
| gccccagtgc tgcaatgata ccgcgagacc cacgctcacc ggctccagat ttatcagcaa | 4140 |
| taaaccagcc agccggaagg gccgagcgca gaagtggtcc tgcaacttta tccgcctcca | 4200 |
| tccagtctat taattgttgc cgggaagcta gagtaagtag ttcgccagtt aatagtttgc | 4260 |
| gcaacgttgt tgccattgct acaggcatcg tggtgtcacg ctcgtcgttt ggtatggctt | 4320 |
| cattcagctc cggttcccaa cgatcaaggc gagttacatg atcccccatg ttgtgcaaaa | 4380 |
| aagcggttag ctccttcggt cctccgatcg ttgtcagaag taagttggcc gcagtgttat | 4440 |
| cactcatggt tatggcagca ctgcataatt ctcttactgt catgccatcc gtaagatgct | 4500 |
| tttctgtgac tggtgagtac tcaaccaagt cattctgaga atagtgtatg cggcgaccga | 4560 |
| gttgctcttg cccggcgtca cacgggata ataccgcgcc acatagcaga actttaaaag | 4620 |
| tgctcatcat tggaaaacgt tcttcgggc gaaaactctc aaggatctta ccgctgttga | 4680 |
| gatccagttc gatgtaaccc actcgtgcac ccaactgatc ttcagcatct tttactttca | 4740 |
| ccagcgtttc tgggtgagca aaaacaggaa ggcaaaatgc cgcaaaaaag ggaataaggg | 4800 |
| cgacacggaa atgttgaata ctcatactct ccttttca atattattga agcatttatc | 4860 |
| agggttattg tctcatgagc ggatacatat ttgaatgtat ttagaaaaat aaacaaatag | 4920 |

```
gggttccgcg cacatttccc cgaaaagtgc cacctgacgt ctaagagacc attattatca    4980
tgacattaac ctataaaaat aggcgtatca cgaggcccct tcgtcttcaa gaattgtcta    5040
gaggcgcgct taattaatcg cgatggccac atatggagct ctctagaaaa caatatattt    5100
ccaaatgaaa aaaaaatctg ataaaaagtt gactttaaaa aagtatcaat aaatgtatgc    5160
atttctcact agccttaaac tctgcatgaa gtgtttgatg agcagatgaa gacaacatca    5220
tttctagttt cagaaataat aacagcatca aaaccgcagc tgtaactcca ctgagctcac    5280
gttaagtttt gatgtctgaa tatctgacag aactgacata atgagcactg caaggatatc    5340
agacaagtca aaatgaagac agacaaaagt atttttttaat ataaaaatgg tctttatttc    5400
ttcaatacaa ggtaaactac tattgcagtt taagaccaac acaaaagttg gacagcaaat    5460
tgcttaacag tctcctaaag gctgaaaaaa aggaacccat gaaagctaaa agttatgcag    5520
tatttcaagt ataacatcta aaaatgatga aacgatccct aaaggtagag attaactaag    5580
tacttctgct gaaaatgtat taaaatccgc agttgctagg ataccatctt accttgttga    5640
gaaatacagg tctccggcaa cgcaacattc agcagactct ttggcctgct ggaatcagga    5700
aactgcttac tatatacaca tataaaatcc tttggagttg ggcattctga gagacatcca    5760
tttcctgaca ttttgcagtg caactctgca ttccaactca gacaagctcc catgctgtat    5820
ttcaaagcca tttcttgaat agtttaccca gacatccttg tgcaaattgg gaatgaggaa    5880
atgcaatggt acaggaagac aatacagcct tatgtttaga aagtcagcag cgctggtaat    5940
cttcataaaa atgtaactgt ttaccaaata ggaatgtatt tcacttgtaa acacctggt    6000 ccttttttata ttactttttt ttttttttaa ggacacctgc actaatttgc aatcacttgt    6060
atttataaaa gcacacgcac tcctcatttt cttacatttg aagatcagca gaatgtctct    6120
ttcataatgt aataatcata tgcacagttt aaaatatttt ctattacaaa atacagtaca    6180
caagagggtg aggccaaagt ctattacttg aatatattcc aaagtgtcag cactgggggt    6240
gtaaaattac attacatggt atgaataggc ggaattcttt tacaactgaa atgctcgatt    6300
tcattgggat caaaggtaag tactgtttac tatcttcaag agacttcaat caagtcagtg    6360
tatttccaaa gaagcttaaa agattgaagc acagacacag gccacaccag agcctacacc    6420
tgctgcaata agtggtgcta tagaaaggat tcaggaacta acaagtgcat aatttacaaa    6480
tagagatgct ttatcatact ttgcccaaca tgggaaaaaa gacatcccat gagaatatcc    6540
aactgaggaa cttctctgtt tcatagtaac tcatctacta ctgctaagat ggtttgaaaa    6600
gtacccagca ggtgagatgt gttccgggag gtggctgtgt ggcagcgtgt gggaacacga    6660
cacaaagcac cccaccccta tctgcaaatc gctcactgca aggcagtgcc gtaaacagct    6720
gcaacaggca tcacttctgc ataaatgctg tgactcgtta gcatgctgca actgtgttta    6780
aaacctatgc actccgttac caaataatt taagtcccaa acaaatccat gcagcttgct    6840
tcctatgcca aaatatttta gaaagtattc attcttcttt aagaatatgc acgtggatct    6900
acacttccct gggatctgaa gcgatttata cctcagtgca gaagcagttt agtgtcctgg    6960
atctcgggaa ggcagcagcc aaacgtgccc gttttacatt tgaacccatg tgacaacccg    7020
ccttactgag catcgctcta ggaaatttaa ggctgtatcc ttacaacaca agaaccaacg    7080
acagactgca tataaaattc tataaataaa ataggagtg aagtctgttt gacctgtaca    7140
cacagagcat agagataaaa aaaaaaggaa atcaggaatt acgtatttct ataaatgcca    7200
tatattttta ctagaaacac agatgacaag tatatacaac atgtaaatcc gaagttatca    7260
acatgttaac taggaaaaca tttacaagca tttgggtatg caactagatc atcaggtaaa    7320
```

```
aaatcccatt agaaaaatct aagcctcgcc agtttcaaag gaaaaaaacc agagaacgct     7380
cactacttca aagggaaaaa aataaagcat caagctggcc taaacttaat aaggtatctc     7440
atgtaacaac agctatccaa gctttcaagc cacactataa ataaaaacct caagttccga     7500
tcaacgtttt ccataatgca aatcagaacc aaaggcattg gcacagaaag caaaagggga     7560
atgaaagaaa agggctgtac agtttccaaa aggttcttct tttgaagaaa tgtttctgac     7620
ctgtcaaaac atacagtcca gtagaaattt tactaagaaa aagaacacc  ttacttaaaa     7680 aaaaaaaaca acaaaaaaaa caggcaaaaa aacctctcct gtcactgagc tgccaccacc     7740
ccaaccacca cctgctgtgg gctttgtctc ccaagacaaa ggacacacag ccttatccaa     7800
tattcaacat tacttataaa aacgctgatc agaagaaata ccaagtattt cctcacagac     7860
tgttatatcc tttcatcggc aagaagagat gaaatacaac agagtgaata tcaaagaagg     7920
cggcaggagc caccgtggca ccatcaccgg gcagtgcagt gcccaactgc cgtttcctga     7980
gcacgcacag gaagccgtca gtcacatgta ataaccaaa  acctggtaca attgtattac     8040
ggatcccggt ggcgcgccgt ttaaaccctc agctaccgat gtacgggcca gatatacgcg     8100
ttgacattga ttattgacta gttattaata gtaatcaatt acgggtcat  tagttcatag     8160 cccatatatg gagttccgcg ttacataact tacggtaaat ggcccgcctg gctgaccgcc     8220
caacgacccc cgcccattga cgtcaataat gacgtatgtt cccatagtaa cgccaatagg     8280
gactttccat tgacgtcaat gggtggacta tttacggtaa actgcccact tggcagtaca     8340
tcaagtgtat catatgccaa gtacgccccc tattgacgtc aatgacgtta atgggcccgc     8400
ctggcattat gcccagtaca tgaccttatg gactttcct  acttggcagt acatctacgt     8460
attagtcatc gctattacca tggtgatgcg gttttggcag tacatcaatg ggcgtggata     8520
gcggtttgac tcacggggat ttccaagtct ccaccccatt gacgtcaatg ggagtttgtt     8580
ttggcaccaa aatcaacggg actttccaaa atgtcgtaac aactccgccc cattgacgca     8640
aatgggcggt aggcgtgtac ggtgggaggt ctatataagc agagctctct ggctaactag     8700
agaacccact gcttactggc ttatcgaaat taatacgact cactatagca attgcacgtg     8760
tggccacagg taagttaaa  gctcaggtcg agaccgggcc tttgtccggc gctcccttgg     8820
agcctaccta gactcagccg gctctccacg ctttgcctga ccctgcttgc tcaactctac     8880
gtctttgttt cgttttctgt tcctttctct ccacaggctt aagcttggta ccagaaagtt     8940
aacatggctg tcttggggct gctcttctgc ctggtgacat tcccaagctg tgtcctatcc     9000
caggtgcagc tggtggagtc tgggggaggc gtggtccagc ctgggaggtc cctgagactc     9060
tcctgtgcag cctctggatt cacttttcagt gactatcata tggcctgggt ccgccaggct     9120
ccaggcaagg ggctggagtg ggtggcaagc attactcttg atgctaccta cacttactat     9180
cgcgactccg tgcgcggccg cttccaccatc tccagagaca attccaagaa cacgctgtat     9240
ctgcaaatga acagcctgag agctgaggac acggctgtgt attactgtgc gagacatcga     9300
ggctttagcg tctggcttga ttactggggc caaggcaccc tggtcaccgt ctcgtcggct     9360
agcaccaagg gcccatcggt cttccccctg gcaccctcct ccaagagcac ctctgggggc     9420
acagcggccc tgggctgcct ggtcaaggac tacttccccg aaccggtgac ggtgtcgtgg     9480
aactcaggcg ccctgaccag cggcgtgcac accttcccgg ctgtcctaca gtcctcagga     9540
ctctactccc tcagcagcgt ggtgaccgtg ccctccagca gcttgggcac ccagacctac     9600
atctgcaacg tgaatcacaa gcccagcaac accaaggtgg acaagaaagt tgagcccaaa     9660
```

-continued

```
tcttgtgaca aaactcacac atgcccaccg tgcccagcac ctgaactcct gggggaccg      9720
tcagtcttcc tcttccccc aaacccaag  gacaccctca tgatctcccg gaccctgag       9780
gtcacatgcg tggtggtgga cgtgagccac gaagaccctg aggtcaagtt caactggtac     9840
gtggacggcg tggaggtgca taatgccaag acaaagccgc gggaggagca gtacaacagc     9900
acgtaccgtg tggtcagcgt cctcaccgtc ctgcaccagg actggctgaa tggcaaggag     9960
tacaagtgca aggtctccaa caaagccctc ccagccccca tcgagaaaac catctccaaa   10020
gccaagggc  agccccgaga accacaggtg tacaccctgc ccccatcccg ggatgagctg   10080
accaagaacc aggtcagcct gacctgcctg gtcaaaggct tctatcccag cgacatcgcc   10140
gtggagtggg agagcaatgg gcagccggag aacaactaca agaccacgcc tcccgtgctg   10200
gactccgacg gctccttctt cctctacagc aagctcaccg tggacaagag caggtggcag   10260
caggggaacg tcttctcatg ctccgtgatg catgaggctc tgcacaacca ctacacgcag   10320
aagagcctct ccctgtctcc gggtaaatga atcgatgatt ctagatacgg gtccggagga   10380
tccagatccc cctcgctttc ttgctgtcca atttctatta aggttccttt gttccctaa    10440
gtccaactac taaactgggg gatattatga agggccttga gcatctggat tctgcctaat   10500
aaaaaacatt tattttcatt gcaatgatgt atttaaatta tttctgaata ttttactaaa   10560
aagggaatgt gggaggtcag tgcatttaaa acataaagaa atgaagaggg ggatctgtcg   10620
acaagctcta gagagctcac gcgttgatca tgtacaggcc ggccaagctt tcgactagct   10680
tggcacgcca gaaatccgcg cggtggtttt tgggggtcgg gggtgtttgg cagccacaga   10740
cgcccggtgt tcgtgtcgcg ccagtacatg cggtccatgc ccaggccatc caaaaaccat   10800
gggtctgtct gctcagtcca gtcgtggacc tgaccccacg caacgcccaa ataataacc    10860
cccacgaacc ataaaccatt ccccatgggg gaccccgtcc ctaacccacg gggccagtgg   10920
ctatggcagg gcctgccgcc ccgacgttgg ctgcgagccc tgggccttca cccgaacttg   10980
gggggtgggg tggggaaaag gaagaaacgc gggcgtattg gccccaatgg ggtctcggtg   11040
gggtatcgac agagtgccag ccctgggacc gaaccccgcg tttatgaaca acgaccccaa   11100
cacccgtgcg tttattctg  tcttttatt  gccgtcatag cgcgggttcc ttccggtatt   11160
gtctccttcc gtgtttcagt tagcctcccc catctcccga tccggacgag tgctggggcg   11220
tcggtttcca ctatcggcga gtacttctac acagccatcg gtccagacgg ccgcgcttct   11280
gcgggcgatt tgtgtacgcc cgacagtccc ggctccggat cggacgattg cgtcgcatcg   11340
accctgcgcc caagctgcat catcgaaatt gccgtcaacc aagctctgat agagttggtc   11400
aagaccaatg cggagcatat acgcccggag ccgcggcgat cctgcaagct ccggatgcct   11460
ccgctcgaag tagcgcgtct gctgctccat acaagccaac cacggcctcc agaagaagat   11520
gttggcgacc tcgtattggg aatccccgaa catcgcctcg ctccagtcaa tgaccgctgt   11580
tatgcggcca ttgtccgtca ggacattgtt ggagccgaaa tccgcgtgca cgaggtgccg   11640
gacttcgggg cagtcctcgg cccaaagcat cagctcatcg agagcctgcg cgacggacgc   11700
actgacggtg tcgtccatca cagtttgcca gtgatacaca tggggatcag caatcgcgca   11760
tatgaaatca cgccatgtag tgtattgacc gattccttgc ggtccgaatg ggccgaaccc   11820
gctcgtctgg ctaagatcgg ccgcagcgat cgcatccatg gcctccgcga ccggctgcag   11880
aacagcgggc agttcggttt caggcaggtc ttgcaacgtg acaccctgtg cacggcggga   11940
gatgcaatag gtcaggctct cgctgaattc cccaatgtca agcacttccg gaatcgggag   12000
cgcggccgat gcaaagtgcc gataaacata acgatctttg tagaaaccat cggcgcagct   12060
```

```
atttacccgc aggacatatc cacgccctcc tacatcgaag ctgaaagcac gagattcttc   12120
gccctccgag agctgcatca ggtcggagac gctgtcgaac ttttcgatca gaaacttctc   12180
gacagacgtc gcggtgagtt caggcttttt catatctcat gccccccgg gatctgcggc    12240 acgctgttga cgctgttaag cgggtcgctg cagggtcgct cggtgttcga ggccacacgc   12300
gtcaccttaa tatgcgaagt ggacctcgga ccgcgccgcc ccgactgcat ctgcgtgttc   12360
gaattcgcca atgacaagac gctgggcggg gtttgtgtca tcatagaact aaagacatgc   12420
aaatatattt cttccgggga caccgccagc aaacgcgagc aacgggccac ggggatgaag   12480
cagggcggca cctcgctaac ggattcacca ctccaagaat tggagccaat caattcttgc   12540
ggagaactgt gaatgcgcaa accaacccct ggcagaacat atccatcgcg tccgccatct   12600
ccagcagccg cacgcggcgc atctcggggc cgacgcgctg gctacgtctg tgctggcgtt   12660
cgcacaggcc ggccagcgcg cggccggccg gtaccacgcg ttggccacat atggcggccg   12720
ctcgcgatta attaatcgcg atggccacat atggagctct ctagagcttg tcgacagatc   12780
cccctcttca tttctttatg ttttaaatgc actgacctcc cacattccct ttttagtaaa   12840
atattcagaa ataatttaaa tacatcattg caatgaaaat aaatgttttt tattaggcag   12900
aatccagatg ctcaaggccc ttcataatat cccccagttt agtagttgga cttagggaac   12960
aaaggaacct ttaatagaaa ttggacagca agaaagcgag ggggatctgg atcctccgga   13020
gggccctgga tcctcctacg tatctagaat catcgattaa cactctcccc tgttgaagct   13080 cttttgtgacg ggcgagctca ggccctgatg ggtgacttcg caggcgtaga ctttgtgttt   13140
ctcgtagtct gctttgctca gcgtcagggt gctgctgagg ctgtaggtgc tgtccttgct   13200
gtcctgctct gtgacactct cctgggagtt acccgattgg agggcgttat ccaccttcca   13260
ctgtactttg gcctctctgg gatagaagtt attcagcagg cacacaacag aggcagttcc   13320
agatttcaac tgctcatcag atggcgggaa gatgaagaca gatggtgcag ccaccgtacg   13380
tttcagttcc agcttggtcc caggtccaaa cgtgtacccg ctataatact ggtgacagta   13440
gtaagttgca aaatcttcag gttgcagact gctgatggtg agagtgaaat ctgtcccaga   13500
tccactgcca ctgaaccttg atgggacccc cgcttgcaaa gggcttgcat tatagatcag   13560
gagcttaggg gctttccctg gtttctgctg ataccaggcc aagttctcaa aaatgttctg   13620
acttgtcttg caagtgatgg tgactctgtc tcctacagat gcagacaggg aggatggaga   13680
ctgggtcatc tggatgtcac atctcatggc tgggaggaag agcaccaaaa gccctaaaag   13740
ttgaactgga gccatctcga gaattcttaa gcctgtggag agaaaggaac agaaaacgaa   13800
acaaagacgt agagttgagc aagcagggtc aggcaaagcg tggagagccg gctgagtcta   13860
ggtaggctcc aagggagcgc cggacaaagg cccggtctcg acctgagctt taaacttacc   13920 tgtgccaca cgtgcaattg ctatagtgag tcgtattaat ttcgataagc cagtaagcag   13980
tgggttctct agttagccag agagctctgc ttatatagac ctcccaccgt acacgcctac   14040
cgcccatttg cgtcaatggg gcggagttgt tacgacattt tggaaagtcc cgttgatttt   14100
ggtgccaaaa caaactccca ttgacgtcaa tggggtggag acttggaaat cccgtgagt    14160 caaaccgcta tccacgccca ttgatgtact gccaaaaccg catcaccatg gtaatagcga   14220
tgactaatac gtagatgtac tgccaagtag gaaagtccca taaggtcatg tactgggcat   14280
aatgccaggc gggccatttta ccgtcattga cgtcaatagg gggcgtactt ggcatatgat   14340
acacttgatg tactgccaag tgggcagttt accgtaaata gtccacccat tgacgtcaat   14400
```

| | |
|---|---|
| ggaaagtccc tattggcgtt actatgggaa catacgtcat tattgacgtc aatgggcggg | 14460 |
| ggtcgttggg cggtcagcca ggcgggccat ttaccgtaag ttatgtaacg cggaactcca | 14520 |
| tatatgggct atgaactaat gaccccgtaa ttgattacta ttaataacta gtcaataatc | 14580 |
| aatgtcaacg cgtatatctg gcccgtacat cggtaactag tcggaccggc ccgggccacc | 14640 |
| ggtgctcgaa gcttggatcg atccagacat gataagatac attgatgagt ttggacaaac | 14700 |
| cacaactaga atgcagtgaa aaaatgctt tatttgtgaa atttgtgatg ctattgcttt | 14760 |
| atttgtaacc attataagct gcaataaaca agttaacaac aacaattgca ttcattttat | 14820 |
| gtttcaggtt cagggggagg tgtgggaggt tttttaaagc aagtaaaacc tctacaaatg | 14880 |
| tggtatggct gattatgatc tctagtcaag | 14910 |

<210> SEQ ID NO 25
<211> LENGTH: 15083
<212> TYPE: DNA
<213> ORGANISM: Artificial Sequence
<220> FEATURE:
<223> OTHER INFORMATION: Nucleotide sequence of pAIL10V1/puro/MAR(-)

<400> SEQUENCE: 25

| | |
|---|---|
| gcactataca tcaaatattc cttattaacc cctttacaaa ttaaaaagct aaaggtacac | 60 |
| aattttttgag catagttatt aatagcagac actctatgcc tgtgtggagt aagaaaaaac | 120 |
| agtatgttat gattataact gttatgccta cttataaagg ttacagaata ttttttccata | 180 |
| attttcttgt atagcagtgc agctttttcc tttgtggtgt aaatagcaaa gcaagcaaga | 240 |
| gttctattac taaacacagc atgactcaaa aaacttagca attctgaagg aaagtccttg | 300 |
| gggtcttcta cctttctctt ctttttttgga ggagtagaat gttgagagtc agcagtagcc | 360 |
| tcatcatcac tagatggcat ttcttctgag caaaacaggt tttcctcatt aaaggcattc | 420 |
| caccactgct cccattcatc agttccatag gttggaatct aaaatacaca acaattaga | 480 |
| atcagtagtt taacacatta tacacttaaa aatttatat ttaccttaga gctttaaatc | 540 |
| tctgtaggta gtttgtccaa ttatgtcaca ccacagaagt aaggttcctt cacaaagatc | 600 |
| gatctaaagc cagcaaaagt cccatggtct tataaaaatg catagcttta ggaggggagc | 660 |
| agagaacttg aaagcatctt cctgttagtc tttcttctcg tagacttcaa acttatactt | 720 |
| gatgcctttt tcctcctgga cctcagagag gacgcctggg tattctggga gaagtttata | 780 |
| tttccccaaa tcaatttctg ggaaaaacgt gtcactttca aattcctgca tgatccttgt | 840 |
| cacaaagagt ctgaggtggc ctggttgatt catggcttcc tggtaaacag aactgcctcc | 900 |
| gactatccaa accatgtcta ctttacttgc caattccggt tgttcaataa gtcttaaggc | 960 |
| atcatccaaa cttttggcaa gaaaatgagc tcctcgtggt ggttctttga gttctctact | 1020 |
| gagaactata ttaattctgt cctttaaagg tcgattcttc tcaggaatgg agaaccaggt | 1080 |
| tttcctaccc ataatcacca gattctgttt accttccact gaagaggttg tggtcattct | 1140 |
| ttggaagtac ttgaactcgt tcctgagcgg aggccagggt aggtctccgt tcttgccaat | 1200 |
| ccccatattt tgggacacgg cgacgatgca gttcaatgtc cgaaccatga tggcagcggg | 1260 |
| gataaaatcc taccagcctt cacgctagga ttgccgtcaa gtttggcgcg aaatcgcagc | 1320 |
| cctgagctgt cccccccccc aagctcagat ctgagcttgg tccctatggt gagtccgttc | 1380 |
| cgctcttgtg atgatagcca gacaagaaag agacaataca agacaaacac caaatagtag | 1440 |
| aaatagagac aagggtcact tatccgaggg tccctgttcg ggcgccagct gccgcagtcg | 1500 |
| gccgacctga gggtcgccgg ggtctgcggg gggaccctct ggaaagtgaa ggataagtga | 1560 |

-continued

```
cgagcggaga cgggatggcg aacagacaca aacacacaag aggtgaatgt taggactgtt      1620
gcaagtttac tcaaaaaatc agcactcttt tatatcttgg tttacataag catttacata      1680
agatttggat aaattccaaa agaacatagg aaaatagaac actcagagct cagatcagaa      1740
cctttgatac caaaccaagt caggaaacca cttgtctcac atcctcgttt taagaacagt      1800
ttgtaaccaa aaacttactt aagccctggg aaccgcaagg ttgggccaat aaaggctatt      1860
cataataact catgccatga gttttttgcag aataatgttc tattagtcca gccactgtcc     1920
cctccttggt atggaaaatc tttccccaaa agtgcattcc tgttcctaga taaatataat      1980
catgtacctg ttgtttcatg tcgtcttttt cttcttgaga caacatacac caaggaggtc      2040
tagctctggc gagtctttca cgaaaaggga gggatctata taacacttta tagccattga      2100
ctgtaaccca cctatcccaa tttaagtcat atcttcctgt atatggtaag ggggcatctg      2160
ttggtctgta gatgtaaggt cccctataag tccctggttg ccaccacctg tctcctattt      2220
tgacaaaaac actcttttt ccctttttta cttctaggcc tgtggtcaat agtccttgca       2280
cctgttcttc aattgaggtt gagcgtctct ttctattttc tattcccatt tctaacttct      2340
gaatttgagt aaaaatagta ctaaaagata atgattcatt tcttaacata gtaactaata      2400
atctacctat tggattggtc ttattggtaa aaatataatt tttagcaagc attcttattt      2460
ctatttctga aggacaaaat cgatgcggct tgtaagagga agttggctgt ggtccttgcc      2520
tcaggaggaa ggtcgagttc tccgaattgt ttagattgta atcttgcaca gaagagctat      2580
taaaagagtc aagggtgaga gccctgcgag cacgaaccgc aacttccccc aatagcccca      2640
ggcaaagcag agctatgcca agtttgcagc agagaatgaa tatgtctttg tctgatgggc      2700
tcatccgttt gtgcgcagac gggtcgtcct tggtgggaaa caacccttg gctgcttctc       2760 ccctaggtgt aggacactct cgggagttca accatttctg cccaagctca gatctgagct      2820
ttaatgcggt agtttatcac agttaaattg ctaacgcagt caggcaccgt gtatgaaatc      2880
taacaatgcg ctcatcgtca tcctcggcac cgtcaccctg gatgctgtag cataggctt       2940 ggttatgccg gtactgccgg gcctcttgcg ggatatcgtc cattccgaca gcatcgccag      3000
tcactatggc gtgctgctag cgctcttccg cttcctcgct cactgactcg ctgcgctcgg      3060
tcgttcggct gcggcgagcg gtatcagctc actcaaaggc ggtaatacgg ttatccacag      3120
aatcagggga taacgcagga agaacatgt gagcaaaagg ccagcaaaag gccaggaacc       3180
gtaaaaaggc cgcgttgctg gcgttttcc ataggctccg ccccctgac gagcatcaca        3240 aaaatcgacg ctcaagtcag aggtggcgaa acccgacagg actataaaga taccaggcgt      3300
ttccccctgg aagctccctc gtgcgctctc ctgttccgac cctgccgctt accggatacc      3360
tgtccgcctt tctcccttcg ggaagcgtgg cgctttctca tagctcacgc tgtaggtatc      3420
tcagttcggt gtaggtcgtt cgctccaagc tgggctgtgt gcacgaaccc ccgttcagc       3480 ccgaccgctg cgccttatcc ggtaactatc gtcttgagtc aacccggta agacacgact       3540 tatcgccact ggcagcagcc actggtaaca ggattagcag agcgaggtat gtaggcggtg      3600
ctacagagtt cttgaagtgg tggcctaact acggctacac tagaaggaca gtatttggta      3660
tctgcgctct gctgaagcca gttaccttcg gaaaaagagt tggtagctct tgatccggca      3720
aacaaaccac cgctggtagc ggtggttttt tgtttgcaa gcagcagatt acgcgcagaa       3780
aaaaaggatc tcaagaagat cctttgatct tttctacggg gtctgacgct cagtggaacg      3840
aaaactcacg ttaagggatt ttggtcatga gattatcaaa aaggatcttc acctagatcc      3900
```

-continued

```
ttttaaatta aaaatgaagt tttaaatcaa tctaaagtat atatgagtaa acttggtctg    3960
acagttacca atgcttaatc agtgaggcac ctatctcagc gatctgtcta tttcgttcat    4020
ccatagttgc ctgactcccc gtcgtgtaga taactacgat acgggagggc ttaccatctg    4080
gccccagtgc tgcaatgata ccgcgagacc cacgctcacc ggctccagat ttatcagcaa    4140
taaaccagcc agccggaagg gccgagcgca gaagtggtcc tgcaacttta ccgcctcca     4200 tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata ataccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag ggaataaggg    4800
cgacacggaa atgttgaata ctcatactct ccttttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgct taattaatcg cgatggccac atatggagct ctctagaaaa caatatattt    5100
ccaaatgaaa aaaaaatctg ataaaaagtt gactttaaaa agtatcaat aaatgtatgc     5160 atttctcact agcctaaaac tctgcatgaa gtgtttgatg agcagatgaa gacaacatca    5220
tttctagttt cagaaataat aacagcatca aaaccgcagc tgtaactcca ctgagctcac    5280
gttaagtttt gatgtctgaa tatctgacag aactgacata atgagcactg caaggatatc    5340
agacaagtca aaatgaagac agacaaaagt atttttttaat ataaaaatgg tctttatttc    5400
ttcaatacaa ggtaaactac tattgcagtt taagaccaac acaaaagttg gacagcaaat    5460
tgcttaacag tctcctaaag gctgaaaaaa aggaacccat gaaagctaaa agttatgcag    5520
tatttcaagt ataacatcta aaatgatga aacgatccct aaaggtagag attaactaag     5580
tacttctgct gaaaatgtat taaaatccgc agttgctagg ataccatctt accttgttga    5640
gaaatacagg tctccggcaa cgcaacattc agcagactct ttggcctgct ggaatcagga    5700
aactgcttac tatatacaca tataaaatcc tttggagttg ggcattctga gagacatcca    5760
tttcctgaca ttttgcagtg caactctgca ttccaactca gacaagctcc catgctgtat    5820
ttcaaagcca tttcttgaat agtttaccca gacatccttg tgcaaattgg gaatgaggaa    5880
atgcaatggt acaggaagac aatacagcct tatgtttaga aagtcagcag cgctggtaat    5940
cttcataaaa atgtaactgt ttaccaaata ggaatgtatt tcacttgtaa aacacctggt    6000 ccttttttata ttacttttttt ttttttttaa ggacacctgc actaatttgc aatcacttgt    6060
atttataaaa gcacacgcac tcctcatttt cttacatttg aagatcagca gaatgtctct    6120
ttcataatgt aataatcata tgcacagttt aaaatatttt ctattacaaa atacagtaca    6180
caagagggtg aggccaaagt ctattacttg aatatattcc aaagtgtcag cactgggggt    6240
gtaaaattac attacatggt atgaataggc ggaattcttt tacaactgaa atgctcgatt    6300
```

```
tcattgggat caaaggtaag tactgtttac tatcttcaag agacttcaat caagtcagtg    6360
tatttccaaa gaagcttaaa agattgaagc acagacacag gccacaccag agcctacacc    6420
tgctgcaata agtggtgcta tagaaaggat tcaggaacta acaagtgcat aatttacaaa    6480
tagagatgct ttatcatact ttgcccaaca tgggaaaaaa gacatcccat gagaatatcc    6540
aactgaggaa cttctctgtt tcatagtaac tcatctacta ctgctaagat ggtttgaaaa    6600
gtacccagca ggtgagatgt gttccgggag gtggctgtgt ggcagcgtgt gggaacacga    6660
cacaaagcac cccaccccta tctgcaaatc gctcactgca aggcagtgcc gtaaacagct    6720
gcaacaggca tcacttctgc ataaatgctg tgactcgtta gcatgctgca actgtgttta    6780
aaacctatgc actccgttac caaaataatt taagtcccaa acaaatccat gcagcttgct    6840
tcctatgcca aaatatttta gaaagtattc attcttcttt aagaatatgc acgtggatct    6900
acacttccct gggatctgaa gcgatttata cctcagtgca gaagcagttt agtgtcctgg    6960
atctcgggaa ggcagcagcc aaacgtgccc gttttacatt tgaacccatg tgacaacccg    7020
ccttactgag catcgctcta ggaaatttaa ggctgtatcc ttacaacaca gaaccaacg    7080 acagactgca tataaaattc tataaataaa ataggagtg aagtctgttt gacctgtaca    7140
cacagagcat agagataaaa aaaaaaggaa atcaggaatt acgtatttct ataaatgcca    7200
tatattttta ctagaaacac agatgacaag tatatacaac atgtaaatcc gaagttatca    7260
acatgttaac taggaaaaca tttcaagca tttgggtatg caactagatc atcaggtaaa    7320
aaatcccatt agaaaatct aagcctcgcc agtttcaaag gaaaaaaacc agagaacgct    7380
cactacttca aagggaaaaa aataaagcat caagctggcc taaacttaat aaggtatctc    7440
atgtaacaac agctatccaa gctttcaagc cacactataa ataaaaacct caagttccga    7500
tcaacgtttt ccataatgca aatcagaacc aaaggcattg gcacagaaag caaaagggga    7560
atgaaagaaa agggctgtac agtttccaaa aggttcttct tttgaagaaa tgtttctgac    7620
ctgtcaaaac atacagtcca gtagaaattt tactaagaaa aaagaacacc ttacttaaaa    7680
aaaaaaaaca acaaaaaaaa caggcaaaaa aacctctcct gtcactgagc tgccaccacc    7740
ccaaccacca cctgctgtgg gctttgtctc ccaagacaaa ggacacacag ccttatccaa    7800
tattcaacat tacttataaa aacgctgatc agaagaaata ccaagtattt cctcacagac    7860
tgttatatcc tttcatcggc aagaagagat gaaatacaac agagtgaata tcaaagaagg    7920
cggcaggagc caccgtggca ccatcaccgg gcagtgcagt gcccaactgc cgtttcctga    7980
gcacgcacag gaagccgtca gtcacatgta ataaaccaaa acctggtaca attgtattac    8040
ggatcccggt ggcgcgccgt ttaaaccctc agctaccgat gtacgggcca gatatacgcg    8100
ttgacattga ttattgacta gttattaata gtaatcaatt acgggtcat tagttcatag    8160 cccatatatg gagttccgcg ttacataact tacggtaaat ggcccgcctg gctgaccgcc    8220
caacgacccc cgcccattga cgtcaataat gacgtatgtt cccatagtaa cgccaatagg    8280
gactttccat tgacgtcaat gggtggacta tttacggtaa actgcccact ggcagtaca    8340 tcaagtgtat catatgccaa gtacgccccc tattgacgtc aatgacggta atggcccgc    8400 ctggcattat gcccagtaca tgaccttatg ggactttcct acttggcagt acatctacgt    8460
attagtcatc gctattacca tggtgatgcg gttttggcag tacatcaatg ggcgtggata    8520
gcggtttgac tcacggggat ttccaagtct ccaccccatt gacgtcaatg ggagtttgtt    8580
ttggcaccaa aatcaacggg actttccaaa atgtcgtaac aactccgccc cattgacgca    8640
```

```
aatgggcggt aggcgtgtac ggtgggaggt ctatataagc agagctctct ggctaactag    8700
agaacccact gcttactggc ttatcgaaat taatacgact cactatagca attgcacgtg    8760
tggccacagg taagtttaaa gctcaggtcg agaccgggcc tttgtccggc gctcccttgg    8820
agcctaccta gactcagccg gctctccacg ctttgcctga ccctgcttgc tcaactctac    8880
gtctttgttt cgttttctgt tcctttctct ccacaggctt aagcttggta ccagaaagtt    8940
aacatggctg tcttggggct gctcttctgc ctggtgacat cccaagctg tgtcctatcc     9000 caggtcagc tggtggagtc tggggaggc gtggtccagc ctgggaggtc cctgagactc      9060
tcctgtgcag cctctggatt cactttcagt gactatcata tggcctgggt ccgccaggct    9120
ccaggcaagg ggctggagtg ggtggcaagc attactcttg atgctaccta cacttactat    9180
cgcgactccg tgcgcggccg cttccaccatc tccagagaca attccaagaa cacgctgtat   9240
ctgcaaatga acagcctgag agctgaggac acggctgtgt attactgtgc gagacatcga    9300
ggctttagcg tctggcttga ttactgggggc caaggcaccc tggtcaccgt ctcgtcggct   9360
agcaccaagg gcccatcggt cttccccctg gcaccctcct ccaagagcac ctctgggggc    9420
acagcggccc tgggctgcct ggtcaaggac tacttccccg aaccggtgac ggtgtcgtgg    9480
aactcaggcg ccctgaccag cggcgtgcac accttcccgg ctgtcctaca gtcctcagga    9540
ctctactccc tcagcagcgt ggtgaccgtg ccctccagca gcttgggcac ccagacctac    9600
atctgcaacg tgaatcacaa gcccagcaac accaaggtgg acaagaaagt tgagcccaaa    9660
tcttgtgaca aaactcacac atgcccaccg tgcccagcac ctgaactcct ggggggaccg    9720
tcagtcttcc tcttcccccc aaaacccaag gacaccctca tgatctcccg gacccctgag    9780
gtcacatgcg tggtggtgga cgtgagccac gaagaccctg aggtcaagtt caactggtac    9840
gtggacggcg tggaggtgca taatgccaag acaaagccgc gggaggagca gtacaacagc    9900
acgtaccgtg tggtcagcgt cctcaccgtc ctgcaccagg actggctgaa tggcaaggag    9960
tacaagtgca aggtctccaa caaagccctc ccagccccca tcgagaaaac catctccaaa   10020
gccaaagggc agccccgaga accacaggtg tacaccctgc ccccatcccg ggatgagctg   10080
accaagaacc aggtcagcct gacctgcctg gtcaaaggct tctatcccag cgacatcgcc   10140
gtggagtggg agagcaatgg gcagccggag aacaactaca agaccacgcc tcccgtgctg   10200
gactccgacg gctccttctt cctctacagc aagctcaccg tggacaagag caggtggcag   10260
caggggaacg tcttctcatg ctccgtgatg catgaggctc tgcacaacca ctacacgcag   10320
aagagcctct ccctgtctcc gggtaaatga atcgatgatt ctagatacgg gtccggagga   10380
tccagatccc cctcgctttc ttgctgtcca atttctatta aggttccctt tgttccctaa   10440
gtccaactac taaactgggg gatattatga agggccttga gcatctggat tctgcctaat   10500
aaaaaacatt tattttcatt gcaatgatgt atttaaatta tttctgaata ttttactaaa   10560
aagggaatgt gggaggtcag tgcatttaaa acataaagaa atgaagaggg ggatctgtcg   10620
acaagctcta gagagctcac gcgttgatca ttaatcagcc ataccacatt tgtagaggtt   10680
ttacttgctt taaaaaacct cccacacctc cccctgaacc tgaaacataa atgaatgca    10740 attgttgttg ttaacttgtt tattgcagct tataatggtt acaaataaag caatagcatc   10800
acaaatttca caaataaagc atttttttca ctgcattcta gttgtggttt gtccaaactc   10860
atcaatgtat cttatcatgt ctggatcgcg gccgctctag aactagttat taatagtaat   10920
caattacggg gtcattagtt catagcccat atatggagtt ccgcgttaca taacttacgg   10980
taaatggccc gcctggctga ccgcccaacg acccccgccc attgacgtca ataatgacgt   11040
```

```
atgttcccat agtaacgcca atagggactt tccattgacg tcaatgggtg gagtatttac   11100
ggtaaactgc ccacttggca gtacatcaag tgtatcatat gccaagtacg cccctattg    11160
acgtcaatga cggtaaatgg cccgcctggc attatgccca gtacatgacc ttatgggact   11220
ttcctacttg gcagtacatc tacgtattag tcatcgctat taccatggtg atgcggtttt   11280
ggcagtacat caatgggcgt ggatagcggt ttgactcacg gggatttcca agtctccacc   11340
ccattgacgt caatgggagt ttgttttggc accaaaatca acgggacttt ccaaaatgtc   11400
gtaacaactc cgccccattg acgcaaatgg gcggtaggcg tgtacggtgg gaggtctata   11460
taagcagagc tcgtttagtg aaccgtctag acgatggaga cgccatccac gctgttttga   11520
cctccataga agacaccggg accgatccag cctccgcggc cgggaacggt gcattggaac   11580
gcggattccc cgtgccaaga gtgacgtaag taccgcctat agagtctata ggcccacccc   11640
cttggcttct tatgcatgct ccctgctcc gacccgggct cctcgcccgc cggacccac     11700
aggccaccct caaccgtcct ggccccggac ccaaacccca cccctcactc tgcttctccc   11760
cgcaggagaa ttcgagatcc cggtgccgcc accatcccct gacccacgcc cctgaccct    11820
cacaaggaga cgaccttcca tgaccgagta caagcccacg gtgcgcctcg ccacccgcga   11880
cgacgtcccc cggccgtac gcaccctcgc cgccgcgttc gccgactacc ccgccacgcg    11940
ccacaccgtc gacccggacc gccacatcga gcgggtcacc gagctgcaag aactcttcct   12000
cacgcgcgtc gggctcgaca tcggcaaggt gtgggtcgcg gacgacgcg ccgcggtggc    12060
ggtctggacc acgccggaga gcgtcgaagc ggggcggtg ttcgccgaga tcggcccgcg    12120
catggccgag ttgagcggtt cccggctggc cgcgcagcaa cagatggaag gcctcctggc   12180
gccgcaccgg cccaaggagc ccgcgtggtt cctggccacc gtcggcgtct cgcccgacca   12240
ccagggcaag ggtctgggca gcgccgtcgt gctccccgga gtggaggcgg ccgagcgcgc   12300
cggggtgccc gccttcctgg agacctccgc gccccgcaac ctccccttct acgagcggct   12360
cggcttcacc gtcaccgccg acgtcgagtg cccgaaggac cgcgcgacct ggtgcatgac   12420
ccgcaagccc ggtgcctgac gcccgcccca cgacccgcag cgcccgaccg aaaggagcgc   12480
acgacccat ggctccgacc gaagccgacc cgggcggccc cgccgacccc gcacccgccc    12540
ccgaggccca ccgactctag aggatcataa tcagccatac cacatttgta gaggttttac   12600
ttgctttaaa aaacctccca cacctccccc tgaacctgaa acataaaatg aatgcaattg   12660
ttgttgttaa cttgtttatt gcagcttata atggttacaa ataaagcaat agcatcacaa   12720
atttcacaaa taaagcattt ttttcactgc attctagttg tggtttgtcc aaactcatca   12780
atgtatctta tcatgtctgg ctctagctat cccgccccta actccgccca gttccgccca   12840
ttctccgccc catggctgac taatttttt tatttatgca gaggccgagg ccgcctggag   12900
ttaattaatc gcgatggcca catatggagc tctctagagc ttgtcgacag atccccctct   12960
tcatttcttt atgttttaaa tgcactgacc tcccacattc ccttttagt aaaatattca    13020
gaaataattt aaatacatca ttgcaatgaa aataaatgtt ttttattagg cagaatccag   13080
atgctcaagg cccttcataa tatcccccag tttagtagtt ggacttaggg aacaaaggaa   13140
cctttaatag aaattggaca gcaagaaagc gagggggatc tggatcctcc ggagggccct   13200
ggatcctcct acgtatctag aatcatcgat taacactctc ccctgttgaa gctctttgtg   13260
acgggcgagc tcaggccctg atgggtgact tcgcaggcgt agactttgtg tttctcgtag   13320
tctgctttgc tcagcgtcag ggtgctgctg aggctgtagg tgctgtcctt gctgtcctgc   13380
```

```
tctgtgacac tctcctggga gttacccgat tggagggcgt tatccacctt ccactgtact    13440
ttggcctctc tgggatagaa gttattcagc aggcacacaa cagaggcagt tccagatttc    13500
aactgctcat cagatggcgg gaagatgaag acagatggtg cagccaccgt acgtttcagt    13560
tccagcttgg tcccaggtcc aaacgtgtac ccgctataat actggtgaca gtagtaagtt    13620
gcaaaatctt caggttgcag actgctgatg gtgagagtga atctgtccc agatccactg     13680
ccactgaacc ttgatgggac ccccgcttgc aaagggcttg cattatagat caggagctta    13740
ggggctttcc ctggtttctg ctgataccag gccaagttct caaaaatgtt ctgacttgtc    13800
ttgcaagtga tggtgactct gtctcctaca gatgcagaca gggaggatgg agactgggtc    13860
atctggatgt cacatctcat ggctgggagg aagagcacca aaagccctaa aagttgaact    13920
ggagccatct cgagaattct taagcctgtg gagagaaagg aacagaaaac gaaacaaaga    13980
cgtagagttg agcaagcagg gtcaggcaaa gcgtggagag ccggctgagt ctaggtaggc    14040
tccaagggag cgccggacaa aggcccggtc tcgacctgag cttttaaactt acctgtggcc   14100
acacgtgcaa ttgctatagt gagtcgtatt aatttcgata agccagtaag cagtgggttc    14160
tctagttagc cagagagctc tgcttatata gacctcccac cgtacacgcc taccgcccat    14220
ttgcgtcaat ggggcggagt tgttacgaca ttttggaaag tcccgttgat tttggtgcca    14280
aaacaaactc ccattgacgt caatggggtg gagacttgga atccccgtg agtcaaaccg     14340
ctatccacgc ccattgatgt actgccaaaa ccgcatcacc atggtaatag cgatgactaa    14400
tacgtagatg tactgccaag taggaaagtc ccataaggtc atgtactggg cataatgcca    14460
ggcgggccat ttaccgtcat tgacgtcaat aggggggcgta cttggcatat gatacacttg    14520
atgtactgcc aagtgggcag tttaccgtaa atagtccacc cattgacgtc aatggaaagt    14580
ccctattggc gttactatgg gaacatacgt cattattgac gtcaatgggc ggggtcgtt     14640
gggcggtcag ccaggcgggc catttaccgt aagttatgta acgcggaact ccatatatgg    14700
gctatgaact aatgacccg taattgatta ctattaataa ctagtcaata atcaatgtca    14760
acgcgtatat ctggcccgta catcggtaac tagtcggacc ggcccgggcc accggtgctc    14820
gaagcttgga tcgatccaga catgataaga tacattgatg agtttggaca aaccacaact    14880
agaatgcagt gaaaaaaatg ctttatttgt gaaatttgtg atgctattgc tttatttgta    14940
accattataa gctgcaataa acaagttaac aacaacaatt gcattcattt tatgtttcag    15000
gttcaggggg aggtgtggga ggttttttaa agcaagtaaa acctctacaa atgtggtatg    15060
gctgattatg atctctagtc aag                                           15083
```

<210> SEQ ID NO 26
<211> LENGTH: 14937
<212> TYPE: DNA
<213> ORGANISM: Artificial Sequence
<220> FEATURE:
<223> OTHER INFORMATION: Nucleotide sequence of pAIGFRLCb2/MAR(-)

<400> SEQUENCE: 26

```
gcactataca tcaaatattc cttattaacc cctttacaaa ttaaaaagct aaaggtacac      60
aatttttgag catagttatt aatagcagac actctatgcc tgtgtggagt aagaaaaaac    120
agtatgttat gattataact gttatgccta cttataaagg ttacagaata tttttccata    180
attttcttgt atagcagtgc agcttttttcc tttgtggtgt aaatagcaaa gcaagcaaga    240
gttctattac taaacacagc atgactcaaa aaacttagca attctgaagg aaagtccttg    300
gggtcttcta cctttctctt cttttttgga ggagtagaat gttgagagtc agcagtagcc    360
```

-continued

| | |
|---|---|
| tcatcatcac tagatggcat ttcttctgag caaaacaggt tttcctcatt aaaggcattc | 420 |
| caccactgct cccattcatc agttccatag gttggaatct aaaatacaca aacaattaga | 480 |
| atcagtagtt taacacatta tacacttaaa aattttatat ttaccttaga gctttaaatc | 540 |
| tctgtaggta gtttgtccaa ttatgtcaca ccacagaagt aaggttcctt cacaaagatc | 600 |
| gatctaaagc cagcaaaagt cccatggtct tataaaaatg catagcttta ggaggggagc | 660 |
| agagaacttg aaagcatctt cctgttagtc tttcttctcg tagacttcaa acttatactt | 720 |
| gatgcctttt tcctcctgga cctcagagag gacgcctggg tattctggga gaagtttata | 780 |
| tttccccaaa tcaatttctg ggaaaaacgt gtcactttca aattcctgca tgatccttgt | 840 |
| cacaaagagt ctgaggtggc ctggttgatt catggcttcc tggtaaacag aactgcctcc | 900 |
| gactatccaa accatgtcta ctttacttgc caattccggt tgttcaataa gtcttaaggc | 960 |
| atcatccaaa cttttggcaa gaaaatgagc tcctcgtggt ggttctttga gttctctact | 1020 |
| gagaactata ttaattctgt cctttaaagg tcgattcttc tcaggaatgg agaaccaggt | 1080 |
| tttcctaccc ataatcacca gattctgttt accttccact gaagaggttg tggtcattct | 1140 |
| ttggaagtac ttgaactcgt tcctgagcgg aggccagggt aggtctccgt tcttgccaat | 1200 |
| ccccatattt tgggacacgg cgacgatgca gttcaatggt cgaaccatga tggcagcggg | 1260 |
| gataaaatcc taccagcctt cacgctagga ttgccgtcaa gtttggcgcg aaatcgcagc | 1320 |
| cctgagctgt ccccccccc aagctcagat ctgagcttgg tccctatggt gagtccgttc | 1380 |
| cgctcttgtg atgatagcca gacaagaaag agacaataca agacaaacac caaatagtag | 1440 |
| aaatagagac aagggtcact tatccgaggg tccctgttcg ggcgccagct gccgcagtcg | 1500 |
| gccgacctga gggtcgccgg ggtctgcggg gggaccctct ggaaagtgaa ggataagtga | 1560 |
| cgagcggaga cgggatggcg aacagacaca acacacaag aggtgaatgt taggactgtt | 1620 |
| gcaagtttac tcaaaaaatc agcactcttt tatatcttgg tttacataag catttacata | 1680 |
| agatttggat aaattccaaa gaacataggg aaaatagaac actcagagct cagatcagaa | 1740 |
| cctttgatac caaaccaagt caggaaaacca cttgtctcac atcctcgttt taagaacagt | 1800 |
| ttgtaaccaa aaacttactt aagccctggg aaccgcaagg ttgggccaat aaaggctatt | 1860 |
| cataataact catgccatga gttttttgcag aataatgttc tattagtcca gccactgtcc | 1920 |
| cctccttggt atggaaaatc tttcccccaaa agtgcattcc tgttcctaga taaatataat | 1980 |
| catgtacctg ttgtttcatg tcgtcttttt cttcttgaga caacatacac caaggaggtc | 2040 |
| tagctctggc gagtctttca cgaaaaggga gggatctata taacacttta tagccattga | 2100 |
| ctgtaaccca cctatcccaa tttaagtcat atcttcctgt atatggtaag ggggcatctg | 2160 |
| ttggtctgta gatgtaaggt cccctataag tccctggttg ccaccacctg tctcctattt | 2220 |
| tgacaaaaac actcttttt ccctttttta cttctaggcc tgtggtcaat agtccttgca | 2280 |
| cctgttcttc aattgaggtt gagcgtctct ttctattttc tattcccatt tctaacttct | 2340 |
| gaatttgagt aaaaatagta ctaaaagata atgattcatt tcttaacata gtaactaata | 2400 |
| atctacctat tggattggtc ttattggtaa aaatataatt tttagcaagc attcttattt | 2460 |
| ctatttctga aggacaaaat cgatgcggct tgtaagagga agttggctgt ggtccttgcc | 2520 |
| tcaggaggaa ggtcgagttc tccgaattgt ttagattgta atcttgcaca gaagagctat | 2580 |
| taaaagagtc aagggtgaga gccctgcgag cacgaaccgc aacttccccc aatagcccca | 2640 |
| ggcaaagcag agctatgcca agtttgcagc agagaatgaa tatgtctttg tctgatgggc | 2700 |

```
tcatccgttt gtgcgcagac gggtcgtcct tggtgggaaa caacccttg gctgcttctc      2760 ccctaggtgt aggacactct cgggagttca accatttctg cccaagctca gatctgagct      2820
ttaatgcggt agtttatcac agttaaattg ctaacgcagt caggcaccgt gtatgaaatc      2880
taacaatgcg ctcatcgtca tcctcggcac cgtcaccctg gatgctgtag gcataggctt      2940
ggttatgccg gtactgccgg gcctcttgcg ggatatcgtc cattccgaca gcatcgccag      3000
tcactatggc gtgctgctag cgctcttccg cttcctcgct cactgactcg ctgcgctcgg      3060
tcgttcggct gcggcgagcg gtatcagctc actcaaaggc ggtaatacgg ttatccacag      3120
aatcagggga taacgcagga agaacatgt gagcaaaagg ccagcaaaag gccaggaacc       3180
gtaaaaaggc cgcgttgctg gcgttttttcc ataggctccg ccccctgac gagcatcaca      3240 aaaatcgacg ctcaagtcag aggtggcgaa acccgacagg actataaaga taccaggcgt      3300
ttccccctgg aagctccctc gtgcgctctc ctgttccgac cctgccgctt accggatacc      3360
tgtccgcctt tctcccttcg ggaagcgtgg cgctttctca tagctcacgc tgtaggtatc      3420
tcagttcggt gtaggtcgtt cgctccaagc tgggctgtgt gcacgaaccc cccgttcagc      3480
ccgaccgctg cgccttatcc ggtaactatc gtcttgagtc caacccggta agacacgact      3540
tatcgccact ggcagcagcc actggtaaca ggattagcag agcgaggtat gtaggcggtg      3600
ctacagagtt cttgaagtgg tggcctaact acggctacac tagaaggaca gtatttggta      3660
tctgcgctct gctgaagcca gttaccttcg gaaaaagagt tggtagctct tgatccggca      3720
aacaaaccac cgctggtagc ggtggttttt ttgtttgcaa gcagcagatt acgcgcagaa      3780
aaaaaggatc tcaagaagat cctttgatct tttctacggg gtctgacgct cagtggaacg      3840
aaaactcacg ttaagggatt ttggtcatga gattatcaaa aaggatcttc acctagatcc      3900
ttttaaatta aaaatgaagt tttaaatcaa tctaaagtat atatgagtaa acttggtctg      3960
acagttacca atgcttaatc agtgaggcac ctatctcagc gatctgtcta tttcgttcat      4020
ccatagttgc ctgactcccc gtcgtgtaga taactacgat acgggagggc ttaccatctg      4080
gccccagtgc tgcaatgata ccgcgagacc cacgctcacc ggctccagat ttatcagcaa      4140
taaaccagcc agccggaagg gccgagcgca gaagtggtcc tgcaacttta tccgcctcca      4200
tccagtctat taattgttgc cgggaagcta gagtaagtag ttcgccagtt aatagtttgc      4260
gcaacgttgt tgccattgct acaggcatcg tggtgtcacg ctcgtcgttt ggtatggctt      4320
cattcagctc cggttcccaa cgatcaaggc gagttacatg atcccccatg ttgtgcaaaa      4380
aagcggttag ctccttcggt cctccgatcg ttgtcagaag taagttggcc gcagtgttat      4440
cactcatggt tatggcagca ctgcataatt ctcttactgt catgccatcc gtaagatgct      4500
tttctgtgac tggtgagtac tcaaccaagt cattctgaga atagtgtatg cggcgaccga      4560
gttgctcttg cccggcgtca cacgggata taccgcgcc acatagcaga actttaaaag       4620
tgctcatcat tggaaaacgt tcttcgggggc gaaaactctc aaggatctta ccgctgttga      4680
gatccagttc gatgtaaccc actcgtgcac ccaactgatc ttcagcatct tttactttca      4740
ccagcgtttc tgggtgagca aaaacaggaa ggcaaaatgc cgcaaaaaag gaataagggg      4800
cgacacggaa atgttgaata ctcatactct tcctttttca atattattga agcatttatc      4860
agggttattg tctcatgagc ggatacatat ttgaatgtat ttagaaaaat aaacaaatag      4920
gggttccgcg cacatttccc cgaaaagtgc cacctgacgt ctaagagacc attattatca      4980
tgacattaac ctataaaaat aggcgtatca cgaggccctt tcgtcttcaa gaattgtcta      5040
gaggcgcgct taattaatcg cgatggccac atatggagct ctctagaaaa caatatattt      5100
```

-continued

```
ccaaatgaaa aaaaaatctg ataaaaagtt gactttaaaa aagtatcaat aaatgtatgc   5160
atttctcact agccttaaac tctgcatgaa gtgtttgatg agcagatgaa gacaacatca   5220
tttctagttt cagaaataat aacagcatca aaaccgcagc tgtaactcca ctgagctcac   5280
gttaagtttt gatgtctgaa tatctgacag aactgacata atgagcactg caaggatatc   5340
agacaagtca aaatgaagac agacaaaagt attttttaat ataaaaatgg tctttatttc   5400
ttcaatacaa ggtaaactac tattgcagtt taagaccaac acaaaagttg gacagcaaat   5460
tgcttaacag tctcctaaag gctgaaaaaa aggaacccat gaaagctaaa agttatgcag   5520
tatttcaagt ataacatcta aaaatgatga aacgatccct aaaggtagag attaactaag   5580
tacttctgct gaaaatgtat taaaatccgc agttgctagg ataccatctt accttgttga   5640
gaaatacagg tctccggcaa cgcaacattc agcagactct ttggcctgct ggaatcagga   5700
aactgcttac tatatacaca tataaaatcc tttggagttg ggcattctga gagacatcca   5760
tttcctgaca ttttgcagtg caactctgca ttccaactca gacaagctcc catgctgtat   5820
ttcaaagcca tttcttgaat agtttaccca gacatccttg tgcaaattgg gaatgaggaa   5880
atgcaatggt acaggaagac aatacagcct tatgtttaga aagtcagcag cgctggtaat   5940
cttcataaaa atgtaactgt ttaccaaata ggaatgtatt tcacttgtaa acacctggt    6000 ccttttata ttactttttt ttttttttaa ggacacctgc actaatttgc aatcacttgt    6060
atttataaaa gcacacgcac tcctcatttt cttacatttg aagatcagca gaatgtctct   6120
ttcataatgt aataatcata tgcacagttt aaaatatttt ctattacaaa atacagtaca   6180
caagagggtg aggccaaagt ctattacttg aatatattcc aaagtgtcag cactgggggt   6240
gtaaaattac attacatggt atgaataggc ggaattcttt tacaactgaa atgctcgatt   6300
tcattgggat caaggtaag tactgtttac tatcttcaag agacttcaat caagtcagtg    6360
tatttccaaa gaagcttaaa agattgaagc acagacacag gccacaccag agcctacacc   6420
tgctgcaata agtggtgcta tagaaaggat tcaggaacta acaagtgcat aatttacaaa   6480
tagagatgct ttatcatact ttgcccaaca tgggaaaaaa gacatcccat gagaatatcc   6540
aactgaggaa cttctctgtt tcatagtaac tcatctacta ctgctaagat ggtttgaaaa   6600
gtacccagca ggtgagatgt gttccgggag gtggctgtgt ggcagcgtgt gggaacacga   6660
cacaaagcac cccaccccta tctgcaaatc gctcactgca aggcagtgcc gtaaacagct   6720
gcaacaggca tcacttctgc ataaatgctg tgactcgtta gcatgctgca actgtgttta   6780
aaacctatgc actccgttac caaaataatt taagtcccaa acaaatccat gcagcttgct   6840
tcctatgcca aaatatttta gaaagtattc attcttcttt aagaatatgc acgtggatct   6900
acacttccct gggatctgaa gcgatttata cctcagtgca gaagcagttt agtgtcctgg   6960
atctcgggaa ggcagcagcc aaacgtgccc gttttacatt tgaacccatg tgacaacccg   7020
ccttactgag catcgctcta ggaaatttaa ggctgtatcc ttacaacaca agaaccaacg   7080
acagactgca tataaaattc tataaataaa aataggagtg aagtctgttt gacctgtaca   7140
cacagagcat agagataaaa aaaaaaggaa atcaggaatt acgtatttct ataaatgcca   7200
tatattttta ctagaaacac agatgacaag tatatacaac atgtaaatcc gaagttatca   7260
acatgttaac taggaaaaca tttacaagca tttgggtatg caactagatc atcaggtaaa   7320
aaatcccatt agaaaaatct aagcctcgcg agtttcaaag gaaaaaaacc agagaacgct   7380
cactacttca aagggaaaaa aataaagcat caagctggcc taaacttaat aaggtatctc   7440
```

```
atgtaacaac agctatccaa gctttcaagc cacactataa ataaaaacct caagttccga   7500
tcaacgtttt ccataatgca aatcagaacc aaaggcattg gcacagaaag caaaaaggga   7560
atgaaagaaa agggctgtac agtttccaaa aggttcttct tttgaagaaa tgtttctgac   7620
ctgtcaaaac atacagtcca gtagaaattt tactaagaaa aaagaacacc ttacttaaaa   7680
aaaaaaaaca acaaaaaaaa caggcaaaaa aacctctcct gtcactgagc tgccaccacc   7740
ccaaccacca cctgctgtgg gctttgtctc ccaagacaaa ggacacacag ccttatccaa   7800
tattcaacat tacttataaa aacgctgatc agaagaaata ccaagtattt cctcacagac   7860
tgttatatcc tttcatcggc aagaagagat gaaatacaac agagtgaata tcaaagaagg   7920
cggcaggagc caccgtggca ccatcaccgg gcagtgcagt gcccaactgc cgtttcctga   7980
gcacgcacag gaagccgtca gtcacatgta ataaaccaaa acctggtaca attgtattac   8040
ggatcccggt ggcgcgccgt ttaaaccctc agctaccgat gtacgggcca gatatacgcg   8100
ttgacattga ttattgacta gttattaata gtaatcaatt acgggtcat tagttcatag    8160
cccatatatg gagttccgcg ttacataact tacggtaaat ggcccgcctg gctgaccgcc   8220
caacgacccc cgcccattga cgtcaataat gacgtatgtt cccatagtaa cgccaatagg   8280
gactttccat tgacgtcaat gggtggacta tttacggtaa actgcccact tggcagtaca   8340
tcaagtgtat catatgccaa gtacgccccc tattgacgtc aatgacggta atggcccgc    8400
ctggcattat gcccagtaca tgaccttatg ggactttcct acttggcagt acatctacgt   8460
attagtcatc gctattacca tggtgatgcg gttttggcag tacatcaatg ggcgtggata   8520
gcggtttgac tcacggggat ttccaagtct ccaccccatt gacgtcaatg ggagtttgtt   8580
ttggcaccaa aatcaacggg actttccaaa atgtcgtaac aactccgccc cattgacgca   8640
aatgggcggt aggcgtgtac ggtgggaggt ctatataagc agagctctct ggctaactag   8700
agaacccact gcttactggc ttatcgaaat taatacgact cactatagca attgcacgtg   8760
tggccacagg taagtttaaa gctcaggtcg agaccgggcc tttgtccggc gctcccttgg   8820
agcctaccta gactcagccg gctctccacg ctttgcctga ccctgcttgc tcaactctac   8880
gtctttgttt cgttttctgt tcctttctct ccacaggctt aagcttggta ccgagctcgg   8940
atccactagt ccagtgtggt ggaattcgcc cttatggagt ttgggctgag ctggttttc    9000
cttgttgcta tattaaaagg tgtccagtgt gaggttcagc tggtgcagtc tggggaggc    9060
ttggtaaagc ctggggggtc cctgagactc tcctgtgcag cctctggatt caccttcagt   9120
agctttgcta tgcactgggt tcgccaggct ccaggaaaag gtctggagtg gatatcagtt   9180
attgatactc gtggtgccac atactatgca gactccgtga agggccgatt caccatctcc   9240
agagacaatg ccaagaactc cttgtatctt caaatgaaca gcctgagagc cgaggacact   9300
gctgtgtatt actgtgcaag actgggggaac ttctactacg gtatggacgt ctggggccaa   9360
gggaccacgg tcaccgtctc ctcagcttcc accaagggcc catcggtctt ccccctggca   9420
ccctcctcca agagcacctc tgggggcaca gcggccctgg gctgcctggt caaggactac   9480
ttccccgaac cggtgacggt gtcgtggaac tcaggcgccc tgaccagcgg cgtgcacacc   9540
ttcccggctg tcctacagtc ctcaggactc tactccctca gcagcgtggt gaccgtgccc   9600
tccagcagct tgggcaccca gacctacatc tgcaacgtga atcacaagcc cagcaacacc   9660
aaggtggaca gaaagttga gcccaaatct tgtgacaaaa ctcacacatg cccaccgtgc    9720
ccagcacctg aactcctggg gggaccgtca gtcttcctct tccccccaaa acccaaggac   9780
accctcatga tctcccggac ccctgaggtc acatgcgtgg tggtggacgt gagccacgaa   9840
```

```
gaccctgagg tcaagttcaa ctggtacgtg gacggcgtgg aggtgcataa tgccaagaca   9900
aagccgcggg aggagcagta acacagcacg taccgtgtgg tcagcgtcct caccgtcctg   9960
caccaggact ggctgaatgg caaggagtac aagtgcaagg tctccaacaa agccctccca  10020
gcccccatcg agaaaaccat ctccaaagcc aagggcagc cccgagaacc acaggtgtac  10080
accctgcccc catcccggga tgagctgacc aagaaccagg tcagcctgac ctgcctggtc  10140
aaaggcttct atcccagcga catcgccgtg gagtgggaga gcaatgggca gccggagaac  10200
aactacaaga ccacgcctcc cgtgctggac tccgacggct ccttcttcct ctacagcaag  10260
ctcaccgtgg acaagagcag gtggcagcag gggaacgtct tctcatgctc cgtgatgcat  10320
gaggctctgc acaaccacta cacgcagaag agcctctccc tgtctccggg taaatgaatc  10380
gatgattcta gatacgggtc cggaggatcc agatccccct cgctttcttg ctgtccaatt  10440
tctattaaag gttcctttgt tccctaagtc caactactaa actggggat attatgaagg  10500
gccttgagca tctggattct gcctaataaa aaacatttat tttcattgca atgatgtatt  10560
taaattattt ctgaatattt tactaaaaag gaatgtggg aggtcagtgc atttaaaaca  10620
taaagaaatg aagaggggga tctgtcgaca agctctagag agctcacgcg ttgatcatgt  10680
acaggccggc caagctttcg actagcttgg cacgccagaa atccgcgcgg tggttttggg  10740
gggtcggggg tgtttggcag ccacagacgc ccggtgttcg tgtcgcgcca gtacatgcgg  10800
tccatgccca ggccatccaa aaaccatggg tctgtctgct cagtccagtc gtggacctga  10860
ccccacgcaa cgcccaaaat aataaccccc acgaaccata aaccattccc catgggggac  10920
cccgtcccta acccacgggg ccagtggcta tggcagggcc tgccgccccg acgttggctg  10980
cgagccctgg gccttcaccc gaacttgggg ggtggggtgg ggaaaaggaa gaaacgcggg  11040
cgtattggcc ccaatggggt ctcggtgggg tatcgacaga gtgccagccc tgggaccgaa  11100
ccccgcgttt atgaacaaac gacccaacac ccgtgcgttt tattctgtct ttttattgcc  11160
gtcatagcgc gggttccttc cggtattgtc tccttccgtg tttcagttag cctcccccat  11220
ctcccgatcc ggacgagtgc tggggcgtcg gtttccacta tcggcgagta cttctacaca  11280
gccatcggtc cagacggccg cgcttctgcg ggcgatttgt gtacgcccga cagtcccggc  11340
tccggatcgg acgattgcgt cgcatcgacc ctgcgcccaa gctgcatcat cgaaattgcc  11400
gtcaaccaag ctctgataga gttggtcaag accaatgcgg agcatatacg cccggagccg  11460
cggcgatcct gcaagctccg gatgcctccg ctcgaagtag cgcgtctgct gctccataca  11520
agccaaccac ggcctccaga agaagatgtt ggcgacctcg tattgggaat ccccgaacat  11580
cgcctcgctc cagtcaatga ccgctgttat gcggccattg tccgtcagga cattgttgga  11640
gccgaaatcc gcgtgcacga ggtgccggac ttcggggcag tcctcggccc aaagcatcag  11700
ctcatcgaga gcctgcgcga cggacgcact gacggtgtcg tccatcacag tttgccagtg  11760
atacacatgg ggatcagcaa tcgcgcatat gaaatcacgc catgtagtgt attgaccgat  11820
tccttgcggt ccgaatgggc cgaacccgct cgtctggcta agatcggccg cagcgatcgc  11880
atccatggcc tccgcgaccg gctgcagaac agcgggcagt tcggtttcag gcaggtcttg  11940
caacgtgaca ccctgtgcac ggcgggagat gcaataggtc aggctctcgc tgaattcccc  12000
aatgtcaagc acttccggaa tcgggagcgc ggccgatgca aagtgccgat aaacataacg  12060
atctttgtag aaaccatcgg cgcagctatt tacccgcagg acatatccac gccctcctac  12120
atcgaagctg aaagcacgag attcttcgcc ctccgagagc tgcatcaggt cggagacgct  12180
```

```
gtcgaacttt tcgatcagaa acttctcgac agacgtcgcg gtgagttcag gcttttcat    12240 atctcattgc cccccgggat ctgcggcacg ctgttgacgc tgttaagcgg gtcgctgcag   12300
ggtcgctcgg tgttcgaggc cacacgcgtc accttaatat gcgaagtgga cctcggaccg   12360
cgccgccccg actgcatctg cgtgttcgaa ttcgccaatg acaagacgct gggcggggtt   12420
tgtgtcatca tagaactaaa gacatgcaaa tatatttctt ccggggacac cgccagcaaa   12480
cgcgagcaac gggccacggg gatgaagcag ggcggcacct cgctaacgga ttcaccactc   12540
caagaattgg agccaatcaa ttcttgcgga gaactgtgaa tgcgcaaacc aacccttggc   12600
agaacatatc catcgcgtcc gccatctcca gcagccgcac gcggcgcatc tcggggccga   12660
cgcgctgggc tacgtcttgc tggcgttcgc acaggccggc cagcgcgcgg ccggccggta   12720
ccacgcgttg gccacatatg gcggccgctc gcgattaatt aatcgcgatg ccacatatg    12780 gagctctcta gagcttgtcg acagatcccc ctcttcattt ctttatgttt taaatgcact   12840
gacctcccac attcccttt tagtaaaata ttcagaaata atttaaatac atcattgcaa    12900
tgaaaataaa tgtttttat taggcagaat ccagatgctc aaggcccttc ataatatccc    12960
ccagtttagt agttggactt agggaacaaa ggaaccttta atagaaattg acagcaaga    13020 aagcgagggg gatctggatc ctccggaggg ccccttctcc ctctaacact ctcccctgtt   13080
gaagctcttt gtgacgggcg agctcaggcc ctgatgggtg acttcgcagg cgtagacttt   13140
gtgtttctcg tagtctgctt tgctcagcgt cagggtgctg ctgaggctgt aggtgctgtc   13200
cttgctgtcc tgctctgtga cactctcctg ggagttaccc gattggaggg cgttatccac   13260
cttccactgt actttggcct ctctgggata gaagttattc agcaggcaca caacagaggc   13320
agttccagat ttcaactgct catcagatgg cgggaagatg aagacagatg gtgcagccac   13380
tgtacgtttg atctccacct tggtcccttg gccgaaagtg tgaggtaaac gactactctg   13440
atgacagtaa tacactgcga aatcttcagg ctccagtcta ctgatggtga gggtgaaatc   13500
tgtcccagat ccactgccac tgaacctatc ggggatccct gagagggact gggatgcata   13560
cttgatgaga agccttggag cctgacctgg tttctgctgg taccagtgta agctactacc   13620
aatgctctga ctggcccggc aggagagggt ggctctctcg cctggagaca cagacagggt   13680
acctgggctc tgagtcagca caatttcacc cctggaggct ggaacccaga gcagcagaaa   13740
cccaatgagt tgtgatggcg acatgttaaa cgctagaatt cttaagcctg tggagagaaa   13800
ggaacagaaa acgaaacaaa gacgtagagt tgagcaagca gggtcaggca aagcgtggag   13860
agccggctga gtctaggtag gctccaaggg agcgccggac aaaggcccgg tctcgacctg   13920
agctttaaac ttacctgtgg ccacacgtgc aattgctata gtgagtcgta ttaatttcga   13980
taagccagta agcagtgggt tctctagtta gccagagagc tctgcttata tagacctccc   14040
accgtacacg cctaccgccc atttgcgtca atggggcgga gttgttacga cattttggaa   14100
agtcccgttg attttggtgc caaaacaaac tcccattgac gtcaatgggg tggagacttg   14160
gaaatccccg tgagtcaaac cgctatccac gcccattgat gtactgccaa accgcatca   14220 ccatggtaat agcgatgact aatacgtaga tgtactgcca gtaggaaag tcccataagg   14280 tcatgtactg ggcataatgc caggcggcc atttaccgtc attgacgtca ataggggggcg   14340 tacttggcat atgatacact tgatgtactg ccaagtgggc agtttaccgt aaatagtcca   14400
cccattgacg tcaatggaaa gtccctattg gcgttactat gggaacatac gtcattattg   14460
acgtcaatgg gcggggtcg ttgggcggtc agccaggcgg gccatttacc gtaagttatg   14520
taacgcggaa ctccatatat gggctatgaa ctaatgaccc cgtaattgat tactattaat   14580
```

| | |
|---|---:|
| aactagtcaa taatcaatgt caacgcgtat atctggcccg tacatcggta actagtcgga | 14640 |
| ccgccgcgga ctagtgcccg ggccaccggt gctcgaagct tggatcgatc cagacatgat | 14700 |
| aagatacatt gatgagtttg gacaaaccac aactagaatg cagtgaaaaa aatgctttat | 14760 |
| ttgtgaaatt tgtgatgcta ttgctttatt tgtaaccatt ataagctgca ataaacaagt | 14820 |
| taacaacaac aattgcattc attttatgtt tcaggttcag ggggaggtgt gggaggtttt | 14880 |
| ttaaagcaag taaaacctct acaaatgtgg tatggctgat tatgatctct agtcaag | 14937 |

<210> SEQ ID NO 27
<211> LENGTH: 15110
<212> TYPE: DNA
<213> ORGANISM: Artificial Sequence
<220> FEATURE:
<223> OTHER INFORMATION: Nucleotide sequence of pAIGFRLCb2/puro/MAR(-)

<400> SEQUENCE: 27

| | |
|---|---:|
| gcactataca tcaaatattc cttattaacc cctttacaaa ttaaaaagct aaaggtacac | 60 |
| aattttttgag catagttatt aatagcagac actctatgcc tgtgtggagt aagaaaaaac | 120 |
| agtatgttat gattataact gttatgccta cttataaagg ttacagaata ttttccata | 180 |
| atttctcttgt atagcagtgc agcttttttcc tttgtggtgt aaatagcaaa gcaagcaaga | 240 |
| gttctattac taaacacagc atgactcaaa aaacttagca attctgaagg aaagtccttg | 300 |
| gggtcttcta cctttctctt ctttttttgga ggagtagaat gttgagagtc agcagtagcc | 360 |
| tcatcatcac tagatggcat ttcttctgag caaaacaggt tttcctcatt aaaggcattc | 420 |
| caccactgct cccattcatc agttccatag gttggaatct aaaatacaca acaattaga | 480 |
| atcagtagtt taacacatta tacacttaaa aatttttatat ttaccttaga gctttaaatc | 540 |
| tctgtaggta gtttgtccaa ttatgtcaca ccacagaagt aaggttcctt cacaaagatc | 600 |
| gatctaaagc cagcaaaagt cccatggtct tataaaaatg catagcttta ggaggggagc | 660 |
| agagaacttg aaagcatctt cctgttagtc tttcttctcg tagacttcaa acttatactt | 720 |
| gatgcctttt tcctcctgga cctcagagag gacgcctggg tattctggga gaagtttata | 780 |
| tttcccccaaa tcaatttctg ggaaaaacgt gtcactttca aattcctgca tgatccttgt | 840 |
| cacaaagagt ctgaggtggc ctggttgatt catggcttcc tggtaaacag aactgcctcc | 900 |
| gactatccaa accatgtcta ctttacttgc caattccggt tgttcaataa gtcttaaggc | 960 |
| atcatccaaa cttttggcaa gaaaatgagc tcctcgtggt ggttctttga gttctctact | 1020 |
| gagaactata ttaattctgt cctttaaagg tcgattcttc tcaggaatgg agaaccaggt | 1080 |
| tttcctaccc ataatcacca gattctgttt accttccact gaagaggttg tggtcattct | 1140 |
| ttggaagtac ttgaactcgt tcctgagcgg aggccagggt aggtctccgt tcttgccaat | 1200 |
| ccccatattt tgggacacgg cgacgatgca gttcaatggt cgaaccatga tggcagcggg | 1260 |
| gataaaatcc taccagcctt cacgctagga ttgccgtcaa gtttggcgcg aaatcgcagc | 1320 |
| cctgagctgt cccccccccc aagctcagat ctgagcttgg tccctatggt gagtccgttc | 1380 |
| cgctcttgtg atgatagcca gacaagaaag agacaataca agacaaacac caaatagtag | 1440 |
| aaatagagac aagggtcact tatccgaggg tccctgttcg ggcgccagct gccgcagtcg | 1500 |
| gccgacctga gggtcgccgg ggtctgcggg gggacccctct ggaaagtgaa ggataagtga | 1560 |
| cgagcggaga cgggatggcg aacagacaca aacacacaag aggtgaatgt taggactgtt | 1620 |
| gcaagtttac tcaaaaaatc agcactcttt tatatcttgg tttacataag catttacata | 1680 |

-continued

```
agatttggat aaattccaaa agaacatagg aaaatagaac actcagagct cagatcagaa    1740
cctttgatac caaaccaagt caggaaacca cttgtctcac atcctcgttt taagaacagt    1800
ttgtaaccaa aaacttactt aagccctggg aaccgcaagg ttgggccaat aaaggctatt    1860
cataataact catgccatga gttttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca gtttgcagc agagaatgaa tatgtctttg tctgatgggc    2700
tcatccgttt gtgcgcagac gggtcgtcct tggtgggaaa caaccccttg ctgcttctc    2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag catagggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga agaacatgt gagcaaaagg ccagcaaaag gccaggaacc    3180
gtaaaaaggc cgcgttgctg gcgttttttcc ataggctccg ccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc aacccggta agacacgact    3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaagagt tggtagctct tgatccggca    3720
aacaaaccac cgctggtagc ggtggttttt tgtttgcaa gcagcagatt acgcgcagaa    3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
```

-continued

```
gccccagtgc tgcaatgata ccgcgagacc cacgctcacc ggctccagat ttatcagcaa    4140
taaaccagcc agccggaagg gccgagcgca gaagtggtcc tgcaacttta tccgcctcca    4200
tccagtctat taattgttgc cgggaagcta gagtaagtag ttcgccagtt aatagtttgc    4260
gcaacgttgt tgccattgct acaggcatcg tggtgtcacg ctcgtcgttt ggtatggctt    4320
cattcagctc cggttcccaa cgatcaaggc gagttacatg atcccccatg ttgtgcaaaa    4380
aagcggttag ctccttcggt cctccgatcg ttgtcagaag taagttggcc gcagtgttat    4440
cactcatggt tatggcagca ctgcataatt ctcttactgt catgccatcc gtaagatgct    4500
tttctgtgac tggtgagtac tcaaccaagt cattctgaga atagtgtatg cggcgaccga    4560
gttgctcttg cccggcgtca cacgggata taccgcgcc acatagcaga actttaaaag    4620
tgctcatcat tggaaaacgt tcttcggggc gaaaactctc aaggatctta ccgctgttga    4680
gatccagttc gatgtaaccc actcgtgcac ccaactgatc ttcagcatct tttactttca    4740
ccagcgtttc tgggtgagca aaaacaggaa ggcaaaatgc cgcaaaaaag gaataagggg    4800
cgacacggaa atgttgaata ctcatactct tccttttca atattattga agcatttatc    4860
agggttattg tctcatgagc ggatacatat ttgaatgtat ttagaaaaat aaacaaatag    4920
gggttccgcg cacatttccc cgaaaagtgc cacctgacgt ctaagagacc attattatca    4980
tgacattaac ctataaaaat aggcgtatca cgaggccctt tcgtcttcaa gaattgtcta    5040
gaggcgcgct taattaatcg cgatggccac atatggagct ctctagaaaa caatatattt    5100
ccaaatgaaa aaaaaatctg ataaaaagtt gactttaaaa aagtatcaat aaatgtatgc    5160
atttctcact agccttaaac tctgcatgaa gtgtttgatg agcagatgaa gacaacatca    5220
tttctagttt cagaaataat aacagcatca aaaccgcagc tgtaactcca ctgagctcac    5280
gttaagtttt gatgtctgaa tatctgacag aactgacata atgagcactg caaggatatc    5340
agacaagtca aaatgaagac agacaaaagt attttttaat ataaaatgg tctttatttc    5400 ttcaatacaa ggtaaactac tattgcagtt taagaccaac acaaaagttg acagcaaat    5460 tgcttaacag tctcctaaag gctgaaaaaa aggaacccat gaaagctaaa agttatgcag    5520
tatttcaagt ataacatcta aaatgatga acgatccct aaaggtagag attaactaag    5580
tacttctgct gaaaatgtat taaaatccgc agttgctagg ataccatctt accttgttga    5640
gaaatacagg tctccggcaa cgcaacattc agcagactct ttggcctgct ggaatcagga    5700
aactgcttac tatatacaca tataaaatcc tttggagttg ggcattctga gagacatcca    5760
tttcctgaca ttttgcagtg caactctgca ttccaactca gacaagctcc catgctgtat    5820
ttcaaagcca tttcttgaat agtttaccca gacatccttg tgcaaattgg gaatgaggaa    5880
atgcaatggt acaggaagac aatacagcct tatgtttaga aagtcagcag cgctggtaat    5940
cttcataaaa atgtaactgt ttaccaaata ggaatgtatt tcacttgtaa acacctggt    6000 ccttttata ttactttttt tttttttaa ggacacctgc actaatttgc aatcacttgt    6060
atttataaaa gcacacgcac tcctcatttt cttacatttg aagatcagca gaatgtctct    6120
ttcataatgt aataatcata tgcacagttt aaaatatttt ctattacaaa atacagtaca    6180
caagagggtg aggccaaagt ctattacttg aatatattcc aaagtgtcag cactggggt    6240 gtaaaattac attcatggt atgaataggc ggaattcttt tacaactgaa atgctcgatt    6300
tcattgggat caaaggtaag tactgtttac tatcttcaag agacttcaat caagtcagtg    6360
tatttccaaa gaagcttaaa agattgaagc acagacacag gccacaccag agcctacacc    6420
```

-continued

```
tgctgcaata agtggtgcta tagaaaggat tcaggaacta acaagtgcat aatttacaaa    6480
tagagatgct ttatcatact ttgcccaaca tgggaaaaaa gacatcccat gagaatatcc    6540
aactgaggaa cttctctgtt tcatagtaac tcatctacta ctgctaagat ggtttgaaaa    6600
gtacccagca ggtgagatgt gttccgggag gtggctgtgt ggcagcgtgt gggaacacga    6660
cacaaagcac cccaccccta tctgcaaatc gctcactgca aggcagtgcc gtaaacagct    6720
gcaacaggca tcacttctgc ataaatgctg tgactcgtta gcatgctgca actgtgttta    6780
aaacctatgc actccgttac caaaataatt taagtcccaa acaaatccat gcagcttgct    6840
tcctatgcca aaatatttta gaaagtattc attcttcttt aagaatatgc acgtggatct    6900
acacttccct gggatctgaa gcgatttata cctcagtgca gaagcagttt agtgtcctgg    6960
atctcgggaa ggcagcagcc aaacgtgccc gttttacatt tgaacccatg tgacaacccg    7020
ccttactgag catcgctcta ggaaatttaa ggctgtatcc ttacaacaca agaaccaacg    7080
acagactgca tataaaattc tataaataaa aataggagtg aagtctgttt gacctgtaca    7140
cacagagcat agagataaaa aaaaaggaa atcaggaatt acgtatttct ataaatgcca    7200 tatatttta ctagaaacac agatgacaag tatatacaac atgtaaatcc gaagttatca    7260
acatgttaac taggaaaaca tttacaagca tttgggtatg caactagatc atcaggtaaa    7320
aaatcccatt agaaaatct aagcctcgcc agtttcaaag gaaaaaaacc agagaacgct    7380
cactacttca aagggaaaaa aataaagcat caagctggcc taaacttaat aaggtatctc    7440
atgtaacaac agctatccaa gctttcaagc cacactataa ataaaaacct caagttccga    7500
tcaacgtttt ccataatgca aatcagaacc aaaggcattg gcacagaaag caaaaaggga    7560
atgaaagaaa agggctgtac agtttccaaa aggttcttct tttgaagaaa tgtttctgac    7620
ctgtcaaaac atacagtcca gtagaaattt tactaagaaa aaagaacacc ttacttaaaa    7680
aaaaaaaaca acaaaaaaaa caggcaaaaa aacctctcct gtcactgagc tgccaccacc    7740
ccaaccacca cctgctgtgg gctttgtctc ccaagacaaa ggacacacag ccttatccaa    7800
tattcaacat tacttataaa aacgctgatc agaagaaata ccaagtattt cctcacagac    7860
tgttatatcc tttcatcggc aagaagagat gaaatacaac agagtgaata tcaaagaagg    7920
cggcaggagc caccgtggca ccatcaccgg gcagtgcagt gcccaactgc cgtttcctga    7980
gcacgcacag gaagccgtca gtcacatgta ataaccaaa acctggtaca attgtattac    8040
ggatcccggt ggcgcgccgt ttaaaccctc agctaccgat gtacgggcca gatatacgcg    8100
ttgacattga ttattgacta gttattaata gtaatcaatt acgggtcat tagttcatag    8160 cccatatatg gagttccgcg ttacataact tacggtaaat ggcccgcctg gctgaccgcc    8220
caacgacccc cgcccattga cgtcaataat gacgtatgtt cccatagtaa cgccaatagg    8280
gactttccat tgacgtcaat gggtggacta tttacggtaa actgcccact tggcagtaca    8340
tcaagtgtat catatgccaa gtacgccccc tattgacgtc aatgacggta atggcccgc    8400 ctggcattat gcccagtaca tgaccttatg ggactttcct acttggcagt acatctacgt    8460
attagtcatc gctattacca tggtgatgcg gttttggcag tacatcaatg ggcgtggata    8520
gcggtttgac tcacggggat ttccaagtct ccaccccatt gacgtcaatg ggagtttgtt    8580
ttggcaccaa aatcaacggg actttccaaa atgtcgtaac aactccgccc cattgacgca    8640
aatgggcggt aggcgtgtac ggtgggaggt ctatataagc agagctctct ggctaactag    8700
agaacccact gcttactggc ttatcgaaat taatacgact cactatagca attgcacgtg    8760
tggccacagg taagtttaaa gctcaggtcg agaccgggcc tttgtccggc gctcccttgg    8820
```

-continued

| | |
|---|---|
| agcctaccta gactcagccg gctctccacg ctttgcctga ccctgcttgc tcaactctac | 8880 |
| gtctttgttt cgttttctgt tcctttctct ccacaggctt aagcttggta ccgagctcgg | 8940 |
| atccactagt ccagtgtggt ggaattcgcc cttatggagt ttgggctgag ctgggttttc | 9000 |
| cttgttgcta tattaaaagg tgtccagtgt gaggttcagc tggtgcagtc tggggggaggc | 9060 |
| ttggtaaagc ctggggggtc cctgagactc tcctgtgcag cctctggatt cacccttcagt | 9120 |
| agctttgcta tgcactgggt tcgccaggct ccaggaaaag gtctggagtg gatatcagtt | 9180 |
| attgatactg tggtgccac atactatgca gactccgtga agggccgatt caccatctcc | 9240 |
| agagacaatg ccaagaactc cttgtatctt caaatgaaca gcctgagagc cgaggacact | 9300 |
| gctgtgtatt actgtgcaag actggggaac ttctactacg gtatggacgt ctggggccaa | 9360 |
| gggaccacgg tcaccgtctc ctcagcttcc accaagggcc catcggtctt cccctggca | 9420 |
| ccctcctcca agagcacctc tgggggcaca gcggccctgg gctgcctggt caaggactac | 9480 |
| ttccccgaac cggtgacggt gtcgtggaac tcaggcgccc tgaccagcgg cgtgcacacc | 9540 |
| ttcccggctg tcctacagtc ctcaggactc tactccctca gcagcgtggt gaccgtgccc | 9600 |
| tccagcagct tgggcaccca gacctacatc tgcaacgtga atcacaagcc cagcaacacc | 9660 |
| aaggtggaca gaaagttga gcccaaatct tgtgacaaaa ctcacacatg cccaccgtgc | 9720 |
| ccagcacctg aactcctggg gggaccgtca gtcttcctct tccccccaaa acccaaggac | 9780 |
| accctcatga tctcccggac ccctgaggtc acatgcgtgg tggtggacgt gagccacgaa | 9840 |
| gaccctgagg tcaagttcaa ctggtacgtg gacggcgtgg aggtgcataa tgccaagaca | 9900 |
| aagccgcggg aggagcagta caacagcacg taccgtgtgg tcagcgtcct caccgtcctg | 9960 |
| caccaggact ggctgaatgg caaggagtac aagtgcaagg tctccaacaa agccctccca | 10020 |
| gcccccatcg agaaaaccat ctccaaagcc aaagggcagc cccgagaacc acaggtgtac | 10080 |
| accctgcccc catcccggga tgagctgacc aagaaccagg tcagcctgac ctgcctggtc | 10140 |
| aaaggcttct atcccagcga catcgccgtg gagtgggaga gcaatgggca gccggagaac | 10200 |
| aactacaaga ccacgcctcc cgtgctggac tccgacggct ccttcttcct ctacagcaag | 10260 |
| ctcaccgtgg acaagagcag gtggcagcag gggaacgtct tctcatgctc cgtgatgcat | 10320 |
| gaggctctgc acaaccacta cacgcagaag agcctctccc tgtctccggg taaatgaatc | 10380 |
| gatgattcta gatacgggtc cggaggatcc agatccccct cgctttcttg ctgtccaatt | 10440 |
| tctattaaag gttcctttgt tccctaagtc caactactaa actgggggat attatgaagg | 10500 |
| gccttgagca tctggattct gcctaataaa aaacatttat tttcattgca atgatgtatt | 10560 |
| taaattattt ctgaatattt tactaaaaag gaatgtggg aggtcagtgc atttaaaaca | 10620 |
| taaagaaatg aagagggga tctgtcgaca agctctagag agctcacgcg ttgatcatta | 10680 |
| atcagccata ccacatttgt agaggtttta cttgctttaa aaaacctccc acacctcccc | 10740 |
| ctgaacctga aacataaaat gaatgcaatt gttgttgtta acttgtttat tgcagcttat | 10800 |
| aatggttaca ataaagcaa tagcatcaca aatttcacaa ataaagcatt tttttcactg | 10860 |
| cattctagtt gtggtttgtc caaactcatc aatgtatctt atcatgtctg gatcgcggcc | 10920 |
| gctctagaac tagttattaa tagtaatcaa ttacggggtc attagttcat agcccatata | 10980 |
| tggagttccg cgttacataa cttacggtaa atggcccgcc tggctgaccg cccaacgacc | 11040 |
| cccgcccatt gacgtcaata atgacgtatg ttcccatagt aacgccaata gggactttcc | 11100 |
| attgacgtca atgggtggag tatttacggt aaactgccca cttggcagta catcaagtgt | 11160 |

```
atcatatgcc aagtacgccc cctattgacg tcaatgacgg taaatggccc gcctggcatt   11220
atgcccagta catgaccttta tgggactttc ctacttggca gtacatctac gtattagtca   11280
tcgctattac catggtgatg cggttttggc agtacatcaa tgggcgtgga tagcggtttg   11340
actcacgggg atttccaagt ctccacccca ttgacgtcaa tgggagtttg ttttggcacc   11400
aaaatcaacg ggactttcca aaatgtcgta caactccgc cccattgacg caaatgggcg   11460
gtaggcgtgt acggtgggag gtctatataa gcagagctcg tttagtgaac cgtctagacg   11520
atggagacgc catccacgct gttttgacct ccatagaaga caccgggacc gatccagcct   11580
ccgcggccgg gaacggtgca ttggaacgcg gattccccgt gccaagagtg acgtaagtac   11640
cgcctataga gtctataggc cacccccctt ggcttcttat gcatgctccc ctgctccgac   11700
ccgggctcct cgcccgcccg gacccacagg ccaccctcaa ccgtcctggc cccggaccca   11760
aaccccaccc ctcactctgc ttctccccgc aggagaattc gagatcccgg tgccgccacc   11820 atccctgac ccacgcccct gaccctcac aaggagacga ccttccatga ccagtacaa   11880 gcccacggtg cgcctcgcca ccgcgacga cgtccccgg gccgtacgca ccctcgccgc   11940
cgcgttcgcc gactaccccg ccacgcgcca caccgtcgac ccggaccgcc acatcgagcg   12000
ggtcaccgag ctgcaagaac tcttcctcac gcgcgtcggg ctcgacatcg gcaaggtgtg   12060
ggtcgcggac gacggcgccg cggtggcggt ctggaccacg ccggagagcg tcgaagcggg   12120
ggcggtgttc gccgagatcg gcccgcgcat ggccgagttg agcggttccc ggctggccgc   12180
gcagcaacag atggaaggcc tcctggcgcc gcaccggccc aaggagcccg cgtggttcct   12240
ggccaccgtc ggcgtctcgc ccgaccacca gggcaagggt ctgggcagcg ccgtcgtgct   12300
ccccggagtg gaggcggccg agcgcgccgg ggtgcccgcc ttcctggaga cctccgcgcc   12360
ccgcaacctc cccttctacg agcggctcgg cttcaccgtc accgccgacg tcgagtgccc   12420
gaaggaccgc gcgacctggt gcatgacccg caagcccgt gcctgacgcc cgccccacga   12480
cccgcagcgc ccgaccgaaa ggagcgcacg accccatggc tccgaccgaa gccgacccgg   12540
gcggccccgc cgaccccgca cccgcccccg aggcccaccg actctagagg atcataatca   12600
gccataccac atttgtagag gttttacttg ctttaaaaaa cctcccacac ctcccctga   12660 acctgaaaca taaatgaat gcaattgttg ttgttaactt gtttattgca gcttataatg   12720
gttacaaata aagcaatagc atcacaaatt tcacaaataa agcatttttt tcactgcatt   12780
ctagttgtgg tttgtccaaa ctcatcaatg tatcttatca tgtctggctc tagctatccc   12840
gcccctaact ccgcccagtt ccgcccattc tccgccccat ggctgactaa ttttttttat   12900
ttatgcagag gccgaggccg cctgagtta attaatcgcg atggccacat atggagctct   12960
ctagagcttg tcgacagatc ccctcttca tttctttatg ttttaaatgc actgacctcc   13020
cacattccct ttttagtaaa atattcagaa ataatttaaa tacatcattg caatgaaaat   13080
aaatgttttt tattaggcag aatccagatg ctcaaggccc ttcataatat cccccagttt   13140
agtagttgga cttagggaac aaaggaacct ttaatagaaa ttggacagca agaaagcgag   13200
ggggatctgt atcctccgga gggcccttc tccctctaac actctcccct gttgaagctc   13260
tttgtgacgg gcgagctcag gccctgatgg gtgacttcgc aggcgtagac tttgtgtttc   13320
tcgtagtctg ctttgctcag cgtcaggtt ctgctgaggc tgtaggtgct gtccttgctg   13380
tcctgctctg tgacactctc ctgggagtta cccgattgga gggcgttatc caccttccac   13440
tgtactttgg cctctctggg atagaagtta ttcagcaggc acacaacaga ggcagttcca   13500
gatttcaact gctcatcaga tggcgggaag atgaagacag atggtgcagc cactgtacgt   13560
```

```
ttgatctcca ccttggtccc ttggccgaaa gtgtgaggta aacgactact ctgatgacag    13620
taatacactg cgaaatcttc aggctccagt ctactgatgg tgagggtgaa atctgtccca    13680
gatccactgc cactgaacct atcgggatc cctgagaggg actgggatgc atacttgatg     13740
agaagccttg gagcctgacc tggtttctgc tggtaccagt gtaagctact accaatgctc    13800
tgactggccc ggcaggagag ggtggctctc tcgcctggag acacagacag ggtacctggg    13860
ctctgagtca gcacaatttc accoctggag gctggaaccc agagcagcag aaacccaatg    13920
agttgtgatg gcgacatgtt aaacgctaga attcttaagc ctgtggagag aaaggaacag    13980
aaaacgaaac aaagacgtag agttgagcaa gcagggtcag gcaaagcgtg gagagccggc    14040
tgagtctagg taggctccaa gggagcgccg gacaaaggcc cggtctcgac ctgagctta    14100 aacttacctg tggccacacg tgcaattgct atagtgagtc gtattaattt cgataagcca    14160
gtaagcagtg ggttctctag ttagccagag agctctgctt atatagacct cccaccgtac    14220
acgcctaccg cccatttgcg tcaatgggc ggagttgtta cgacattttg gaaagtcccg     14280
ttgattttgg tgccaaaaca aactcccatt gacgtcaatg gggtggagac ttggaaatcc    14340
ccgtgagtca aaccgctatc cacgcccatt gatgtactgc caaaaccgca tcaccatggt    14400
aatagcgatg actaatacgt agatgtactg ccaagtagga aagtcccata aggtcatgta    14460
ctgggcataa tgccaggcgg gccatttacc gtcattgacg tcaataggg gcgtacttgg     14520 catatgatac acttgatgta ctgccaagtg ggcagtttac cgtaaatagt ccacccattg    14580
acgtcaatgg aaagtcccta ttggcgttac tatgggaaca tacgtcatta ttgacgtcaa    14640
tgggcggggg tcgttgggcg gtcagccagg cgggccattt accgtaagtt atgtaacgcg    14700
gaactccata tatgggctat gaactaatga ccccgtaatt gattactatt aataactagt    14760
caataatcaa tgtcaacgcg tatatctggc ccgtacatcg gtaactagtc ggaccgccgc    14820
ggactagtgc ccgggccacc ggtgctcgaa gcttggatcg atccagacat gataagatac    14880
attgatgagt ttggacaaac cacaactaga atgcagtgaa aaaaatgctt tatttgtgaa    14940
atttgtgatg ctattgcttt atttgtaacc attataagct gcaataaaca agttaacaac    15000
aacaattgca ttcattttat gtttcaggtt caggggagg tgtgggaggt tttttaaagc     15060
aagtaaaacc tctacaaatg tggtatggct gattatgatc tctagtcaag               15110
```

US 7,326,567 B2

PLASMID SYSTEM FOR MULTIGENE EXPRESSION

This application claims the benefit of U.S. Provisional Patent Application No. 60/519,230; filed Nov. 12, 2003 which is herein incorporated by reference in its entirety.

FIELD OF THE INVENTION

A plasmid system which facilitates construction of a single amplifiable expression plasmid for multi-subunit proteins.

BACKGROUND OF THE INVENTION

Development of any mammalian cell based protein therapeutic requires an efficient expression system. Ideally, if a multi-subunit protein (e.g., an antibody) must be produced, each polypeptide should be expressed from a single plasmid. Construction of expression vectors containing multiple genes, using commercially available expression plasmids, is problematic. Typically, the multiple cloning sites (MCS), of currently available expression plasmids, are inadequate for insertion of multiple expression cassettes. The multiple cloning sites of currently available expression plasmids contain relatively few restriction sites. Ideally, an expression plasmid for expression of multiple polypeptides would contain a large multiple cloning site containing many common and rare restriction sites.

The present invention provides, inter alia, an ideal generic plasmid expression system which can help maintain uniformity in vector construction, decrease variability in downstream processing, facilitate running multiple protein therapeutic projects simultaneously, and reduce cycle time significantly. The present invention includes such a generic plasmid platform for mammalian expression and its use for the production of various polypeptides. The platform is flexible enough to be used for expression of simple proteins, such as interferon, as well as large, complex, multi-subunit proteins, such as antibodies.

SUMMARY OF THE INVENTION

The present invention provides a plasmid system comprising in separate containers:

(a) a first universal transfer vector comprising the following, first multiple cloning site: Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma III, Xba I, Sac I, Mlu I, Bcl I, Bsr GI, Bss HII; (b) a second universal transfer vector comprising the following, second multiple cloning site: Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma III, Xba I, Sac I, Nde I, Msc I, Nru I, Pac I, Bss HII; and (c) an amplifiable vector comprising the following, third multiple cloning site: Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I. In an embodiment of the invention, the plasmid system comprises: a first universal transfer vector comprising the plasmid map of FIG. 2, a second universal transfer vector comprising the plasmid map of FIG. 1 and an amplifiable vector comprising the plasmid map of FIG. 3. In another embodiment, the multiple cloning site of the first universal transfer vector comprises the nucleotide sequence set forth in SEQ ID NO: 11; the multiple cloning site of the second universal transfer vector comprises the nucleotide sequence set forth in SEQ ID NO: 12; and the multiple cloning site of the amplifiable vector comprises the nucleotide sequence set forth in SEQ ID NO: 10. In an embodiment of the invention, any of the universal transfer vectors or the amplifiable vector comprises a matrix attachment region (MAR; e.g., chicken lysozyme MAR).

In another embodiment of the invention, the plasmid system comprises only the first and second universal transfer vectors (supra).

In an embodiment of the invention, at least one of the plasmids comprises a promoter (e.g., SRα promoter, MMTV LTR, human cytomegalovirus (hCMV) immediate early promoter and murine cytomegalovirus (mCMV) immediate early promoter) located upstream of or within the multiple cloning site. Preferably, in this embodiment, the first universal transfer vector comprises the plasmid map of FIG. 10; the second universal transfer vector comprises the plasmid map of FIG. 11; and the amplifiable vector comprises the plasmid map of FIG. 9. In this embodiment, the first universal transfer vector can comprise the nucleotide sequence set forth in SEQ ID NO: 5; the second universal transfer vector comprise the nucleotide sequence set forth in SEQ ID NO: 4; and the amplifiable vector comprises the nucleotide sequence set forth in SEQ ID NO: 13.

Another embodiment of the present invention includes the plasmid system wherein at least one of the universal transfer vectors comprises a terminator/polyA addition site located in the multiple cloning site wherein the location of the terminator/polyA addition site is such that a gene located in the multiple cloning site would be operably linked to the terminator/polyA addition site.

The amplifiable vector in the plasmid system of the invention may comprise a selectable marker for amplification, such as the DHFR gene.

In an embodiment of the invention, the plasmid system of the present invention comprises in separate containers: (a) a first universal transfer vector comprising the nucleotide sequence set forth in SEQ ID NO: 2; (b) a second universal transfer vector comprising the nucleotide sequence set forth in SEQ ID NO: 1; and (c) an amplifiable vector comprising the nucleotide sequence set forth in SEQ ID NO: 3.

An embodiment of the invention includes a plasmid system wherein the first or second universal transfer vector comprises a first set of one or more expression cassettes, the other universal transfer vector comprise a second set of one or more expression cassettes and the amplifiable vector comprises said first set and second set of expression cassettes; wherein the expression cassettes encode an immunogloblin heavy chain and an immunogloblin light chain (e.g., anti-IGFR1, anti-IL10 or anti-IL5 immunoglobulin chains); for example wherein (a) the first set of one or more expression cassettes comprises an anti-IL5 immunoglobulin heavy chain gene expression cassette and the second set of one or more expression cassettes comprises an anti-IL5 immunoglobulin light chain gene expression cassette; (b) the first set or one or more expression cassette comprises an anti-IGFR1 immunoglobulin heavy chain gene expression cassette and the second set of one or more expression cassette comprises an anti-IGFR1 immunoglobulin light chain gene expression cassette; (c) the first set of one or more expression cassettes comprises an expression cassette comprising a bicistronic gene expression cassette which bicistronic gene comprises an anti-IGFR1 immunoglobulin light chain gene and an IL2 receptor α gene wherein said genes are linked by an internal ribosome entry sequence (IRES) and the second set of one or more expression cassettes is an anti-IGFR1 immunoglobulin heavy chain gene expression cassette and a hygromycin resistance gene (Hyg-b) expression cassette; or (d) the first set of one or more expression cassettes comprises an anti-IL10 immunoglobulin heavy chain gene expression cassette and the second set of one or more expression cassettes comprises an anti-IL10 immunoglobulin light chain gene expression cassette and a hygromycin resistance gene expression cassette. In an embodiment of the invention, the amplifiable vector comprises a plasmid map as set forth in a figure selected from FIGS. 4-7. For example, the amplifiable vector can comprise a nucleotide sequence selected from SEQ ID NOs: 6-9.

In an embodiment of the present invention, the plasmid system includes the amplifiable vectors pinAIL10/MAR(−); pAIL10V1 /puro/MAR(−); pAIGFRLCb2/MAR(−) or pAIGFRLCb2V1/puro/MAR(−). In an embodiment of the invention, the plasmids pinAIL10/MAR(−); pAIL10V1/puro/MAR(−); pAIGFRLCb2/MAR(−) and pAIGFRLCb2V1/puro/MAR(−) are characterized by FIGS. 13-16, respectively. In another embodiment of the invention, the plasmids pinAIL10/MAR(−); pAIL10V1/puro/MAR(−); pAIGFRLCb2/MAR(−) and pAIGFRLCb2V1/puro/MAR(−) comprise a nucleotide sequence selected from SEQ ID NOs: 24-27.

The present invention also provides a method for expressing a protein comprising two or more types of polypeptide comprising the steps of (a) introducing a set of one or more expression cassettes into a first universal transfer vector; (b) introducing one or more different expression cassettes into a second universal transfer vector; (c) moving the cassettes from the transfer vectors into an amplifiable vector; (d) causing expression of said cassettes; and (e) optionally, isolating/purifying the polypeptide; wherein said vectors are provided in a kit of the present invention. In one embodiment of the invention, the first universal transfer vector comprises the plasmid map of FIG. 2 or FIG. 10, or the nucleotide sequence set forth in SEQ ID NO: 2 or SEQ ID NO: 5. In another embodiment, the second universal transfer vector comprises the plasmid map of FIG. 1 or FIG. 11 or the nucleotide sequence set forth in SEQ ID NO: 1 or SEQ ID NO: 4. In another embodiment of the invention, the amplifiable vector comprises the plasmid map of FIG. 3 or FIG. 9 or the nucleotide sequence set forth in SEQ ID NO: 3 or SEQ ID NO: 13.

In an embodiment of the method, an anti-IGFR heavy chain or anti-IL10 heavy is expressed in an amplifiable vector, comprising a MAR and either the hygromycin resistance gene or the puromycin resistance gene, which selected from pinAIL10/MAR(−); pAIL10V1/puro/MAR(−); pAIGFRLCb2/MAR(−) and pAIGFRLCb2V1/puro/MAR(−). In an embodiment of the invention, the plasmids pinAIL10/MAR(−); pAIL10V1/puro/MAR(−); pAIGFRLCb2/MAR(−) and pAIGFRLCb2V1/puro/MAR(−) are characterized by FIGS. 13-16, respectively. In another embodiment of the invention, the plasmids pinAIL10/MAR(−); pAIL10V1/puro/MAR(−); pAIGFRLCb2/MAR(−) and pAIGFRLCb2V1/puro/MAR(−) comprise a nucleotide sequence selected from SEQ ID NOs: 24-27.

In an embodiment of the method for expressing a protein comprising two or more types of polypeptide, the expression cassettes encode an immunoglobulin heavy or light chain (e.g., anti-IGFR1, anti-IL5 or anti-IL10 immunoglobulin chain); for example: (i) one expression cassette encodes an anti-IL5 immunoglobulin heavy chain and the other expression cassette encodes an anti-IL5 immunoglobulin light chain; (ii) one expression cassette encodes an anti-IGFR1 immunoglobulin heavy chain (e.g., SEQ ID NO: 17 or 21 or any polynucleotide encoding a polypeptide comprising the amino acid sequence of SEQ ID NO: 18 or 22) and the other expression cassette encodes an anti-IGFR1 immunoglobulin light chain (e.g., SEQ ID NO: 15 or 19 or any polynucleotide encoding a polypeptide comprising the amino acid sequence of SEQ ID NO: 16 or 20); (iii) one expression cassette comprises a bicistronic gene encoding an anti-IGFR1 immunoglobulin light chain and an IL2 receptor α-subunit which are linked by an internal ribosome entry sequence (IRES) and the other expression cassette encodes an anti-IGFR1 immunoglobulin heavy chain and HYG-B; or (iv) one expression cassettes encodes an anti-IL10 immunoglobulin heavy chain and the other expression cassette encodes an anti-IL10 immunoglobulin light chain and HYG-B.

In an embodiment of the invention, the amplifiable vector comprises a plasmid map in a figure selected from FIGS. 4-7. The amplifiable vector may comprise a nucleotide sequence selected from SEQ ID NOs: 6-9.

The scope of the present invention also encompasses any product produced by any of the methods of the invention for producing a polypeptide (e.g., any immunoglobulin chain, such as that of an anti-IGFR1, anti-IL5 or anti-IL10 antibody).

In an embodiment of the method for expressing a protein comprising two or more types of polypeptide, expression is caused in a cell (e.g., a eukaryotic cell such as a CHO cell).

The present invention also comprises a method for producing an anti-IGFR1 antibody comprising the steps of (a) introducing an expression cassette comprising a polynucleotide encoding a polypeptide comprising an amino acid sequence selected from SEQ ID NOs: 18 and 22 or an expression cassette comprising a polynucleotide encoding a polypeptide comprising an amino acid sequence selected from SEQ ID NOs: 16 and 20 into a first universal transfer vector comprising the following, first multiple cloning site: Bss HII, Pme I, Sna B1, Hin dIII, Asp 718, Kpn I, Pae R71, Xho I, Sal I, Acc I, Hinc II, Cla I, Eco RV, Eco RI, Pst I, EcoO 109I, Eco 0109I, Apa I, Xma I, Bsp EI, Bam H1, Dsa I, Eag I, Ecl XI, Not I, Sac II, Xma III, Xba I, Sac I, Mlu I, Bcl I, Bsr GI, Bss HII (e.g., pUHLS or PUHSRstopLS); (b) introducing the other expression cassette, not introduced into said first vector, into a second universal transfer vector comprising the following, second multiple cloning site: Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma II, Xba I, Sac I, Nde I, Msc I, Nru I, Pac I, Bss HII (e.g., pULLS or PULSRstopLS); (c) optionally, moving the cassettes from the transfer vectors into an amplifiable vector comprising the following, third multiple cloning site: Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I (e.g., pXBLS or PSRXBLS); (d) causing expression of said cassettes; and (e) optionally isolating/purifying the antibody. The polynucleotide encoding a polypeptide comprising an amino acid sequence selected from SEQ ID NOs: 18 and 22 can comprise a nucleotide sequence selected from SEQ ID NOs: 17 and 21. The polynucleotide encoding a polypeptide comprising an amino acid sequence selected from SEQ ID NOs: 16 and 20 can comprise a nucleotide sequence selected from SEQ ID NOs: 15 and 19. In one embodiment of the invention, the expression cassettes are operably linked to a human cytomegalovirus (hCMV) promoter. The scope of the present invention includes embodiments wherein the expression cassettes mentioned above are linked to an immunoglobulin constant region such as that of any one of κ or γ1 or γ2 or γ3 or γ4.

The present invention also provides a kit comprising the plasmid system of the invention and one or more components selected from: (i) sterile, distilled water; (ii) calcium phosphate transformation reagents $CaCl_2$ and 2× HEPES buffered saline; (iii) DEAE-dextran transformation reagents chloroquine in Phosphate buffered saline and phosphate buffered saline; (iv) DOTAP/cholesterol extruded liposomes; (v) transformation competent *E. coli*; (vi) Dulbecco/Vogt modified Eagle's minimal essential medium (DMEM); (vii) Fetal calf serum; (viii) luria broth media; and (ix) paper instructions for usage of the plasmid system.

One embodiment of the present invention includes a single stranded or double stranded polynucleotide (e.g., an oligonucleotide primer) comprising a nucleotide sequence of SEQ ID NO: 10, 11 or 12.

The present invention also includes a plasmid comprising a nucleotide sequence selected from the group consisting of SEQ ID NOs: 6-9.

BRIEF DESCRIPTION OF THE FIGURES

The scope of the present invention includes any plasmid or plasmid system containing a plasmid that comprises a plasmid map substantially identical to any of the following plasmid maps.

VDJ (Anti-IGFR1 heavy chain of 11D8 hybridoma): Start: 8214 End: 8641
IgG1(Anti-IGFR1 heavy chain of 11D8 hybridoma): Start: 7234 End: 8214
Beta Globin Poly A signal (b-globin pA): Start: 6971 End: 7209
TK-Hygromycin: Start: 5053 End: 6925
AP$^r$: Start: 3965 End: 4828
pBR ORI: Start: 3207 End: 3207
pBR322 sequences: Start: 3020 End: 5033
pBR322 sequences: Start: 2811 End: 3019
MMTV-LTR: Start: 1348 End: 2810
DHFR cDNA: Start: 601 End: 1347

Figure 1:
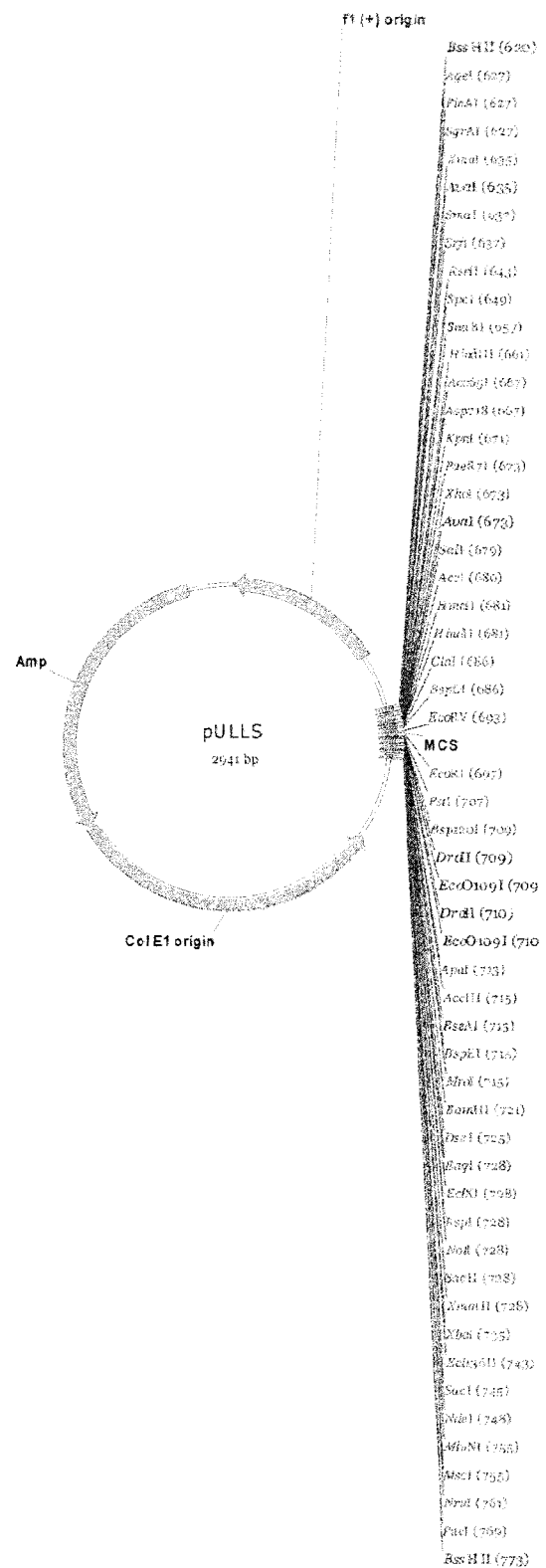
FIG. 1. Plasmid map of universal transfer vector pULLS.
Amp: Start: 1955 End: 2812
Col E1 origin: Start: 1012 End: 1952
Multiple Cloning Site (MCS): Start: 620 End: 772
f1 (+) origin: Start: 3 End: 459
Figure 2:
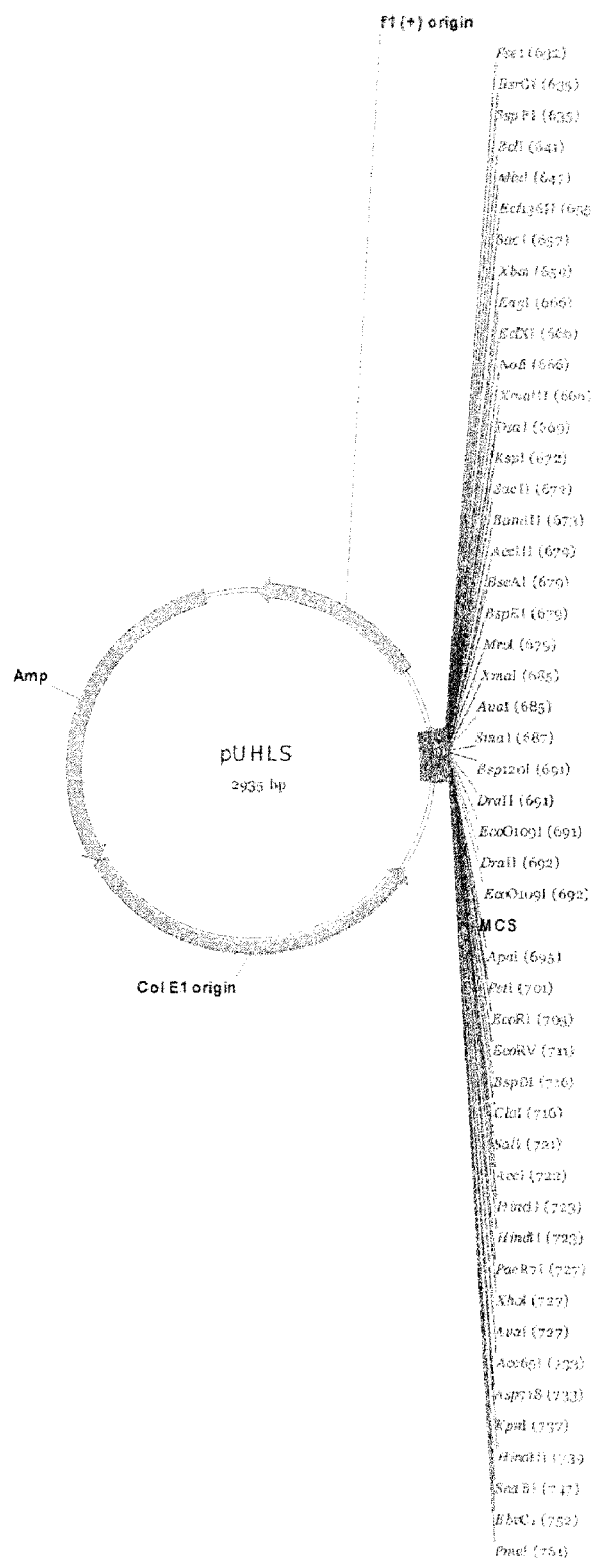
FIG. 2. Plasmid map of universal transfer vector pUHLS.
Amp: Start: 1949 End: 2806
MCS: Start: 620 End: 766
f1 (+) origin: Start: 3 End: 459
Col E1 origin: Start: 1006 End: 1946
Figure 3:
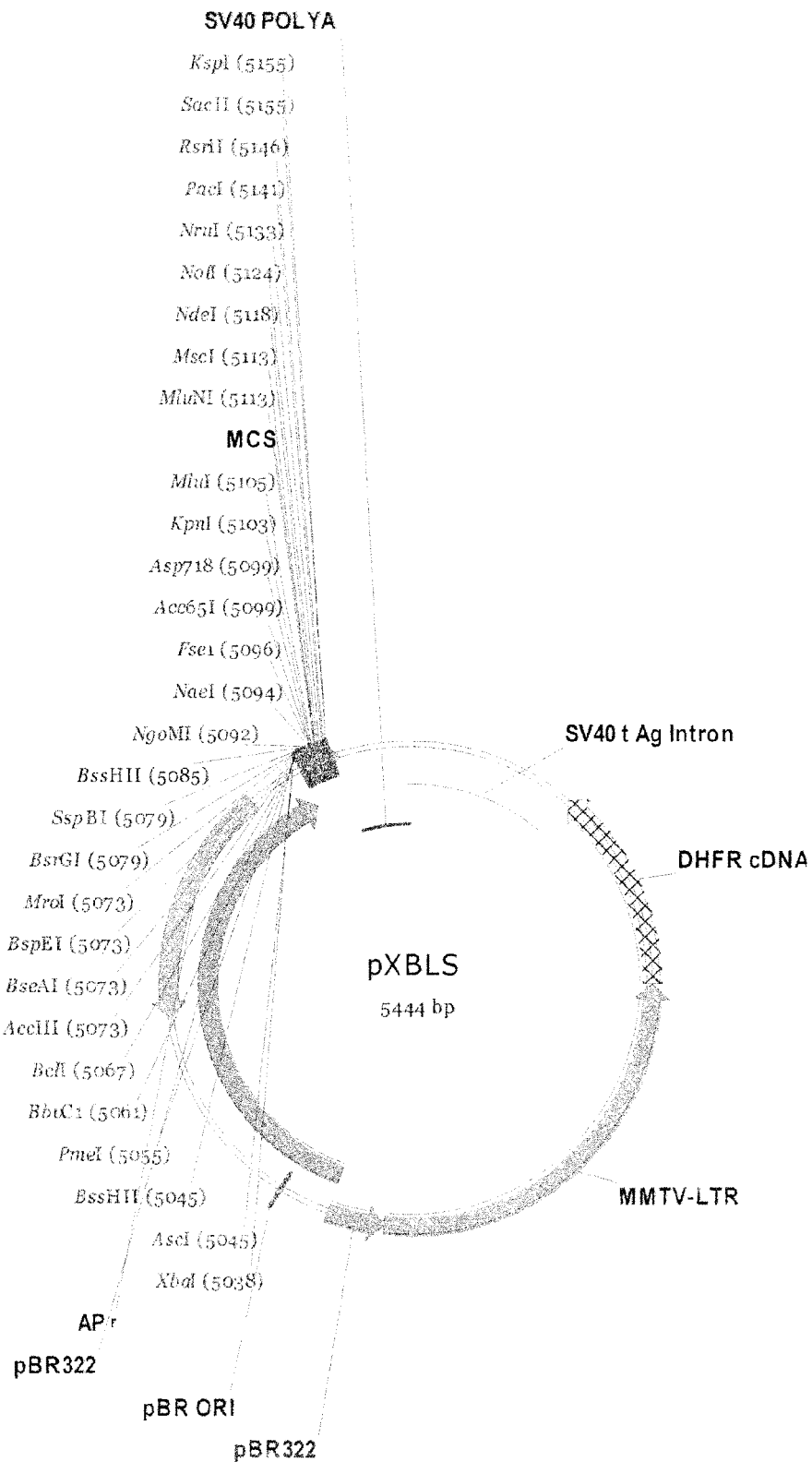
FIG. 3. Plasmid map of amplifiable vector pXBLS.
SV40 T-antigen (t Ag) Intron: Start: 5431 End: 600
SV40 POLY A signal: Start: 5184 End: 5432
MCS: Start: 5037 End: 5183
Ampicillin resistance (Amp): Start: 3965 End: 4828
pBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347.
Figure 4:
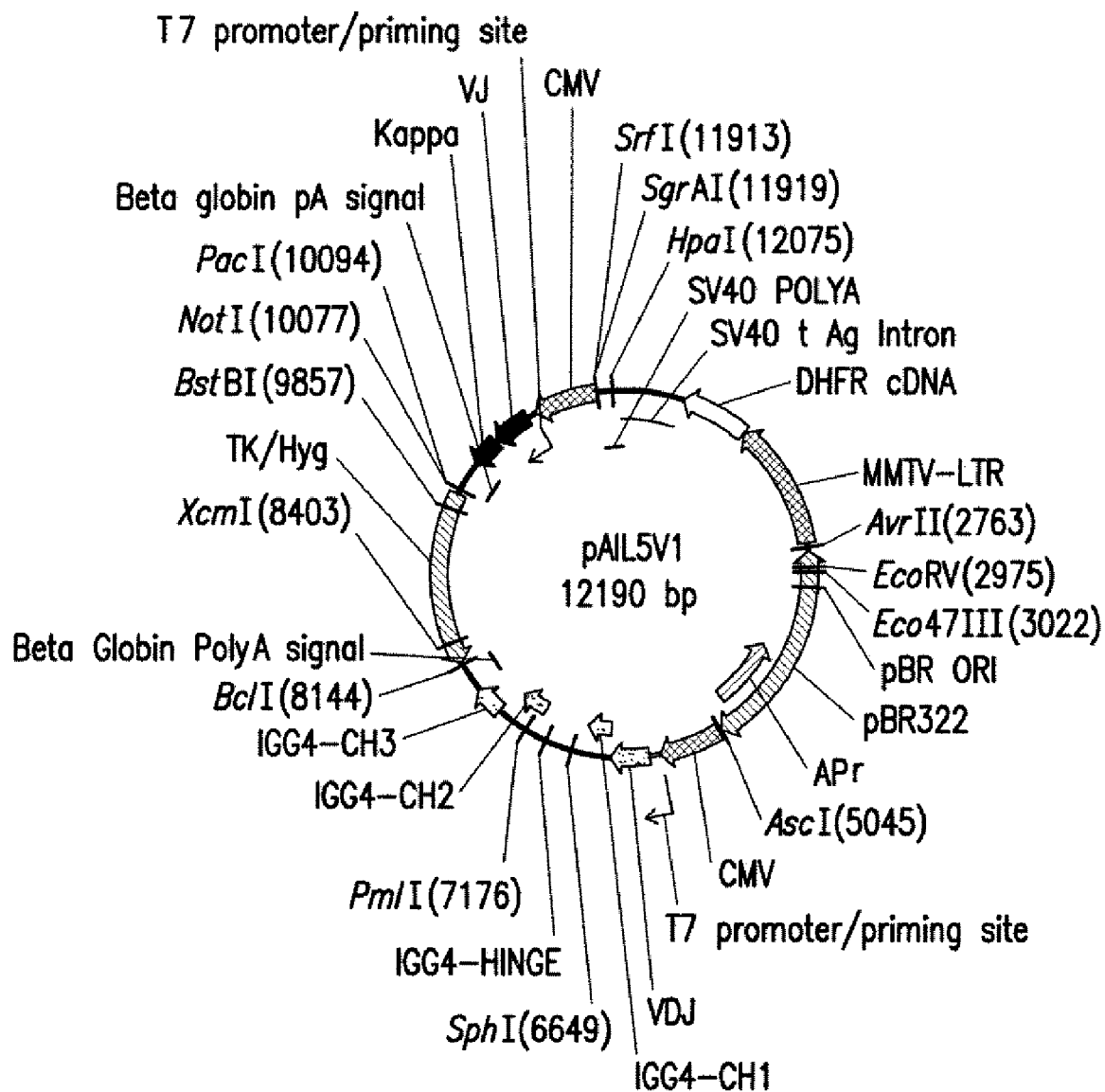
FIG. 4. Plasmid map of pAIL5V1.
The anti-IL-5 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK/Hyg).
SV40 t Ag Intron: Start: 12177 End: 600
SV40 POLYA signal: Start: 11930 End: 12178
CMV Promoter: Start: 11238 End: 11892
T 7 promoter/priming site: Start: 11219 End: 11238
VDJ (Anti-IL-5 light chain): Start: 10718 End: 11148
IGκ (Anti-IL-5 light chain): Start: 10382 End: 10717
Beta Globin Poly A signal: Start: 10126 End: 10374
TK/Hyg: Start: 8161 End: 10033
Beta Globin Poly A signal: Start: 7877 End: 8115
IGG4-CH3 (Anti-IL-5 antibody heavy chain): Start: 7517 End: 7834
IGG4-CH2 (Anti-IL-5 antibody heavy chain): Start: 7087 End: 7419
IGG4-HINGE (Anti-IL-5 antibody heavy chain): Start: 6933 End: 6968
IGG4-CH1 (Anti-IL-5 antibody heavy chain): Start: 6247 End: 6540
VDJ (Anti-IL-5 antibody heavy chain): Start: 5813 End: 6247
T 7 promoter/priming site: Start: 5723 End: 5742
CMV Promoter: Start: 5069 End: 5723
AP$^r$ (Ampicillin resistance): Start: 3965 End: 4828
PBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347
Figure 5:
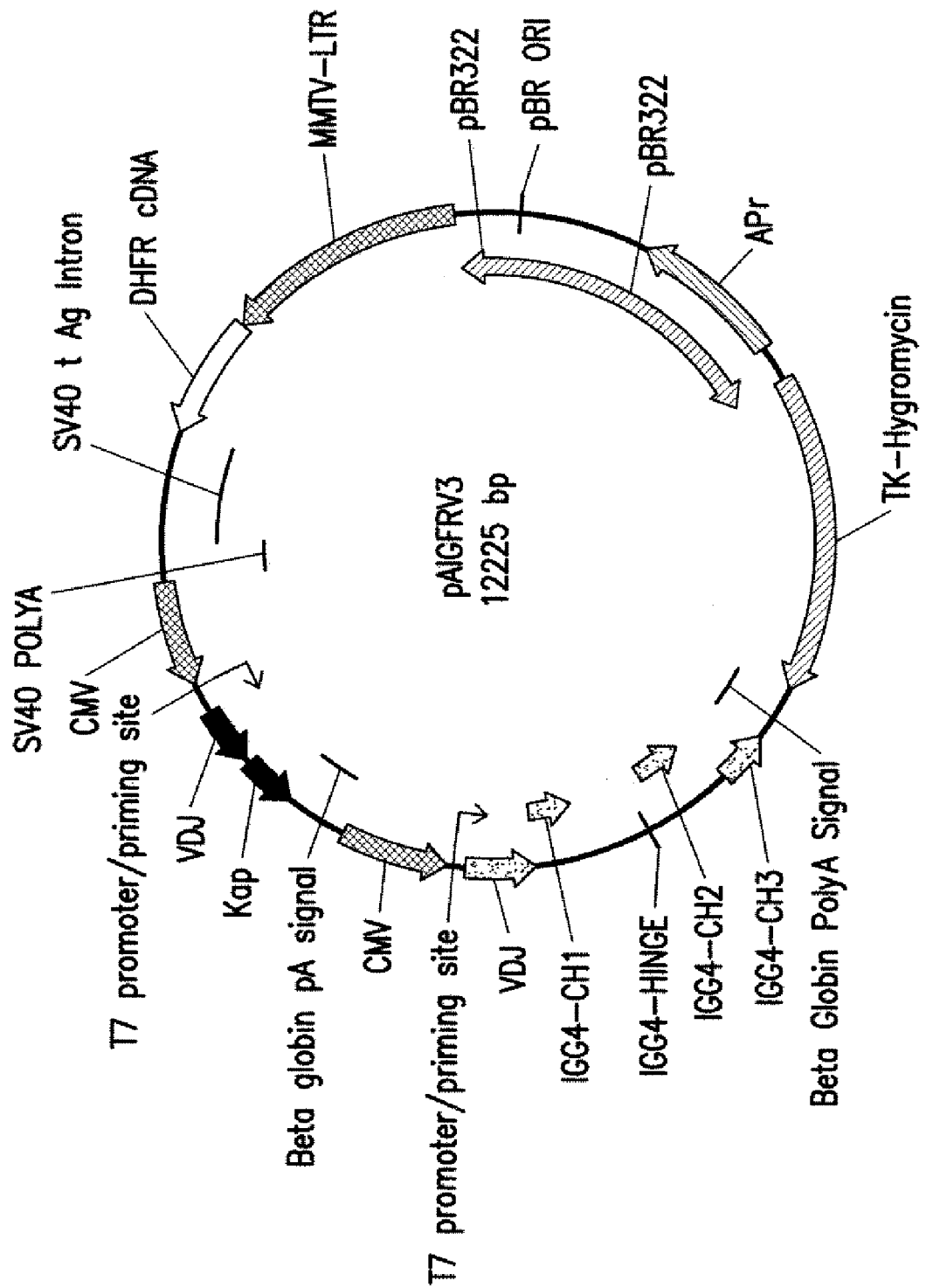
FIG. 5. Plasmid map of pAIGFRV3.
The anti-IGFR1 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK-Hygromycin). The DHFR cDNA, along with its promoter (MMTV-LTR) for plasmid amplification and the hygromycin B coding sequence, along with its TK promoter for selection in mammalian cells, are shown.
AP(R): Start: 3965 End: 4828
IgG1 non genomic region: Start: 7234 End: 8214
VDJ of IGFR1 of 11D8 hybridoma: Start: 8214 End: 8641
DHFR cDNA: Start: 601 End: 1347
SV40 t Ag Intron: Start: 11603 End: 600
Kappa chain of hu-antiIGFR gene: Start: 9761 End: 10096
VDJ Domain of hu-anti IGFR gene for light chain: Start: 10097 End: 10477
pBR322 sequence: Start: 2811 End: 3019
pBR322 sequence: Start: 3020 End: 5033
TK-Hygromycin: Start: 5053 End: 6925
Beta Globin Poly A signal: Start: 6971 End: 7209
Beta globin pA signal: Start: 9505 End: 9753
SV40 POLYA: Start: 11356 End: 11604
MMTV-LTR: Start: 1348 End: 2810
CMV promoter: Start: 10664 End: 11318
T 7 promoter/priming site: Start: 8723 End: 8742
CMV promoter: Start: 8742 End: 9396
T 7 promoter/priming site: Start: 10645 End: 10664
pBR ORI: Start: 3207 End: 3207
Figure 6:
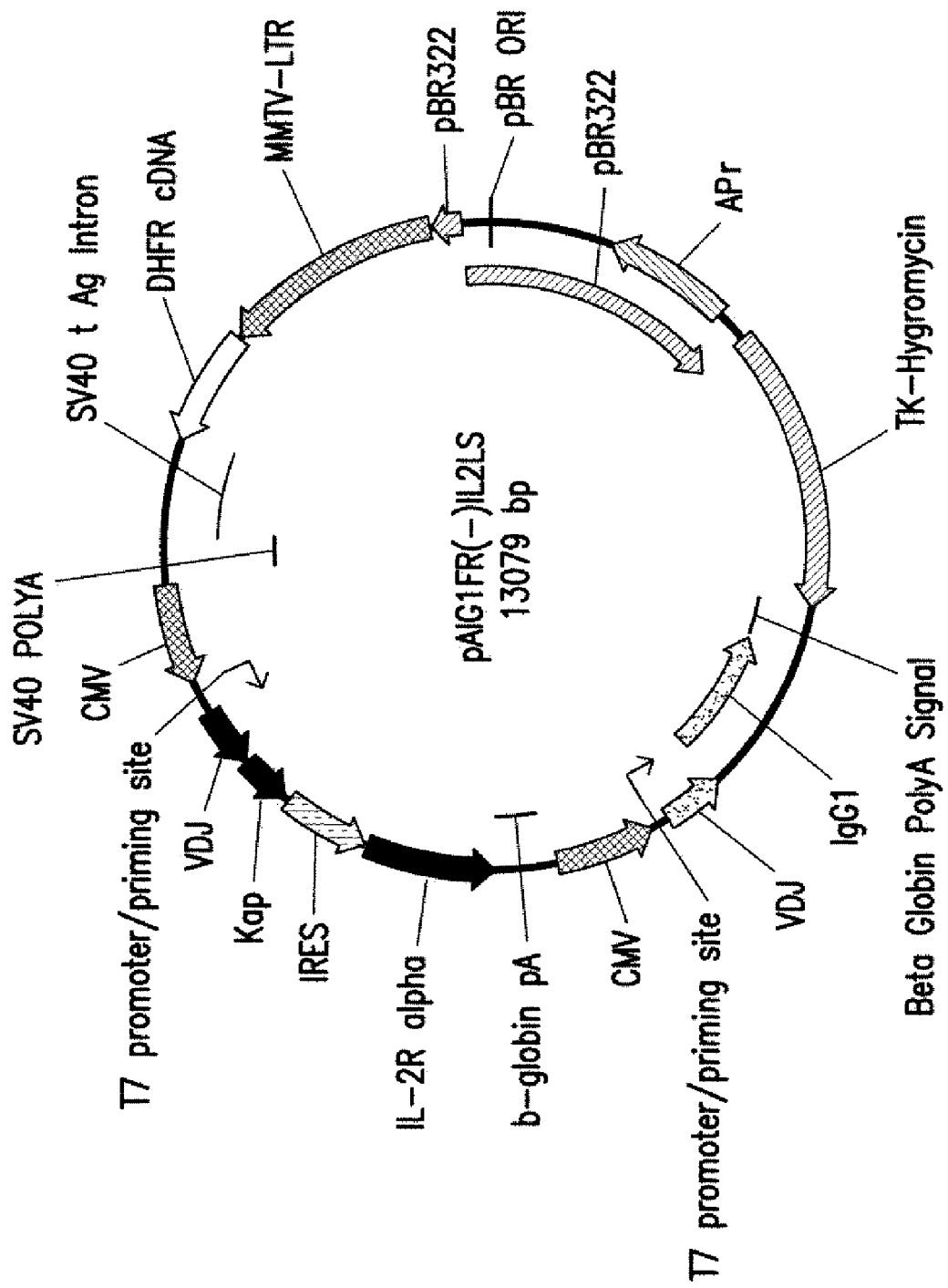
FIG. 6. Plasmid map of pAIG1FR(−)IL2LS.
This plasmid drives expression of the anti-IGFR1 antibody and the membrane domain of the IL2 receptor. Three independent expression cassettes containing four genes including heavy and light chain anti-IGFR1, truncated IL2 receptor and hygromycin B are incorporated into the multiple cloning site of pXBLS.
SV40 t Ag Intron: Start: 13066 End: 600
SV40 POLYA: Start: 12819 End: 13067
CMV: Start: 12115 End: 12769
T7 promoter/priming site: Start: 12096 End: 12115
VDJ (Anti-IGFR1 light chain): Start: 11548 End: 11928
Kappa (Kap; Anti-IGFR1 light chain): Start: 11212 End: 11547
IRES: Start: 10621 End: 11195
IL-2R alpha: Start: 9787 End: 10615
Beta Globin Poly A signal (β-globin pA)Start: 9505 End: 9753
CMV: Start: 8742 End: 9396
T7 promoter/priming site: Start: 8723 End: 8742
Figure 7:
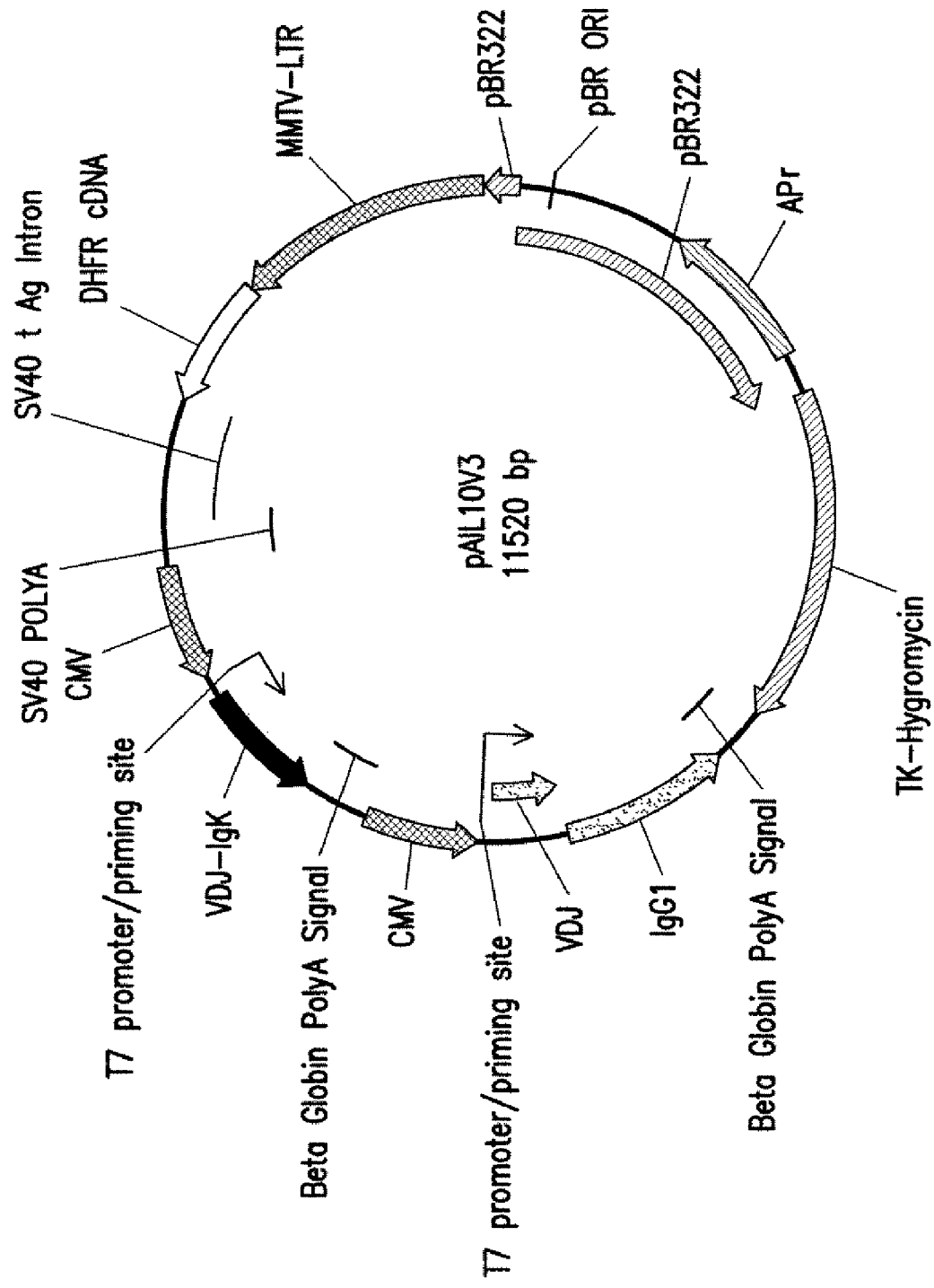

FIG. 7. Plasmid map of pAIL10V3.

The plasmid drives expression of anti-IL10. The anti-IL10 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK-Hygromycin). The dhfr cDNA, along with its promoter (MMTV-LTR) for plasmid amplification and the hygromycin B coding sequence, along with its TK promoter for selection in mammalian cells, are shown.

SV40 t Ag Intron: Start: 11507 End: 600
SV40 POLYA signal: Start: 11260 End: 11508
CMV: Start: 10568 End: 11222
T7 promoter/priming site: Start: 10549 End: 10568
VDJ-IgK (anti-IL10 rat antibody 12G8 light chain): Start: 9739 End: 10468
Beta globin Poly A signal: Start: 9478 End: 9726
CMV promoter: Start: 8715 End: 9369
T7 promoter/priming site: Start: 8696 End: 8715
VDJ (anti-IL10 rat antibody 12G8 heavy chain): Start: 8214 End: 8644
IgG1 non genomic region (anti-IL10 rat antibody 12G8 heavy chain): Start: 7234 End: 8214
Beta Globin Poly A signal: Start: 6971 End: 7209
TK promoter driving Hygromycin gene (TK-Hygromycin): Start: 5053 End: 6925
AP$^r$: Start: 3965 End: 4828
pBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347

Figure 8:
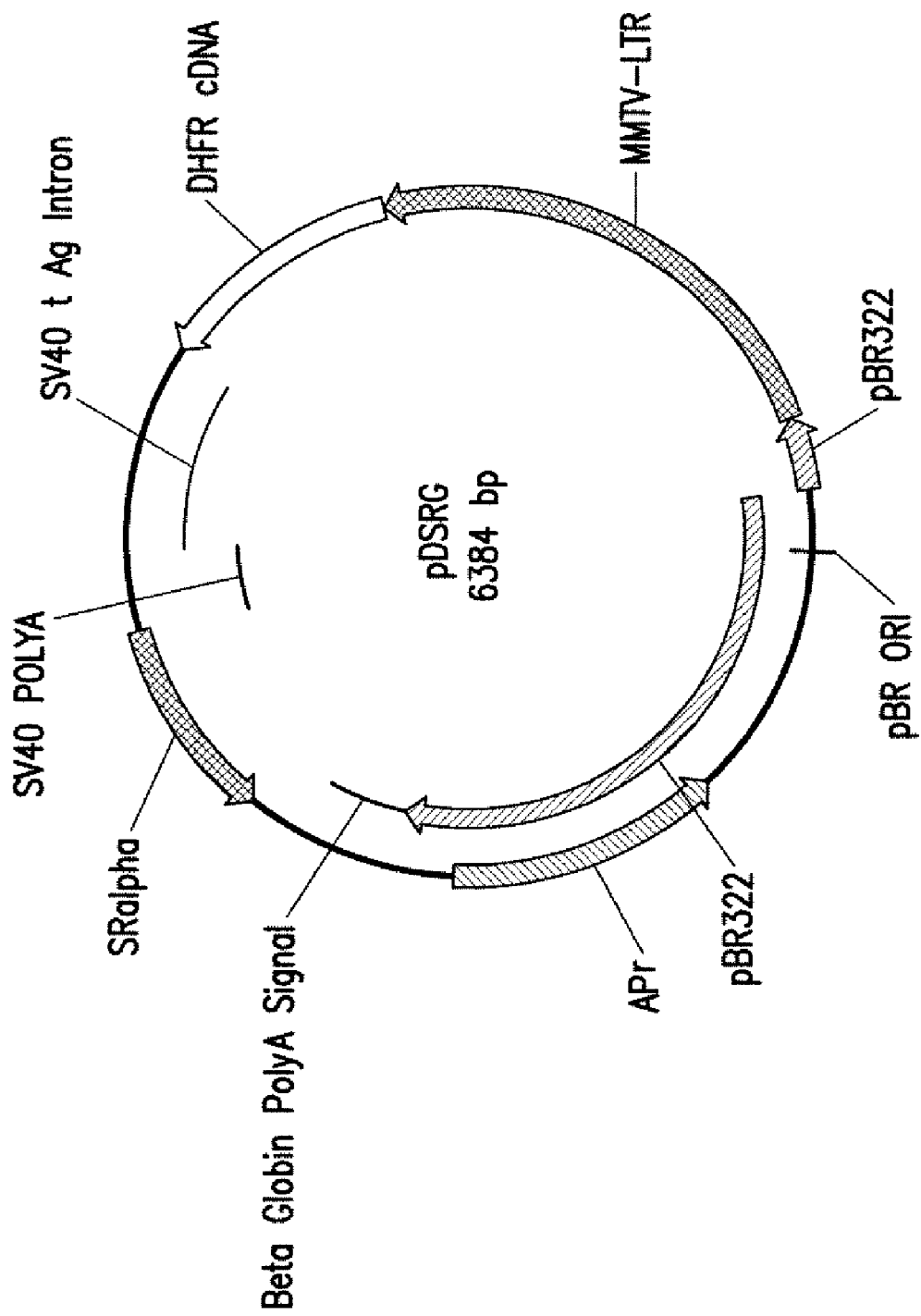

FIG. 8. Plasmid map of pDSRG.

This plasmid is deposited at the American Type Culture Collection (10801 University Boulevard; Manassas, Va. 20110-2209), under catalogue number 68233. The plasmid includes the SRα promoter, a strong SV40-based promoter and the dihydrofolate reductase (DHFR) cDNA for plasmid amplification in the presence of methotrexate in dhftr(-) Chinese hamster ovary (CHO) cells.

SV40 t Ag Intron: Start: 6371 End: 600
SV40 POLYA signal: Start: 6124 End: 6372
SRα promoter: Start: 5486 End: 6123
Beta Globin Poly A signal: Start: 5038 End: 5298
Ap$^r$: Start: 3965 End: 4828
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347

Figure 9:
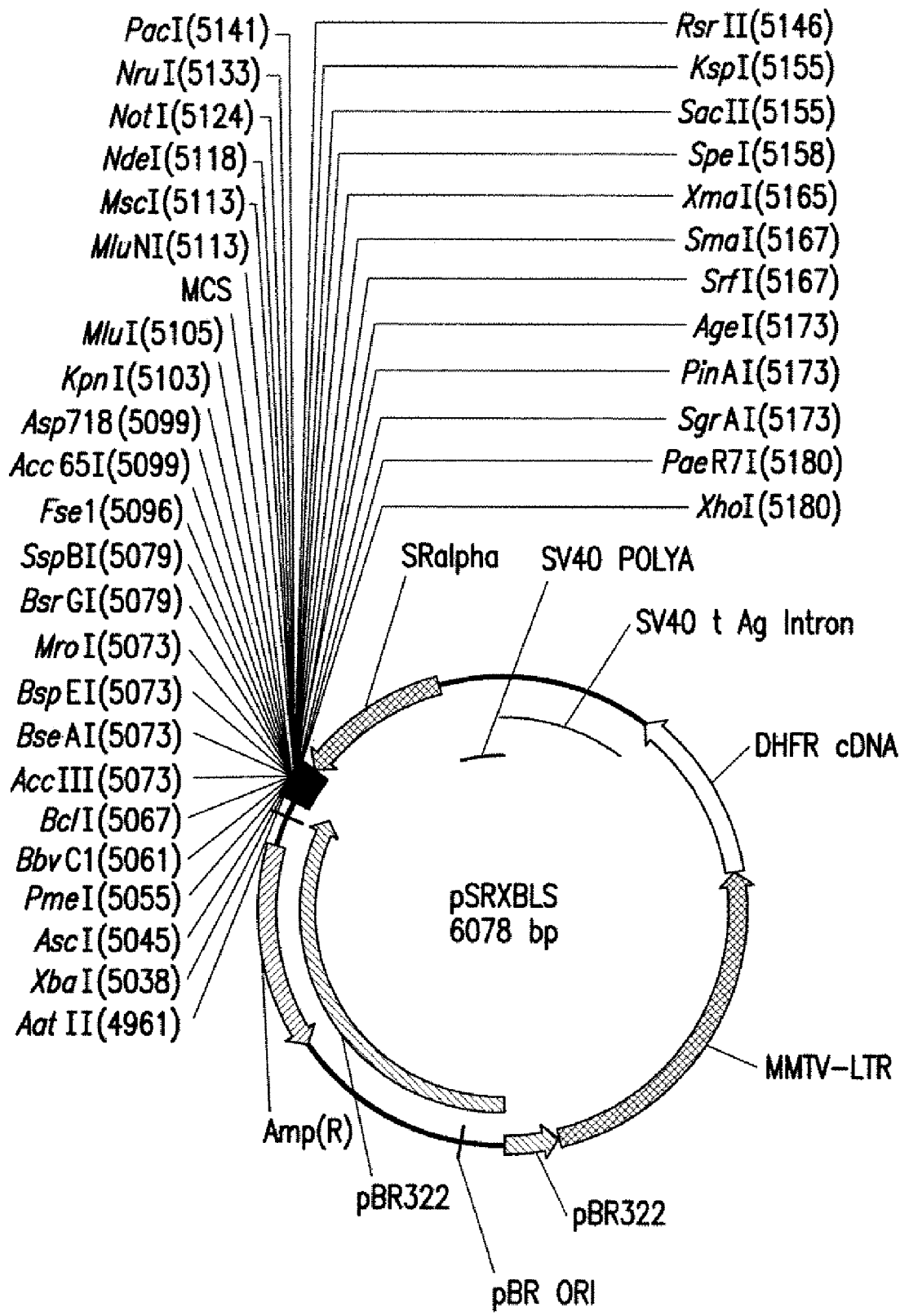

FIG. 9. Plasmid map of pSRXBLS.

pSRXBLS is the direct descendent of pDSRG replacing its own multiple cloning site with a large multiple cloning site. PSRXBLS is the progenitor plasmid of pXBLS.

SV40 t Ag Intron: Start: 6065 End: 600
SV40 POLYA signal: Start: 5818 End: 6066
SRα promoter: Start: 5180 End: 5817
MCS: Start: 5038 End: 5179
Amp(R): Start: 3965 End: 4828
pBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347.

Figure 10:
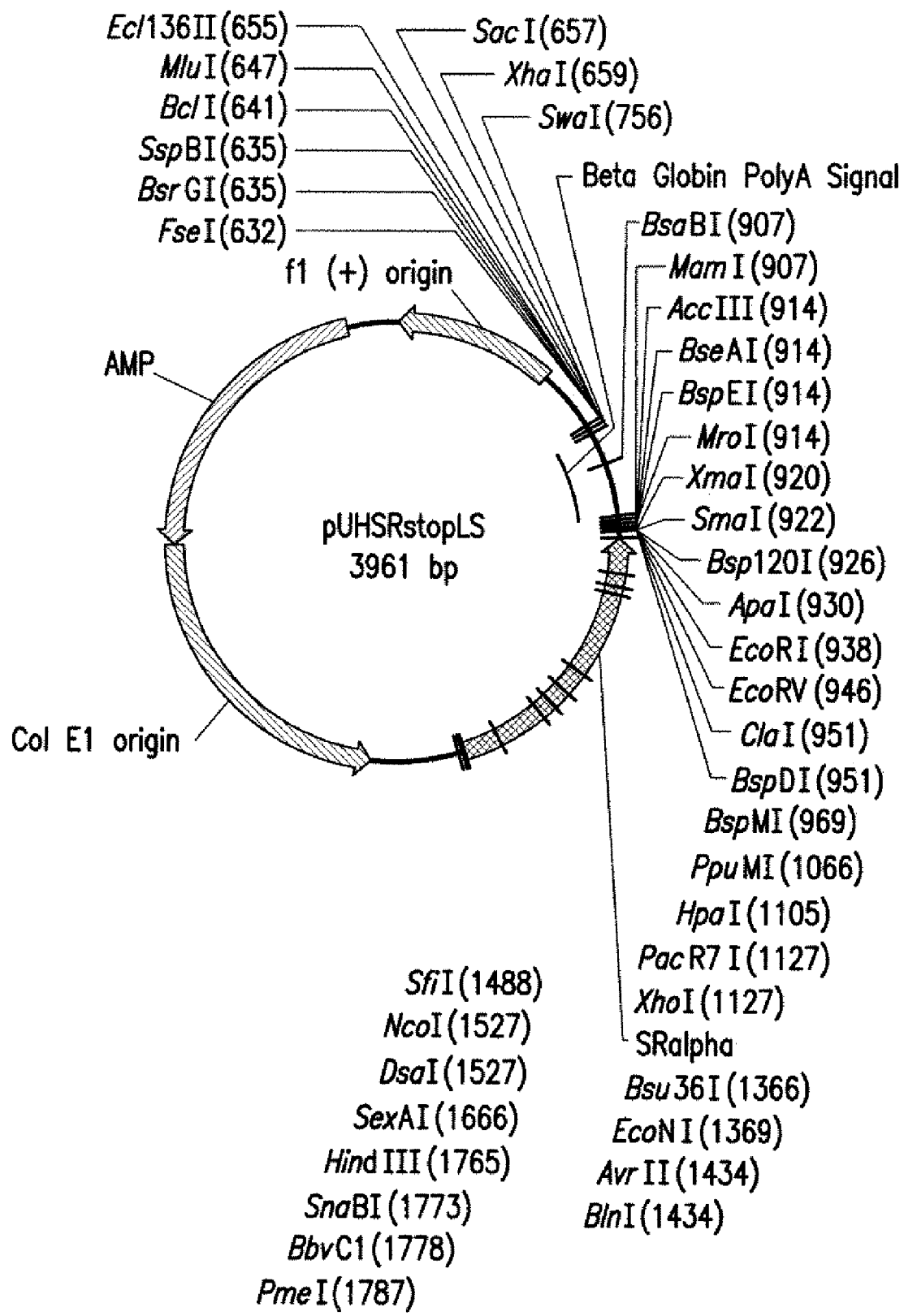

FIG. 10. Plasmid map of pUHSRstopLS.

pUHSRstopLS is the descendent plasmid to pUHLS carrying the SRα promoter and 249 bp of chicken β-globin terminator. This plasmid alone can be used to express any gene of interest. Also, it can be used as a transfer vector to transfer a complete expression cassette of part of a complex protein to pXBLS where all the expression cassettes can be assembled on a single plasmid.

Amp: Start: 2975 End: 3832
Col E1 origin: Start: 2032 End: 2972
Srα promoter with Intron: Start: 955 End: 1764
Beta Globin Poly A signal: Start: 673 End: 911
f1 (+) origin: Start: 3 End: 459

Figure 11:
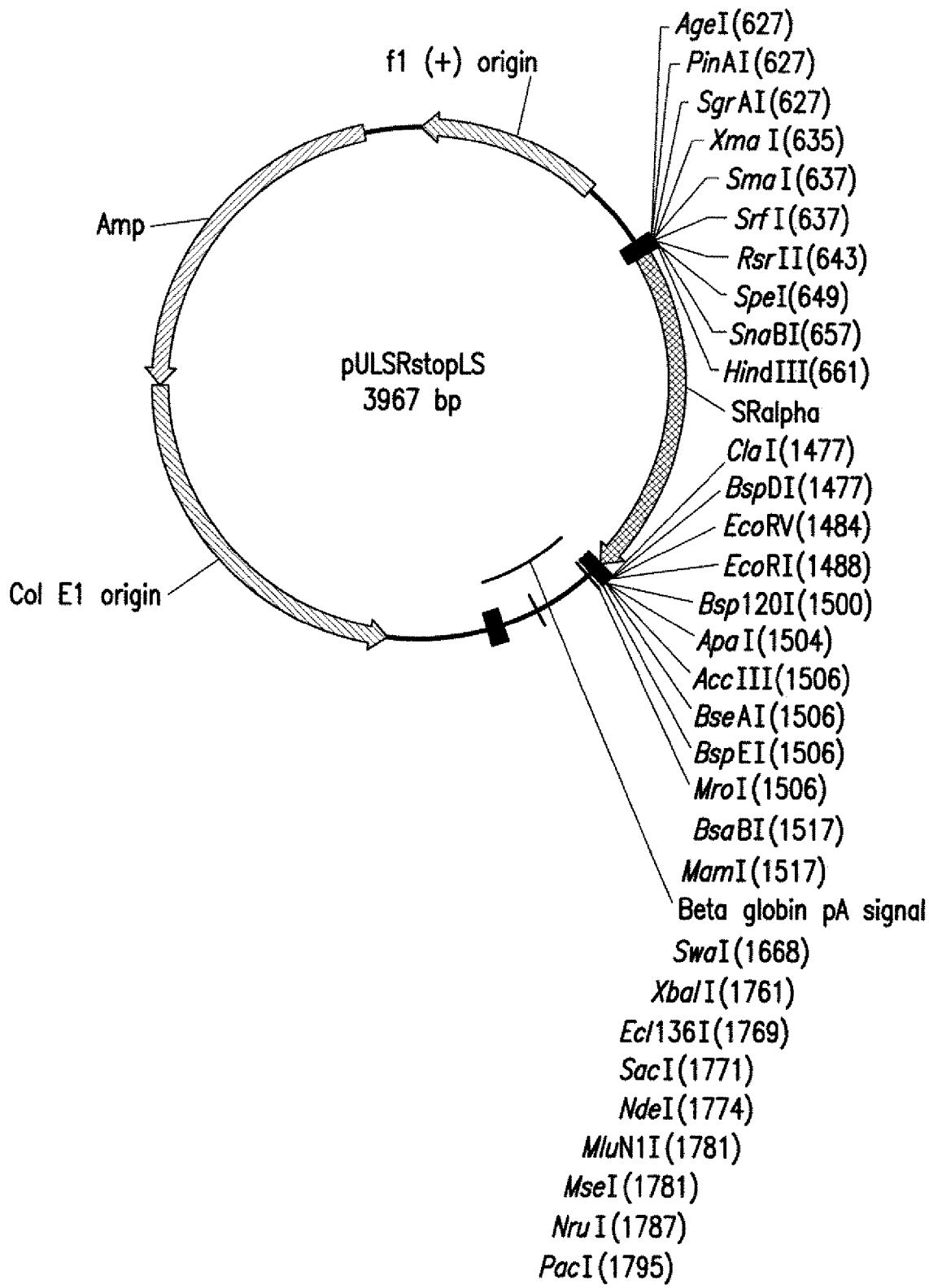

FIG. 11. Plasmid map of pULSRstopLS.

pULSRstopLS is the descendent plasmid to pULLS carrying the SRα promoter and a 249 bp of chicken β-globin terminator. This plasmid alone can be used to express any gene of interest. Also, it can be used as a transfer vector to transfer a complete expression cassette of part of a complex protein to pXBLS where all the expression cassettes can be assembled on a single plasmid.

Amp: Start: 2981 End: 3838
Col E1 origin: Start: 2038 End: 2978
Beta globin poly A signal: Start: 1512 End: 1760
Srα promoter: Start: 665 End: 1474
f1 (+) origin: Start: 3 End: 459

Figure 12:
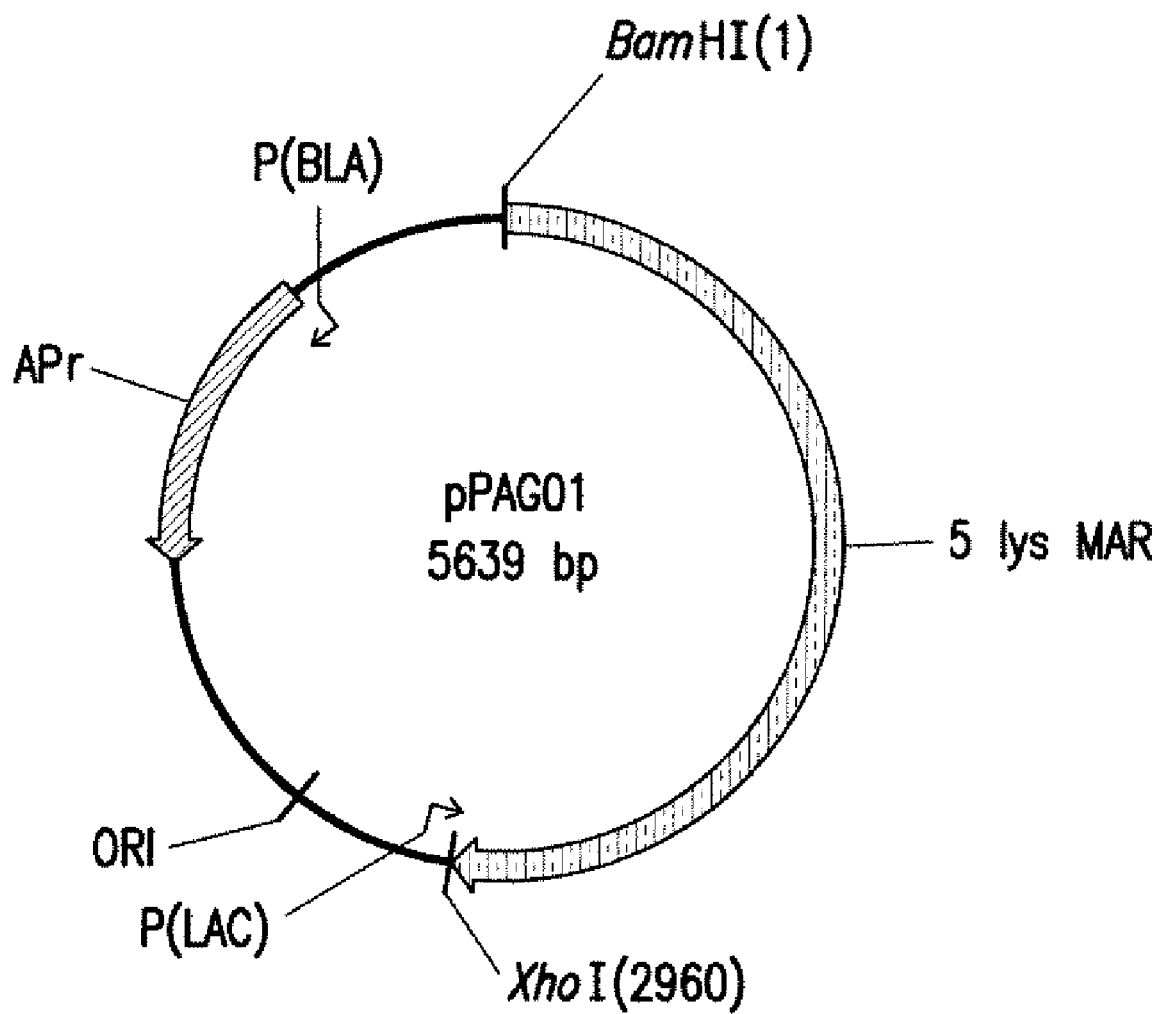

FIG. 12. Plasmid map of pPAG01.

This plasmid contains Selexis's (Geneva, Switzerland) ~3 kb chicken lysozyme MAR, flanked by Xba1 and BamH1 site.

AP(R) (bla gene-Ap(r) determinant): Start: 4165 End: 5022
Selexis Inc. 5' lys MAR: Start: 1 End: 2960
P(LAC): Start: 3043 End: 3043
P(BLA) (bla gene promoter): Start: 5057 End: 5057
Replication Origin ORI (RNaseH cleavage point): Start: 3403 End: 3403

Figure 13:
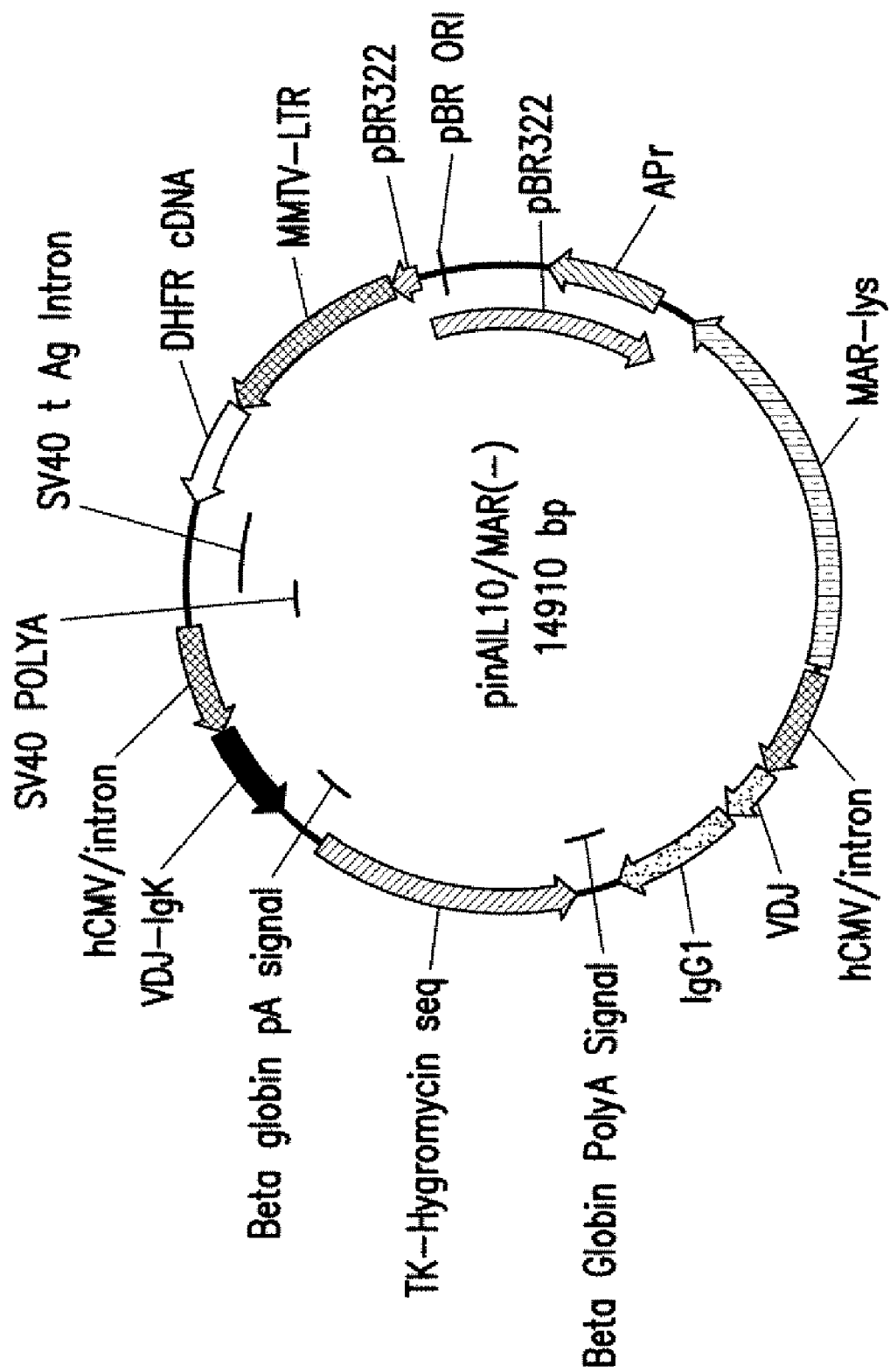

FIG. 13. Plasmid map of pinAIL10/MAR(-).

The figure describes the map of plasmid, pinAIL10/MAR (-), that has the chicken lysozyme MAR element juxtaposed to the heavy chain expression cassette of the anti-IL10 gene containing the hygromycin resistance marker.

AP(R): Start: 3965 End: 4828
MAR-lys (MAR-lys is Matrix Attachment Region): Start: 5087 End: 8045
VDJ (VDJ region of anti-IL10 (12G8)): Start: 8928 End: 9369
IgG1 (IgG1 non genomic region): Start: 9374 End: 10354
DHFR cDNA: Start: 601 End: 1347
SV40 t Ag Intron: Start: 14897 End: 600
VDJ-IgK (VDJ-IgK for 12G8 light chain (anti-IL10)): Start: 13026 End: 13755
pBR322: Start: 2811 End: 3019
pBR322: Start: 3020 End: 5033
TK-Hygromycin: Start: 10663 End: 12672
Beta Globin Poly A signal: Start: 10379 End: 10617
Beta globin pA signal: Start: 12765 End: 13013
SV40 POLYA: Start: 14650 End: 14898

MMTV-LTR: Start: 1348 End: 2810
hCMV/intron (Human CMV promoter with hybrid intron): Start: 8077 End: 8918
hCMV/intron (Human CMV promoter and hybrid intron): Start: 13771 End: 14612
pBR ORI: Start: 3207 End: 3207

Figure 14:
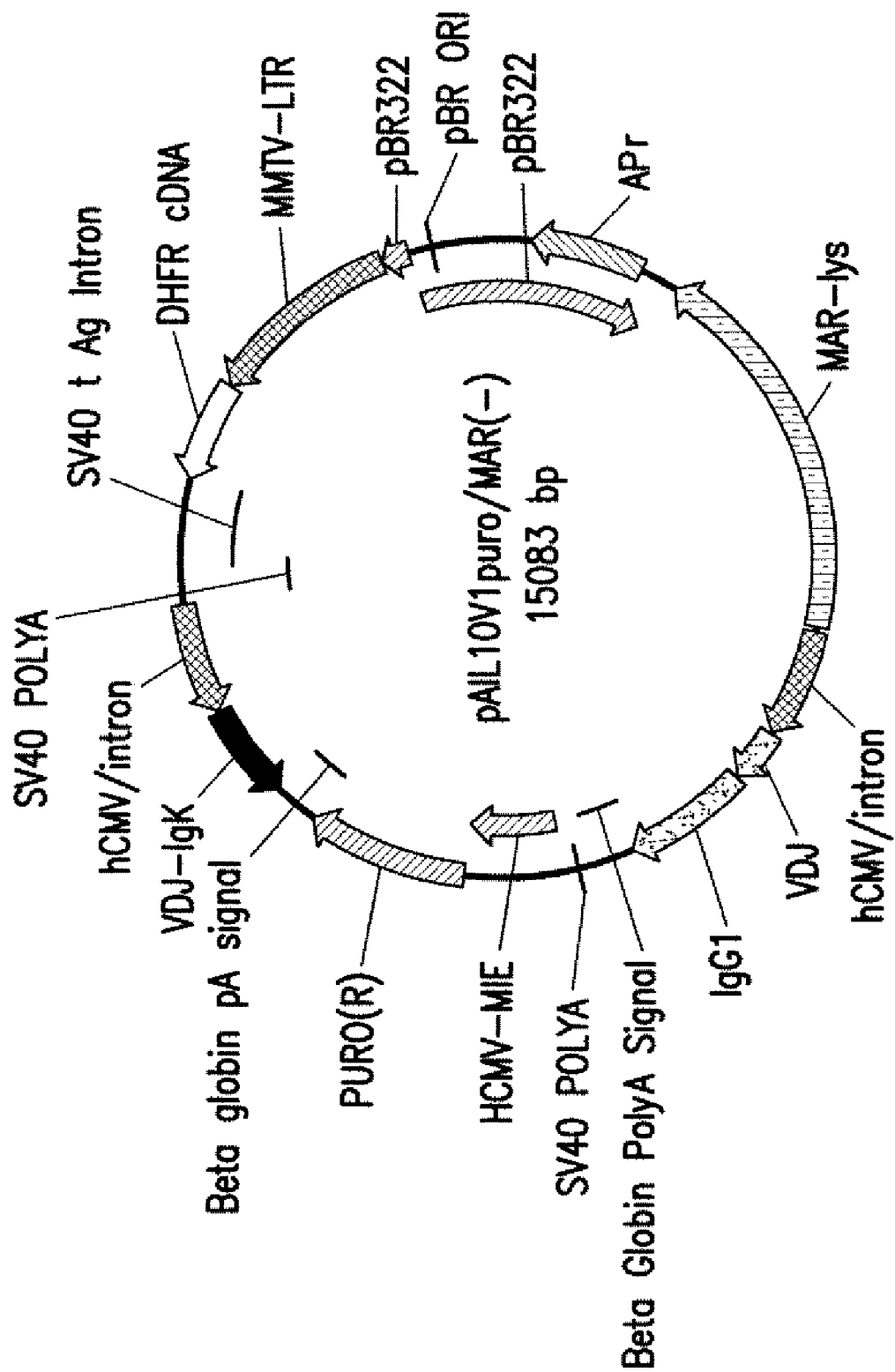

FIG. 14. Plasmid map of pAIL10V1/puro/MAR(−).

The figure describes the map of plasmid, pAIL10/puro/MAR(−), that has chicken lysozyme MAR element juxtaposed to the heavy chain expression cassette of the anti-IL10 gene containing the puromycin instead of the hygromycin resistance marker.
AP: Start: 3965 End: 4828
MAR-lys (MAR-lys is Matrix Attachment Region): Start: 5087 End: 8045
VDJ: Start (VDJ region of anti-IL10 (12G8)): 8928 End: 9369
IgG1 (IgG1 non genomic region): Start: 9374 End: 10354
PURO: Start: 11674 End: 12905
DHFR cDNA: Start: 601 End: 1347
SV40 t Ag Intron: Start: 15070 End: 600
VDJ-IgK (VDJ-IgK for 12G8 light chain (anti-IL10)): Start: 13199 End: 13928
(Complementary)
pBR322: Start: 2811 End: 3019
pBR322: Start: 3020 End: 5033
Beta Globin Poly A signal: Start: 10379 End: 10617
SV40 POLYA: Start: 10784 End: 10789
Beta globin pA signal: Start: 12938 End: 13186
SV40 POLYA: Start: 14823 End: 15071
MMTV-LTR: Start: 1348 End: 2810
hCMV/intron (Human CMV promoter with hybrid intron): Start: 8077 End: 8918
HCMV-MIE: Start: 10902 End: 11660
hCMV/intron (Human CMV promoter and hybrid intron): Start: 13944 End: 14785
(Complementary)
pBR ORI: Start: 3207 End: 3207

Figure 15:
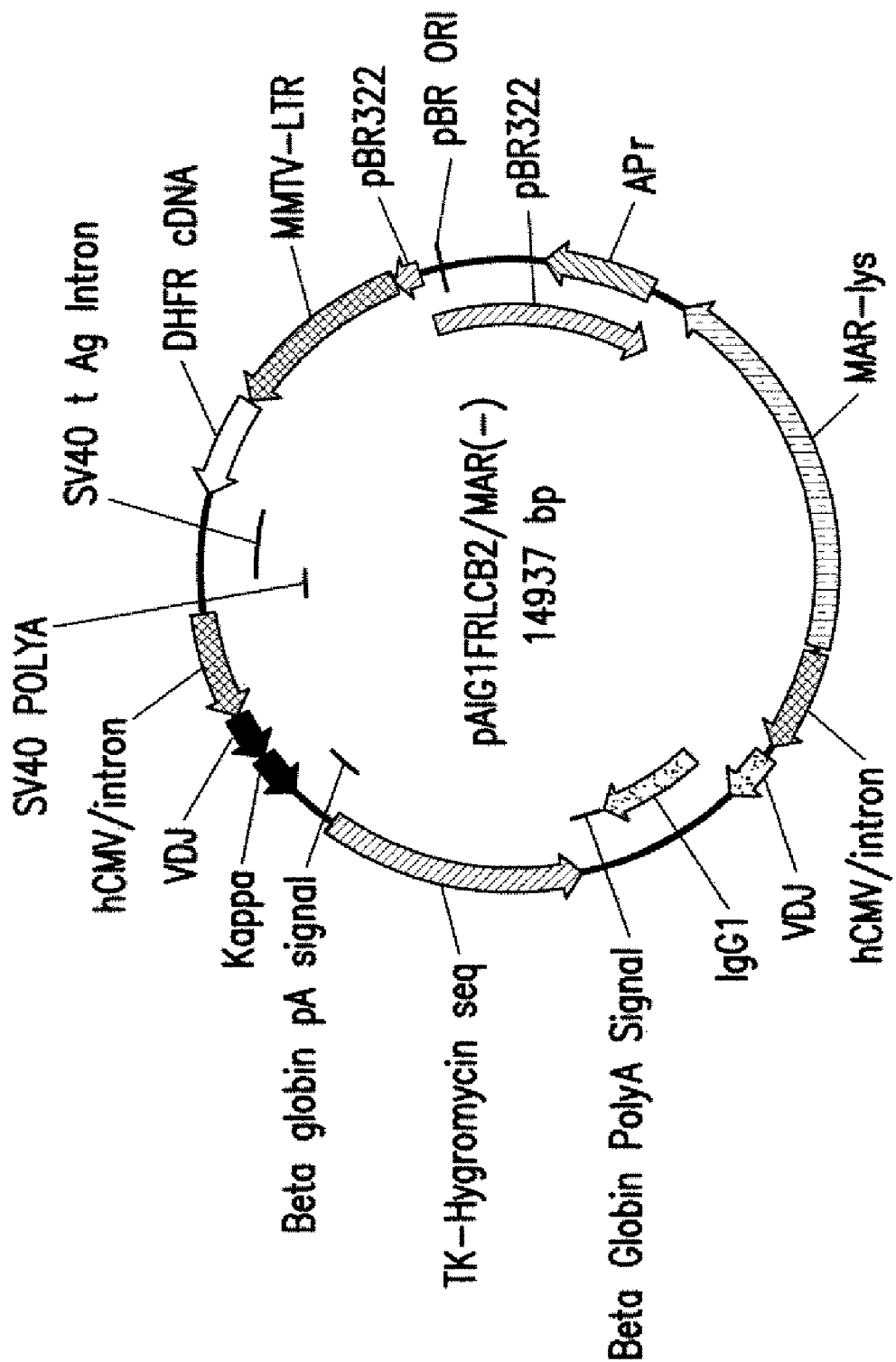

FIG. 15. Plasmid map of pAIGFRLCb2/MAR(−).

The figure describes the map of plasmid, that has chicken lysozyme MAR element juxtaposed to the heavy chain expression cassette of the anti-IGFR1 gene containing the hygromycin resistance marker.
AP(R): Start: 3965 End: 4828
MAR-lys (MAR-lys is Matrix Attachment Region): Start: 5087 End: 8045
VDJ (VDJ of IGFR1 of 11 D8 hybridoma): Start: 8974 End: 9401
IgG1 (IgG1 non genomic region): Start: 9401 End: 10381
DHFR cDNA: Start: 601 End: 1347
SV40 t Ag Intron: Start: 14924 End: 600
Kappa (Kappa Chain): Start: 13063 End: 13386
VDJ (VDJ of IGFR1 (LCb, human germline sequence)): Start: 13387 End: 13764
pBR322: Start: 2811 End: 3019
pBR322: Start: 3020 End: 5033
TK-Hygromycin: Start: 10690 End: 12699
Beta Globin Poly A signal: Start: 10406 End: 10644
Beta globin pA signal: Start: 12792 End: 13040
SV40 POLYA: Start: 14677 End: 14925
MMTV-LTR: Start: 1348 End: 2810
hCMV/intron (Human CMV promoterwith hybrid intron): Start: 8077 End: 8918
hCMV/intron (Human CMV promoter and hybrid intron): Start: 13786 End: 14627
pBR ORI: Start: 3207 End: 3207

Figure 16:
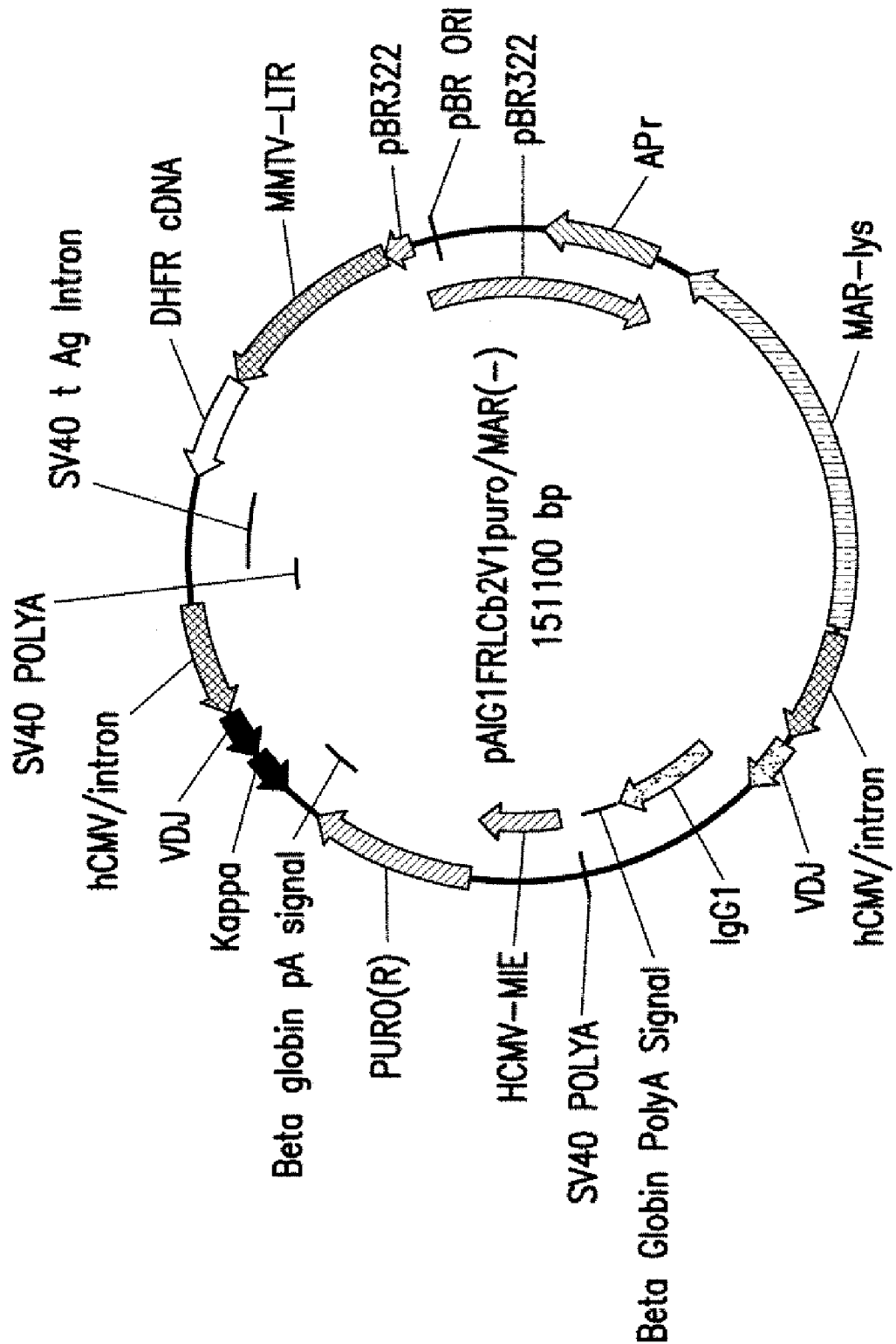

FIG. 16. Plasmid map of pAIGFRLCb2V1/puro/MAR(−).

The figure describes the map of plasmid, that has chicken lysozyme MAR element juxtaposed to the heavy chain expression cassette of the anti-IGFR1 gene containing the puromycin instead of the hygromycin resistance marker.
AP(R): Start: 3965 End: 4828
MAR-lys (MAR-lys is Matrix Attachment Region): Start: 5087 End: 8045
VDJ (VDJ of IGFR1 of 11D8 hybridoma): Start: 8974 End: 9401
IgG1 (IgG1 non genomic region): Start: 9401 End: 10381
PURO(R): Start: 11701 End: 12932
DHFR cDNA: Start: 601 End: 1347
SV40 t Ag Intron: Start: 15097 End: 600
Kappa (Kappa Chain): Start: 13236 End: 13559
VDJ (VDJ of IGFR1 (LCb, human germline sequence)): Start: 13560 End: 13937
pBR322: Start: 2811 End: 3019
pBR322: Start: 3020 End: 5033
Beta Globin Poly A signal: Start: 10406 End: 10644
SV40 POLYA: Start: 10811 End: 10816
Beta globin pA signal: Start: 12965 End: 13213
SV40 POLYA: Start: 14850 End: 15098
MMTV-LTR: Start: 1348 End: 2810
hCMV/intron (Human CMV promoter with hybrid intron): Start: 8077 End: 8918
HCMV-MIE: Start: 10929 End: 11687
hCMV/intron (Human CMV promoter and hybrid intron): Start: 13959 End: 14800
pBR ORI: Start: 3207 End: 3207

DETAILED DESCRIPTION

The present invention provides a plasmid system useful for recombinant protein expression in any cell, for example in a mammalian cell, a bacterial cell, a yeast cell or an insect cell. The plasmid system is amenable to any cell based expression of a broad range of recombinant proteins, ranging from simple proteins, such as interferon, to complex proteins, such as antibodies. The system offers many common and rare restriction sites to accommodate a variety of expression cassettes. It also provides flexibility in the choice of various elements of an expression cassette, such as a promoter, enhancer, and terminator, as well as an antibiotic resistance marker. The plasmids can also be used as simple transfer vectors. The system offers potential for both transient as well as stable expression. The pXBLS vector carries the dihydrofolate reductase (DHFR) coding region for selection and amplification of the plasmid in DHFR deficient mammalian cells, e.g. CHO DXB-11 and CHO DG44. Thus, the system can be used for isolating stable clones, harnessing gene amplification and selection. The plasmid system includes two universal transfer plasmids, pUHLS and pULLS, which are useful for carrying out expression of the parts of a complex protein such as an antibody. Thus, the system offers options of co-transfection with universal vectors and single transfection with pXBLS. The ability of the plasmid system to cause such segregated expression of various parts is advantageous since it is sometimes necessary to take a deeper insight into the expression of individual units of a multi-subunit protein in order to analyze the overall expression of the complex protein. The system can also be used to address the effect of directional variability, resulting from the orientation of the multiple genes in the plasmid for the expression of multi-subunit proteins. Thus, a strategy in placing multiple expression cassettes can be arrived at for optimal expression of a complex protein.

The plasmid system of the invention has been demonstrated to direct high levels of expression of multiple polypeptides including anti-IL5 antibody, anti-IGFR1 antibody, IL2 receptor membrane domain, and anti-IL10 antibody. Other proteins may also be expressed in the plasmid system of the invention including interferon, fibrinogen, ion channels, bacterial porins (e.g., ompF), and the nicotinic acetylcholine receptor (nAChR).

In one embodiment of the invention, the plasmid system comprises the light and heavy chain of the fully human, monoclonal anti-IGFR1 antibody 15H12/19D12 which may also be referred to as 15H12 or as 19D12.

The parts to the plasmid system can be provided separately or, conveniently, together as part of a kit.

The present invention includes any of the polynucleotide comprising or consisting of a nucleotide sequence set forth, below, in Table 1, individually or as part of a plasmid system or kit. Polynucleotides of the invention can be in any form, including circular, linear, double-stranded or single-stranded.

TABLE 1

Polynucleotides of the invention.

| Polynucleotide | Sequence Identifier |
| --- | --- |
| pULLS | SEQ ID NO: 1 |
| pUHLS | SEQ ID NO: 2 |
| pXBLS | SEQ ID NO: 3 |
| pULSRstopLS | SEQ ID NO: 4 |
| pUHSRstopLS | SEQ ID NO: 5 |
| pAIL5V1 | SEQ ID NO: 6 |
| pAIGFRV3 | SEQ ID NO: 7 |
| pAIG1FR(−)IL2LS | SEQ ID NO: 8 |
| pAIL10V3 | SEQ ID NO: 9 |
| pXBLS multiple cloning site | SEQ ID NO: 10 |
| pUHLS multiple cloning site | SEQ ID NO: 11 |
| pULLS multiple cloning site | SEQ ID NO: 12 |
| pSRXBLS | SEQ ID NO: 13 |
| pDSRG | SEQ ID NO: 14 |
| Nucleotide sequence encoding the 15H12 and 19D12 light chain variable region-including signal peptide (15H12/19D12 LC) | SEQ ID NO: 15 |
| Amino acid sequence of the 15H12 and 19D12 light chain variable region-including signal peptide | SEQ ID NO: 16 |
| Nucleotide sequence encoding the 15H12 and 19D12 heavy chain variable region including signal peptide (15H12/19D12 HC) | SEQ ID NO: 17 |
| Amino acid sequence of the 15H12 and 19D12 heavy chain variable region including signal peptide | SEQ ID NO: 18 |
| Nucleotide sequence encoding the 15H12/19D12 light chain F (LCF) | SEQ ID NO: 19 |
| Amino acid sequence of the 15H12/19D12 light chain F | SEQ ID NO: 20 |
| Nucleotide sequence encoding the 15H12/19D12 heavy chain A (HCA) | SEQ ID NO: 21 |
| Amino acid sequence of the 15H12/19D12 heavy chain A | SEQ ID NO: 22 |
| Nucleotide sequence of the chicken lysozyme MAR element | SEQ ID NO: 23 |
| pinAIL10/MAR(−) | SEQ ID NO: 24 |
| pAIL10V1/puro/MAR(−) | SEQ ID NO: 25 |
| pAIGFRLCb2/MAR(−) | SEQ ID NO: 26 |
| PAIGFRLCb2/puro/MAR(−) | SEQ ID NO: 27 |

Molecular Biology

In accordance with the present invention there may be employed conventional molecular biology, microbiology, and recombinant DNA techniques within the skill of the art. Such techniques are explained in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" includes the polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA or peptide, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

As used herein, the term "oligonucleotide" refers to a nucleic acid, generally of no more than about 300 nucleotides (e.g., 30, 40, 50, 60, 70, 80, 90, 150, 175, 200, 250, 300), that may be hybridizable to a genomic DNA molecule, a cDNA molecule, or an mRNA molecule encoding a gene, mRNA, cDNA, or other nucleic acid of interest. Oligonucleotides are usually single-stranded, but may be double-stranded. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" refers to a series of two or more amino acids in a protein, peptide or polypeptide.

"Protein", "peptide" or "polypeptide" includes a contiguous string of two or more amino acids.

The term "isolated polynucleotide" or "isolated polypeptide" includes a polynucleotide (e.g., RNA or DNA molecule, or a mixed polymer) or a polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"PCR amplification" of DNA as used herein includes the use of polymerase chain reaction (PCR) to increase the concentration of a particular DNA sequence within a mixture of DNA sequences. For a description of PCR see Saiki, eta., Science (1988) 239:487. Genes can be amplified, for example, in a plasmid in a cell. Cells harboring a plasmid containing an amplifiable, selectable marker, but lacking an endogenous marker gene, such as DHFR, can be selected with increasing amounts of a selecting agent, such as methotrexate (e.g., if the DHFR gene is on the plasmid). Typically, this procedure will cause the copy number of the plasmid containing the amplifiable, selectable marker in the cell to increase.

The term "host cell" includes any cell of any organism that is selected, modified, transfected, transformed, grown, or used or manipulated in any way, for the production of a substance by the cell, for example the expression or replication, by the cell, of a gene, a DNA or RNA or a protein. For example, a host cell may be a bacteria such as E. coli or an eukaryotic cell such as a CHO cell.

A "cassette" or an "expression cassette" refers to a DNA coding sequence or segment of DNA that codes for an expression product (e.g., peptide or RNA) that can be inserted into a vector at defined restriction sites. The DNA coding sequence can be operably linked to a promoter and/or to a terminator and/or polyA signal.

The sequence of a nucleic acid may be determined by any method known in the art (e.g., chemical sequencing or enzymatic sequencing). "Chemical sequencing" of DNA includes methods such as that of Maxam and Gilbert (Proc. Natl. Acad. Sci. USA (1977) 74:560), in which DNA is randomly cleaved using individual base-specific reactions. "Enzymatic sequencing" of DNA includes methods such as that of Sanger (Sanger, et al., Proc. Natl. Acad. Sci. USA (1977) 74:5463).

The present invention includes nucleic acids of the invention flanked by natural regulatory (expression control) sequences, which may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

"Internal ribosome entry sites" "IRES" are commonly known in the art. Internal ribosome entry sites have been identified in a several genes including eIF4G (Johannes et a., RNA 4: 1500-1513 (1998)), DAP5 (Henis-Korenblit et al., Molecular and Cellular Biology 20: 496-506 (2000)), c-Myc.(Stoneley et al., Molecular and Cellular Biology 20: 1162-1169 (2000)), NF-κ-b repressing factor (Oumard et al., Molecular and Cellular Biology 20: 2755-2759 (2000)), VEGF (Huez et al., Molecular and Cellular Biology 18: 6178-6190 (1998)), FGF-2 (Creancier et al., Journal of Cell Biology 150: 275-281 (2000)), PDGF-B (Bernstein et al., Journal of Biological Chemistry 272: 9356-9362 (1997)), X-linked inhibitor of apoptosis (XIAP) (Holcik et al., Oncogene 19: 4174-4177 (2000)), Apaf-1 (Coldwell et a., Oncogene 19: 899-905 (2000)) and BiP (Macejak et al., Nature 353: 90-94 (1991)).

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention.

A coding sequence is "under the control of", "functionally associated with", "operably linked to" or "operably associated with" transcriptional and translational control sequences in a cell when the sequences direct or regulate expression of the sequence. For example, a promoter operably linked to a gene will direct RNA polymerase mediated transcription of the coding sequence into RNA, preferably mRNA, which then may be RNA spliced (if it contains introns) and, optionally, translated into a protein encoded by the coding sequence. A terminator/polyA signal operably linked to a gene terminates transcription of the gene into RNA and directs addition of a poly A signal onto the RNA.

The terms "express" and "expression" mean allowing or causing the information in a gene, RNA or DNA sequence to become manifest; for example, producing a protein by activating the cellular functions involved in transcription and translation of a corresponding gene. "Express" and "expression" include transcription of DNA to RNA and RNA to protein. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species. Examples of transformation methods which are very well known in the art include liposome delivery, electroporation, $CaPO_4$ transformation, DEAE-Dextran transformation, microinjection and viral infection.

The present invention includes vectors which comprise polynucleotides of the invention. The term "vector" may refer to a vehicle (e.g., a plasmid) by which a DNA or RNA sequence can be introduced into a host cell, so as to transform the host and, optionally, promote expression and/or replication of the introduced sequence.

The polynucleotides of the invention may be expressed in an expression system. The term "expression system" means a host cell and compatible vector which, under suitable conditions, can express a protein or nucleic acid which is carried by the vector and introduced to the host cell. Common expression systems include E. coli host cells and plasmid vectors, insect host cells and baculovirus vectors, and mammalian host cells and vectors such as plasmids, cosmids, BACs, YACs and viruses such as adenovirus and adenovirus associated virus (AAV).

Plasmids

In one embodiment, the present invention comprises a kit comprising a first universal transfer vector comprising a multiple cloning site, a replication origin, and a selectable marker; a second universal transfer vector comprising a multiple cloning site, a replication origin, and a selectable marker and an amplifiable vector comprising a multiple cloning site, a promoter, a replication origin or a chromosomal integration site, a poly-adenylation site and an amplifiable selectable marker. Generally, the multiple cloning sites comprise about 20, 25 or 30 restriction sites.

Plasmids of the present invention may include any of several amplifiable markers known in the art. Use of amplifiable markers is discussed in Maniatis, *Molecular Biology: A Laboratory Manual*, Cold Spring Harbor Laboratory, New York (1989)). Useful selectable markers for gene amplification in drug-resistant mammalian cells include DHFR (MTX (methotrexate) resistance) (Alt et al., J. Biol. Chem. 253:1357 (1978); Wigler et al., Proc. Natl. Acad. Sci. USA 77:3567 (1980)); metallothionein (cadmium resistance) (Beach et al., Proc Natl. Acad. Sci. USA 78:210 (1981)); CAD (N-(phosphonoacetyl)-1-aspartate (PALA) resistance) (Wahl et al., J. Biol. Chem. 254: 8679 (1979)); adenylate deaminase (coformycin resistance) (Debatisse et al., Mol. Cell. Biol. 6:1776 (1986)); IMP 5'-dehydrogenase (mycophenolic acid resistance) (Huberman et al., Proc. Natl. Acad. Sci. USA 78:3151 (1981)) and other markers known in the art (as reviewed, for example, in Kaufman et al., Meth. Enzymology 185:537-566 (1988)).

In one embodiment, the metallothionein 11 A gene under the control of a metallothionein promoter is an amplifiable marker in cell lines such as CHO-K1. Amplification can be induced by addition of $Cd^{2+}$ or $Zn^{2+}$ to the cell culture.

Plasmids of the invention may include other eukaryotic, non-amplifiable selectable markers known in the art. In an embodiment of the invention, the drug-resistance marker is the hygromycin B gene which confers resistance to hygromycin. Other markers include the G418 resistance gene. The plasmids of the invention may also include a prokaryotic antibiotic resistance marker such as the ampicillin resistance gene or the kanamycin resistance gene.

Plasmids of the invention may also include a matrix attachment region (MAR). Generally, MARs are DNA sequences capable of specific binding to nuclear proteins that are part of a fibrillar nuclear matrix analogous to the cytoskeleton. In one embodiment, the MAR is the chicken lysozyme MAR.

Promoters which may be used to control gene expression include, but are not limited to, SRα promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), the mouse CMV immediate early promoter, the SV40 early promoter region (Benoist, et al., Nature 290:304-310 (1981)), the *Orgyia pseudotsugata* immediate early promoter, the herpes thymidine kinase promoter (Wagner, et al., Proc. Natl. Acad. Sci. USA 78:1441-1445 (1981)), the regulatory sequences of the metallothionein gene (Brinster, et al., Nature 296:39-42 (1982)); prokaryotic expression vectors such as the β-lactamase promoter (Villa-Komaroff, et al., Proc. Natl. Acad. Sci. USA 75:3727-3731 (1978)), or the tac promoter (DeBoer, et al., Proc. Natl. Acad. Sci. USA 80:21-25 (1983)); and promoter elements from yeast or other fungi such as the GAL1, GAL4 or GAL10 promoter, the ADH (alcohol dehydrogenase) promoter, PGK (phosphoglycerol kinase) promoter or the alkaline phosphatase promoter.

Viral long terminal repeat promoters such as the mouse mammary tumor virus long terminal repeat (MMTV-LTR) (Fasel et al., EMBO J. 1(1):3-7 (1982)), the moloney murine sarcoma virus long terminal repeat (Reddy et al., Proc. Natl. Acad. Sci. USA 77(9): 5234-5238 (1980)), the moloney murine leukemia virus long terminal repeat (Van Beveren et al., Proc. Natl. Acad. Sci. USA 77(6): 3307-3311 (1980)), the HIV LTR (Genbank Accession No. AB100245), the bovine foamy virus LTR (Genbank Accession No. NC_001831), RSV 5'-LTR (Genbank Accession No. K00087), the HIV-2 LTR (Genbank Accession No. NC_001722), an avian retroviral LTR (Ju et al., Cell 22: 379-386 (1980)) and the human herpesvirus LTR (Genbank Accession No. NC_001806) may be included in the plasmids of the present invention.

Other acceptable promoters include the human CMV promoter, the human CMV5 promoter, the murine CMV promoter, the EF1α promoter, the SV40 promoter, a hybrid CMV promoter for liver specific expression (e.g., made by conjugating CMV immediate early promoter with the transcriptional promoter elements of either human α1-antitrypsin (HAT) or albumin (HAL) promoter), or promoters for hepatoma specific expression (e.g., wherein the transcriptional promoter elements of either human albumin (HAL; about 1000 bp) or human α1-antitrypsin (HAT, about 2000 bp) are combined with a 145 bp long enhancer element of human α1-microglobulin and bikunin precursor gene (AMBP); HAL-AMBP and HAT-AMBP).

In addition, bacterial promoters, such as the T7 RNA Polymerase promoter or the tac promoter, may be used to control expression.

A promoter (e.g., SRα promoter) may be linked to the cassette and then moved into a transfer vector (e.g., pULLS or PUHLS). In another embodiment, the transfer vector can contain a promoter upstream of the multiple cloning site (e.g., pULSRstopLS or pUHSRstopLS). When a gene, not linked to a promoter, is inserted into the multiple cloning site, it will be operably linked to the upstream promoter.

In yet another embodiment of the invention, a gene in a transfer vector, not linked to a promoter, can be moved into the amplifiable vector comprising a promoter (e.g., SRα promoter) upstream of the multiple cloning site (e.g., pSRX-BLS). When the unlinked gene is placed in the multiple cloning site, it will become operably linked to the promoter.

Plasmids of the invention may also include a polyadenylation signal/terminator for termination of the transcription of a gene in the plasmid and for the addition of a polyA tail to the transcript. For example, the chicken β-globin terminator/polyA signal may be included in a plasmid of the invention. Other acceptable poly A signals include the SV40 Poly A signal and the bovine growth hormone poly A signal.

In one embodiment of the invention, the amplifiable vector comprises a multiple cloning site including the following restriction sites: Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv CI, Pme I, Bss HII, Asc I, Xba I; for example, wherein the amplifiable vector multiple cloning site is that of pXBLS:

```
             AscI                        BclI      BsrGI  (SEQ ID NO: 10)
             ~~~~~~~~                    ~~~~~~    ~~~~~~
                        PmeI
                        ~~~~~~~~~~
     XbaI    BssHII         BbvCI        BspEI
     ~~~~~~  ~~~~~~~~       ~~~~~~~~     ~~~~~~

1  AAATCTAGAG GCGCGCCGTT TAAACCCTCA GCTGATCATC CGGATGTACA
     TTTAGATCTC CGCGCGGCAA ATTTGGGAGT CGACTAGTAG GCCTACATGT
             Fse1           MluI         NdeI        NruI
             ~~~~~~~~~~     ~~~~~~       ~~~~~~      ~~~~
     BssHII          KpnI         MscI         NotI
     ~~~~~~~~        ~~~~~~       ~~~~~~       ~~~~~~~~~~

51  GCGCGCGGCC GGCCGGTACC ACGCGTTGGC CACATATGGC GGCCGCTCGC
     CGCGCGCCGG CCGGCCATGG TGCGCAACCG GTGTATACCG CCGGCGAGCG
             PacI         SacII       Srf1           XhoI
             ~~~~~~~~~~   ~~~~~~~~    ~~~~~~~~~      ~~~~~~
     NruI       RsrII       SpeI      XmaI    SgrAI
     ~~         ~~~~~~~~    ~~~~~~    ~~~~~~  ~~~~~~~~~~

101  GATTAATTAA CGGACCGCCG CGGACTAGTG CCCGGGCCAC CGGTGCTCGA
     CTAATTAATT GCCTGGCGGC GCCTGATCAC GGGCCCGGTG GCCACGAGCT
     XhoI
     ~

151  GAAAA
     CTTTT.
```

In an embodiment of the invention, a universal transfer vector comprises a multiple cloning site including the following restriction sites: Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma III, Xba I, Sac I, Mlu I, Bcl I, Bsr GI, Bss HII; for example, wherein the transfer vector multiple cloning site is that of pUHLS:

```
           AscI                        HindIII     PaeR7I    (SEQ ID NO: 11)
           ~~~~~~~~~~                  ~~~~~~      ~~~~~~
                    PmeI     SnaBI         KpnI
                    ~~~~~~   ~~~~~~        ~~~~~~
     XmaI                                            XhoI
     ~~~                                             ~~~~~~
         BssHII         BbvCl              Asp718
         ~~~~~~~        ~~~~~~~            ~~~~~~~

1  GGGGGCGCGC CGTTTAAACC CTCAGCTACG TAAAGCTTGG TACCCTCGAG
     CCCCCGCGCG GCAAATTTGG GAGTCGATGC ATTTCGAACC ATGGGAGCTC
             ClaI                                  BspEI
             ~~~~~~                                ~~~~~~~
     HincII    EcoRV         PstI
     ~~~~~~    ~~~~~~        ~~~~~~
       SalI                         XmaI
       ~~~~                         ~~~~~~
       AccI         EcoRI     ApaI              BamHI
       ~~~~         ~~~~~~    ~~~~~~            ~~~

51  GTCGACATCG ATGATATCGA ATTCCTGCAG GGGCCCCCCG GTCCGGAGG
     CAGCTGTAGC TACTATAGCT TAAGGACGTC CCCGGGGGGC CAGGCCTCC
           NotI            MluI        BsrGI
           ~~~~~~~~~       ~~~~~~      ~~~~~~~
                    SacI
                    ~~~~~~
      BamHI      XbaI           BclI          Fse1
      ~~~~       ~~~~~~         ~~~~~~        ~~~~~~~~

101  ATCCGCGGCC GCTCTAGAGA GCTCACGCGT TGATCATGTA CAGGCCGGCC
     TAGGCGCCGG CGAGATCTCT CGAGTGCGCA ACTAGTACAT GTCCGGCCGG
             XmaI
             ~~~
        BssHII
        ~~~~~~~

151  AGCGCGCCCC
     TCGCGCGGGG.
```

A universal transfer vector may comprise a multiple cloning site including the following restriction sites: Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst 1, Eco O109I, Eco O109I, Apa I, Xma I, Bsp EI, Bam H1, Dsa I, Eag I, Ecl XI, Not I, Sac II, Xma III, Xba I, Sac I, Nde I, Msc I, Nru I, Pac I, Bss HII; for example, wherein the transfer vector multiple cloning site is that of pULLS:

transformed. Examples of suitable *E. coli* include DH1, DH5, DH5α, XL1-Blue, SURE, SCS110, OneShot Top 10, and HB101.

Plasmids may be introduced into a cell by any of the many methods which are commonly known in the art. For example, a plasmid of the invention can be used to transform a cell by the calcium phosphate method, electroporation, the DEAE-dextran method or the liposome method.

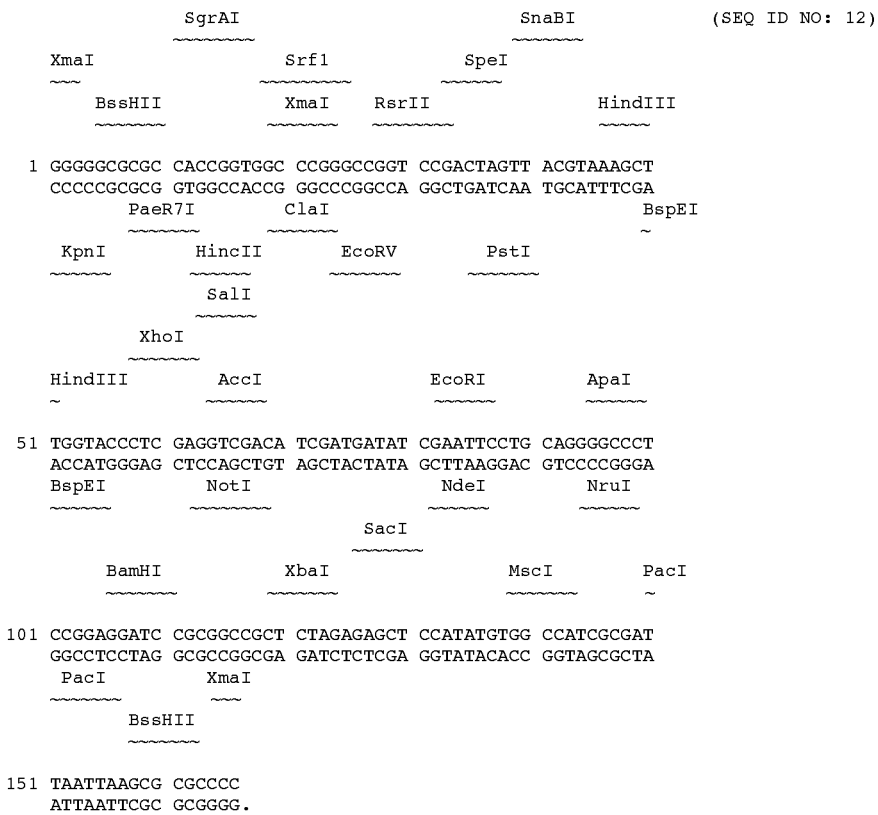

(SEQ ID NO: 12)

The present invention contemplates amplifiable vectors or universal transfer vectors comprising the above-referenced multiple cloning sites in the orientation shown or in the opposite orientation.

The plasmids of the present invention can be introduced into any cell line for expression of the target polypeptides. In one embodiment of the invention, the plasmids are introduced into a mammalian cell line, preferably a Chinese hamster ovary (CHO) cell line. A commonly used cell line is DHFR-CHO cell line which can be transformed to the DHFR⁺ phenotype using DHFR cDNA as an amplifiable dominant marker. One such known DHFR-CHO cell line is DX-B11 or DG-44. In another embodiment, the plasmids of the invention can be introduced into a lower eukaryotic cell line, such as from *S. cerevisiae, K. lactis, P. pastoris, C. albicans* or *A. fumigatus*. Further, the plasmids of the invention may also be introduced into higher eukaryotic non-mammalian cell lines such as from insect cells (e.g., *Drosophila melanogaster*, sf9 cells, sf21 cells), amphibian cells (e.g., *X. laevis*), plant cells (e.g., *A. thaliana*) and avian cells.

Plasmids of the invention can also be introduced into a bacterial cell. In one embodiment, competent *E. coli* are The plasmids of the invention can include any gene or combination of genes. In an embodiment of the invention the plasmids include heavy and light chain immunoglobulin genes. The immunoglobulin chains may be part of antibodies which specifically recognize any antigen such as IL-5, IGFR1 or IL-10. Receptors or receptor subunits may also be expressed. For example, a gene encoding the IL-2 receptor or a portion thereof (e.g., membrane domain) can be included in a plasmid of the invention.

U.S. patent application Ser. No. 10/443,466; filed May 22, 2003, which is herein incorporated by reference in its entirety, sets forth the nucleotide and amino acid sequences of immunoglobulin light chain and heavy chain variable regions of anti-IGFR1 antibodies. Any of the light and heavy chain variable regions disclosed therein can be incorporated into the plasmid system of the invention and expressed. In one embodiment, the anti-IGFR1 antibody light chain variable region is encoded by the nucleotide sequence set forth in SEQ ID NO: 15 or 19 or is any polynucleotide encoding a polypeptide comprising the amino acid sequence of SEQ ID NO: 16 or 20 and/or the anti-IGFR1 antibody heavy chain variable region is encoded by the nucleotide sequence set forth in SEQ ID NO: 17 or 21 or is any polynucleotide encoding a polypeptide comprising the amino acid sequence of SEQ ID NO: 18 or 22.

Expression cassettes encoding the immunoglobulin heavy and light chain of the anti-IGFR1 antibody can each be introduced into the multiple cloning site of either pULLS or pUHLS. Preferably, the immunoglobulin heavy and light chains, in the expression cassettes, are linked to an immunoglobulin constant region such as γ1, γ4 or κ. Preferably, the expression cassettes are then inserted into the amplifiable vector pXBLS which is then introduced into a cell suitable for causing the expression of the light and heavy chains. For example, the plasmid, pAIGFRV3, which contains the immunoglobulin heavy and light chains of an anti-IGFR1 antibody, can be introduced into a dhfr⁻ mammalian cell line (e.g., CHO-DXB11) wherein the chains are expressed.

Kits

The plasmid system of the invention may be provided in a kit. The kits of the invention may include, in addition to the plasmid system, any reagent which may be employed in the use of the plasmid system. In one embodiment, the kit includes reagents necessary for transformation of the plasmids into mammalian cells. For example, the kit may include reagents for a calcium phosphate transformation procedure: calcium chloride, buffer (e.g., 2× HEPES buffered saline), and sterile, distilled water. In another embodiment, the kit includes reagents for a DEAE-Dextran transformation: Chloroquine in PBS, DEAE-dextran in PBS and Phosphate buffered saline. In yet another embodiment, reagents for a liposome transformation are included in the kit: Liposomes extruded from DOTAP/cholesterol extruded liposomes. For example, the kit may include the cationic lipid-based transfection reagent Lipofectamine™ (Invitrogen Life Technologies; Carlsbad, Calif.).

The kit may include reagents required for bacterial transformation of the plasmids of the invention. For example, the kit may include transformation competent bacteria (e.g., DH1, DH5, DH5α, XL1-Blue, SURE, SCS110, OneShot Top 10, or HB101).

The kit may include growth media or reagents required for making growth media. For example, in one embodiment, the kit can include fetal calf serum or DMEM (Dulbecco/Vogt modified Eagle's (Harry Eagle) minimal essential medium) for growth of mammalian cells. In another embodiment, the kit can contain powdered Luria broth media or Luria broth plates containing an appropriate antibiotic (e.g., ampicillin or kanamycin) for growing bacteria.

Components supplied in the kit may be provided in appropriate vials or containers (e.g., plastic or glass vials). The kit can include appropriate label directions for storage, and appropriate instructions for usage.

Protein Expression and Purification

Polypeptides produced in the plasmid system of the invention can be purified by standard methods, including, but not limited to, salt or alcohol precipitation, affinity chromatography (e.g., used in conjunction with a purification tag), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in "*Guide to Protein Purification*", *Methods in Enzymology*, Vol. 182, M. Deutscher, Ed., 1990, Academic Press, New York, N.Y.

Particularly where a polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Polypeptides of the invention may be fused with a second polypeptide or polynucleotide moiety, which may be referred to as a "tag". A tag may be used, for example, to facilitate purification or detection of the polypeptide after expression. A fused polypeptide may be constructed, for example, by in-frame insertion of a polynucleotide encoding the tag on the 5' or 3' end of the polynucleotide encoding the polypeptide to be expressed. The fused polynucleotide may then be expressed in the plasmid system of the invention. Such tags include glutathione-S-transferase (GST), hexahistidine (His6) tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

EXAMPLES

The following examples are provided to further describe the present invention and should not be construed as a limitation thereof. The scope of the present invention includes any and all plasmids set forth, below, in the following examples either individually or as part of a kit. Also included within the scope of the invention are any and all of the methods which are set forth below in the following examples.

Example 1

Construction of Amplifiable Cloning Vectors, pSRXBLS and pXBLS

This example describes the construction of the mammalian expression vectors, pSRXBLS and pXBLS. A large multicloning site was inserted in the plasmid pDSRG downstream of the SRα promoter, to generate pSRXBLS. pXBLS, a derivative of pSRXBLS, is devoid of any promoter. Both of the plasmids can serve as amplifiable vectors into which more than one expression cassette, e.g., for the heavy and light chain cDNAs of an antibody gene, can be easily inserted.

A multiple cloning site of 155 bp, pDSRG-xba-xho, was designed, synthesized by PCR and cloned initially in the TA Cloning Vector (Invitrogen; Carlsbad, Calif.). It was later cloned at the XhoI and XbaI sites of pDSRG, resulting in pSRXBLS. The SRα promoter was retained in the pSRXBLS vector.

pSRXBLS was further digested with XhoI and HindIII to remove the SRα promoter. The ends were then filled in by Klenow and religated, regenerating the HindIII site, to construct pXBLS.

Example 2

Construction of Universal Transfer Vectors pUHLS, pULLS and Their Descendents This example describes the construction of universal transfer vectors, each having a large multiple cloning site, and their descendents, each carrying a promoter and a terminator/poly A addition site. pUHLS and pULLS are the universal transfer vectors, and pUHSRstopLS and pULSRstopLS are their corresponding descendents that carry the SRα promoter and the chicken β-globin terminator. The plasmid system is so constructed that different subunits of a large, complex protein can be expressed in these vectors separately. Later, the expression cassettes for each subunit can be transferred to a single vector, such as pXBLS or pSRXBLS, to facilitate transfection, integration and equimolar production of a multi-subunit protein.

Two multiple cloning sites, Universal Plasmid Primer 1 of 160 bp and Universal Plasmid Primer 2 of 166 bp, were designed to construct pUHLS and pULLS. Both of the cloning sites were synthesized by PCR, cloned in the TA Cloning Vector (Invitrogen) and later cloned at the BssHII sites of the pCRScript vector (Stratagene). Thus, the original multiple cloning site of pCRScript was replaced with newly synthesized multiple cloning sites. The new vectors, pUHLS and pULLS, were derived from the Universal Plasmid Primer 1 and Universal Plasmid Primer 2, respectively.

A 249 bp region of the chicken β-globin terminator, derived from pDSRG by digestion with BamHI and XbaI, was inserted in both pUHLS and pULLS at the BamHI and XbaI sites to generate pUHstopLS and pULstopLS, respectively. The SRα promoter and its accompanying intron, derived from pDSRG by digestion with HindIII and SalI, was inserted in pUHstopLS and pULstopLS at the HindIII and XhoI sites to generate pUHSRstopLS and pULSRstopLS, respectively.

Example 3

Construction of pAIL5V1

The construction of pAIL5V1 for the expression of heavy and light antibody chains in a single vector is described here. Aside from variations in their orientations, two types of plasmids have been constructed. The first carries only the dhfr marker for selection with amplification. The second type of expression plasmid carries the dhfr marker, along with the gene for hygromycin resistance (Hyg). This adds versatility, allowing selection with or without amplification.

The heavy chain gene of the anti-huIL5 human monoclonal antibody, (MAb) was isolated and inserted in the pUHSRstopLS vector (supra) at the EcoRI and XmaI sites to generate pUSRHLS. The light chain gene of the anti-huIL5 MAb was isolated and inserted in pULSRstopLS at the EcoRI and ApaI sites to generate pUSRLLS.

The hCMV minimal promoter, derived from pcDNA3.1 (Invitrogen; Carlsbad, Calif.) by digestion with NruI and EcoRI, replaced the SRα promoter, which was removed by digestion with SnaBI and EcoRI, in pUSRHLS and pUSRLLS to generate pUhCMVHLS and pUhCMVLLS. The TK-hygromycin gene (TK/Hyg) was inserted in pUhCMVHLS at the FseI sites to construct pUHhyg(+)hCMVLS and pUHhyg(−)hCMVLS. The light chain antibody cassette was transferred from pUhCMVLLS, by digestion with PacI and SrfI, to pXBLS at the PacI and SrfI sites to construct pAIL5L(−)hCMVLS and pAIL5L(+)hCMVLS. The heavy chain antibody cassette was transferred from pUHhyg(−)hCMVLS to pAIL5L(−)hCMVLS at the BssHII sites to generate pAIL5V1.

Example 4

Construction of pAIGFRV3 cDNAs encoding the variable regions from a hybridoma expressing an anti-IGFR1 monoclonal antibody 19D12/15H12 were isolated and cloned in TA cloning vectors (Invitrogen; Carlsbad, Calif.). The light and heavy chain amino acid and nucleotide sequences of antibody 19D12/15H12 are set forth in U.S. patent application Ser. No. 10/443,466; filed May 22, 2003 which is herein incorporated by reference in its entirety. The heavy chain was transferred from the EcoRI and ApaI sites of the TA vector containing cDNA for heavy chain of variable region of anti-IGFR1 to the same sites of pUhCMVHLS (supra) to construct pUhCMVIGFRHLS containing cDNA for light chain of anti-IGFR1. For selection, a TK-hygromycin resistance cassette was inserted at the FseI site of pUhCMVIGFRHLS to construct pUhCMVHyg(−)IGFRHLS. The light chain was transferred from the EcoRI and BbsI sites of the TA plasmid to the same sites of pUhCMVLLS (supra) to construct pUhCMVIGFRLLS. The entire light chain expression cassette was then transferred from pUhCMVIGFRLLS to pXBLS at the PacI and SrfI sites to construct pAIGFRLLS. The heavy chain expression cassette, along with the hygromycin expression cassette, was transferred to pAIGFRLLS at the BssHII sites to construct pAIGFRV1 and pAIGFRV3 (pIAGFRV1 is essentially identical to pAIGFRV3 except that the orientation of the heavy chain and the TK-Hyg genes are opposite).

Example 5

Construction of pAIL10V3 cDNAs encoding the variable regions of 12G8, a rat antibody which recognizes IL-10 were isolated. The heavy chain variable region of 12G8 was transferred to KpnI and ApaI site of pUhyg(−)IG1FRhuH plasmid to construct pUIL10H. The pUhyg(−)IG1FrhuH plasmid carries the modified cDNA for variable region of IGFR1 along with IgG1 cDNA and TK-Hygromycin cassette. The light chain variable region of 12G8 was transferred to the EcoRI and ApaI sites of pAIL5(−)hCMVLS to construct pAIL10(−)L. The heavy chain expression cassette from the pUIL10H was transferred to pAIL10(−)L at BssHII restriction sites to construct pAIL10V3.

Example 6

Construction of pAIG1FR(−)IL2LS pAIG1FR(−)IL2LS was constructed in a three step process. The construction process started with transfer of an IRES-IL2Rα element to pULstopLS. The plasmid containing the IRES-IL2Rα, pme18IRES, was digested with SpeI and NotI restriction enzymes and the NotI site was completely filled in using Klenow enzyme to derive the IRES-IL2Rα element. Simultaneously, pULstopLS was digested with EcoRV and SpeI enzymes and the SpeI site was filled in, using the Klenow enzyme, and ligated with the IRES-IL2Rα element to construct pULstopIRESIL2R. pULstopIRESIL2R was further digested with SpeI and XbaI enzyme and SpeI site was completely filled in with Klenow enzyme. Also pUhCMVIGFRLLS was digested with XbaI and BspEI enzymes and the BspEI site was completely filled in using Klenow enzyme and ligated with the XbaI-SpeI fragment that was generated from pULstopIRESIL2R to construct pUIGFRL-IRESIL2R. The heavy chain expression cassette of IGFR1 was transferred from pUhyg(−)IG1FRhuH to pUIGFRL-IRESIL2R at BssHII restriction sites to construct pAIG1 FR(−)IL2LS.

Example 7

Development of Cell Lines for Expressing Anti-IGFR1 Monoclonal Antibody 19D12

In this example, the development and growth of cell lines for expressing the 19D12 antibody (LCF/HCA) are presented.

DXB11 Cell Culture. Cells were grown in MEM Alpha Medium with ribonucleosides and deoxyribonucleosides (GIBCO Cat. # 12571-063; Gibco-Invitrogen Corp; Carlsbad, Calif.) plus 10% FBS (HyClone Cat. # SH30071.03; Hyclone; Logan, Utah).

Hygromycin selection media. Cells were split at 48 hours post-transfection. Cells were grown in MEM Alpha Medium without ribonucleosides and deoxyribonucleosides (GIBCO Cat. # 12561-056) plus 10% Dialyzed FBS (HyClone Cat. # SH30079.03) plus Hygromycin B (CLONTECH Cat. # 8057-1; BD Biosciences-Clontech; Palo Alto, Calif.) at 300 µg/mL.

Subcloning media. Subcloning was performed in MEM Alpha Medium without ribonucleosides and deoxyribonucleosides (GIBCO Cat. # 12561-056) plus 10% Dialyzed FBS (HyClone Cat. # SH30079.03).

Methotrexate (MTX) amplification media. Methotrexate amplification was carried out in MEM Alpha Medium without ribonucleosides and deoxyribonucleosides (GIBCO Cat. # 12561-056) plus 10% Dialyzed FBS (HyClone Cat. # SH30079.03) plus MTX (Sigma Cat. # M8407; Sigma-Aldrich Corp; St. Louis, Mo.) at 20, 80 and 320 nM, respectively.

Media for adaptation to serum free suspension. Adaptation to serum free suspension was performed in CHO Protein-Free Medium (Sigma Cat. # C5467) supplemented with 20 ml/L L-Glutamine-200 mM (GIBCO Cat. # 25030-081) and 10 ml/L Lipids (Cholesterol rich) (Sigma Cat. # L4646).

Feed medium for 3L production batch. L-Glutamine-200 mM (GIBCO Cat. # 25030-081) and Glucose Solution (Sigma Cat. # G8769) were served as the feed during production runs.

Transfection and Subcloning method. DXB11 cells were trypsinized, counted and plated @ 2×10$^6$ cells/T25 flask on the day before transfection, so that they became 50-90% confluent on the day of transfection. Transfections were performed using 2.5 µg DNA (pAIGFRV3)/T25 flask and LipofectAMINE PLUS™ reagent (GIBCO, cat. # 10964-013). As per the vendor's instructions, the DNA was first complexed with PLUS reagent, the DNA-PLUS complex was mixed with LipofectAMINE reagent and the DNA-PLUS-LipofectAMINE complex was then used to transfect the cells. The cells were incubated at 37° C. at 5% $CO_2$ for 3 hours. Following incubation, DXB11 cell culture medium was added to the desired volume, the cells and medium were transferred to a T75 flask, and the cells were grown for 2 days. The medium was exchanged with hygromycin selection medium, and the cells were grown for 10 days to 2 weeks. Some cells were banked at this stage, and the remaining cells were subcloned in 96 well plates.

Subcloning was initiated in 96 well plates with subcloning media. Single clones were successively grown in 24 well plates, 6 well plates, T-25 flasks and T-75 flasks, following detection of satisfactory expression by ELISA at each stage. Methotrexate media was added on 20-30% confluent cultures for amplification. Amplification was carried out at 20, 40, 80, and 320 nM methotrexate for 10 days to 2 weeks. Following amplification, the media was exchanged with the subcloning media and the cells were allowed to grow to ~10% confluence. The cells were subjected to another round of subcloning at this stage. Following the second round of subcloning, the cells were subjected to adaptation to serum free suspension culture with the designated media at the T-25 flask stage. Serum was sequentially eliminated from the media by dilution with serum free adaptation medium, and the cells were finally transferred to shake flasks with 2.5% serum. The remaining serum was eliminated by subsequent dilution (splitting) of the cultures. The serum free culture was scaled to 3 liters.

Example 8

Propagation of Cells Expressing Anti-IL5 Antibody

Cells carrying pAIL5V1 from a frozen vial are thawed and propagated in suspension using Sigma CHO protein-free medium (C-5467 supplemented with 0.57 g/L L-glutamine). All cultures are maintained in a 37° C., 7.5% $CO_2$ incubator or on a rocker bag platform set at 37° C. and supplying 7.5% $CO_2$. The inoculum train begins in a shake flask and is continuously passaged and scaled-up until there is enough culture to start a 20-Liter bag with a 2-liter working volume. When the bag reaches the predetermined split criteria, it is scaled up to a 10-liter working volume. When the bag reaches the predetermined split criteria, it is split and the remaining culture will be used to start another 20-liter rocker bag (10-liter working volume) in parallel. When the two rocker bags reach the appropriate split density, they are used to seed the production bioreactor. Shake flasks and rocker bags are typically split at 1:4 dilutions when the viable cell density reaches 1-1.5×10$^6$ viable cells/mL. The inoculum pool is diluted 1:4 going into the bioreactor.

Flow diagram illustrating the propagation process:

Vial↓

Thaw

SF-250V (C-5467 CHO media supplemented with L-glutamine)↓

20 mL, then to 60 mL (2 passages)

SF-1000V (C-5467 CHO media supplemented with L-glutamine)

250mL (1 passage), then create another SF-1000V with a 250mL working volume.↓

20-liter rocker bag (C-5467 CHO media supplemented with L-glutamine)

2 L (1passage), then to 10 L (1passage), then create another 20-liter bag with 10 L working volume.↓

Production Bioreactor at quarter volume (C-5467 CHO media supplemented with L-glutamine)

60 L (1 passage), then to full volume (200 L)

Example 9

Process for Purifying Anti-IL10 Antibody

This example describes the process for purifying the anti-IL10 antibody encoded by pAIL10V3 from a 200 liter CHO cell fermentation. The steps include:

Harvesting of cell culture supernatant by filtration with a positively charged CUNO filter in series with a 0.2 µm filter.

Affinity chromatography on Amersham rProtein-A SepharoseTM Fast Flow (4 L) eluted by a pH 3.0 step.

Viral Inactivation by incubation at pH 3.5 for 1 hour at 20-22° C., followed by pH adjustment to 5.5.

Cation exchange chromatography on EMD Fractogel® SE HiCap (4 L) at pH 5.5 eluted with a 20 BV gradient to 250 mM NaCl.

Concentration (2×)/Diafiltration (10×) into 20 mM Tris, pH 8.0.

Anion exchange chromatography on Amersham Q SepharoseTM Fast Flow (4 L) in flow-through mode. The unretained peak is pooled and adjusted to pH 5.5.

Viral Filtration with Planova filters: one 0.1 m² Planova 35 in series with 2-4 0.1 m² Planova 20 filters.

Final concentration (6-10×) and diafiltration (10×) into 20 mM sodium acetate followed by filtration (0.2 µm).

This process yields material that is >99% pure by RP-HPLC. Overall yield is 70%.

Example 10

Expression of Anti-IGFR1 and Anti-IL-10 Antibody

In this example, expression plasmids including the anti-IGFR and anti-IL-10 antibody chains were constructed wherein the antibody chain genes were situated, in the plasmids, adjacent to a MAR element (Selexis; Geneva, Switzerland; Kim et al., J. Biotechnol. 107(2): 95-105 (2004); Stief et al., Nature 341: 343-345 (1989); Phi-Van etal., Mol. Cell. Biol. 10: 2302-2307 (1990); Kalos et al., Mol. Cell. Biol. 15: 198-207 (1995)). The MAR element is a ~3 kb DNA element that aids the expression of a recombinant gene which is stably integrated in the host chromosome following incorporation into the cell.

The MAR element was inserted into the mammalian expression plasmids, pAIL10Vi, having anti-IL10 along with hygromycin expression cassette, pAIL10V1/puro, having anti-IL10 along with puromycin instead of hygromycin expression cassette, pAIGFRLCb2V1, having anti-IGFR1 along with hygromycin expression cassette, and pAIGFRLCb2V1/puro, having anti-IGFR1 along with puromycin instead of hygromycin expression cassette. Each plasmid already contained four independent mammalian expression cassettes.

The vector, pPAG01 contained the ~3 kb chicken lysozyme matrix attachment region (MAR) DNA element. One of the universal vectors, pULLS was digested by restriction enzymes, Age1 and BamH1 and was religated, following end filling by Klenow enzyme, to construct vector pULLSmod. The pPAG01 plasmid was digested by BamH1 and Xba1 to transfer the MAR element over to pULLSmod at the same sites to construct the plasmid pULMAR. The MAR element was finally transferred to the plasmids expressing anti-IL10 and anti-IGFR1. pULMAR was digested with BssHII and the fragment containing MAR element was transferred to the Asc1 sites of the plasmids pAIL10Vi, pAIL10V1/puro, pAIGFRLCb2V1 and pAIGFRLCb2V1/puro to construct pinAIL10/MAR(-), pAIL10V1/puro/MAR(-), pAIGFRLCb2/MAR(-) and pAIGFRLCb2/puro/MAR(-), respectively.

The MAR containing plasmids were introduced into the CHO cell line, DXB11 cells and the antibody chains were expressed. Expression of the antibody chains were confirmed by ELISA as well as HPLC analysis. In the HPLC analysis, the proteins isolated from the CHO cells was fractionated using a reverse-phase column or a protein-A column. Eluted protein was detected spectrophotometrically at $A_{280\ nm}$.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

I claim:

1. A plasmid system comprising in separate containers:
   (a) a first universal transfer vector comprising the following, first multiple cloning site, which multiple cloning site comprises the following restriction sites:
   Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma III, Xba I, Sac I, Mlu I, Bcl I, Bsr GI, Bss HII; wherein said restriction sites are in said orientation or in a reverse orientation;
   (b) a second universal transfer vector comprising the following, second multiple cloning site, which multiple cloning site comprises the following restriction sites:
   Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Bam H1, Dsa I, Eag I, Ecl XI, Not I, Sac II, Xma III, Xba I, Sac I, Nde I, Msc I, Nru I, Pac I, Bss HII;
   wherein said restriction sites are in said orientation or in a reverse orientation; and
   (c) an amplifiable vector comprising the following, third multiple cloning site, which multiple cloning site comprises the following restriction sites:
   Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I;
   wherein said restriction sites are in said orientation or in a reverse orientation; and wherein the first universal transfer vector, the second universal transfer vector and the amplifiable vector are in separate containers.

2. The plasmid system of claim 1 wherein at least one of the plasmids comprises a promoter located upstream of or within the multiple cloning site.

3. The plasmid system of claim 2 wherein the promoter is selected from SRα promoter, mouse mammary tumor virus long terminal repeat (MMTV LTR), human cytomegalovirus (hCMV) immediate early promoter and murine cytomegalovirus (mCMV) immediate early promoter.

4. The plasmid system of claim 1 wherein at least one of the universal transfer vectors comprises a terminator/polyA addition site.

5. The plasmid system of claim 1 wherein the amplifiable vector comprises a DHFR gene.

6. The plasmid system of claim 1 wherein one or more of said plasmids comprises a polynucleotide encoding an immunoglobulin light chain or an immunoglobulin heavy chain.

7. The plasmid system of claim 1 wherein the first universal transfer vector, second universal transfer vector or the emplifieble vector comprises a matrix attachment region.

8. The plasmid system of claim 7 wherein the amplifiable vector comprises a polynucleotide encoding (a) an anti-IGFR1 antibody heavy chain or an anti-IL10 antibody heavy chain; and (b) a polynucleotide encoding a puromycin resistance marker or a hygromycin resistance marker.

9. The plasmid system of claim 1 wherein said first universal transfer vector comprises a matrix attachment region.

10. The plasmid system of claim 9 wherein said matrix attachment region comprises the nucleotide sequence set forth in SEQ ID NO: 23.

11. The plasmid system of claim 1 wherein said second universal transfer vector comprises a matrix attachment region.

12. The plasmid system of claim 11 wherein said matrix attachment region comprises the nucleotide sequence set forth in SEQ ID NO: 23.

13. The plasmid system of claim 1 wherein said amplifiable vector comprises a matrix attachment region.

14. The plasmid system of claim 13 wherein said matrix attachment region comprises the nucleotide sequence set forth in SEQ ID NO: 23.

15. A plasmid system comprising (a) a first universal transfer vector comprising a first multiple cloning site wherein said first multiple cloning site comprises nucleotides 620-766 of the nucleotide sequence set forth in SEQ ID NO: 2; (b) a second universal transfer vector comprising a second multiple cloning site wherein said second multiple cloning site comprises nucleotides 620-772 of the nucleotide sequence set forth in SEQ ID NO: 1; and (c) an amplifiable vector comprising a third multiple cloning site wherein said third multiple cloning site comprises nucleotides 5037-5183 of the nucleotide sequence set forth in SEQ ID NO: 3; wherein the first universal transfer vector, the second universal transfer vector and the amplifiable vector are in separate containers.

16. A plasmid system comprising:
(a) a first universal transfer vector comprising the nucleotide sequence set forth in SEQ ID NO: 2;
(b) a second universal transfer vector comprising the nucleotide sequence set forth in SEQ ID NO: 1; and
(c) an amplifiable vector comprising the nucleotide sequence set forth in SEQ ID NO: 3; wherein the first universal transfer vector, the second universal transfer vector and the amplifiable vector are in separate containers.

17. A method for producing two or more polypeptides comprising the steps of:
(a) introducing a set of one or more expression cassettes encoding one or more of said polypeptides, wherein each cassette is operably associated with a promoter, into a first universal transfer vector comprising a first multiple cloning site which multiple cloning site comprises the following restriction sites: BsB HII, Pme I, Sna BI, Hin dIII, Asp 718, Kpn I, Pae R71, Xho I, Sal I, Acc I, Hinc II, Cla I, Eco RV, Eco RI, Psi I, Eco O109I, Eco O109I, Apa I, Xma I, Bsp EI, Ram HI, Dsa I, Eag I, Ecl XI, Not I, Sac II, Xma III, Xba I, Sac I, Mlu I, Bcl I, Bsr GI, and Bss HII; wherein said restriction sites are in said orientation or in a reverse orientation;
(b) introducing a set of one or more different expression cassettes encoding one or more of said polypeptides, wherein each cassette is operably associated with a promoter, into a second universal transfer vector comprising a second multiple cloning site which multiple cloning site comprises the following restriction sites:
Bss HII, Sgr AI, Xma I, Rsr II, Spe I, Sna BI, Hin dIII, Asp 718, Kpn I, Pae RTI, Xho I, Sal I, Acc I, Hinc II, Cla I, Eco RV, Eco RI, Pst I, Eco O109I, Eco O109I, Apa I, Bsp EI, Bam HI, Dsa I, Eag i, Ecl XI, Not I, Sac II, Xma III, Xba I, Sac I, Nde I, Msc I, Nru I, Pac I, and Bss HII;
wherein said restriction sites are in said orientation or in a reverse orientation;
(c) introducing the cassettes and promoters from the transfer vectors in (a) and (b) into an amplifiable vector comprising a third multiple cloning site which multiple cloning site comprises the following restriction sites:
Sgr AI, Srf I, Xma I, Spe I, Sac II, Rsr II, Pac I, Nru I, Not I, Nde I, Msc I, Mlu I, Kpn I, Fse I, Bss HII, Bsr GI, Bsp EI, Bcl I, Bbv C1, Pme I, Bss HII, Asc I, and Xba I;
wherein said restriction sites are in said orientation or in a reverse orientation; and wherein the first universal transfer vector, the second universal transfer vector and the amplifiable vector are in separate containers; and
(d) introducing the amplifiable vector, comprising said cassettes, into a host cell under conditions allowing expression of the polypeptides.

18. The method of claim 17 wherein the first universal transfer vector, the second universal transfer vector or the amplifiable vector comprises a matrix attachment region.

19. The method of claim 18 wherein the amplifiable vector comprises a polynucleotide encoding (a) an anti-IGFR1 antibody heavy chain operably associated with a promoter or an anti-IL10 antibody heavy chain, operably associated with a promoter; and (b) a polynucleotide encoding a puromycin resistance marker, operably associated with a promoter, or a hygromycin resistance marker operably associated with a promoter.

20. The method of claim 18 wherein the amplifiable vector, following step (c), is characterized by a plasmid map selected from the group consisting of FIGS. 13-16.

21. The method of claim 17 further comprising purifying one or more of the polypeptides.

22. The method of claim 17 wherein one set of the expression cassettes comprises a polynucleotide encoding an anti-IL5 immunoglobulin heavy chain and the other set of expression cassettes comprises a polynucleotide encoding an anti-IL5 immunoglobulin light chain.

23. The method of claim 17 wherein one set of expression cassettes comprises a polynucleotide, operably associated with a promoter, which polynucleotide encodes an anti-IGFR1 immunoglobulin heavy chain and the other set of expression cassettes comprises a polynucleotide, operably associated with a promoter, which polynucleotide encodes an anti-IGFR1 immunoglobulin light chain.

24. The method of claim 17 wherein one set of expression cassettes comprises a bicistronic gene, operably associated with a promoter, encoding an anti-IGFR1 immunoglobulin light chain and an IL2 receptor α-subunit which are linked by an internal ribosome entry sequence (IRES) and the other set of expression cassettes comprises a polynucleotide, operably associated with a promoter, encoding an anti-IGFR1 immunoglobulin heavy chain and a polynucleotide, operably associated with a promoter, encoding a HYG-B polypeptide.

25. The method of claim 17 wherein one set of expression cassettes comprises a polynucleotide, operably associated with a promoter, encoding an anti-IL10 immunoglobulin heavy chain and the other set of expression cassettes comprises a polynucleotide, operably associated with a promoter, encoding an anti-IL10 immunoglobulin light chain and a polynucleotide, operably associated with a promoter, encoding a HYG-B polypeptide.

26. A method for producing an anti-IGFR1 antibody comprising the steps of:
   (a) introducing an expression cassette comprising a polynucleotide encoding a polypeptide comprising an amino acid sequence selected from SEQ ID NOs: 18 and 22, wherein said polynucleotide is operably associated with a promoter,
   or an expression cassette comprising a polynucleotide encoding a polypeptide comprising an amino acid sequence selected from SEQ ID NOs: 16 and 20, wherein said polynucleotide is operably associated with a promoter, into a first universal transfer vector comprising a first multiple cloning site which multiple cloning site comprises the following restriction sites: Bss HII, Pme I, Sna BI, Hin dIII, Asp 718, Kpn I, Pae R71, Xho I, Sal I, Acc I, Hinc II, Cla I, Eco RV, Eco RI, Pst I, Eco OI09I, Eco OI09I, Apa I, Xma I, Bsp EI, Bam HI, Dsa I, Eag I, Ecl XI, Not I, Sac II, Xma III, Xba I, Sac I, Mlu I, Bcl I, Bsr GI, and Bss HII; wherein said restriction sites are in said orientation or in a reverse orientation;
   (b) introducing the other expression cassette, not introduced into said first vector, into a second universal transfer vector comprising a second multiple cloning site which multiple cloning site comprises the following restriction sites:
   Bss HII, Sgr AI, Xma I, Rsr II, Spe I, Sna BI, Hin dIII, Asp 718, Kpn I, Pae R71, Xho I, Sal I, Acc I, Hinc II, Cla I, Eco RV, Eco RI, Pst I, Eco O1091, Eco O1091, Apa I, Bsp EI, Bam HI, Dsa I, Eag I, Ecl XI, Not I, Sac II, Xma III, Xba I, Sac I, Nde I, Msc I, Nru I, Pac I, and Bss HII;
   wherein said restriction sites are in said orientation or in a reverse orientation;
   (c) introducing the cassettes from the transfer vectors in (a) and (b) into an amplifiable vector comprising a third multiple cloning site which multiple cloning site comprises the following restriction sites: Sgr AI, Srf I, Xma I, Spe I, Sac II, Rsr II, Pac I, Nru I, Not I, Nde I, Msc I, Mlu I, Kpn I, Fse I, Bss HII, Bsr GI, Bsp EI, Bcl I, Bbv Cl, Pme I, Bss HII, Asc I, and Xba I;
   wherein said restriction sites are in said orientation or in a reverse orientation; and wherein the first universal transfer vector, the second universal transfer vector and the amplifiable vector are in separate containers; and
   (d) introducing the amplifiable vector, comprising said cassettes, into a host cell under conditions allowing expression of the polypeptides.

27. The method of claim 26 further comprising purifying one or more of the polypeptides.

28. The method of claim 26 wherein the polynucleotide encoding a polypeptide comprising an amino acid sequence selected from SEQ ID NOs: 18 and 22 comprises a nucleotide sequence selected from SEQ ID NOs: 17 and 21.

29. The method of claim 26 wherein the polynucleotide encoding a polypeptide comprising an amino acid sequence selected from SEQ ID NOs: 16 and 20 comprises a nucleotide sequence selected from SEQ ID NOs: 15 and 19.

30. The method of claim 26 wherein the promoter is a human cytomegalovirus (hCMV) promoter.

31. The method of claim 26 comprising the steps of:
   (a) introducing an expression cassette comprising a polynucleotide, operably associated with a promoter, encoding a polypeptide comprising the amino acid sequence set forth in SEQ ID NO: 22 or an expression cassette comprising a polynucleotide, operably associated with a promoter, encoding a polypeptide comprising an amino acid sequence set forth in SEQ ID NO: 20 into a first universal transfer vector comprising a first multiple cloning site which multiple cloning site comprises the following restriction sites: Bss HII, Pme I, Sna BI, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI Bam HI, Dsa I, Eag I, Ecl XI, Not I, Sac II, Xma III, Xba I, Sac I, Mlu I, Bcl I, Bsr GI, and Bss HII;
   wherein said restriction sites are in said orientation or in a reverse orientation;
   (b) introducing the other expression cassette, not introduced into said first vector, into a second universal transfer vector comprising, a second multiple cloning site which multiple cloning site comprises the following restriction sites:
   Bss Hil, Sgr AI, Xma I, Rsr II, Spe I, Sna BI, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Bam HI, Dsa I, Eag I, Ecl XI, Not I, Sac II, Xma III, Xba I, Sac I, Nde I, Msc I, Nru I, Pac I, and Bss HII;
   wherein said restriction sites are in said orientation or in a reverse orientation;
   (c) introducing the cassettes from the transfer vectors in (a) and (b) into an amplifiable vector comprising a third multiple cloning site which multiple cloning site comprises the following restriction sites:
   Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv Cl, Pme I, Bss HII, Asc I, and Xba I;
   wherein said restriction sites are in said orientation or in a reverse orientation; and wherein the first universal transfer vector, the second universal transfer vector and the amplifiable vector are in separate containers; and
   (d) introducing the amplifiable vector, comprising said cassettes, into a host cell under conditions allowing expression of the polypeptides.

32. The method of claim 31 wherein the polynucleotide encoding the polypeptide comprising the amino acid sequence set forth in SEQ ID NO: 22 comprises a nucleotide sequence set forth in SEQ ID NO: 21.

33. The method of claim 31 wherein the polynucleotide encoding the polypeptide comprising the amino acid sequence set forth in SEQ ID NO: 20 comprises a nucleotide sequence set forth in SEQ ID NO: 19.

34. The method of claim 31 further comprising purifying one or more of the polypeptides.

35. The method of claim 26 comprising the steps of:
   (a) introducing an expression cassette comprising a polynucleotide, operably associated with a promoter, encoding a polypeptide comprising the amino acid sequence set forth in SEQ ID NO: 16 or an expression cassette comprising a polynucleotide, operably associated with a promoter, encoding a polypeptide comprising an amino acid sequence set forth in SEQ ID NO: 18 into a first universal transfer vector comprising a first multiple cloning site which multiple cloning site comprises the following restriction sites: Bss HII, Pme I, Sna BI, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam HI, Dsa I, Eag I, Ecl XI, Not I, Sac II, Xma III, Xba I, Sac I, Mlu I, Bcl I, Bsr GI, and Bss HII;

wherein said restriction sites are in said orientation or in a reverse orientation;

(b) introducing the other expression cassette, not introduced into said first vector, into a second universal transfer vector comprising a second multiple cloning site which multiple cloning site comprises the following restriction sites:

Bss HII, Sgr AI, Xma I, Rsr II, Spe I, Sna BI, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Bam HI, Dsa I, Eag I, Ecl XI, Not I, Sac II, Xma III, Xba I, Sac I, Nde I, Msc I, Nru I, Pac I, and Bss HII;

wherein said restriction sites are in said orientation or in a reverse orientation;

(c) introducing the cassettes from the transfer vectors in (a) and (b) into an amplifiable vector comprising a third multiple cloning site which multiple cloning site comprises the following restriction sites:

Sgr AI, Srf I, Xma I, Spe I, Sac II, Rsr II, Pac I, Nru I, Not I, Nde I, Msc I, Mlu I, Kpn I, Fse I, Bss HII, Bsr GI, Bsp EI, Bcl I, Bbv CI, Pme I, Bss HII, Asc I, and Xba I;

wherein said restriction sites are in said orientation or in a reverse orientation; and wherein the first universal transfer vector, the second universal transfer vector and the amplifiable vector are in separate containers; and (d) introducing the amplifiable vector, comprising said cassettes, into a host cell under conditions allowing expression of the polypeptides.

36. The method of claim 35 wherein the polynucleotide encoding the polypeptide comprising the amino acid sequence set forth in SEQ ID NO: 16 comprises a nucleotide sequence set forth in SEQ ID NO: 15.

37. The method of claim 35 wherein the polynucleotide encoding the polypeptide comprising the amino acid sequence set forth in SEQ ID NO: 18 comprises a nucleotide sequence set forth in SEQ ID NO: 17.

38. The method of claim 35 further comprising purifying one or more of the polypeptides.

39. A kit comprising the plasmid system of claim 1 and one or more components selected from
   (i) sterile, distilled water;
   (ii) calcium phosphate transformation reagents $CaCl_2$ and 2×HEPES buffered saline;
   (iii) DEAE-dextran transformation reagents chloroquine in Phosphate buffered saline and phosphate buffered saline;
   (iv) DOTAP/cholesterol extruded liposomes;
   (v) Transformation competent *E.coli;*
   (vi) Dulbecco/Vogt modified Eagle's minimal essential medium (DMEM);
   (vii) Fetal calf serum;
   (viii) Luria broth media; and
   (ix) paper instructions for usage of the plasmid system.

* * * * *